(12) United States Patent
Farren

(10) Patent No.: US 9,687,575 B2
(45) Date of Patent: Jun. 27, 2017

(54) UV DEVICES, SYSTEMS AND METHODS FOR UV STERILIZATION

(71) Applicant: BlueMorph LLC, Oakland, CA (US)

(72) Inventor: Alexander Farren, Oakland, CA (US)

(73) Assignee: BlueMorph, LLC, Oakland, CA (US)

(*) Notice: Subject to any disclaimer, the term of this patent is extended or adjusted under 35 U.S.C. 154(b) by 309 days.

(21) Appl. No.: 14/302,375

(22) Filed: Jun. 11, 2014

(65) Prior Publication Data

US 2014/0356229 A1 Dec. 4, 2014

Related U.S. Application Data

(63) Continuation-in-part of application No. 14/091,311, filed on Nov. 26, 2013, which is a
(Continued)

(51) Int. Cl.

| | |
|---|---|
| *A61L 2/00* | (2006.01) |
| *G21G 1/00* | (2006.01) |
| *A61L 2/10* | (2006.01) |
| *H01J 37/244* | (2006.01) |
| *A23L 3/28* | (2006.01) |
| *A61L 9/20* | (2006.01) |

(52) U.S. Cl.
CPC .......... *A61L 2/10* (2013.01); *A23L 3/28* (2013.01); *A61L 9/20* (2013.01); *H01J 37/244* (2013.01);
(Continued)

(58) Field of Classification Search
CPC ...................................... A61L 2/10; A23L 3/28
(Continued)

(56) References Cited

U.S. PATENT DOCUMENTS

| | | |
|---|---|---|
| 1,788,906 A | 1/1931 | Brown |
| 2,194,463 A | 3/1940 | Powley |
| (Continued) | | |

FOREIGN PATENT DOCUMENTS

| | | |
|---|---|---|
| CN | 2608008 Y | 3/2004 |
| CN | 201481833 U | 5/2010 |
| (Continued) | | |

OTHER PUBLICATIONS

International Search Report and Written Opinion under Patent Cooperation Treat (PCT) for PCT/US2011/38826; Sep. 12, 2011; 8 pages.
(Continued)

*Primary Examiner* — Kevin Joyner
(74) *Attorney, Agent, or Firm* — Duane Morris LLP; Siegfried J. W. Ruppert

(57) ABSTRACT

Provided herein are ultraviolet (UV) devices, systems, and methods for UV disinfection and sterilization, more specifically, UV devices, systems, and methods for UV disinfection and sterilization of a container, room, space or defined environment. The systems, UV devices, and methods are particularly useful for the UV disinfection and sterilization of a container used in the food and dairy industry and for containers used in the process of fermentation for an alcoholic beverage. Provided are also UV devices, systems, and methods for inhibiting the growth of one or more species of microorganisms present in a container, room, space or defined environment, preferably for inhibiting the growth of one or more species of microorganisms present on an interior surface of a container, room, space or defined environment.

64 Claims, 74 Drawing Sheets

Related U.S. Application Data continuation-in-part of application No. 13/650,028, filed on Oct. 11, 2012, now Pat. No. 9,387,268, which is a continuation-in-part of application No. 13/314,007, filed on Dec. 7, 2011, which is a continuation-in-part of application No. 13/308,383, filed on Nov. 30, 2011, now abandoned, which is a continuation-in-part of application No. 13/151,196, filed on Jun. 1, 2011, now Pat. No. 9,044,521, which is a continuation of application No. PCT/US2011/063827, filed on Dec. 7, 2011, which is a continuation-in-part of application No. 13/151,196, filed on Jun. 1, 2011, and a continuation-in-part of application No. PCT/US2011/038826, filed on Jun. 1, 2011, which is a continuation of application No. PCT/US2014/042013, filed on Jun. 11, 2014, which is a continuation-in-part of application No. 14/091,311, filed on Nov. 26, 2013.

(60) Provisional application No. 61/350,414, filed on Jun. 1, 2010.

(52) U.S. Cl.
CPC ....... *A61L 2202/14* (2013.01); *A61L 2202/16* (2013.01); *A61L 2202/23* (2013.01); *A61L 2202/25* (2013.01); *A61L 2209/212* (2013.01); *H01J 2237/0245* (2013.01); *H01J 2237/22* (2013.01)

(58) Field of Classification Search
USPC .......................................... 422/24; 250/492.1
See application file for complete search history.

(56) References Cited

U.S. PATENT DOCUMENTS

| | | |
|---|---|---|
| 2,499,153 A | 2/1950 | Nicholson |
| 3,906,236 A | 9/1975 | Callahan |
| 4,150,164 A | 4/1979 | Gerek |
| 4,396,582 A | 8/1983 | Kodera |
| 4,786,812 A | 11/1988 | Humphreys |
| 4,830,968 A | 5/1989 | Thornton et al. |
| 4,871,559 A | 10/1989 | Dunn et al. |
| 4,877,964 A | 10/1989 | Tanaka |
| 5,020,183 A | 6/1991 | Grant, Jr. |
| 5,597,597 A | 1/1997 | Newman |
| 5,744,094 A | 4/1998 | Castberg et al. |
| 5,920,075 A | 7/1999 | Whitehead |
| 6,074,565 A | 6/2000 | Buckner |
| 6,110,424 A | 8/2000 | Maiden |
| 6,299,770 B1 | 10/2001 | Diener |
| 6,368,554 B1 | 4/2002 | Wajsfeiner et al. |
| 6,396,068 B1 | 5/2002 | Sweatt |
| 6,403,030 B1 | 6/2002 | Horton, III |
| 6,517,776 B1 | 2/2003 | Rodgers et al. |
| 6,524,529 B1 | 2/2003 | Horton, III |
| 6,579,495 B1 | 6/2003 | Maiden |
| 6,592,816 B1 | 7/2003 | Ebel |
| 6,646,270 B2 | 11/2003 | Cunningham |
| 6,665,326 B2 | 12/2003 | Kusunose |
| 6,953,940 B2 | 10/2005 | Leighley |
| 7,081,636 B2 | 7/2006 | Moruzzi |
| 7,390,417 B2 | 6/2008 | Kuhlmann |
| 7,443,903 B2 | 10/2008 | Leonardo |
| 7,547,893 B1 | 6/2009 | Tantillo |
| 7,829,016 B2 | 11/2010 | Deal et al. |
| 8,125,333 B2 | 2/2012 | Ressler |
| 8,519,356 B2 | 8/2013 | Boyle |
| 8,921,813 B2 | 12/2014 | Palmer |
| 9,006,683 B2 | 4/2015 | Wen |
| 9,013,116 B2 | 4/2015 | Porter |
| 9,045,358 B2 | 6/2015 | Greuel |
| 2002/0063954 A1 | 5/2002 | Horton |
| 2002/0122742 A1 | 9/2002 | Wajsfelner |
| 2002/0122743 A1 | 9/2002 | Huang |
| 2003/0067768 A1 | 4/2003 | Shiau |
| 2006/0011263 A1 | 1/2006 | Till |
| 2006/0032199 A1 | 2/2006 | Beam |
| 2006/0042205 A1 | 3/2006 | Kalous |
| 2006/0284109 A1 | 12/2006 | Scheir |
| 2007/0140435 A1 | 6/2007 | Schwieker |
| 2008/0073595 A1 | 3/2008 | Thiruppathi |
| 2008/0095661 A1 | 4/2008 | Kohler |
| 2008/0199353 A1 | 8/2008 | Mlodzinski |
| 2008/0206095 A1 | 8/2008 | Duthie |
| 2008/0240978 A1 | 10/2008 | Sorensen et al. |
| 2008/0253941 A1 | 10/2008 | Wichers |
| 2009/0010826 A1 | 1/2009 | Shin |
| 2009/0148358 A1 | 6/2009 | Wind |
| 2009/0274576 A1 | 11/2009 | Ressler |
| 2010/0187443 A1 | 7/2010 | Leben |
| 2010/0266445 A1 | 10/2010 | Campagna |
| 2011/0031203 A1 | 2/2011 | Chapman |
| 2011/0049391 A1 | 3/2011 | Yang |
| 2011/0079590 A1 | 4/2011 | Lin |
| 2011/0143000 A1 | 6/2011 | Fiset |
| 2011/0165018 A1 | 7/2011 | Lynn |
| 2011/0286883 A1 | 11/2011 | Hecht |
| 2011/0305597 A1 | 12/2011 | Farren |
| 2012/0121457 A1 | 5/2012 | Farren |
| 2013/0175460 A1 | 7/2013 | Farren |
| 2013/0323118 A1 | 12/2013 | Krueger |
| 2014/0161663 A1 | 6/2014 | Farren |

FOREIGN PATENT DOCUMENTS

| | | |
|---|---|---|
| CN | 202724291 U | 2/2013 |
| CN | 202961251 U | 6/2013 |
| CN | 203169632 U | 9/2013 |
| CN | 104340508 A | 2/2015 |
| DE | 3500487 A1 | 7/1986 |
| DE | 4407183 A1 | 9/1995 |
| DE | 29812427 U1 | 4/1999 |
| EP | 1120121 A2 | 8/2001 |
| GB | 495499 A | 11/1938 |
| GB | 556912 A | 10/1943 |
| GB | 2454642 A | 5/2009 |
| JP | H0280509 U | 6/1990 |
| JP | H1024092 A | 1/1998 |
| JP | 2001171621 A | 6/2001 |
| JP | 2001247108 A | 9/2001 |
| JP | 2015157646 A | 9/2015 |
| KR | 846075 B1 | 7/2008 |
| KR | 20100122422 A | 11/2010 |
| KR | 20110070267 A | 6/2011 |
| KR | 20150028154 A | 3/2015 |
| KR | 20150042959 A | 4/2015 |
| WO | WO90/05909 | 5/1990 |
| WO | WO 02/36437 A1 | 5/2002 |
| WO | WO2004/064875 A2 | 8/2004 |
| WO | WO2007/035907 | 3/2007 |
| WO | WO 2009/086053 A1 | 7/2009 |
| WO | WO2010/021506 A2 | 2/2010 |
| WO | WO2010/133698 A2 | 11/2010 |
| WO | WO 2011/153288 A1 | 12/2011 |
| WO | WO 2015/080768 A1 | 6/2015 |
| WO | WO2015/116833 A1 | 8/2015 |

OTHER PUBLICATIONS

International Search Report and Written Opinion under Patent Cooperation Treat (PCT) for PCT/US11/63827; Dated Apr. 18, 2012; 10 pages.
International Search Report from the International Searching Authority issued Oct. 28, 2016 for PCT/US2016/044924.
Written Opinion from the International Searching Authority issued Oct. 28, 2016 for PCT/US2016/044924.

| Length | Model | Description | Type* | Diameter/Base | UVC Output Watts | UV pW/cm² @1m |
|---|---|---|---|---|---|---|
| 6" | GML370 | Hot Cathode | PL-S9W/TUV | PL-S | 2.4 | |
| 6" | GML180 | Hot Cathode | G 4T5 | T5/mini bi-pin | 0.5 | 5.4 |
| 6" | GML170 | Hot Cathode | OZ4T5 | T5/mini bi-pin | 0.5 | 5.4 |
| 9" | GML195 | Hot Cathode | G 6T5 | T5/mini bi-pin | 1.0 | 11 |
| 9" | GML190 | Hot Cathode | OZ 6T5 | T5/mini bi-pin | 1.1 | 11 |
| 12" | GML205 | Hot Cathode | G 8T5 | T5/mini bi-pin | 1.6 | 17 |
| 12" | GML125 | Slimline | G12T5½L/BP | T5/mini bi-pin | 6.0 | 66 |
| 12" | GML075 | Slimline | G12T5½VH/BP | T5/mini bi-pin | 6.0 | 66 |
| 12" | GML405 | High Output | GPH357T5L/HO | Four-pin | 8.5 | 92 |
| 14" | AAWHO/14 | High Output | Custom | Four-pin | 12 | 106 |
| 16" | GML020 | Cold Cathode | 782 L 10 | T5/single-pin | 2.0/2.8 | 20/28 |
| 16" | GML120 | Cold Cathode | 782 VH 10 | T5/single-pin | 2.0/2.8 | 20/28 |
| 16" | GML060 | Slimline | G10T5½L | T5/single-pin | 5.3 | 55 |
| 16" | GML350 | Slimline | G10T5½L-4P | T5/four-pin | 5.3 | 55 |
| 16" | GML070 | Slimline | G10T5½LVH | T5/single-pin | 5.3 | 55 |
| 18" | GML430 | Hot Output | GSL406T5L/HO | Four-pin | 10.0 | 108 |
| 18" | GML210 | Hot Cathode | G15T8 | T8/medium bi-pin | 3.6 | 38 |
| 18" | GML215 | Hot Cathode | G25T8 | T8/medium bi-pin | 5.0 | 54 |
| 18" | GML410 | High Output | GSL406T5L/HO | Single-pin | 10.0 | 100 |
| 22" | AAWHO/22 | High Output | GPH550T5/HO/4 | Four-pin | 18 | 174 |
| 22" | GML225MBP | High Output | CUSTOM | T5 15mm Bi-pin | 18 | 157 |
| 24" | GML435 | High Output | GPH610T5L/HO | Four-pin | 16.2 | 175 |
| 24" | GML0224/4PNO | High Output | CUSTOM | T5 15mm Four-pin | 20 | 168 |
| 24" | GML0244PO | High Output | CUSTOM | T5 15mm Four-pin | 20 | 168 |
| 27" | GML025 | Cold Cathode | 782 L 20 | T5/single-pin | 3.9/5.5 | 35/52 |
| 27" | GML290 | Cold Cathode | 782 VH 20 | T5/single-pin | 3.9/5.5 | 35/52 |
| 27" | GML325 | Slimline | GSL591 | T5/single-pin | | |
| 27" | GML355 | Slimline | S24T5-4P | T5/four-pin | | |
| 27" | GML415 | High Output | GPH610T5L/HO | Single-pin | 16.2 | 140 |
| 30" | GML030 | Cold Cathode | 782 L 25½ | T5/single-pin | 7.3 | 75 |
| 36" | GML010 | Cold Cathode | 782 L 30 | T5/single-pin | 5.2/8.3 | 46/73 |
| 36" | GML035 | Cold Cathode | 782 VH 29 | T5/mini bi-pin | 5.7/9.1 | 50/80 |
| 36" | GML040 | Cold Cathode | 782 H 30 | T5/single-pin | 5.2/8.3 | 46/73 |
| 36" | GML220 | Hot Cathode | G30T8 | T8/medium bi-pin | 8.3 | 85 |
| 36" | GML005 | Slimline | G36T6L | T5/single-pin | 13.8 | 120 |
| 36" | GML100 | Slimline | G36T6L-4P | T5/four-pin | 12.7 | 110 |
| 36" | GML090 | Slimline | G36T6VH | T5/single-pin | 13.8 | 120 |
| 36" | GML095 | Slimline | G37T6VH | T5/single-pin | 15.2 | 124 |
| 36" | GML420 | High Output | GSL843T5L/HO | Single-pin | 25 | 195 |
| 36" | GML440 | High Output | GSL843T5L/HO/4 | Four-pin | 25 | 195 |
| 48" | GML425 | High Output | GSL1148T5L/HO | Single-pin | 36.1 | 250 |
| 48" | GML445 | High Output | GSL1148T5L/HO/4 | Four-pin | 36.1 | 250 |
| 64" | GML015 | Slimline | G64T5L | T5/single-pin | 26.7 | 190 |
| 64" | GML017 | High Output | GXO64T5L H/O | Single-pin | 46 | 370 |
| 64" | GML140 | Slimline | G84T5VH | T5/single-pin | 26.7 | 190 |
| 64" | GML270 | Slimline | G64T5L-4P | T5/four-pin | 26.7 | 190 |

FIG. 17

5" Parabolic Diffuser
10' Sections

7" Parabolic Diffuser
10' Sections

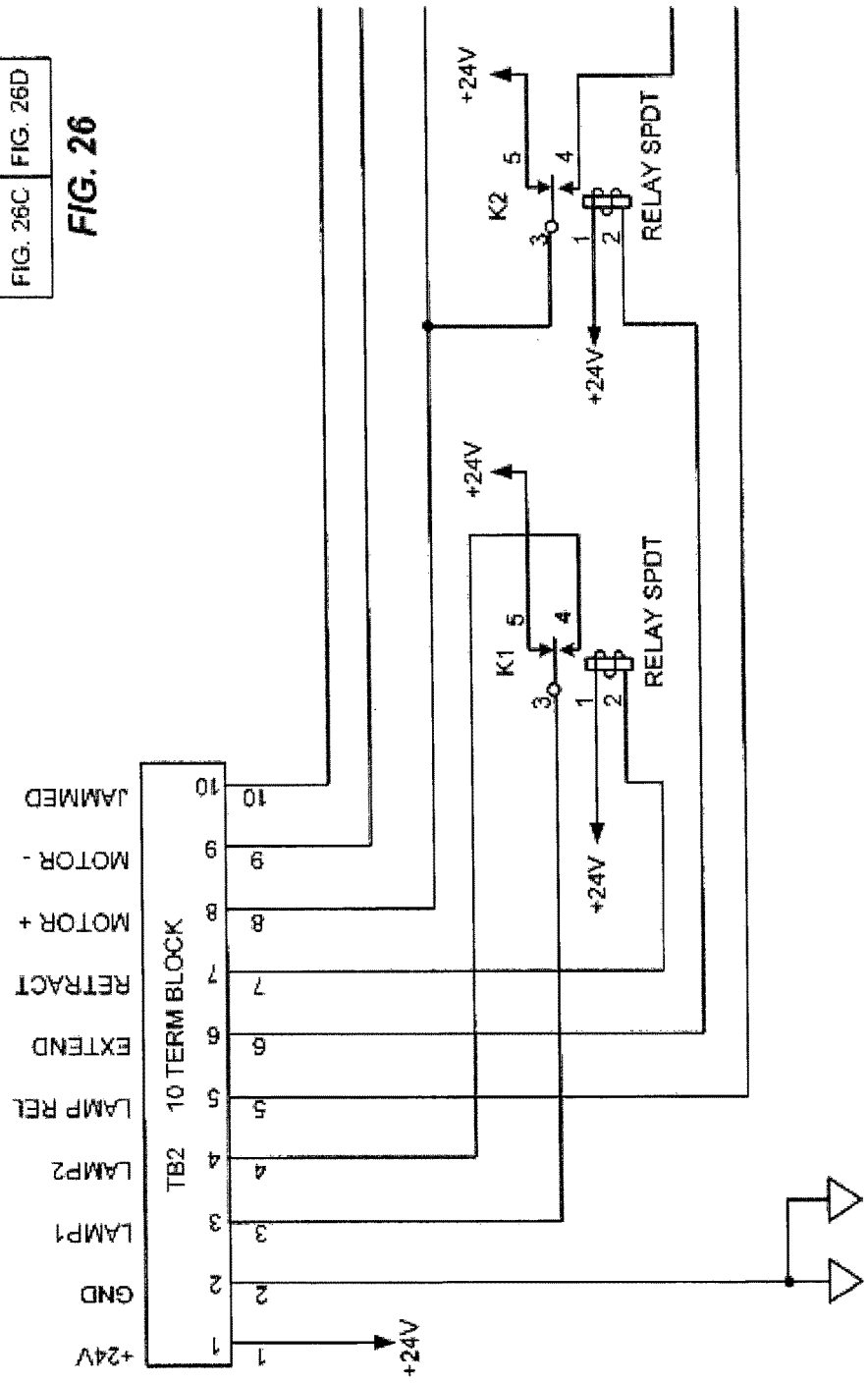

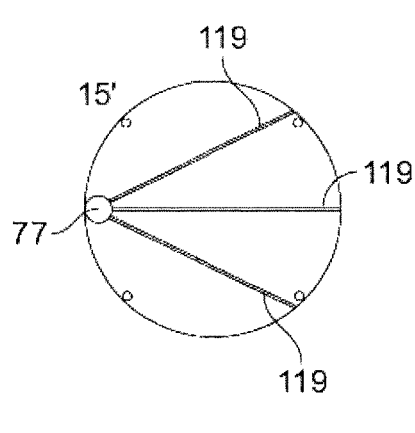
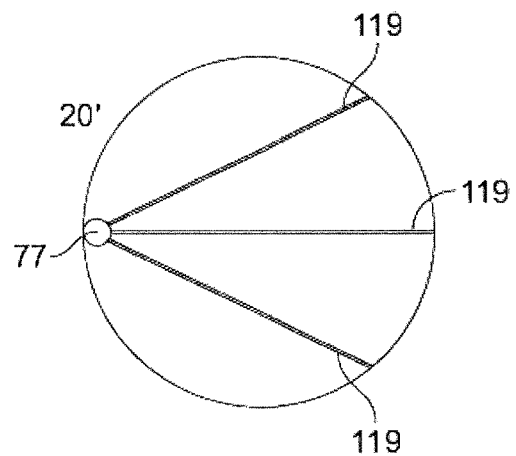
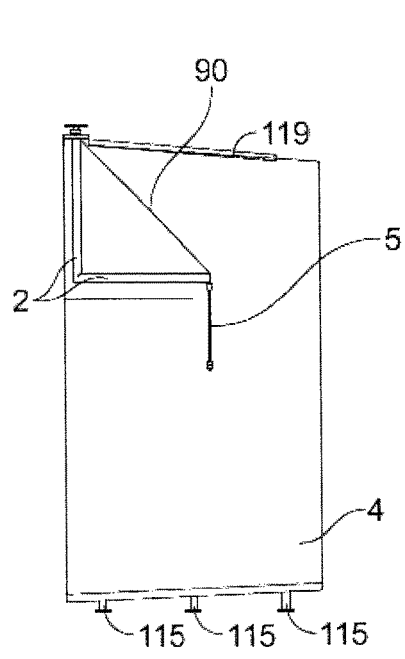
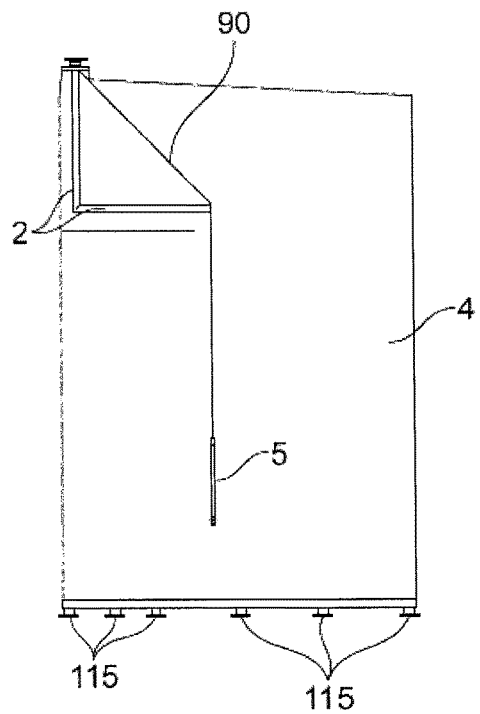
FIG. 34B FIG. 34C

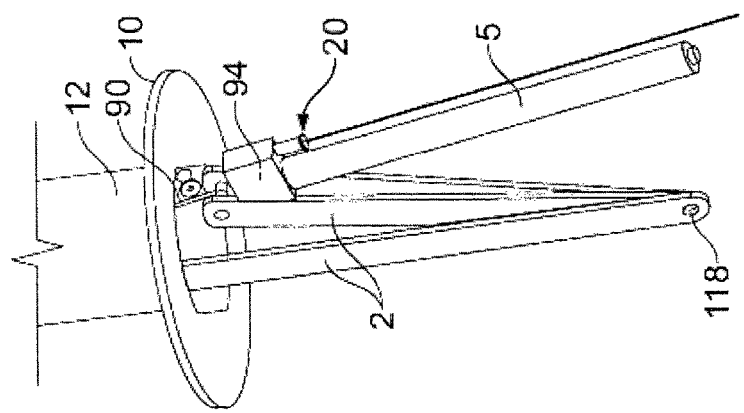
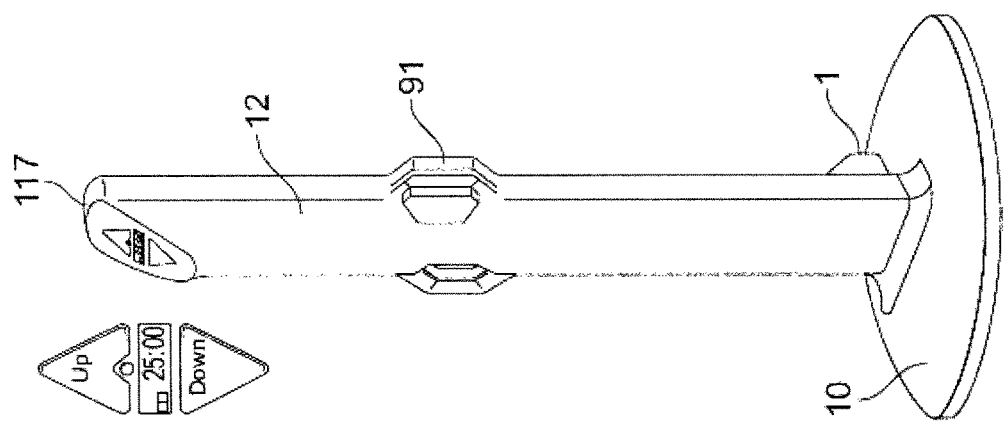
FIG. 35B
FIG. 35A

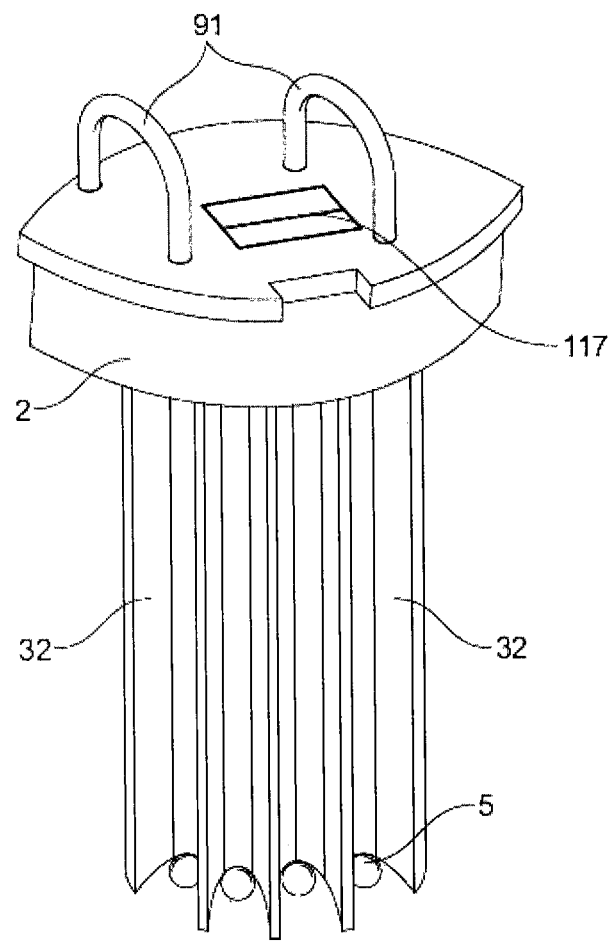
FIG. 37A
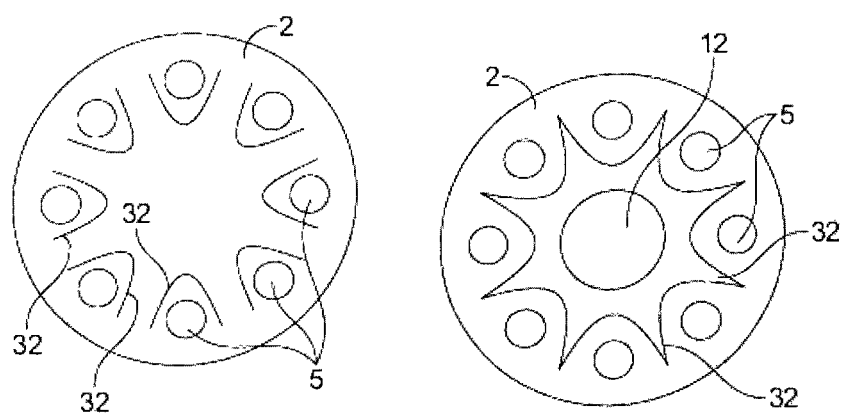
FIG. 37C  FIG. 37B

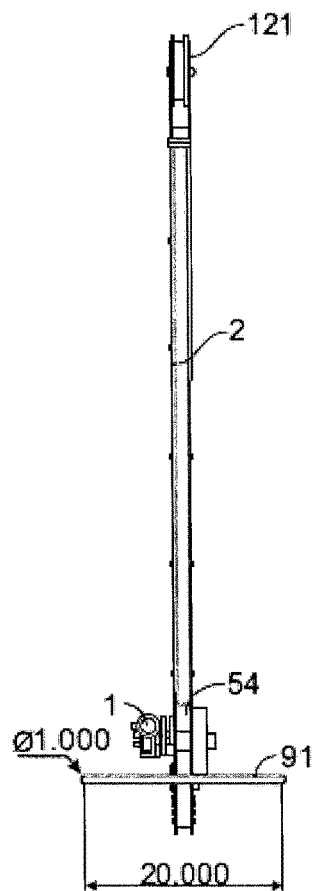
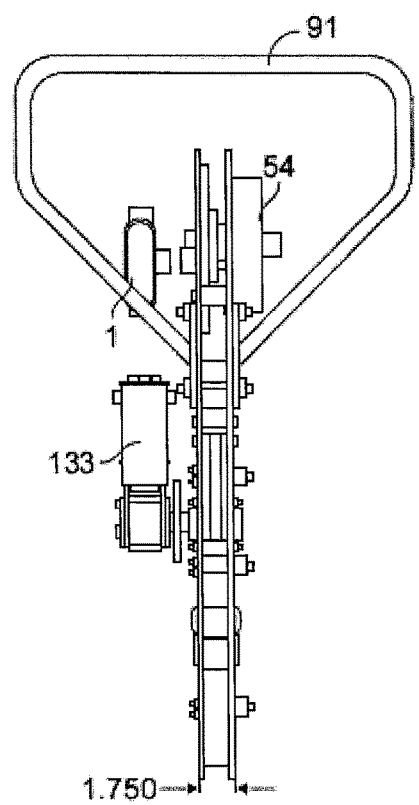
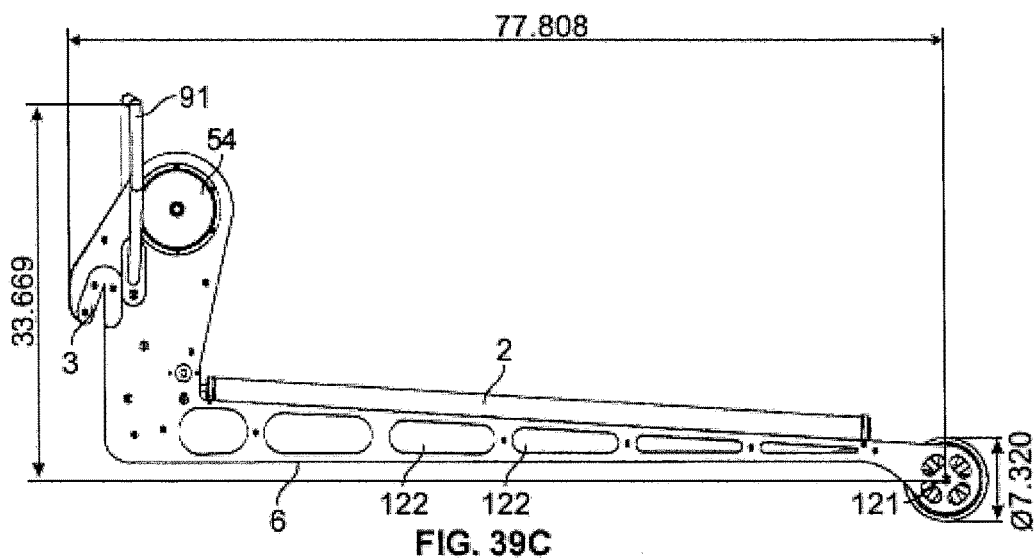
FIG. 39A
FIG. 39B
FIG. 39C

UV DEVICES, SYSTEMS AND METHODS FOR UV STERILIZATION

CROSS-REFERENCE TO RELATED APPLICATIONS

This patent application is a continuation-in-part application of U.S. application Ser. No. 14/091,311, filed Nov. 26, 2013, which is a continuation-in-part application of U.S. application Ser. No. 13/650,028, filed Oct. 11, 2012, which is a continuation-in-part application of U.S. application Ser. No. 13/314,007, filed Dec. 7, 2011, which is a continuation-in-part application of U.S. application Ser. No. 13/308,383, filed Nov. 30, 2011, now abandoned, which is a continuation-in-part application of U.S. application Ser. No. 13/151,196, filed Jun. 1, 2011, which claims the benefit of U.S. provisional patent application Ser. No. 61/350,414, entitled "UV Sterilization Of Containers," filed Jun. 1, 2010, the disclosures of which are incorporated herein by reference in their entirety by reference for all purposes. U.S. application Ser. No. 13/314,007, filed Dec. 7, 2011, also claims benefit of PCT patent application Ser. No. PCT/US2011/63827, filed Dec. 7, 2011, which is (i) a continuation-in-part application of U.S. application Ser. No. 13/151,196, filed Jun. 1, 2011, and (ii) a continuation-in-part application of PCT/US 11/38826, filed Jun. 1, 2011, each (i) and (ii) claiming the benefit of U.S. provisional patent application Ser. No. 61/350,414, entitled "UV Sterilization Of Containers," filed Jun. 1, 2010, the disclosures of which are incorporated herein by reference in their entirety by reference for all purposes.

FIELD OF INVENTION

The present invention relates generally to compositions, systems and methods for ultraviolet (UV) disinfection, and more specifically, to compositions, systems and methods for UV disinfection of a container, and more particularly to compositions, systems and methods for UV disinfection of a container used in the food and dairy industry or in the process of fermentation for an alcoholic beverage. More specifically, the present invention relates to portable UV devices and uses thereof in methods of sterilization and sanitization of interior surfaces of containers. The present invention also relates to compositions, systems and methods for UV disinfection of a room, a space or a defined environment.

BACKGROUND OF THE INVENTION

It has been well established that ultraviolet (UV) light has germicidal properties. Specifically, the mechanism by which UV light kills microorganisms is by damaging the genetic material, the deoxyribonucleic acid (DNA), of the microorganisms. Wavelengths between 200-300 nm have been shown to initiate a photoreaction between adjacent pyrimidines. Pyrimidine bases, such as cytosine and thymine, have conjugated double bonds and as such absorb UV light. The photoreaction between adjacent thymine or cytosine bases proceeds at an exceedingly rapid rate (on the order of picoseconds). There are two possible products. The most common is the formation of a cyclobutane ring between the two pyrimidines (Fu et al., 1997, *Applied and Environ Microbiol* 63(4):1551-1556). The other photoproduct is a (6-4) pyrimidone. The formation of these dimers leads to "kinks" within the structure of the DNA inhibiting the formation of proper transcriptional and replicational templates. Cytosine cyclobutane photodimers are susceptible to deamination and can therefore induce point mutations, specifically the CC (two adjacent cytosines) are converted into TT (two adjacent thymines) via the SOS Response system in both eukaryotic and prokaryotic organisms (Fu et al., 2008, *FEMS Microbial Rev* 32(6):908-26; Eller and Gilchrest; 2000, *Pigment Cell Res* 13 Suppl 8:94-7). The inactivation of specific genes via point mutations is one of the mechanisms of how UV-induced genetic damage can lead to cell death or to the inhibition of cell replication. The inability to form proper replicational and transcriptional templates coupled with the increased number of point mutations leads to the deactivation and inability to reproduce of microorganisms.

DNA, specifically has a maximum absorbency of UV light at 253.7 nm. It has been determined that approximately 26,400 microwatt-seconds/cm$^2$ are needed to deactivate 100% of the most resistant bacteria (Osburne et al., 2010, *Environ Microbial*; doi:10.1111/j.1462-2920.2010.02203.x).

UV light is separated into 3 distinct categories: UV-A (315-400 nm), UV-B (280-315 nm), and UV-C (200-280 nm). Since DNA optimally absorbs UV light at 253.7 nm, it is UV-C lamps that are used in most prior art germicidal devices. UV devices are used, e.g., to inactivate microorganisms in laboratory settings.

UV radiation is used for disinfection in hospitals, nurseries, operating rooms, cafeterias and to sterilize vaccines, serums, toxins, municipal waste, and drinking waters.

Current steel vessel and container sanitation protocols involve the use of a pressure wash using a hot water cycle to remove pigments, colloidal deposits, and tartrates following wine fermentations. After the hot water cycle, typically the vessels are washed with a 200 mg/L solution of hypochlorite as a sanitation cycle. This is usually followed by a rinse with citric acid. (Boulton et al., Principles and Practices of Winemaking, page 210, Springer, 1$^{st}$ Edition, Jan. 15, 1996).

Sodium hypochlorite (NaOCl) is often used for disinfecting hospital wastewater in order to prevent the spread of pathogenic microorganisms, causal agents of nosocomial infectious diseases. Chlorine disinfectants in wastewater react with organic matters, giving rise to organic chlorine compounds such as AOX (halogenated organic compounds adsorbable on activated carbon), which are toxic for aquatic organisms and are persistent environmental contaminants (Bohrerova et al., 2008, *Water Research* 42(12):2975-2982). Other protocols follow the removal of pigments, colloidal deposits, and tartrates with a wash with a caustic solution containing sodium hydroxide (typically 3%) and further followed by a final wash with a citric acid solution (typically 3%) to neutralize any remaining sodium hydroxide. There are several disadvantages to using sodium hydroxide and citric acid for sterilization. The primary disadvantage is the necessary use of large amounts of water as a solvent for both solutions. Any potential water saving measure is of great value both economically and environmentally. Further, the reduction in use of extremely caustic sodium hydroxide would be an added environmental benefit.

Other methods currently used for sterilizing fermentation vessels (made from metals and/or wood) include the use of ozone. Prior to 1997, ozone could only be used for sanitation and purification of bottled drinking water in the United States, and it is widely used around the world for this purpose today. In May 1997, an expert panel assembled by the Electric Power Research Institute (EPRI) declared ozone to be Generally Recognized as Safe (GRAS) for use in food processing in the United States. Since then, wineries have embraced the use of ozone. Its use has been generally accepted and documented to be effective for barrel cleaning and sanitation, tank cleaning and sanitation, clean-in-place systems, and for general surface sanitation. Results have shown the same degree of sanitization as that achieved using caustic for a fraction of the cost and wasted water.

However, in the wine industry, ozone systems tend to be mobile (a single unit can be moved to different vessels), with multiple operators in multiple locations. This makes it important that safety features and ozone management systems be in place and that the system itself be reliable and easy to operate.

Natural levels of ozone range from 0.01 ppm to 0.15 ppm and can reach higher concentrations in urban areas. Ozone is an unstable gas and readily reacts with organic substances. It sanitizes by interacting with microbial membranes and denaturating metabolic enzymes.

Ozone is generated by irradiation of an air stream with ultraviolet (UV) light at a wavelength of 185 nm or by passing dry air or oxygen through a corona discharge (CD technology) generator. For low ozone concentrations (ca. 0.14% by weight, or 0.5 grams per hour), the less expensive UV equipment is sufficient. For more demanding situations where higher ozone concentrations (1.0% to 14% by weight) are required, CD systems are used.

The wine industry is using both CD technology and UV (different from the one described herein). Some manufacturers use multiple UV tubes to achieve a desired level of output. Several manufacturers chose to install air-cooled or water-cooled CD generators in their systems. It is really a question of how much ozone at a certain gallons per minute (gpm) is desired for an application. For clean in place (CIP), 20 gpm may be desired, necessitating a larger system, while only 10 gpm at a lower concentration may provide satisfactory barrel washing.

The Occupational Safety and Health Administration (OSHA) has set limits for ozone exposure in the workplace. These limits are for continuous eight-hour exposure of no more than 0.1 ppm, and a short-term exposure limit (STEL) of 15 minutes at 0.3 ppm, not to be exceeded more than twice per eight-hour work day. Consequently, ozone requires monitoring in the workplace if used for environmental or equipment sanitation using, e.g., ozone.

Ozone is known to have adverse physiological effects on humans (Directorate-General of Labour, the Netherlands 1992, 4(92), 62). Technically, there is no minimum threshold for ozone toxicity. Even low concentrations of ozone produce transient irritation of the lungs as well as headaches. Higher concentrations induce severe eye and upper respiratory tract irritation. Chronic exposure to ozone leads to respiratory tract disease and has been associated with reported increases in tumor growth rates. Exposure to ozone levels greater than the maximum thresholds specified by the American Conference of Governmental Industrial Hygienists (ACGIH)/Occupational Safety and Health Administration (OSHA) results in nausea, chest pain, coughing, fatigue and reduced visual acuity. Thus, while ozone provides an efficient means of sterilization, it also poses an occupational hazard to those involved in the sterilization process.

Another bactericidal chemical frequently used to sterilize fermentation vessels is chlorinated trisodium phosphate (TSP). It has been well established that chlorinated TSP is an effective germicidal agent. TSP, however, is also a severe irritant, capable of inducing contact dermatitis in addition to irritating the respiratory tract (Health Hazard Evaluation Report No. HETA-82-281-1503; HETA-82-281-1503). Also, certain microorganisms, such as *Cryptosporidium*, have developed resistance to reactive chlorine compounds. Further, evidence is mounting that organic chemical byproducts of chemical disinfection, especially byproducts of chlorination, are carcinogens and/or toxins for humans. Thus, expensive filtration devices may be required to remove the chemicals. Further, systems based on filtration require frequent replacement and/or cleaning of the filters. In addition, use of chlorinated TSP requires large quantities of water as a solvent and to extensively rinse the container following chemical sterilization. Also, chlorinated compounds are notorious for causing wine fouling. Thus, chemical disinfection is not a viable alternative when chemical purity of a fluid or alcoholic beverage in a fermentation vessel is desired or required.

Ozone sterilization was originally used to purify blood in the late 1800s. In the 1900s, ozonated water was in use for the treatment of multiple types of disease. In the first World War, ozone was used to treat wounds, gangrene and the effects of poisonous gas. Thus, throughout the time period, toxic and/or carcinogenic chemicals have been used in the sterilization of containers used for fermenting alcoholic beverages.

Using the chemical disinfection or ozone disinfection methods, there is also no established protocol for verifying the level of sterilization achieved by using those methods.

Sanitization of food-containing equipment or food-containing containers is a growing concern in the world. An increasing number of people fall ill each year by being exposed to contaminated food or food kept in contaminated containers.

Thus, there is a need in the art for non-toxic and non-carcinogenic methods, systems, and compositions useful for the sterilization of containers, and in particular, for the sterilization of containers for fermenting alcoholic beverages and containers for food and dairy products. There is also a need for providing improved UV devices, systems, and methods for the sanitization of a room, a space or defined environment. The compositions, systems, and methods provided herein meet these and other needs in the art.

BRIEF SUMMARY OF THE INVENTION

The present invention provides compositions, systems, and methods useful for the ultraviolet (UV) sterilization of containers and for the sanitization of rooms, spaces and environments.

The present invention provides a portable UV device. In some embodiments of a portable UV device of the present invention, the portable UV device is a UV device for UV sterilization of an interior surface of a container. In some embodiments of a portable UV device of the present invention, the portable UV device comprises a germicidal UV light source comprising a lamp, a frame to which the germicidal UV light source is attached, a means for positioning the germicidal UV light source at a desired position within a container; and a circuit board controlling one or more functionalities of the portable UV device. The germicidal UV light source of the portable UV device can be movably and inwardly inserted through an opening of the container into the container.

In some embodiments of a portable UV device of the present invention, a portable UV device comprises a means for attaching the portable UV device to the opening of the container.

In some embodiments of a portable UV device of the present invention, a portable UV device comprises a housing housing0 the germicidal UV light source.

In some embodiments of a portable UV device of the present invention, a portable UV device comprises a cable permitting the germicidal UV light source being descended downwardly into the container.

In some embodiments of a UV device of the present invention, a portable UV device comprises an interface. In some embodiments of the portable UV device of the present invention, the interface provides at least one functional button for a function selected from the group of functions consisting of activating the UV device, deactivating the UV device, releasing the germicidal UV light source from a housing, providing time remaining for completing the UV sterilization of the container, and providing time elapsed for UV sterilization of the container. The functionality may result in an audible or visual signal for the user of the UV device.

In some embodiments of a portable UV device of the present invention, a portable UV device comprises a plurality of wheels attached to the frame.

Various means can be used to enhance the functionality of a portable UV device of the present invention. In some embodiments of a portable UV device of the present invention, a portable UV device comprises a reflector partially surrounding the UV light source.

In some embodiments of a portable UV device of the present invention, a portable UV device comprises a rangefinder.

In some embodiments of a portable UV device of the present invention, the one or more functionalities of the circuit board comprises a functionality selected from the group consisting of communicating with a radiofrequency identifier, controlling a movement of the germicidal UV light source within the container, controlling a rate of descent of the germicidal UV light source within the container, controlling a rate of ascent of the germicidal UV light source within the container, controlling a positioning of the germicidal UV light source within the container, controlling activation and deactivation of the germicidal UV light source, relaying UV light intensity via a sensor to the container; uploading and relaying information from the radiofrequency identifier, generating a report on time of sanitization cycle, generating a report on duration of sanitization cycle, generating a report on UV light intensity attained during sanitization cycle, emailing, phoning or texting a report on time of sanitization cycle, emailing, phoning or texting a report on duration of sanitization cycle, emailing, phoning or texting a report on UV light intensity attained during sanitization cycle, and emailing, phoning or texting an alert to an individual that sanitization cycle is complete.

A portable UV device may comprise a plurality of UV lamps arranged in various configurations. In some embodiments of a portable UV device of the present invention, a UV light source comprises a plurality of lamps arranged in a cluster.

In some embodiments of a portable UV device of the present invention, a means for positioning the germicidal UV light source at a desired position within a container comprises a means selected from the group consisting of a pivot attached to the frame, a reel assembly attached to the frame, a plurality of wheels attached to the frame, a cable, and a motor.

A portable UV device of the present invention comprises a germicidal UV light source comprising a lamp. In some embodiments of the portable UV device of the present invention, a lamp is selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.

In some embodiments of a portable UV device of the present invention, the portable UV device comprises a germicidal UV light source. In some embodiments of the portable UV device of the present invention, the germicidal UV light source is a UV-C light source.

In some embodiments of a portable UV device of the present invention, the germicidal UV light source is spring-loaded within the housing.

In some embodiments of a portable UV device of the present invention, the germicidal UV light source is released from the housing prior to being activated.

In another aspect, the present invention provides systems comprising a portable UV device of the present invention and a container. The portable LTV device of a system as described herein, can be any UV device described herein. In some embodiments of a system of the present invention, the portable UV device of the system is a portable UV device comprising a germicidal UV light source comprising a lamp, a frame to which the germicidal UV light source is attached, a means for positioning the germicidal UV light source at a desired position within a container; and a circuit board controlling one or more functionalities of the portable UV device. The UV light source of the portable UV device can be movably and inwardly inserted through an opening of the container into the container.

In some embodiments of a system of the present invention, a portable UV device comprises a means for attaching the portable UV device to the opening of the container.

In some embodiments of a system of the present invention, a portable UV device comprises a housing housing the germicidal UV light source.

In some embodiments of a system of the present invention, a portable UV device comprises a cable permitting the germicidal UV light source being descended downwardly into the container.

In some embodiments of a system of the present invention, a portable UV device comprises an interface. Various interfaces are useful in a system of the present invention. In some embodiments of a system of the present invention, the interface provides at least one functional button for a function selected from the group of functions consisting of activating the UV device, deactivating the UV device, releasing the germicidal UV light source from a housing, providing time remaining for completing the UV sterilization of the container, and providing time elapsed for UV sterilization of the container. The functionality may result in an audible or visual signal for the user of the UV device.

In some embodiments of a system of the present invention, a portable UV device comprises a plurality of wheels attached to the frame.

Various means can be used to enhance the functionality of a portable UV device of a system of the present invention. In some embodiments of a system of the present invention, a portable UV device comprises a reflector partially surrounding the UV light source.

In some embodiments of a system of the present invention, a portable UV device comprises a rangefinder.

In some embodiments of a system of the present invention, the one or more functionalities of a circuit board comprises a functionality selected from the group consisting of communicating with a radiofrequency identifier, controlling a movement of the germicidal UV light source within the container, controlling a rate of descent of the germicidal UV light source within the container, controlling a rate of ascent of the germicidal UV light source within the container, controlling a positioning of the germicidal UV light source within the container, controlling activation and deactivation of the germicidal UV light source, relaying UV light intensity via a sensor to the container; uploading and relaying information from the radiofrequency identifier, generating a report on time of sanitization cycle, generating a report on duration of sanitization cycle, generating a report on UV light intensity attained during sanitization cycle, emailing, phoning or texting a report on time of sanitization cycle, emailing, phoning or texting a report on duration of sanitization cycle, emailing, phoning or texting a report on UV light intensity attained during sanitization cycle, and emailing, phoning or texting an alert to an individual that sanitization cycle is complete.

A portable UV device of a system of the present invention may comprise a plurality of UV lamps arranged in various configurations. In some embodiments of a system of the present invention, a germicidal UV light source comprises a plurality of lamps arranged in a cluster.

In some embodiments of a system of the present invention, a means for positioning the germicidal UV light source at a desired position within a container comprises a means selected from the group consisting of a pivot attached to the frame, a reel assembly attached to the frame, a plurality of wheels attached to the frame, a cable, and a motor.

A portable UV device of a system of the present invention comprises a germicidal UV light source comprising a lamp. In some embodiments of a system of the present invention, a lamp is selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.

In some embodiments of a system of the present invention, the portable UV device comprises a germicidal UV light source. In some embodiments of a system of the present invention, the germicidal UV light source is a UV-C light source.

In some embodiments of a system of the present invention, the germicidal UV light source is spring-loaded within the housing.

In some embodiments of a system of the present invention, the germicidal UV light source is released from the housing prior to being activated.

A system of the present invention may comprise various containers. In some embodiments of a system of the present invention, a container is selected from the group consisting of a container for fermenting an alcoholic beverage and a container for storing or transporting a dairy product, a liquid dairy, a liquid dairy composition or a dry dairy composition.

In another aspect, the present invention provides methods for using a portable 15V device of the present invention. The portable UV devices of the present invention can be used in a variety of methods. In some embodiments a method of the present invention is a method for UV sterilization of an interior surface of a container.

In some embodiments, a method of the present invention comprises the step of movably and inwardly inserting through an opening of a container a germicidal UV light source of a portable UV device and activating the germicidal UV light source. Thereby, the interior surface of the container is sterilized.

In some embodiments of a method of the present invention, a portable UV device is a portable UV device comprising a germicidal UV light source comprising a lamp, a frame to which the germicidal UV light source is attached, a means for positioning the germicidal UV light source at a desired position within a container; and a circuit board controlling one or more functionalities of the portable UV device. The germicidal UV light source of the portable UV device can be movably and inwardly inserted through an opening of the container into the container.

In some embodiments of a method of the present invention, a portable UV device comprises a means for attaching the portable UV device to the opening of the container.

In some embodiments of a method of the present invention, a portable UV device comprises a housing housing the germicidal UV light source.

In some embodiments of a method of the present invention, a portable UV device comprises a cable permitting the germicidal UV light source being descended downwardly into a container.

In some embodiments of a method of the present invention, a portable UV device comprises an interface. Various interfaces are useful in practicing a method of the present invention. In some embodiments of a method of the present invention, the interface provides at least one functional button for a function selected from the group of functions consisting of activating the UV device, deactivating the UV device, releasing the germicidal UV light source from a housing, providing time remaining for completing the UV sterilization of the container, and providing time elapsed for UV sterilization of the container. The functionality may result in an audible or visual signal for the user of the UV device.

In some embodiments of a method of the present invention, a portable UV device comprises a plurality of wheels attached to the frame.

Various means can be used to enhance the functionality of a portable UV device for use in a method of the present invention. In some embodiments of a method of the present invention, a portable UV device comprises a reflector partially surrounding the germicidal UV light source.

In some embodiments of a method of the present invention, a portable UV device comprises a rangefinder.

In some embodiments of a method of the present invention, the one or more functionalities of a circuit board comprises a functionality selected from the group consisting of communicating with a radiofrequency identifier, controlling a movement of the germicidal LTV light source within the container, controlling a rate of descent of the germicidal UV light source within the container, controlling a rate of ascent of the germicidal UV light source within the container, controlling a positioning of the germicidal UV light source within the container, controlling activation and deactivation of the germicidal UV light source, relaying UV light intensity via a sensor to the container; uploading and relaying information from the radiofrequency identifier, generating a report on time of sanitization cycle, generating a report on duration of sanitization cycle, generating a report on UV light intensity attained during sanitization cycle, emailing, phoning or texting a report on time of sanitization cycle, emailing, phoning or texting a report on duration of sanitization cycle, emailing, phoning or texting a report on UV light intensity attained during sanitization cycle, and emailing, phoning or texting an alert to an individual that sanitization cycle is complete.

A portable UV device for use in a method of the present invention may comprise a plurality of UV lamps arranged in various configurations. In some embodiments of a method of the present invention, a germicidal UV light source comprises a plurality of lamps arranged in a cluster.

In some embodiments of a method of the present invention, a means for positioning the germicidal UV light source at a desired position within a container comprises a means selected from the group consisting of a pivot attached to the frame, a reel assembly attached to the frame, a plurality of wheels attached to the frame, a cable, and a motor.

A portable UV device for use in a method of the present invention comprises a germicidal UV light source comprising a lamp. In some embodiments of a method of the present invention, a lamp is selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.

In some embodiments of a method of the present invention, a portable UV device comprises a germicidal UV light source. In some embodiments of a method of the present invention, the germicidal UV light source is a UV-C light source.

In some embodiments of a method of the present invention, a germicidal LTV light source is spring-loaded within the housing.

In some embodiments of a method of the present invention, a germicidal UV light source is released from the housing prior to being activated.

Various containers find use in a method of the present invention. In some embodiments of a method of the present invention, a container is selected from the group consisting of a container for fermenting an alcoholic beverage and a container for storing or transporting a dairy product, a liquid dairy, a liquid dairy composition or a dry dairy composition. In some embodiments, the alcoholic beverage is beer, wine, gin, vodka, or whisky.

In some embodiments of a method of the present invention, one or more species of microorganisms is/are present on an interior surface of a container. Microorganisms on the interior surface of the container can be effectively killed using a method of the present invention. In some embodiments of a method of the present invention, the activation of the germicidal UV light source results in the inhibition of the growth of the one or more species of microorganisms. The one or more species of microorganisms may be selected from the group consisting of *Candida, Kloeckera, Hanseniaspora, Zygosaccharomyces, Schizosaccharomyces, Torulaspora, Brettanomyces, Saccharomycodes, Pichia, Williopsis, Pediococcus, Lactobacillus*, and *Oenococcus*.

Using methods of the present invention effective UV sterilization of an interior surface of a container is achieved. In some embodiments, the growth of one or more species of microorganisms is inhibited by at least 2 log. In some embodiments, the growth of one or more species of microorganisms is inhibited by at least 3 log. In some embodiments, the growth of one or more species of microorganisms is inhibited by at least 4 log. In some embodiments, the growth of one or more species of microorganisms is inhibited by at least 5 log. In some embodiments, the growth of one or more species of microorganisms is inhibited by at least 6 log.

The present invention also provides portable UV devices and systems comprising the portable UV device for the UV sterilization of a room, a space or a defined environment, preferably a surface within the room, space or defined environment. Any portable UV device described herein can be used for the UV sterilization of a room, a space or a defined environment.

The present invention provides methods for the ultraviolet (UV) sterilization of a room, a space or defined environment. In some embodiments, this method comprises the steps of selecting a room, space or defined environment in need of sanitization and exposing the room, space or defined environment to UV sterilization using a portable UV device described herein. For example, the portable UV device may comprise a germicidal UV light source comprising a lamp, a frame to which the germicidal UV light source is attached, a means for positioning the germicidal UV light source at a desired position within a room, space or defined environment; and a circuit board controlling one or more functionalities of the portable UV device.

Some embodiments of a portable UV device of the present invention are set forth in claim format directly below:

1. A portable ultraviolet (UV) device for UV sterilization of an interior surface of a container, the UV device comprising (i) a germicidal UV light source comprising a lamp; (ii) a frame to which the germicidal UV light source is attached; (iii) a means for positioning the germicidal UV light source at a desired position within a container; and (iv) a circuit board controlling one or more functionalities of the portable UV device, wherein the germicidal UV light source can be movably and inwardly inserted through an opening of the container into the container 2. The portable UV device according to claim 1, further comprising a housing housing the germicidal UV light source.

3. The portable UV device according to any one of claims 1 to 2, further comprising a means for attaching the portable UV device to the opening of the container.

4. The portable UV device according to any one of claims 1 to 3, further comprising a cable permitting the germicidal UV light source being descended downwardly into the container.

5. The portable UV device according to any one of claims 1 to 4, further comprising an interface providing at least one functional button for a function selected from the group of functions consisting of activating the portable UV device, deactivating the portable UV device, releasing the germicidal UV light source from a housing, providing time remaining for completing the UV sterilization of the container, and providing time elapsed for UV sterilization of the container.
6. The portable UV device according to any one of claims 1 to 5, further comprising a plurality of wheels attached to the frame.
7. The portable UV device according to any one of claims 1 to 6, further comprising a reflector partially surrounding the UV light source.
8. The portable UV light device according to any one of claims 1 to 7, further comprising a rangefinder.
9. The portable UV device according to any one of claims 1 to 8, wherein the one or more functionalities of the circuit board comprises a functionality selected from the group consisting of communicating with a radiofrequency identifier, controlling a movement of the germicidal UV light source within the container, controlling a rate of descent of the germicidal UV light source within the container, controlling a rate of ascent of the germicidal UV light source within the container, controlling a positioning of the germicidal UV light source within the container, controlling activation and deactivation of the germicidal UV light source, relaying UV light intensity via a sensor to the container; uploading and relaying information from the radiofrequency identifier, generating a report on time of sanitization cycle, generating a report on duration of sanitization cycle, generating a report on UV light intensity attained during sanitization cycle, emailing, phoning or texting a report on time of sanitization cycle, emailing, phoning or texting a report on duration of sanitization cycle, emailing, phoning or texting a report on UV light intensity attained during sanitization cycle, and emailing, phoning or texting an alert to an individual that sanitization cycle is complete,
10. The portable UV device according to any one of claims 1 to 9, wherein the germicidal UV light source comprises a plurality of lamps arranged in a cluster.
11. The portable UV device according to any one of claims 1 to 10, wherein (iii) comprises a means selected from the group consisting of a pivot attached to the frame, a reel assembly attached to the frame, a plurality of wheels attached to the frame, a cable, and a motor.
12. The portable UV device according to any one of claims 1 to 11, wherein the lamp is selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.
13. The portable UV device according to any one of claims 1 to 12, wherein the germicidal UV light source is a UV-C light source.
14. The portable UV device according to any one of claims 2 to 13, wherein the germicidal UV light source is spring-loaded within the housing.
15. The portable UV device according to any one if claims 2 to 14, wherein the germicidal UV light source is released from the housing prior to being activated.

Some embodiments of a system of the present invention are set forth in claim format directly below:
1. A system comprising (i) a portable ultraviolet (UV) device for UV sterilization of an interior surface of a container, the UV device comprising (a) a germicidal UV light source comprising a lamp; (b) a frame to which the germicidal UV light source is attached; (c) a means for positioning the germicidal UV light source at a desired position within a container; and (d) a circuit board controlling one or more functionalities of the portable UV device, wherein the germicidal UV light source can be movably and inwardly inserted through an opening of the container into the container; and (ii) a container.
2. The system according to claim 1, wherein the portable UV device further comprises a housing housing the germicidal UV light source.
3. The system according to any one of claims 1 to 2, wherein the portable UV device further comprises a means for attaching the portable UV device to the opening of the container.
4. The system according to any one of claims 1 to 3, wherein the portable UV device further comprises a cable permitting the germicidal UV light source being descended downwardly into the container.
5. The system according to any one of claims 1 to 4, wherein the portable UV device further comprises an interface providing at least one functional button for a function selected from the group of functions consisting of activating the portable UV device, deactivating the portable UV device, releasing the germicidal UV light source from a housing, providing time remaining for completing the UV sterilization of the container, and providing time elapsed for UV sterilization of the container.
6. The system according to any one of claims 1 to 5, wherein the portable UV device further comprises a plurality of wheels attached to the frame.
7. The system according to any one of claims 1 to 6, wherein the portable UV device further comprises a reflector partially surrounding the germicidal UV light source.
8. The system according to any one of claims 1 to 7, wherein the portable UV device further comprises a rangefinder.
9. The system according to any one of claims 1 to 8, wherein the one or more functionalities of the circuit board comprises a functionality selected from the group consisting of communicating with a radiofrequency identifier, controlling a movement of the germicidal UV light source within the container, controlling a rate of descent of the germicidal UV light source within the container, controlling a rate of ascent of the germicidal UV light source within the container, controlling a positioning of the germicidal UV light source within the container, controlling activation and deactivation of the germicidal UV light source, relaying UV light intensity via a sensor to the container; uploading and relaying information from the radiofrequency identifier, generating a report on time of sanitization cycle, generating a report on duration of sanitization cycle, generating a report on UV light intensity attained during sanitization cycle, emailing, phoning or texting a report on time of sanitization cycle, emailing, phoning or texting a report on duration of sanitization cycle, emailing, phoning or texting a report on UV light intensity attained during sanitization cycle, and emailing, phoning or texting an alert to an individual that sanitization cycle is complete, 10. The system according to any one of claims 1 to 9, wherein the germicidal UV light source comprises a plurality of lamps arranged in a cluster.
11. The system according to any one of claims 1 to 10, wherein (c) comprises a means selected from the group consisting of a pivot attached to the frame, a reel assembly attached to the frame, a plurality of wheels attached to the frame, a cable, and a motor.
12. The system according to any one of claims 1 to 11, wherein the lamp is selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.
13. The system according to any one of claims 1 to 12, wherein the germicidal UV light source is a UV-C light source.
14. The system according to any one of claims 2 to 13, wherein the germicidal UV light source is spring-loaded within the housing.
15. The system according to any one if claims 2 to 14, wherein the germicidal UV light source is released from the housing prior to being activated.
16. The system according to any one of claims 1 to 15, wherein the container is selected from the group consisting of a container for fermenting an alcoholic beverage and a container for storing or transporting a dairy product, a liquid dairy, a liquid dairy composition or a dry dairy composition.
17. The system according to claim 16, wherein the alcoholic beverage is beer, wine, gin, vodka, or whisky.

Some embodiments of a method of the present invention are set forth in claim format directly below:

1. A method for ultraviolet (UV) sterilization of an interior surface of a container, the method comprising the steps of (a) movably and inwardly inserting through an opening of a container a germicidal UV light source of a portable UV device; and (b) activating the germicidal UV light source; whereby the interior surface of the container is sterilized; wherein the germicidal UV light source comprises a lamp and is attached to a portable UV device which comprises (i) a frame to which the germicidal UV light source is attached; (ii) a means for positioning the germicidal UV light source at a desired position within a container; and (iii) a circuit board controlling one or more functionalities of the portable UV device, and wherein the germicidal UV light source can be movably and inwardly inserted through an opening of the container into the container.
2. The method according to claim 1, wherein the portable UV device further comprises a housing housing the germicidal UV light source.
3. The method according to any one of claims 1 to 2, wherein the portable UV device further comprises a means for attaching the portable UV device to the opening of the container.
4. The method according to any one of claims 1 to 3, wherein the portable UV device further comprises a cable permitting the germicidal UV light source being descended downwardly into the container.
5. The method according to any one of claims 1 to 4, wherein the portable UV device further comprises an interface providing at least one functional button for a function selected from the group of functions consisting of activating the portable UV device, deactivating the portable UV device, releasing the germicidal UV light source from a housing, providing time remaining for completing the UV sterilization of the container, and providing time elapsed for UV sterilization of the container.
6. The method according to any one of claims 1 to 5, wherein the portable UV device further comprises a plurality of wheels attached to the frame.
7. The method according to any one of claims 1 to 6, wherein the portable UV device further comprises a reflector partially surrounding the germicidal UV light source.
8. The method according to any one of claims 1 to 7, wherein the portable UV device further comprises a rangefinder.
9. The method according to any one of claims 1 to 8, wherein the one or more functionalities of the circuit board comprises a functionality selected from the group consisting of communicating with a radiofrequency identifier, controlling a movement of the germicidal UV light source within the container, controlling a rate of descent of the germicidal UV light source within the container, controlling a rate of ascent of the germicidal UV light source within the container, controlling a positioning of the germicidal UV light source within the container, controlling activation and deactivation of the germicidal UV light source, relaying UV light intensity via a sensor to the container; uploading and relaying information from the radiofrequency identifier, generating a report on time of sanitization cycle, generating a report on duration of sanitization cycle, generating a report on UV light intensity attained during sanitization cycle, emailing, phoning or texting a report on time of sanitization cycle, emailing, phoning or texting a report on duration of sanitization cycle, emailing, phoning or texting a report on. UV light intensity attained during sanitization cycle, and emailing, phoning or texting an alert to an individual that sanitization cycle is complete,
10. The method according to any one of claims 1 to 9, wherein the germicidal UV light source comprises a plurality of lamps arranged in a cluster.
11. The method according to any one of claims 1 to 10, wherein (ii) comprises a means selected from the group consisting of a pivot attached to the frame, a reel assembly attached to the frame, a plurality of wheels attached to the frame, a cable, and a motor.
12. The method according to any one of claims 1 to 11, wherein the lamp is selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.

13. The method according to any one of claims 1 to 12, wherein the germicidal UV light source is a UV-C light source.

14. The method according to any one of claims 2 to 13, wherein the germicidal UV light source is spring-loaded within the housing.

15. The method according to any one if claims 2 to 14, wherein the germicidal UV light source is released from the housing prior to being activated.

16. The method according to any one of claims 1 to 15, wherein the container is selected from the group consisting of a container for fermenting an alcoholic beverage and a container for storing or transporting a dairy product, a liquid dairy, a liquid dairy composition or a dry dairy composition.

17. The method according to claim 16, wherein the alcoholic beverage is beer, wine, gin, vodka, or whisky.

18. The method according to any one of claims 1 to 17, wherein one or more species of microorganisms is present on the interior surface of the container and wherein the activation of the germicidal UV light source results in inhibiting the growth of the one or more species of microorganisms.

19. The method according to claim 18, wherein the one or more species of microorganisms is selected from the group consisting of *Candida, Kloeckera, Hanseniaspora, Zygosaccharomyces, Schizosaccharomyces, Torulaspora, Brettanomyces, Saccharomycodes, Pichia, Williopsis, Pediococcus, Lactobacillus,* and *Oenococcus*.

20. The method according to any one of claims 18 to 19, wherein the one or more species of microorganisms is *Lactobacillus*.

21. The method according to any one of claims 18 to 20, wherein the growth of the one or more species of microorganisms is inhibited by at least 2 log.

22. The method according to any one of claims 18 to 21, wherein the growth of the one or more species of microorganisms is inhibited by at least 3 log.

23. The method according to any one of claims 18 to 22, wherein the growth of the one or more species of microorganisms is inhibited by at least 4 log.

24. The method according to any one of claims 18 to 23, wherein the growth of the one or more species of microorganisms is inhibited by at least 5 log.

25. The method according to any one of claims 18 to 24, wherein the growth of the one or more species of microorganisms is inhibited by at least 6 log.

26. The method according to any one of claims 1 to 25, wherein the germicidal UV light source is attached to a detector.

27. The method according to claim 26, wherein the detector measures a UV intensity level.

28. The method according to any one of claims 26 to 27, wherein the detector shuts off the germicidal UV light source when a specified UV intensity level is attained.

29. The method according to any one of claims 2 to 28, further comprising the step of releasing the germicidal UV light source from the housing.

30. The method according to any one of claims 1 to 29, further comprising the step of moving the germicidal UV light source longitudinally within the container to a predetermined position.

31. The method according to anyone of claims 1 to 30, further comprising the step of moving the germicidal UV light source laterally within the container to a predetermined position.

32. The method according to anyone of claims 1 to 31, further comprising the step of rotating the germicidal UV Light source within the container.

33. The method according to any one of claims 10 to 32, wherein the UV lamp cluster comprises two to eight UV lamps.

34. The method according to claim 33, wherein the two to eight UV lamps are arranged at an angle of approximate 15 degrees.

BRIEF DESCRIPTION OF THE DRAWINGS

FIG. 17 provides a variety of commercially available UV lamps of different length, shape, and type useful in the present invention (American Air & Water Inc., Hilton Head Island, S.C. 29926, USA). For each UV lamp, the UV-C output is provided in watts and the UV intensity is provided in UV $\mu W/cm^2$ at 1 m. Length as indicated reflects nominal length with standard lamp holders adding 2" overall length. Additional lamp lengths and types are available. *, Ozone is negligible unless noted as OZ for high or VH for very high ozone production.

FIG. 19A, scissor boom folded.

FIG. 20A. closed configuration.

FIGS. 21-25 schematically depict several views of an exemplary embodiment of a UV device of the present invention comprising a telescopic arm as a means for moving a UV light source, here shown as a UV lamp cluster, into a desired or predetermined position. The UV device is shown schematically in various configurations: in its folded position (FIGS. 21A-G), in its load position (FIGS. 22A-G), in its payout position (FIGS. 23A-G), in its horizontal position (FIGS. 24A-G), and in its UV lamp down position (FIGS. 25A-C). Individual parts of this UV device are shown in detail in some of FIGS. 21-25, however, because of providing different overall views of this UV device, not all details or individual parts will be apparent in each of FIGS. 21-25.

FIG. 27A shows a perspective view of the UV light box with the UV lamps in an exposed position. FIG. 27B shows a bottom view of the UV light box with the UV lamps in a closed position. FIG. 27C shows a back view of the UV light box with the UV lamps in an exposed position. FIG. 27D shows a side view of the UV light box with the UV lamps in an exposed position. FIG. 27E shows a top view of the UV light box with the UV lamps in an exposed position. FIG. 27F shows a front view of the UV light box with the UV lamps in an exposed position. FIG. 27G shows a bottom view of the UV light box with the UV lamps in an exposed position.

FIG. 28A schematically depicts a front view of an embodiment of a UV device of the present invention, wherein the UV light source is retracted in a housing. Housing 2, base plate 10, central sleeve 12, hanging hook 84, on/off/reset button 85, central sleeve tightening knob 86, translucent plastic ring 87, metal disc 89, power cord 90, handle 91, handle cap 92, metal sleeve attachment ring 95, power supply access plate 97, optical switch 98. In this embodiment, the power supply access plate is attached to the central sleeve by six screws.

FIG. 28B schematically depicts a top view of an embodiment of a UV device of the present invention, wherein the UV light source is retracted in a housing. Base plate 10, hanging hook 84, on/off/reset button 85, central sleeve tightening knob 86, power cord 90, metal sleeve attachment ring 95.

FIG. 28C schematically depicts a bottom view of an embodiment of a UV device of the present invention, wherein the UV light source is retracted in a housing. Housing 2, UV lamp 5, base plate 10, central sleeve 12, stopping plate 88.

FIG. 28D schematically depicts a front view of an embodiment of a UV device of the present invention, wherein the UV light source is released from a housing.

Figure 1:
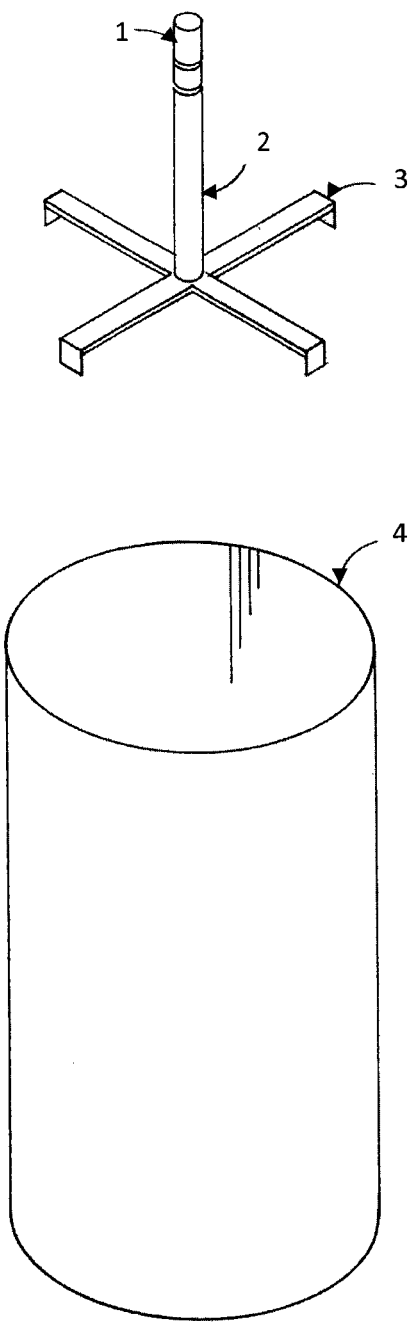
FIG. 1 schematically depicts a UV device of the present invention above a container 4, here a cylindrical fermentation vessel. In the UV device shown, a singular mobile cylindrical UV lamp is retracted in a housing 2, here a protective sleeve. A motorized unit 1 is mounted on top of the protective sleeve. The housing 2 is attached to a mounting bracket 3.

Housing 2, UV lamp 5, base plate 10, central sleeve 12, hanging hook 84, on/off/reset button 85, central sleeve tightening knob 86, translucent plastic ring 87, metal disc 89, power cord 90, handle 91, handle cap 92, UV lamp socket/adaptor 94, metal sleeve attachment ring 95, power supply access plate 97, optical switch 98. In this embodiment, the power supply access plate is attached to the central sleeve by six screws.

Figure 28A:
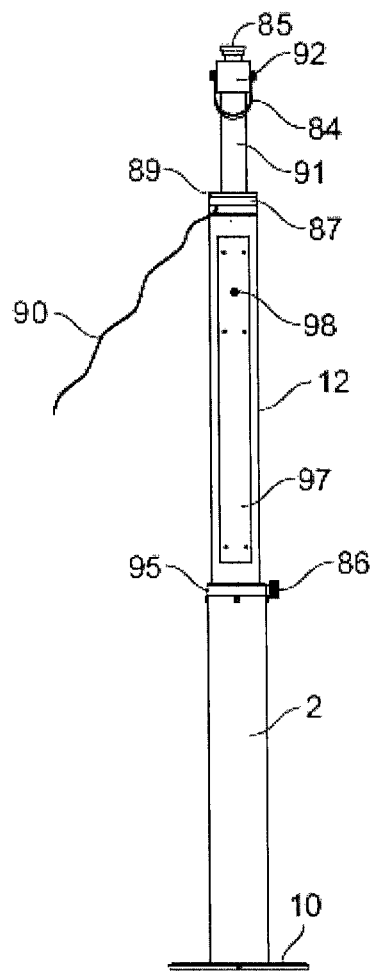
FIGS. 28A through 28H schematically depict details of an embodiment of a UV device of the present invention.
Figure 28B:
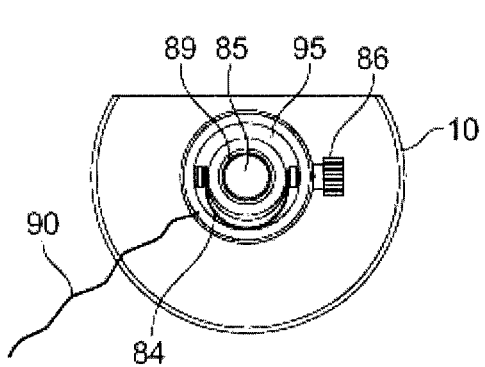
Figure 28C:
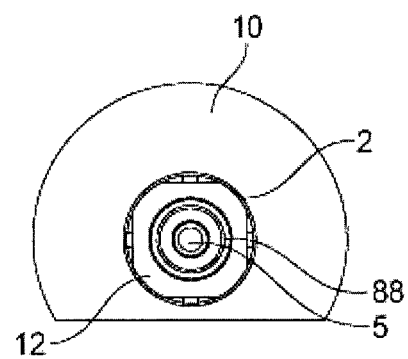
Figure 28D:
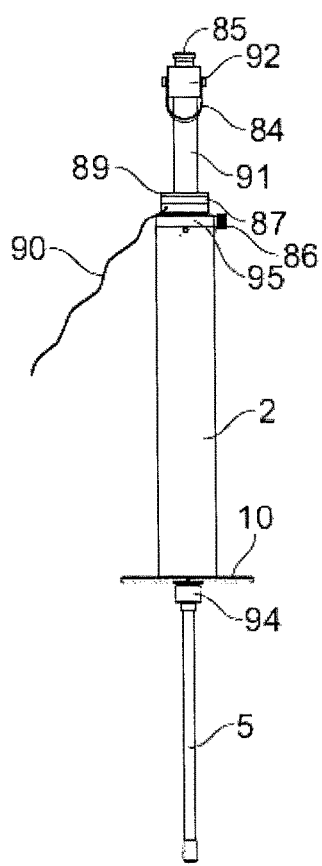
Figure 28E:
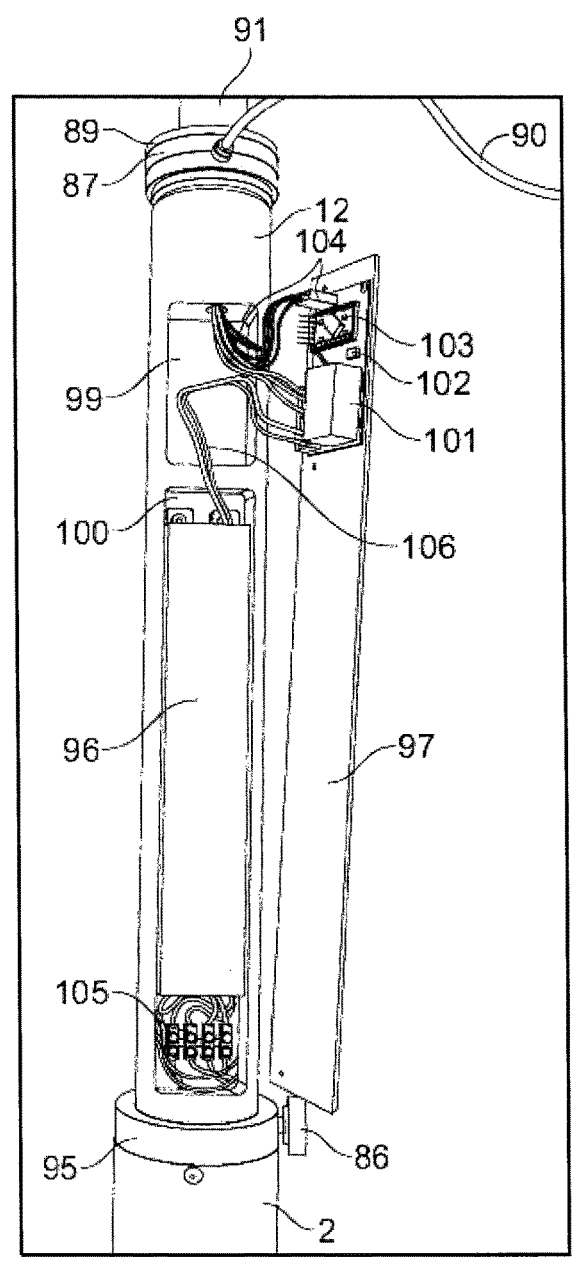

FIG. 28E schematically depicts a detail of an embodiment of a UV device of the present invention, wherein a cover of a central sleeve (power supply access plate 97) is opened to show inner compartments of the central sleeve 12 harboring, among others, a circuit board 103 and a ballast/power supply 96. Housing 2, central sleeve 12, central sleeve tightening knob 86, translucent plastic ring 87, metal disc 89, power cord 90, handle 91, handle cap 92, metal sleeve attachment ring 95, power supply 96, power supply access plate 97, optical switch 98, circuit board cavity 99, power supply cavity 100, AC to DC power converter 101, electronic component 102, circuit board (micro controller) 103, connector and wires (to e.g., LED, optical switch, acoustic speaker) 104, connector and wires to UV light source (e.g., UV lamp 5) 105, connector and wires to power supply 106.

Figure 28F:
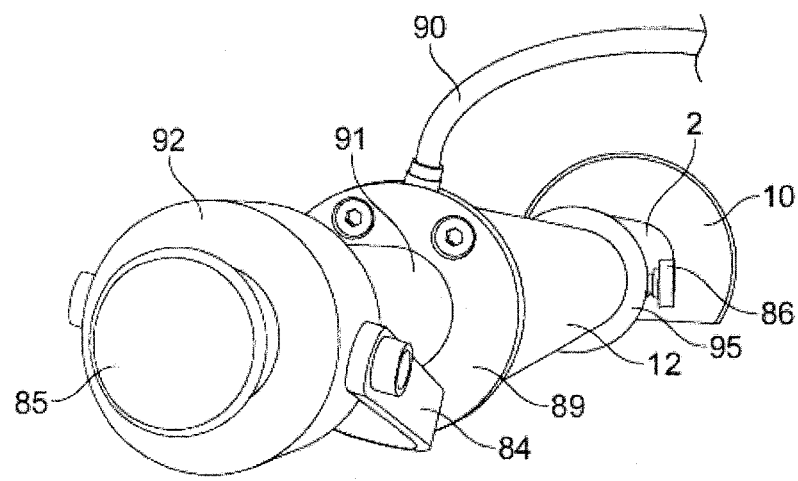

FIG. 28F schematically depicts an upper side view of a detail of an embodiment of a UV device of the present invention, wherein the UV light source is retracted in a housing. Housing 2, base plate 10, central sleeve 12, hanging hook 84, on/off/reset button 85, central sleeve tightening knob 86, metal disc 89, power cord 90, handle 91, handle cap 92, metal sleeve attachment ring 95.

Figure 28G:
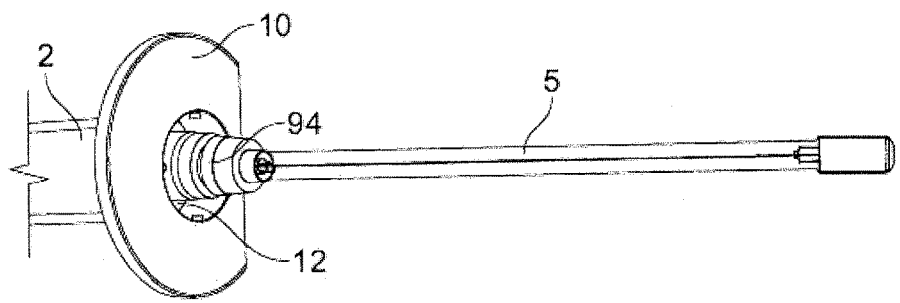

FIG. 28G schematically depicts a side view of an embodiment of a UV device of the present invention, wherein the UV light source is released from a housing. Housing 2, UV lamp 5, base plate 10, central sleeve 12, UV lamp socket/adaptor 94.

Figure 28H:
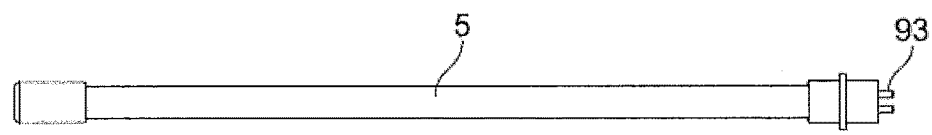

FIG. 28H schematically depicts a UV light source, here a longitudinal UV light bulb. UV lamp 5, pins for UV lamp 93.

Figure 29A:
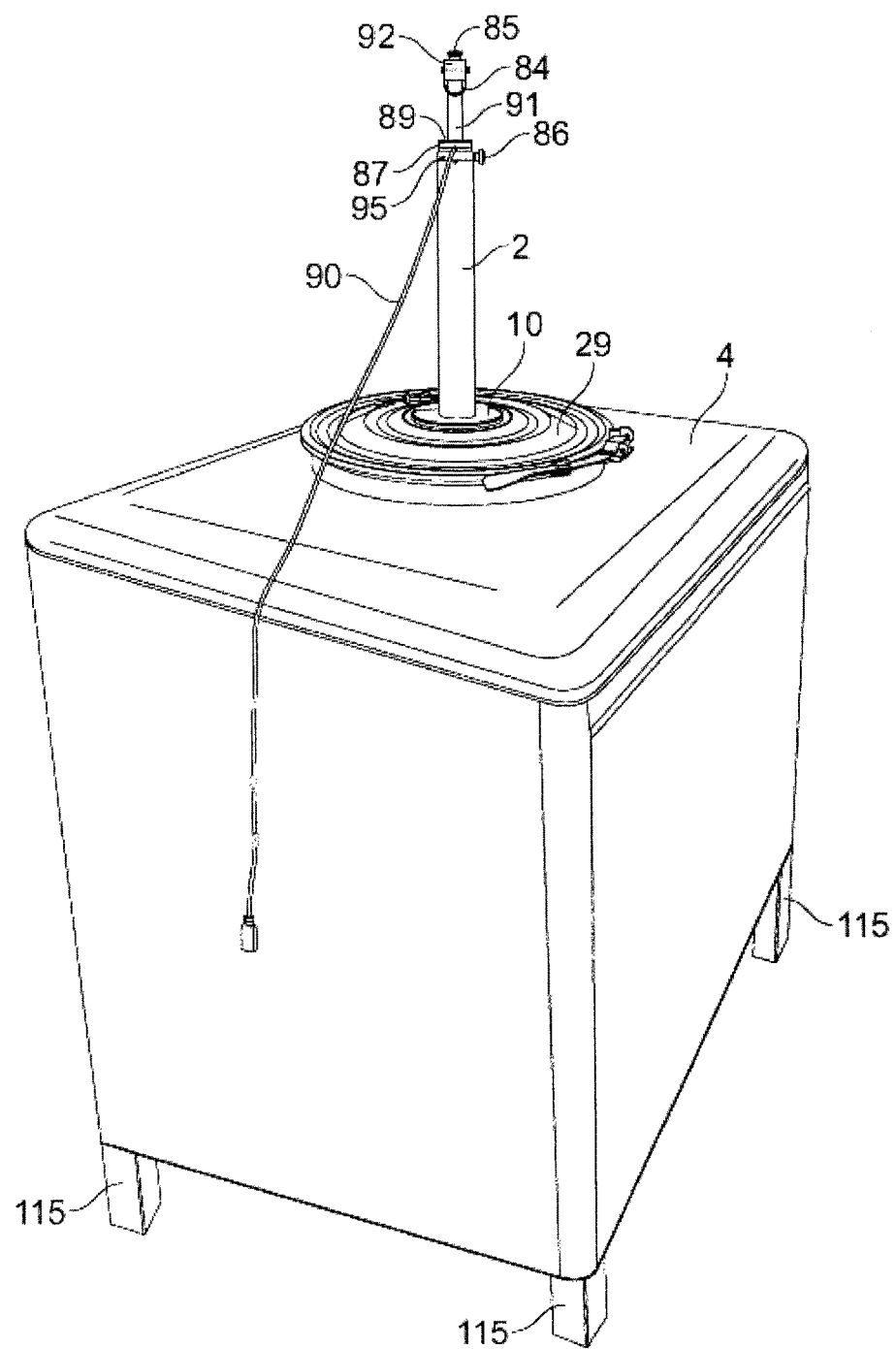

FIG. 29A schematically depicts an embodiment of a UV device of the present invention positioned on top of a container 4 having a lid 29, wherein the central sleeve 12 of the UV device shown in FIGS. 28A, D-G has been moved downwardly through an opening in the lid 29 into the container 4. Housing 2, container 4, base plate 10, lid 29, hanging hook 84, on/off/reset button 85, central sleeve tightening knob 86, translucent plastic ring 87, metal disc 89, power cord 90, handle 91, handle cap 92, metal sleeve attachment ring 95, container support stand 115.

Figure 29B:
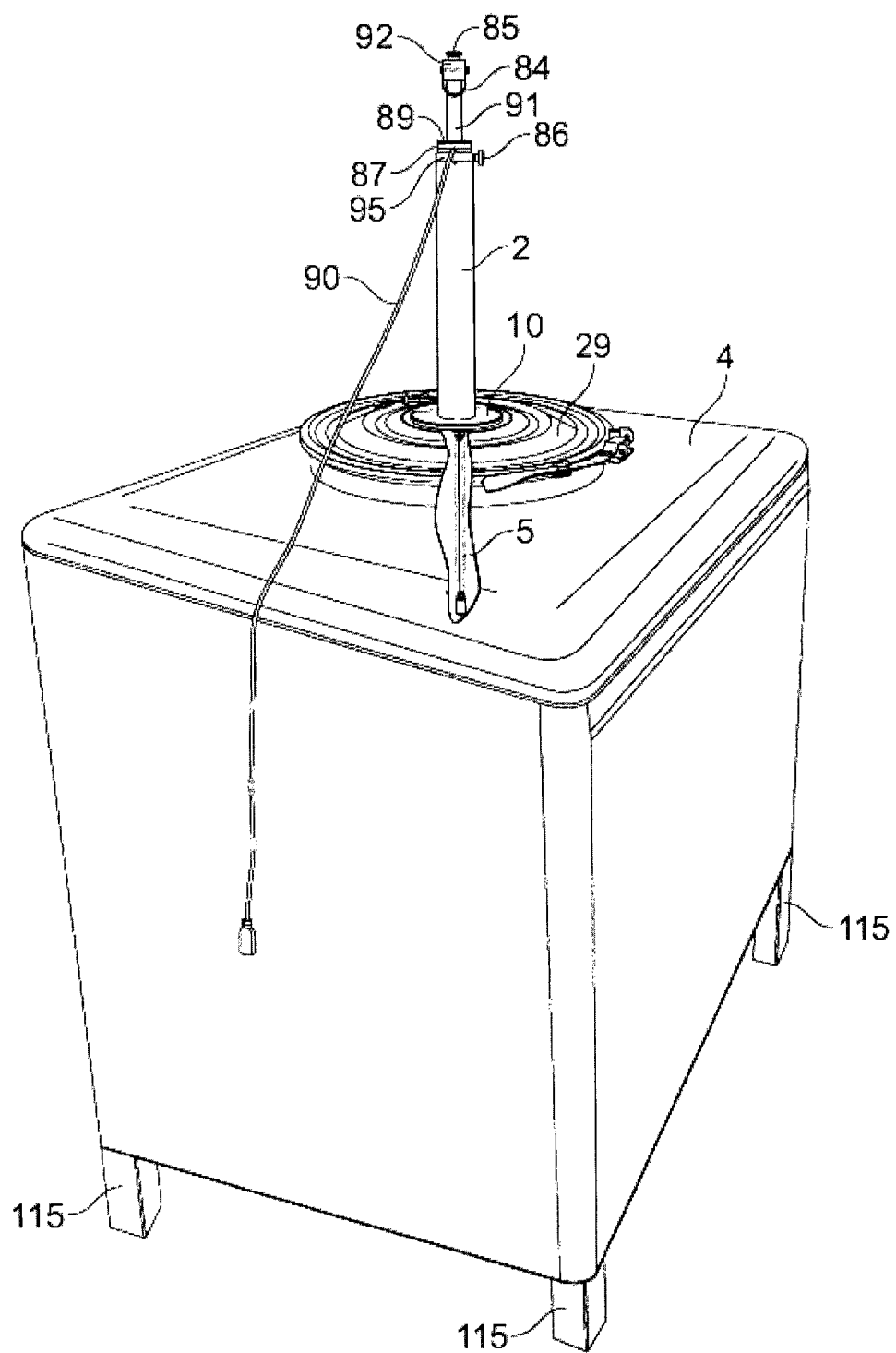

FIG. 29B schematically depicts an embodiment of a UV device of the present invention positioned on top of a container 4 having a lid 29, wherein the central sleeve 12 of the UV device shown in FIGS. 28A, D-G has been moved downwardly through an opening in the lid 29 into the container 4 and wherein the UV light source has been released from the housing 2. Housing 2, container 4, UV lamp 5, base plate 10, lid 29, hanging hook 84, on/off/reset button 85, central sleeve tightening knob 86, translucent plastic ring 87, metal disc 89, power cord 90, handle 91, handle cap 92, metal sleeve attachment ring 95, container support stand 115.

Figure 30:
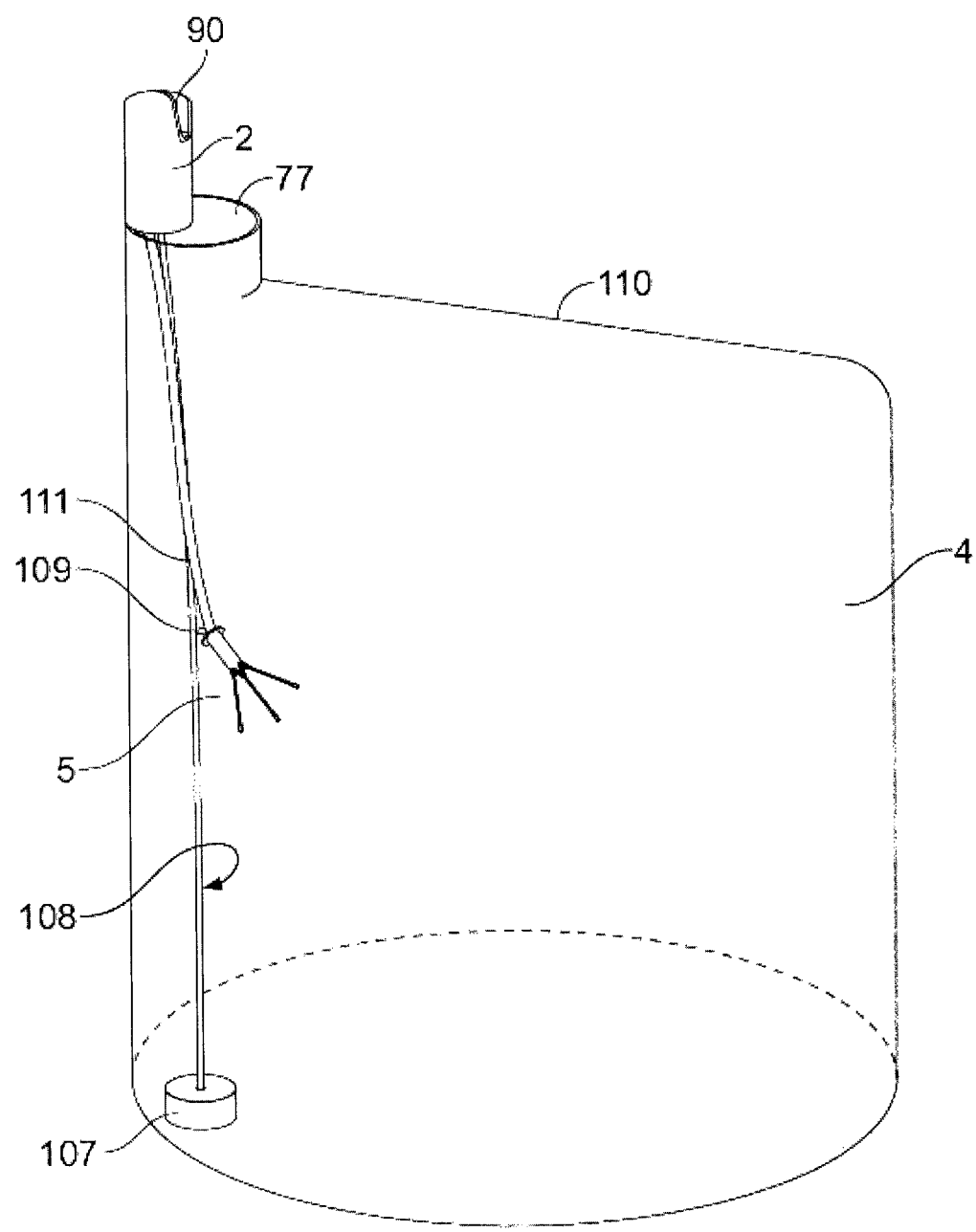

FIG. 30 schematically depicts a UV device of the present invention attached to the top of a container and wherein the UV light source has been inserted through an opening of the container 4 downwardly into the container 4. The UV device shown here comprises a plurality of UV lamps 5 arranged in a UV lamp cluster. Housing 2, container 4, UV lamp(s) 5, manhole or port 77, power cord 90, anchor 107, anchor line 108, anchor connector 109, angled top of container 110, UV lamp cluster line 111.

Figure 31A:
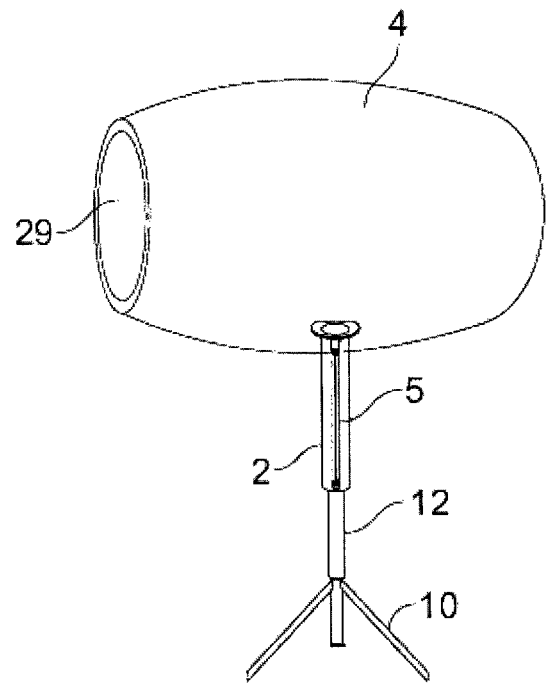
Figure 31B:
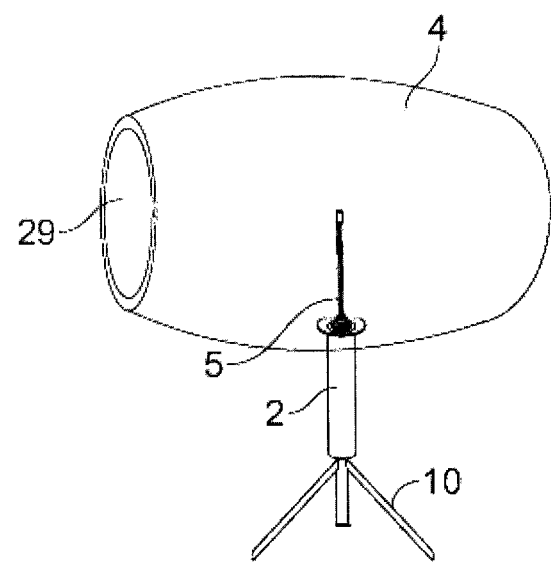

FIGS. 31A and 31B schematically depict the insertion of a UV light source into a container 4 by inserting the UV light source through an opening at the side of the container 4. In FIG. 31A, the UV lamp 5 is shown in the housing 2. In FIG. 31B the UV lamp 5 is released from the housing 2, The housing 2 slides back on a central sleeve 12. While the UV light source is inserted through an opening at a side of a container, the container itself may be positioned to reside on its side so that the UV light source can be moved inwardly into the container from a bottom position. In such configuration, as shown in FIGS. 31A and 31B, the movement of the UV light source within the container is upwardly. Alternatively, a container having an opening on a side wall, may be positioned so that the opening resides on top of the container and the UV light source is inserted into the container and moves downwardly into the container. Housing 2, container 4, UV lamp 5, base plate 10 (here a tripod-like support stand), central sleeve 12, lid 29.

Figure 32:
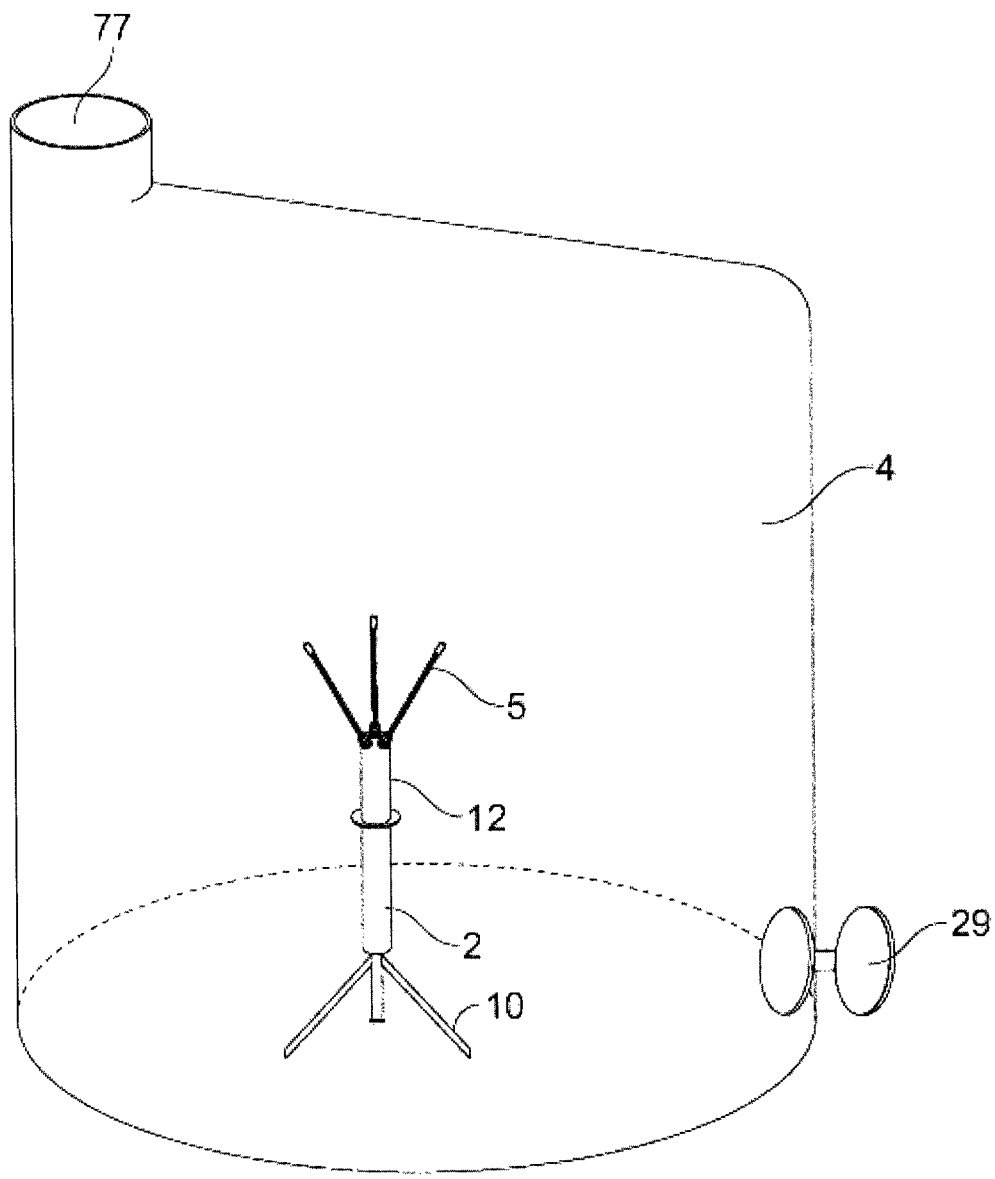

FIG. 32 schematically depicts a UV light source positioned at the bottom of a container 4. The UV light source has been inserted into the container 4 through an opening at the side of the container. Housing 2, container 4, UV lamp 5, base plate 10 (here a tripod-like support stand), central sleeve 12, lid 29, manhole or port 77, In this embodiment, the UV light source comprises a plurality of UV lamps 5 arranged in a UV lamp cluster. In some embodiments, the central sleeve 12 can be extended to permit an upwardly extension and an upwardly positioning of the UV lamps 5.

Figure 33:
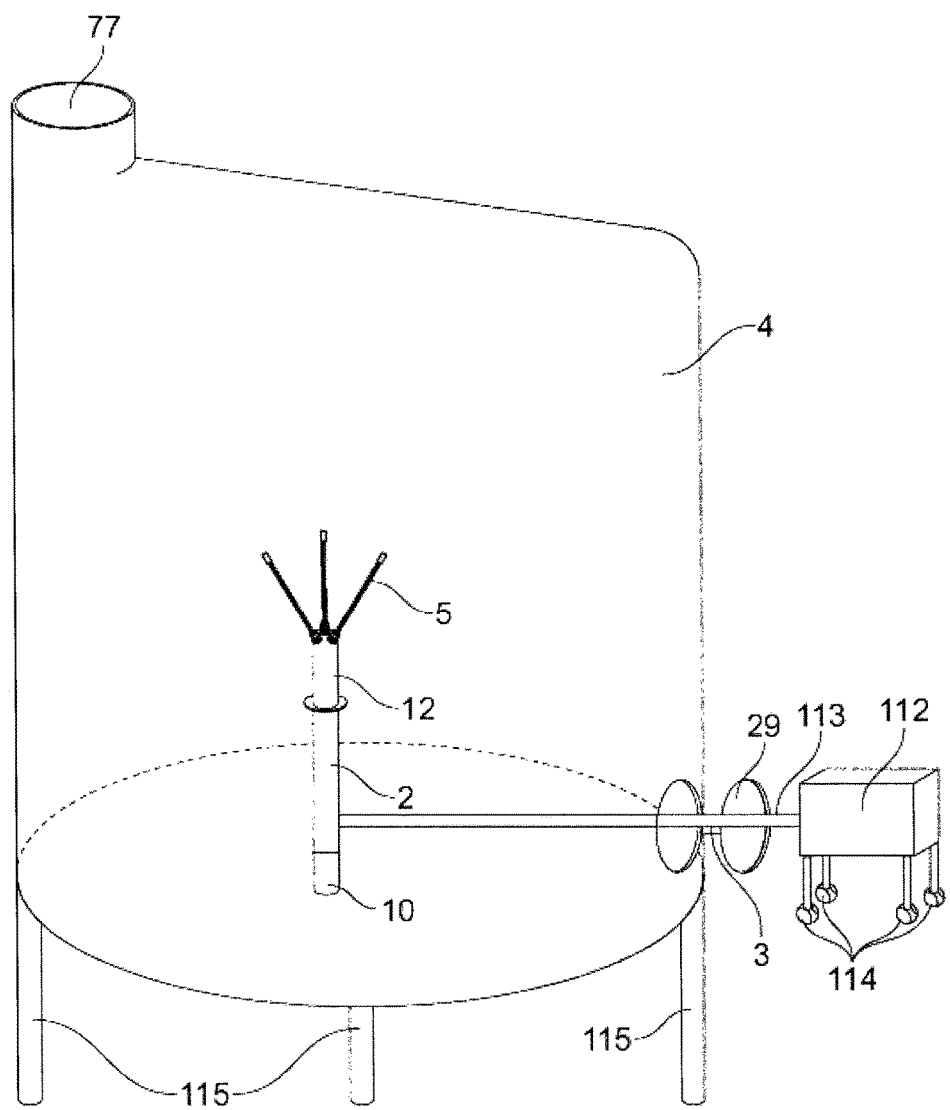

FIG. 33 schematically depicts a UV light source attached to a movable object having wheels. Housing 2, container 4, UV lamp 5, base plate 10 (here a simple support stand), central sleeve 12, lid 29, manhole or port 77, movable object 112, horizontal arm 113, wheels 114, support stand for container 115. In this embodiment, the UV light source comprises a plurality of UV lamps 5 arranged in a UV lamp cluster. In some embodiments, the central sleeve 12 can be extended to permit an upwardly extension and an upwardly positioning of the UV lamps 5.

Figure 34A:
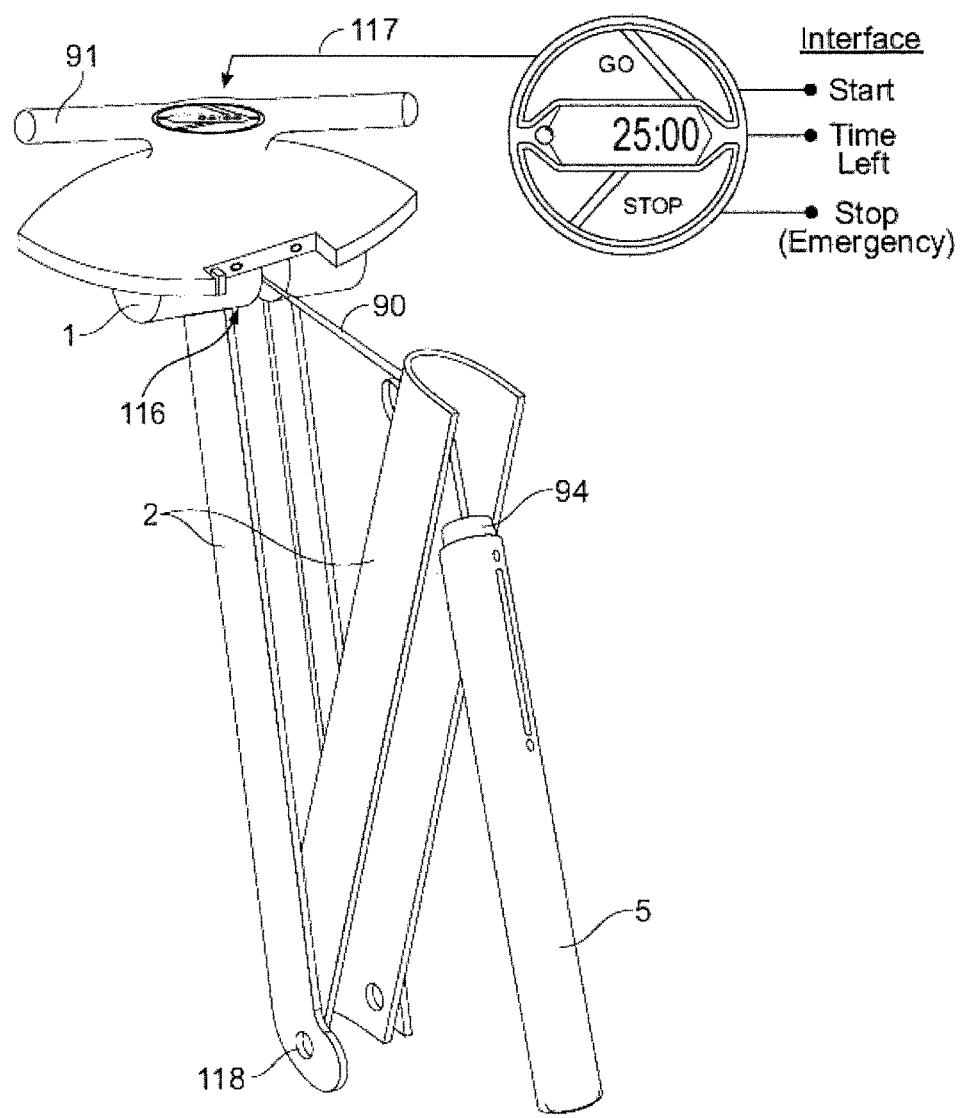
Figure 36A:
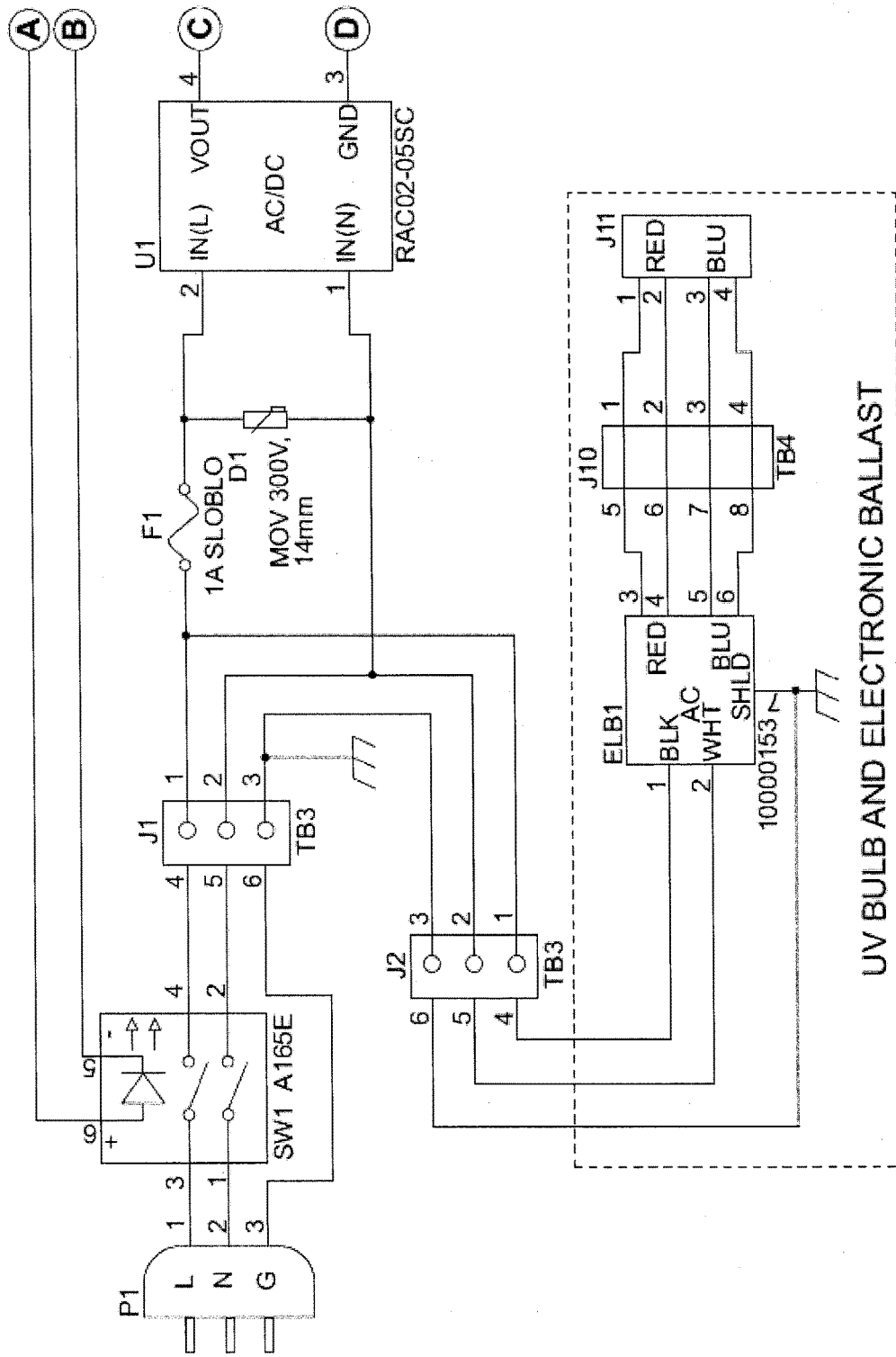
Figure 36B:
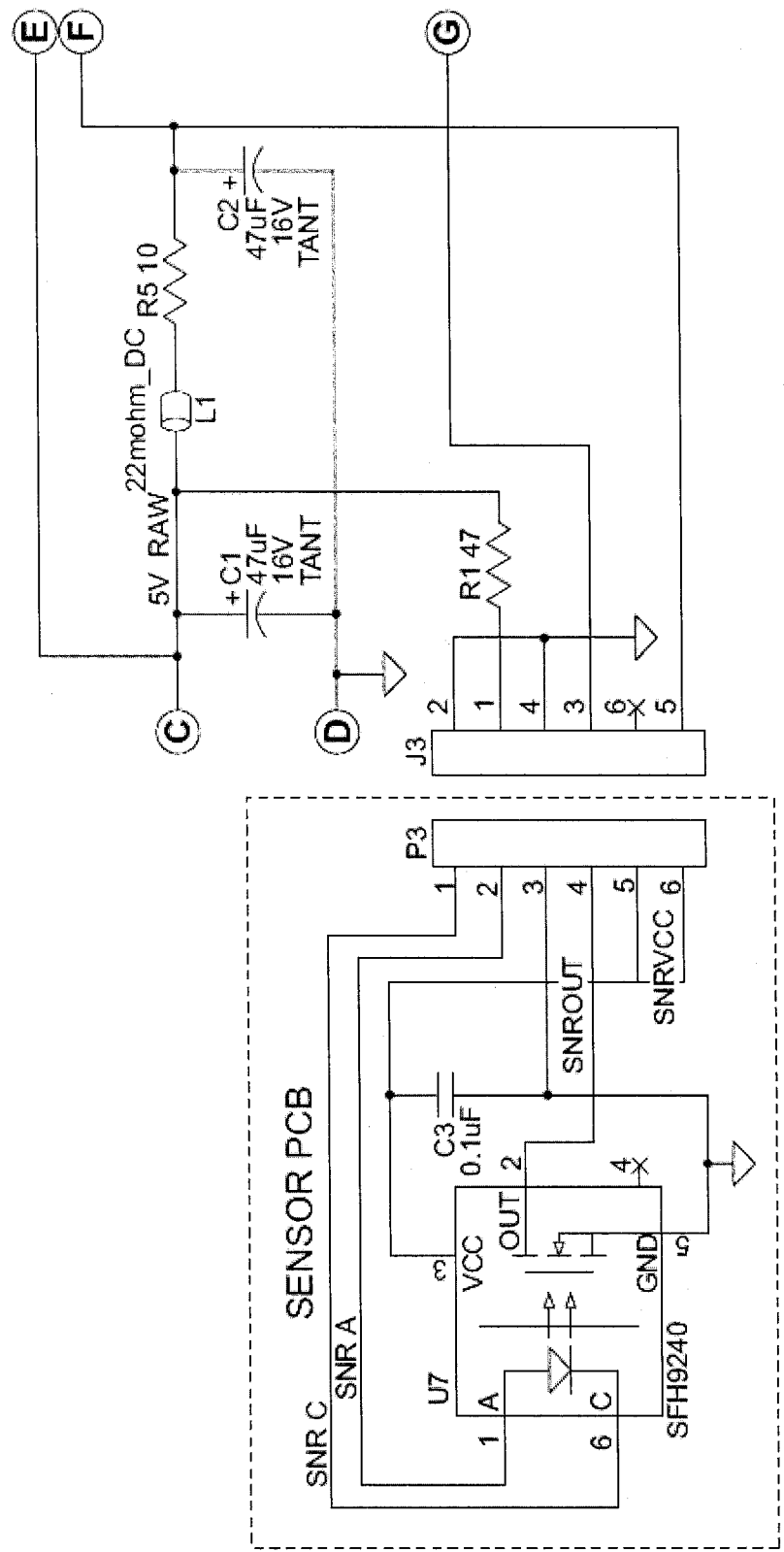
Figure 36C:
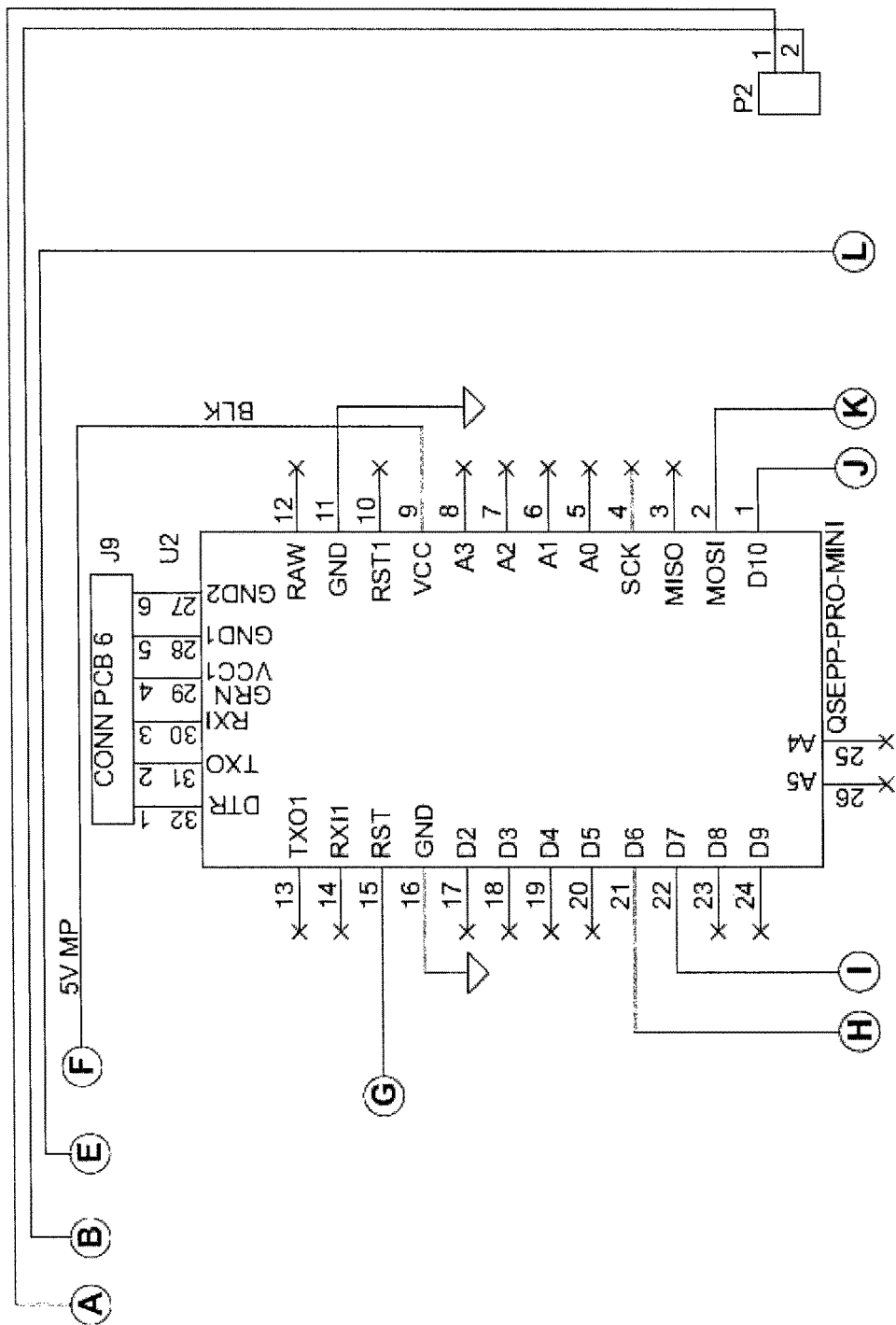
Figure 36D:
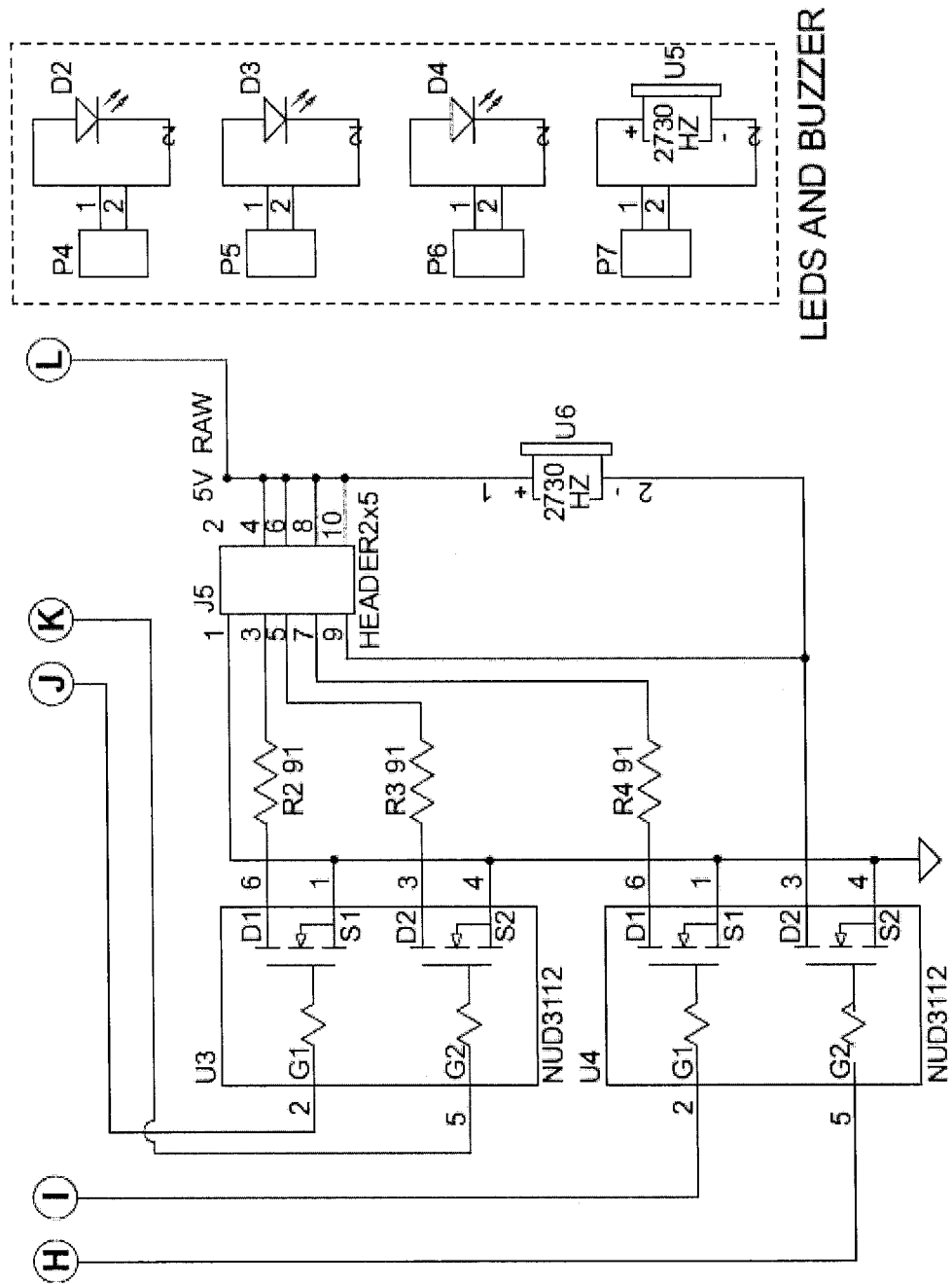

FIG. 34A schematically depicts an embodiment of a UV device of the present invention, wherein a UV light source is released from a housing 2 via a motorized unit 1 and by gravity. Shown to the right is an enlargement of the interface 117 showing buttons for activating (Start) and deactivating (Stop) the UV device. An optional timer shows the time remaining for completing a sterilization cycle. Motorized unit 1, housing 2, UV lamp 5, power cord 90, handle 91, UV lamp socket/adaptor 94, twist lock 116, interface 117, pivot point 118 on housing 2.

FIGS. 34B and 34C schematically depict an attachment of the UV device of FIG. 34A at the top of a closed container 4 and the insertion of the central sleeve 12, housing 2 and UV lamp 5 into the container 4. Housing 2, container 4, UV lamp 5, power cord 90, container support stand 115. FIG. 34B, upper, schematically depicts a top view of a 15 feet (15') container showing a manhole or port 77 through which the UV device can be inserted. Lines 119 radiating from the manhole or port 77 are steel support structures on top of the container. FIG. 34B, lower, shows the housing 2 being extended into a 90 degree angle position with respect to the central sleeve 12 FIG. 34C, upper, schematically depicts a top view of a 20 feet (20') container showing a manhole or port 77 through which the UV device can be inserted. Lines 119 radiating from the manhole or port 77 are steel support structures on top of the container. FIG. 34C, lower, shows the lowering of the UV lamp 5 downwardly into the container 4. The distance of lowering the UV lamp 5 towards the bottom of the container (inwardly and downwardly movement) can be calculated to stop short of the bottom of the shortest container and will be sufficient for the tallest container as long as the distance to the bottom of the container is smaller than the distance to the furthest wall of the container (FIG. 34B). In a taller wider container, the UV light irradiation might stop short of reaching an outer wall, but still sufficient to illuminate the bottom of the container more than the walls (FIG. 34C). The UV device can be configured so that the UV light source (UV lamp 5) can be centered within the container.

FIGS. 35A and 35 B schematically depict an embodiment of a UV device of the present invention. FIG. 35A depicts a UV light source completely retracted into the central sleeve 12 of a UV device standing in an upright position on its base plate 10. Motorized unit 1, central sleeve 12, handle 91, interface 117. An enlargement of the interface 117 showing buttons for up and down movement of the UV lamp and a timer is shown in the upper left part of FIG. 35A.

FIG. 35B schematically depicts the release of the housing 2 and UV lamp 5 from the central sleeve 12 by gravity and a motorized unit 1. Attached to the socket 94 into which the UV lamp 5 is inserted is a guide or range finding device 20 (here schematically a laser depth guide). The broken arrow indicates that the housing 2 can be positioned in an angle ranging from about 0 degree to about 90 degrees with respect to the central sleeve 12. Housing 2, UV lamp 5, central sleeve 12, guide or range-finding device 20, UV lamp socket/adaptor 94, pivot point 118 within housing 2.

FIGS. 36A-D schematically depict a circuit board used in an embodiment of the present invention, UV device UV55. This circuit board includes an optical sensor which begins a timer once the unit is inserted into a drum or container. It also controls a small speaker that emits an audible beep once the cycle has begun and upon completion. It further controls a series of small LED lights that signify at what time point of the cycle the UV55 is in and form a rotating pattern once at the 12 minutes have elapsed. This indicates completion of the cycle for the largest container (550 gallon portable tank) the UV55 was intended for. The LED bulbs blinks once intermittently during the first minute, twice intermittently in the second minute, three times intermittently in the third minute and so on until the twelfth minute.

FIGS. 37A (side view), 37B and 37C (both bottom views) schematically depict a non-limiting embodiment of a UV device of the present invention wherein UV lamps 5 are arranged in a UV lamp cluster and wherein each UV lamp 5 is surrounded by a reflector 32. FIG. 37B schematically depicts an embodiment wherein the reflectors 32 form a contiguous surrounding attached to a central sleeve 12. FIG. 37C schematically depicts an embodiment wherein the reflectors 32 and UV lamps 5 are attached to the housing 2. Reflectors 32 partially surround a UV lamp 5. Housing 2, UV lamp(s) 5, central sleeve 12, handle 91, interface 117, reflector(s) 32.

Figure 38A:
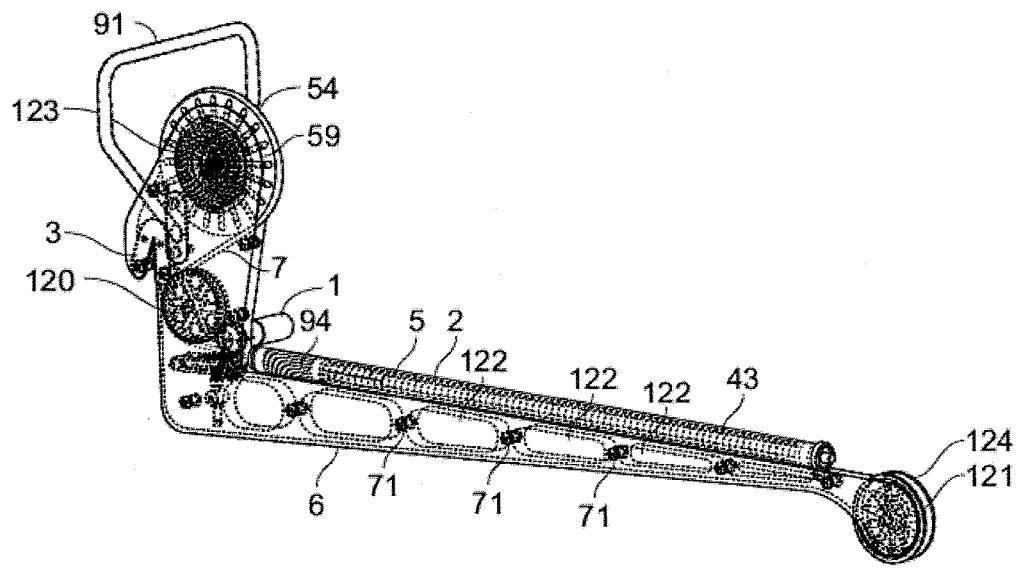

FIGS. 38A (first side view) and 38B (second side view) schematically depict a non-limiting embodiment of a UV device of the present invention, referred to herein as UV device Model BM1. Motorized unit 1, housing 2; mounting bracket 3, UV lamp 5; frame 6, having a first side and a second side; cable 7; spring 43; reel assembly 54; reel assembly flanges 59; cross member support bars(s) 71; handle 91; UV lamp socket/adaptor 94; first cable guide wheel 120; second cable guide wheel 121; openings 122 (within frame 6); first track 124 on first cable guiding wheel 120; cable tightening spring 123. Details of UV device BM1 are described herein.

FIGS. 39A-C schematically depict non-limiting dimensions of a UV device model of the present invention, referred to herein as UV device Model BM1. Parts are as shown for FIGS. 38A and 38B, however, for clarity, not all parts of UV device Model BM1 are shown in FIGS. 39A-C. In some embodiments of UV device Model BM1, the UV device comprises an additional motor 133 driving its torque perpendicular to its axis.

Figure 40A:
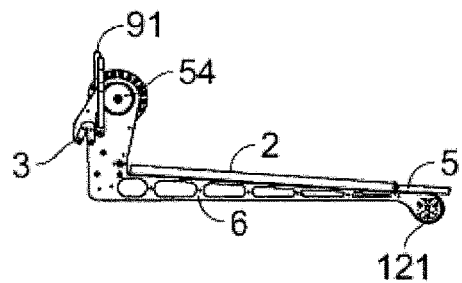
Figure 40B:
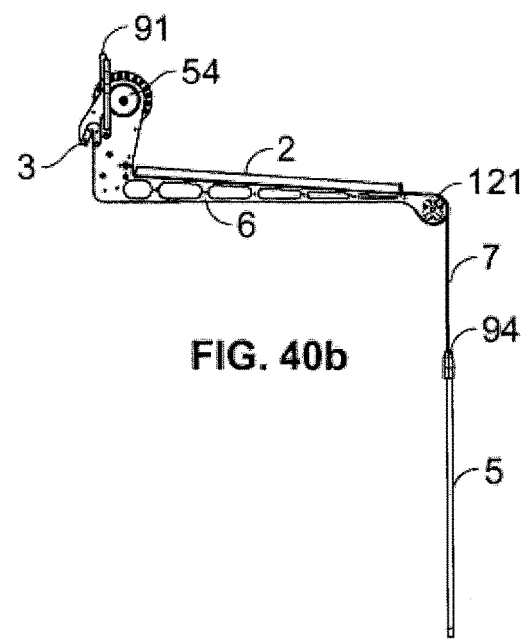
Figure 40C:
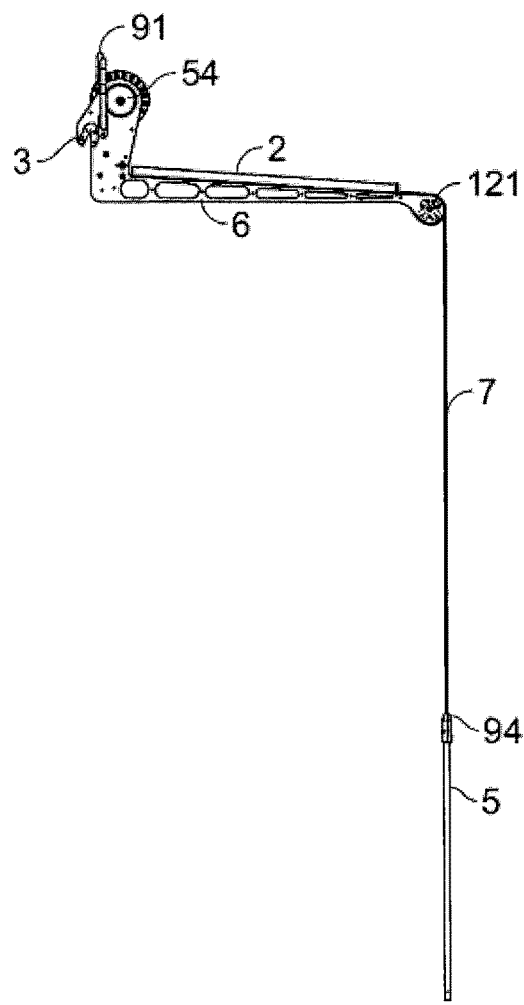

FIGS. 40A-C schematically depict the release of a UV light source from the housing of UV device Model BM1 and the descent of the UV light source downwardly into a container (not shown). FIG. 40A schematically depicts the UV lamp 5 slightly protruding out of the housing 2 and moving onto the first track 124 (not shown) of second cable guide wheel 121. FIG. 40B schematically depicts the UV lamp 5 having moved completely across the first track 124 (not shown) of the second cable guide wheel 121 and being attached to a cable 7 via a UV lamp socket/adaptor 94. FIG. 40C schematically depicts a further downwardly movement of the UV light source into a container (not shown). Housing 2, mounting bracket 3, UV lamp 5, frame 6, cable 7, reel assembly 54, handle 91, UV lamp socket/adaptor 94, second cable guide wheel 121. Details of IN device BM1 are described herein. Not all parts are shown in figure.

Figure 41:
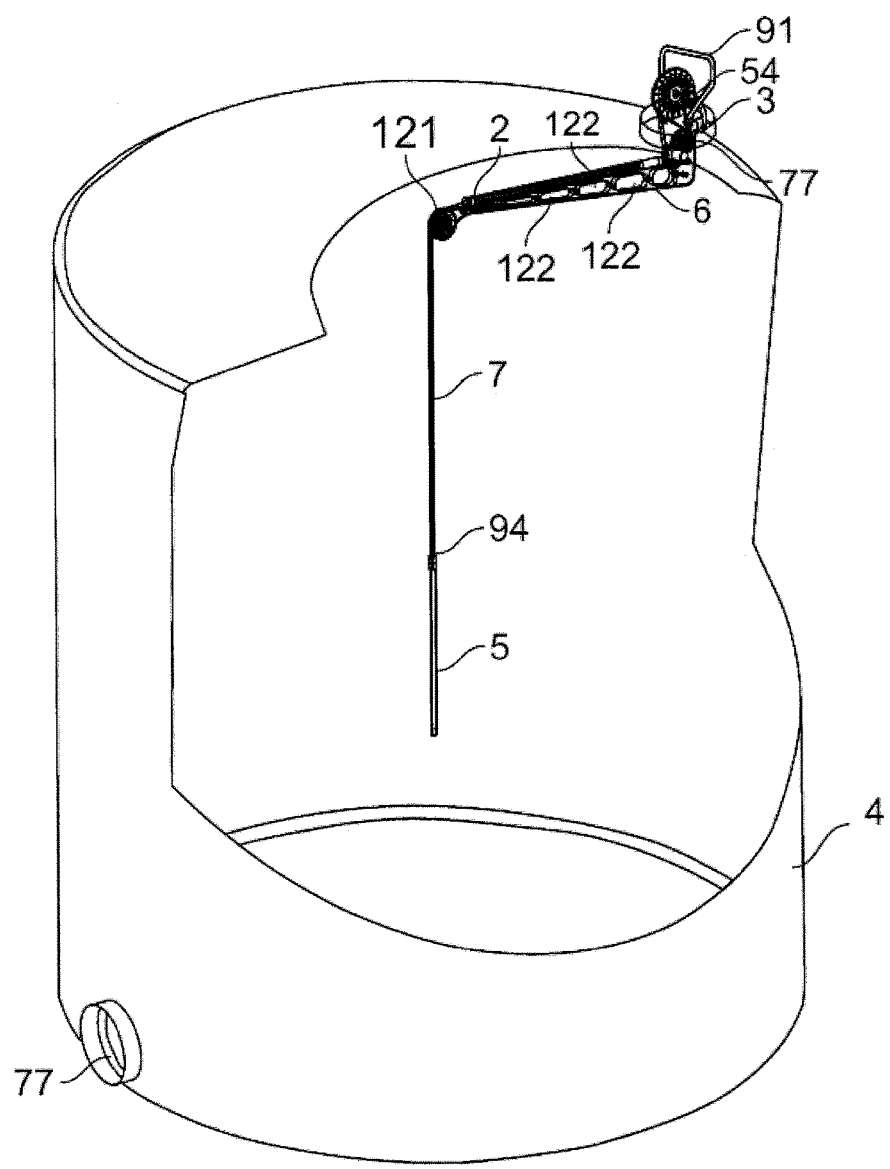

FIG. 41 schematically depicts an attachment of UV device Model BM1 at an opening of a container and the movement of the UV light source from a vertical position into a downwardly position within the container. The container 4, as depicted, has two openings 77, one at the top and one at a bottom side. Housing 2; mounting bracket 3, container 4, UV lamp 5; frame 6; cable 7; reel assembly 54; handle 91; UV lamp socket/adaptor 94; second cable guide wheel 121; openings 122 (within frame 6). Details of UV device BM1 are described herein. Not all parts are shown in figure.

Figure 42:
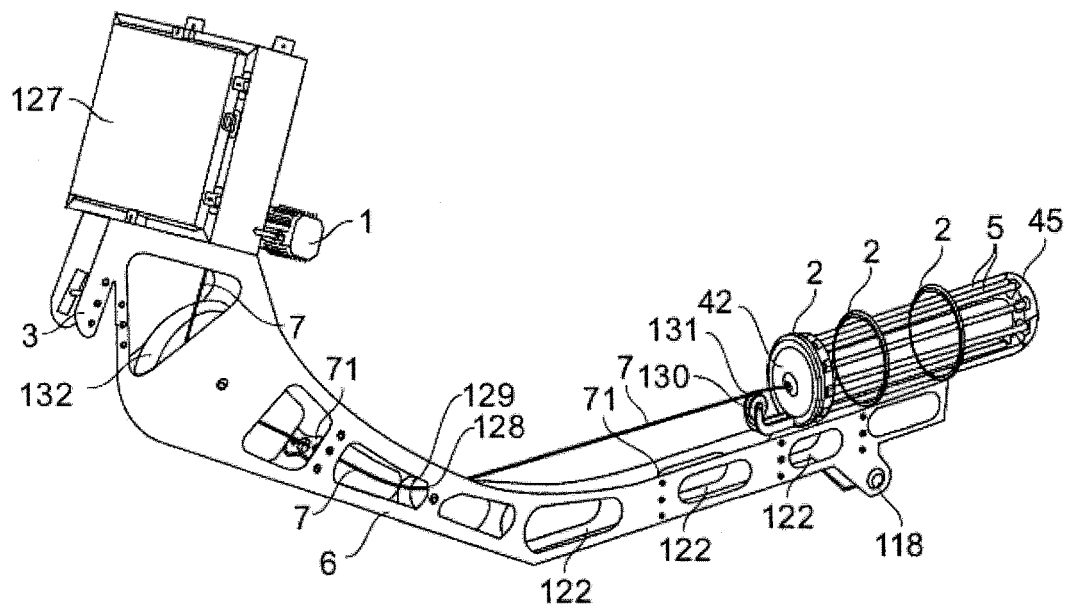

FIG. 42 schematically depicts a non-limiting embodiment of a UV device of the present invention, referred to herein as UV device Model BM2 in its stowed position, i.e., wherein the UV light source is within its housing and the UV light source resides on top of the frame. UV device Model BM2 comprises a UV lamp cluster of eight (8) UV lamps 5. Motorized unit 1, housing 2; mounting bracket 3, UV lamps 5; frame 6, having a first side and a second side; cable 7; cross member support bars(s) 71; UV lamp socket/adaptor 94; openings 122 (within frame 6); box 127; first cable guide wheel 128 with first track 129; second cable guide wheel 130 with second track 131. In this embodiment, cable 7 would insert directly into box 127 and connect with a motor and reel assembly. Optionally, UV device model BM2 comprises a third cable guide wheel 132. The box 127 may harbor a power supply, a circuit board, a reel assembly, a motorized unit, a LED interface, and other components as described herein. Not all parts are shown in figure. Details of UV device BM2 are described herein.

Figure 43:
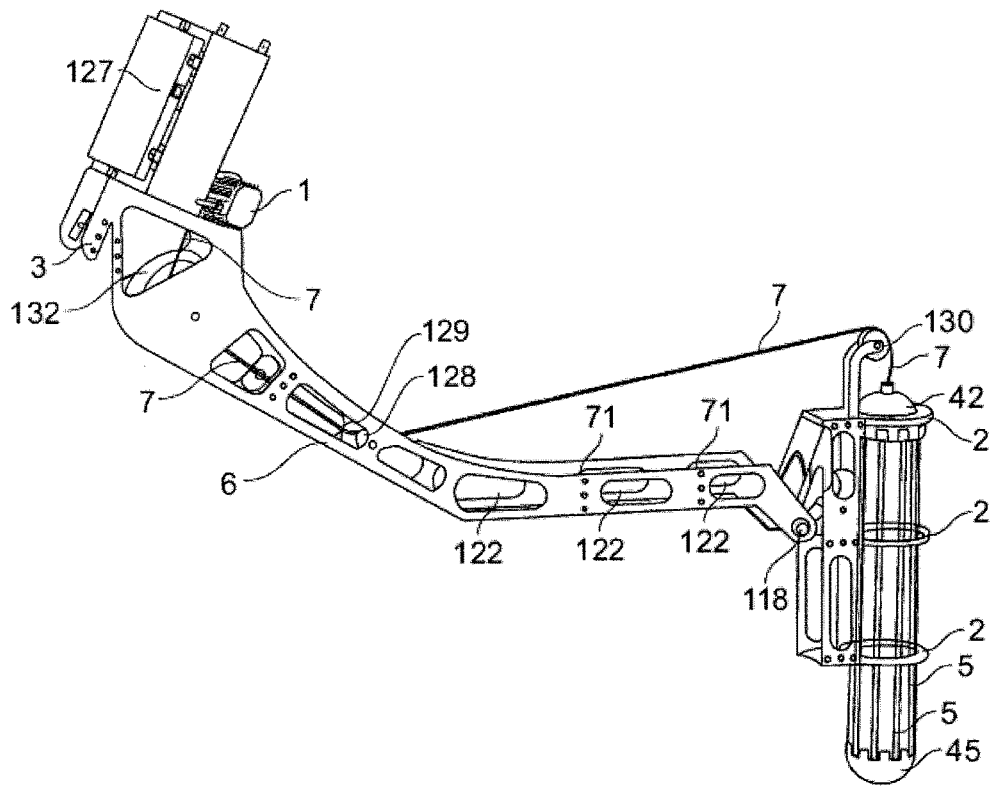

FIG. 43 schematically depicts a non-limiting embodiment of a UV device of the present invention, referred to herein as UV device Model BM2 in its docked position, i.e., the housing 2 and UV lamps 5 are moved into a first vertical position with respect to the frame 6 of the UV device. Parts are as described in FIG. 42. Not all parts are shown in figure. Details of UV device BM2 are described herein.

Figure 44:
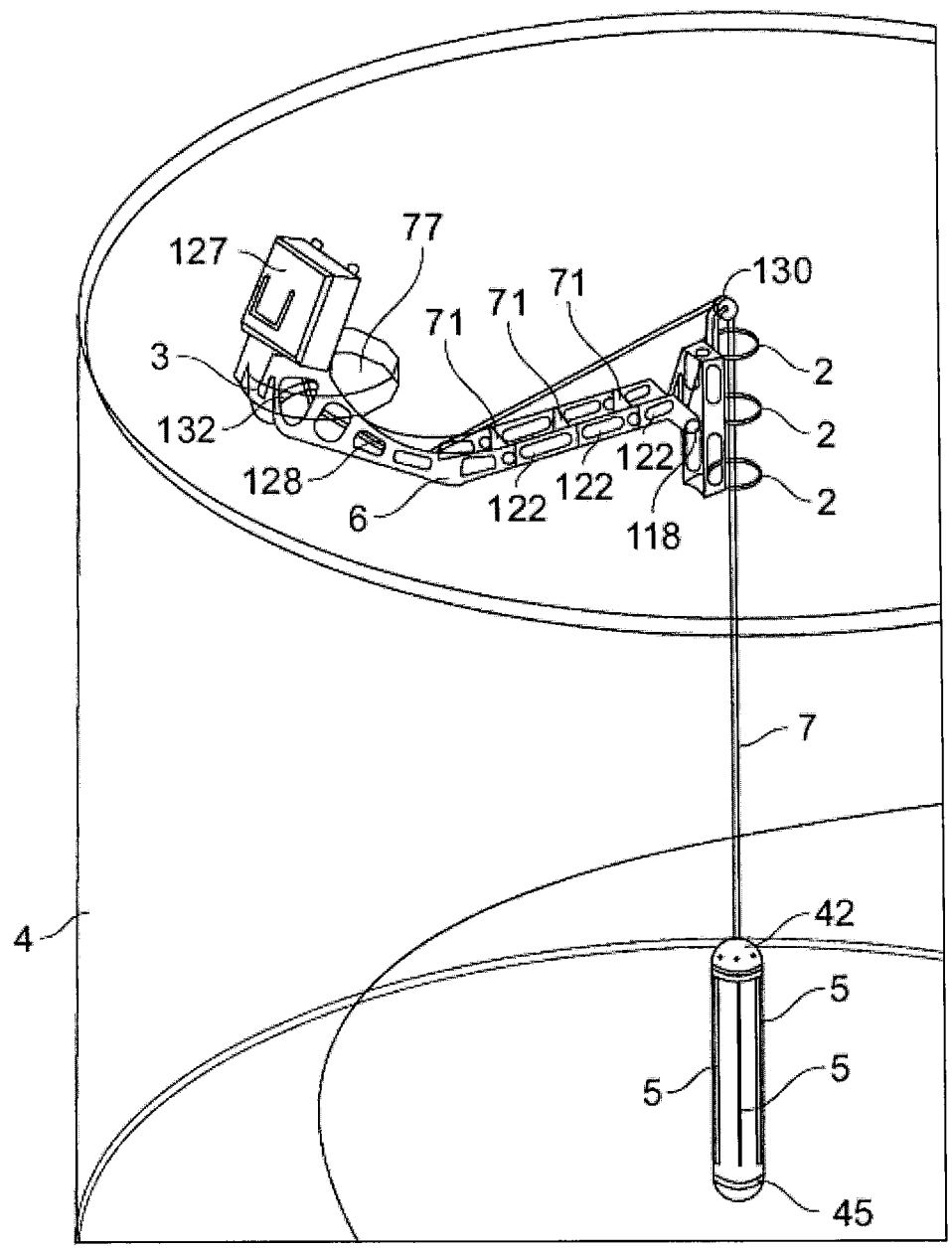

FIG. 44 schematically depicts a non-limiting embodiment of a UV device of the present invention, referred to herein as UV device Model BM2 in its deployed position, i.e., the UV light source (UV lamps 5) is released from the housing 2 and has been moved from the first vertical position (see FIG. 43) into a second vertical position. The second vertical position is further downwardly in the container 4 with respect to its first vertical position (see FIG. 43). Parts are as described in FIG. 42. Not all parts are shown in figure. Details of UV device BM2 are described herein.

Figure 45:
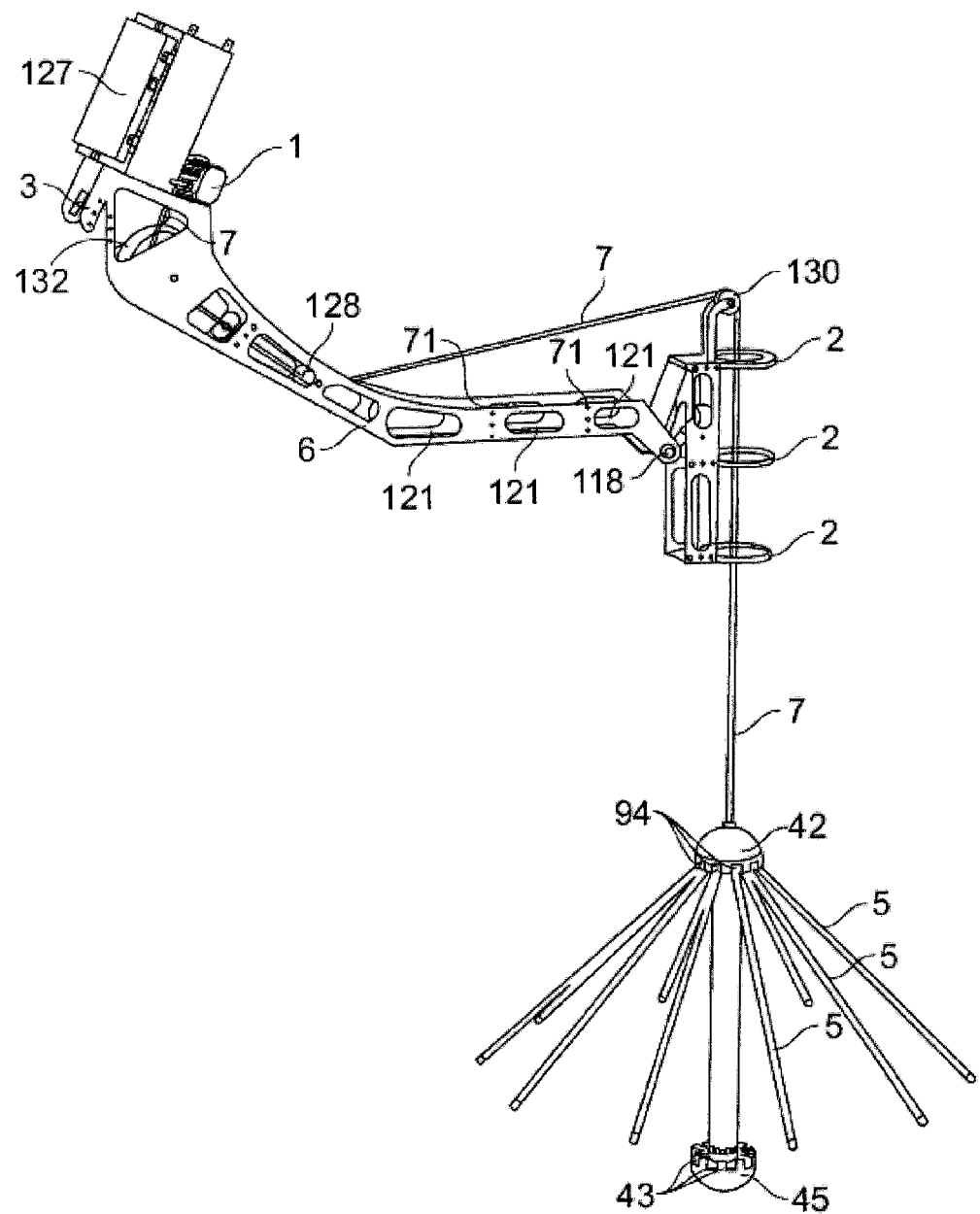

FIG. 45 schematically depicts a non-limiting embodiment of a UV device of the present invention, referred to herein as UV device Model BM2 in its working position, i.e., the UV light source (here a UV lamp cluster of eight (8) UV lamps 5) is released from its attachment at the base plate. Springs 43, UV lamp socket/adapters 94. Other parts are as described in FIG. 42. Not all parts are shown in figure. Details of UV device BM2 are described herein.

Figure 46A:
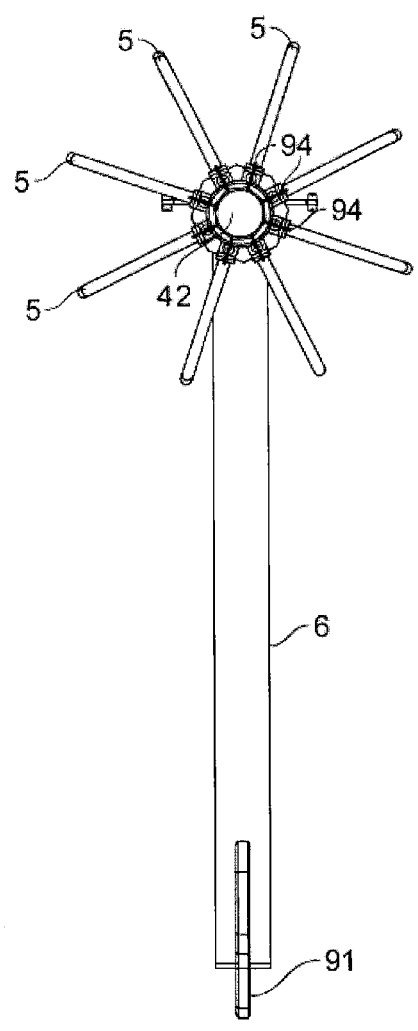
Figure 46B:
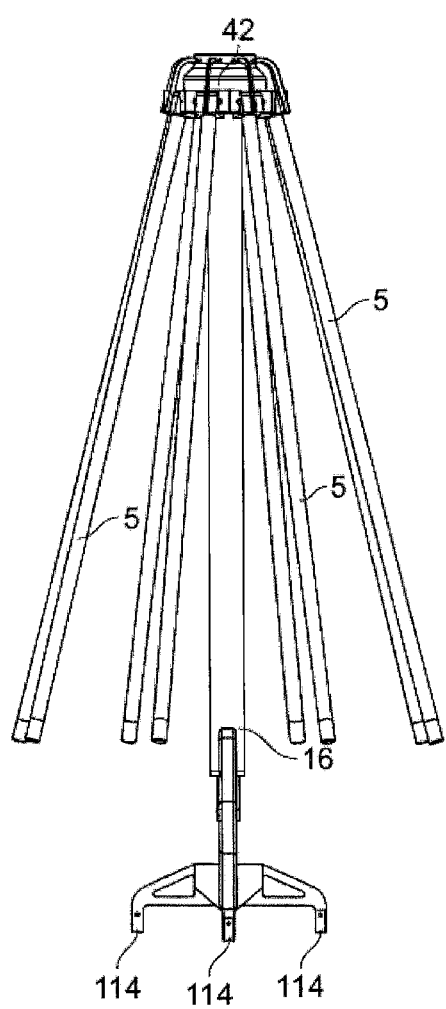
Figure 46C:
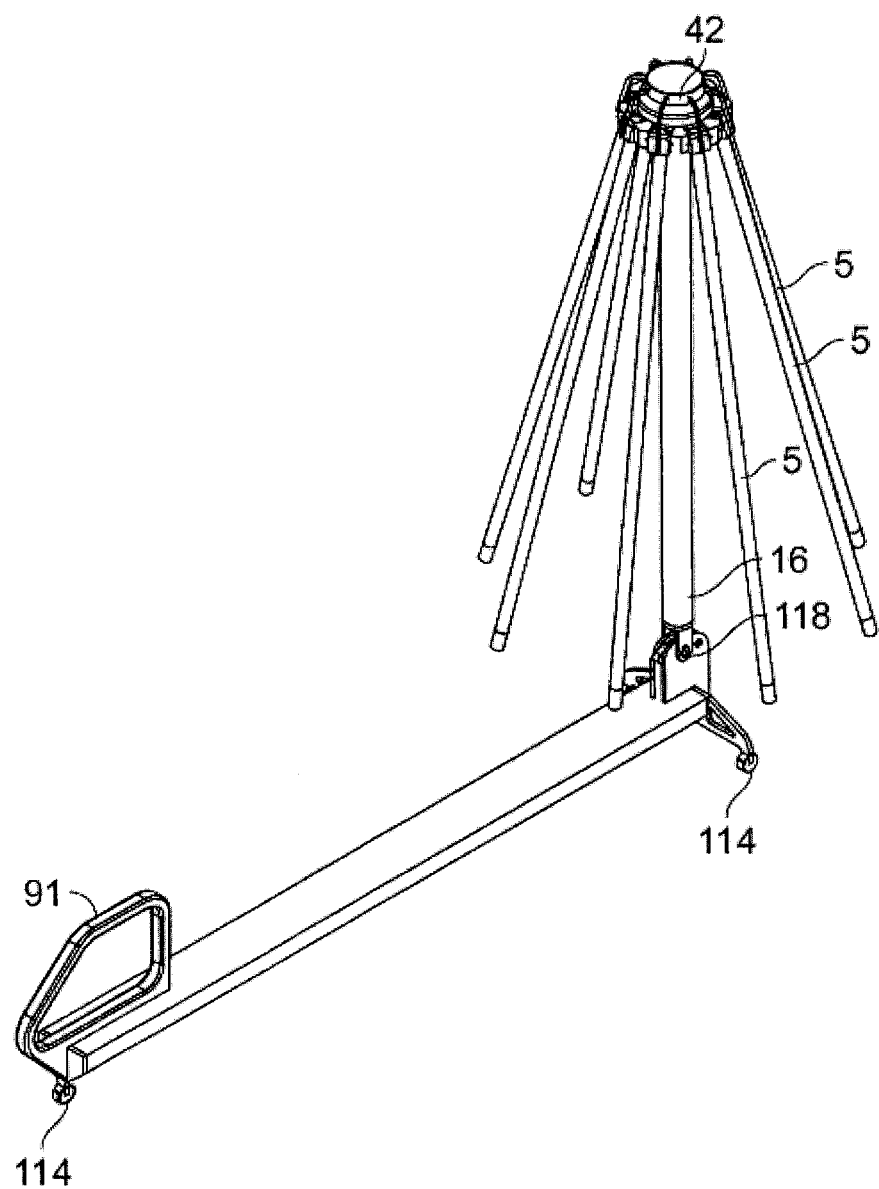
Figure 46D:
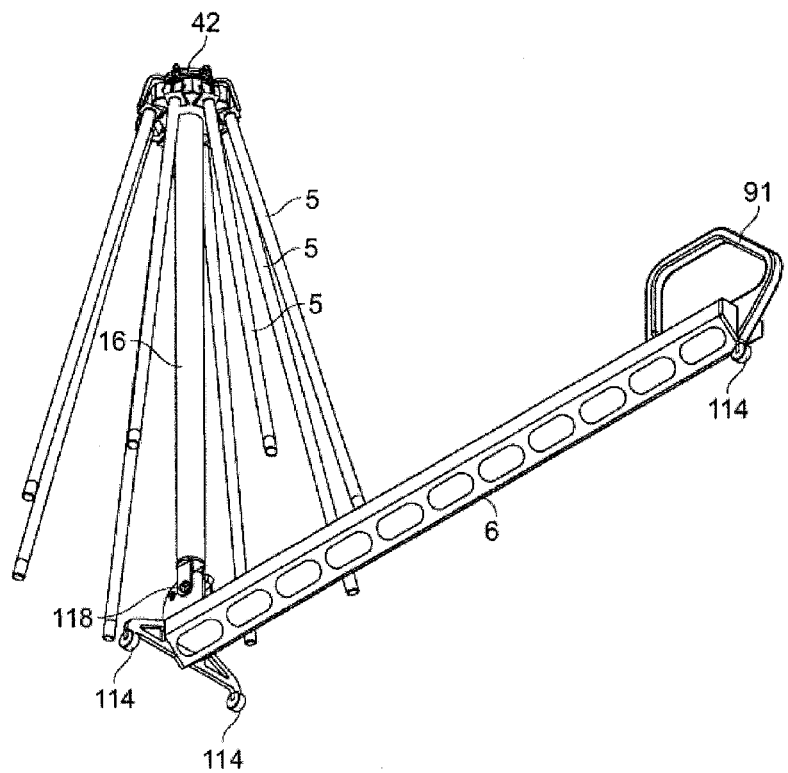
Figure 46E:
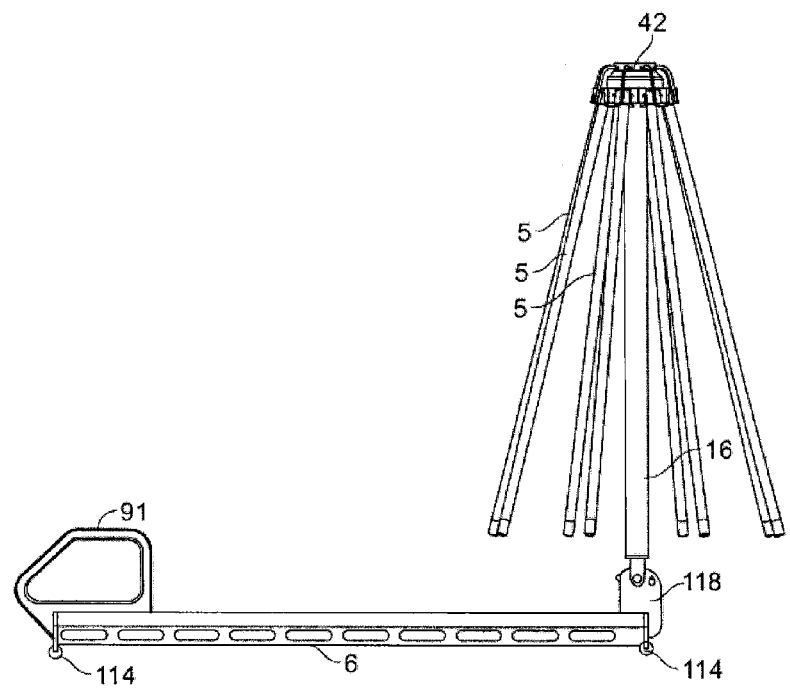

FIGS. 46A-E schematically depict various views of a non-limiting embodiment of a UV device of the present invention, referred to herein as UV device Model BM3 in its deployed position. FIG. 46A, top view; FIG. 46B, right top view; FIG. 46C, lower view; FIG. 46D, front view; FIG. 46E, side view. UV lamp(s) 5, frame 6, central post 16, top plate 42, handle 91, wheels 114, pivot 118.

Figure 47A:
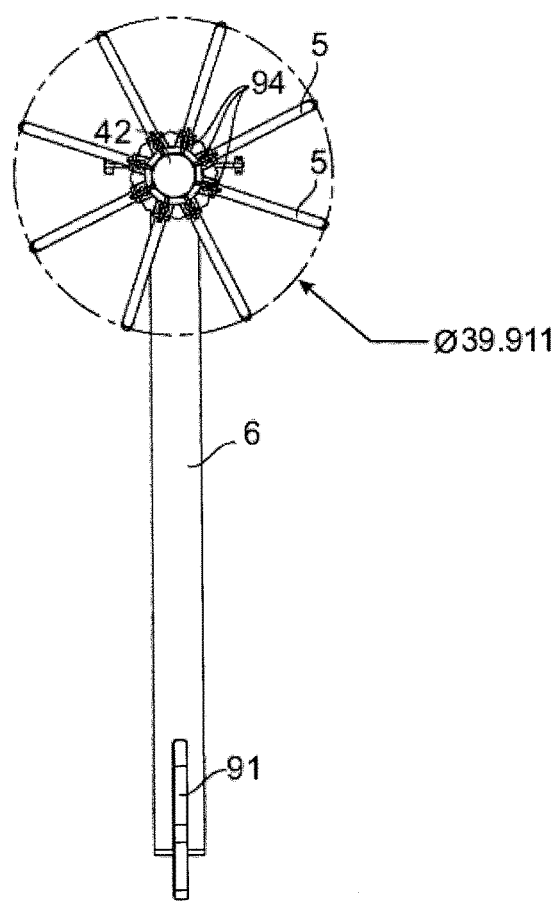
Figure 47B:
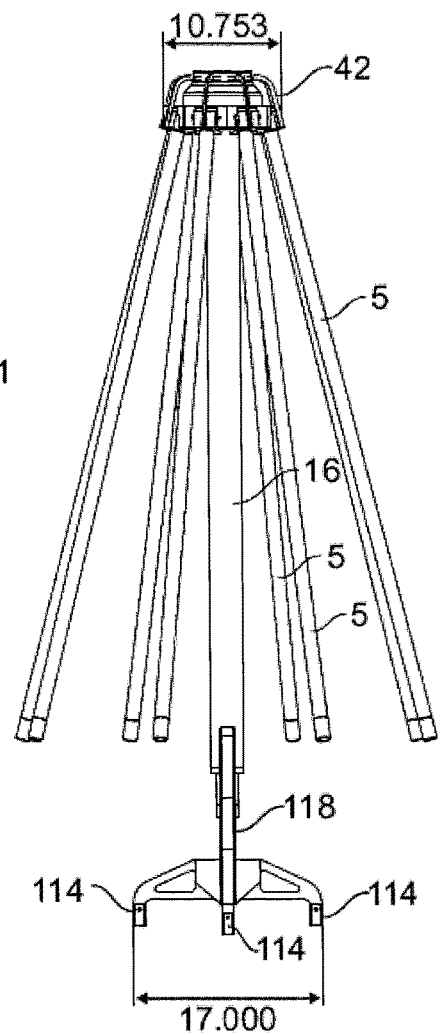
Figure 47C:
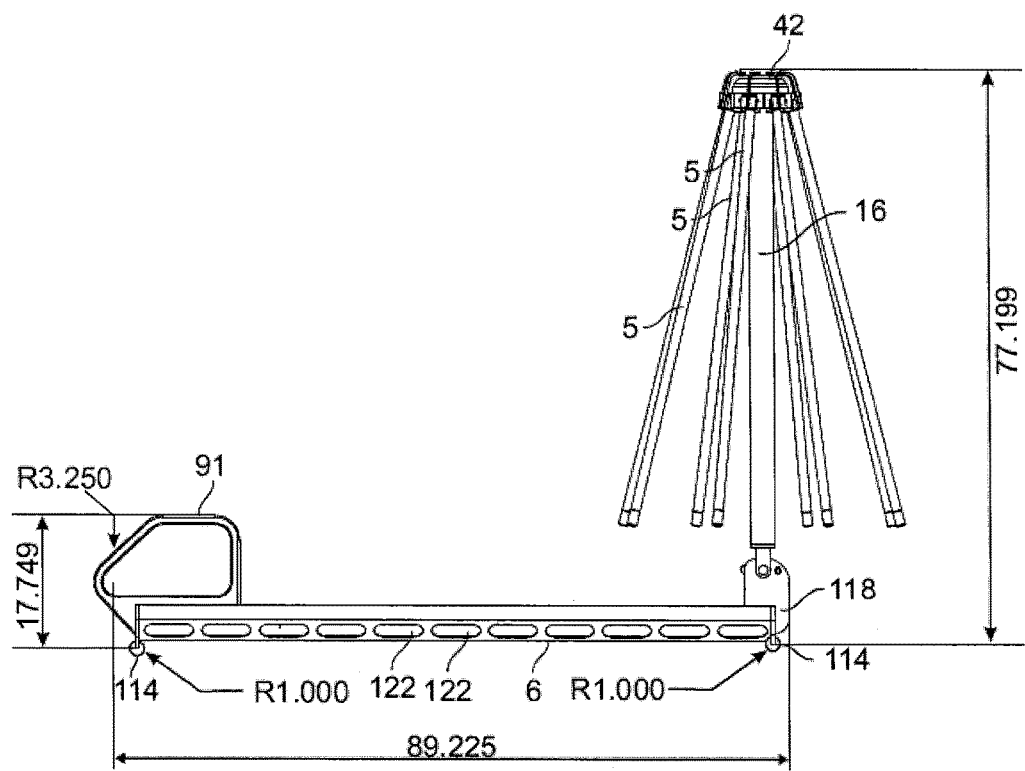

FIGS. 47A-C schematically depict non-limiting dimensions of a UV device model of the present invention, referred to herein as UV device Model BM3. Parts are as shown for FIGS. 46A-E, however, for clarity, not all parts of UV device Model BM3 are shown in FIGS. 47A-C.

Figure 48A:
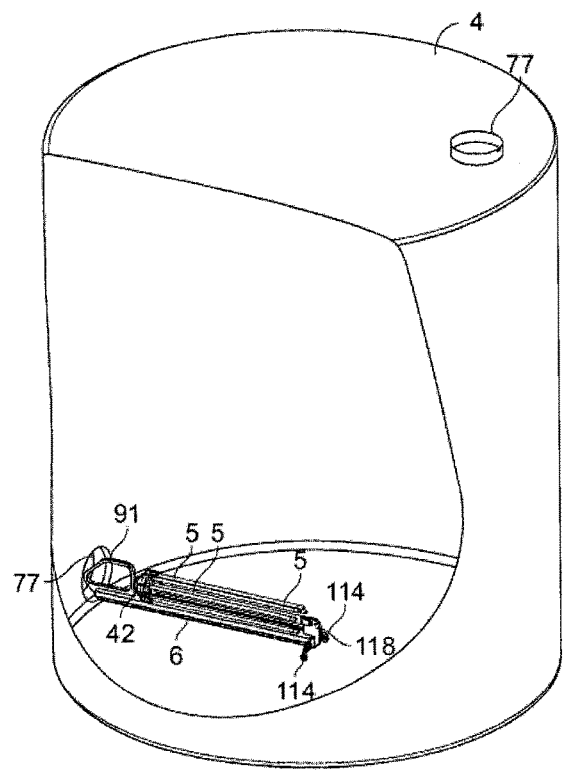
Figure 48B:
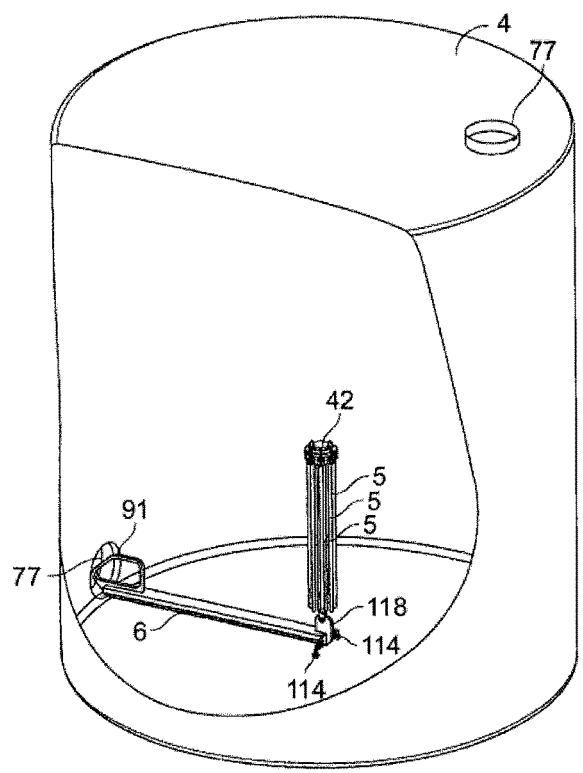
Figure 48C:
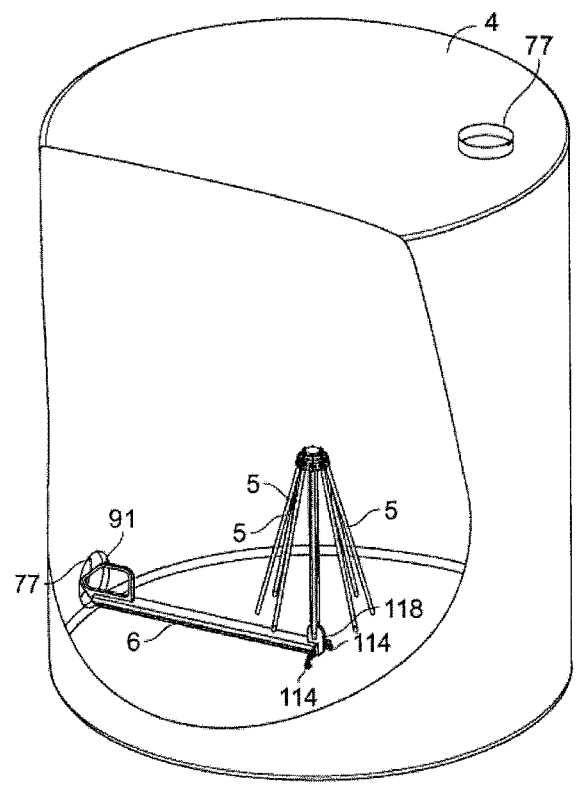
Figure 48D:
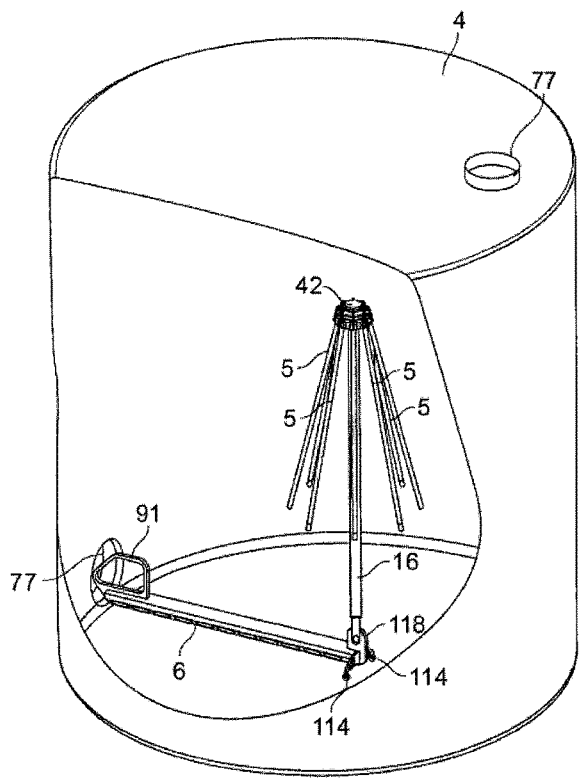

FIGS. 48A-D schematically depict a non-limiting embodiment of a UV device of the present invention, referred to herein as UV device Model BM3 in its working operation. FIG. 48A, the UV device Model BM3 is moved inwardly into a container 4 through an opening 77 at the bottom of the container 4. In this position the UV light source (here a UV lamp cluster of eight (8) UV lamps 5) resides on top of frame 6. FIG. 48B, The UV light source is moved from its horizontal position (see FIG. 48A) into a first vertical position within the container 4 via a pivot arm 118. FIG. 48C schematically depicts the UV lamps 5 at a deployed position, wherein the UV lamps 5 are positioned at an angle with respect to each other. FIG. 48D schematically depicts an optional feature of UV device Model BM3, wherein the central post 16 can be extended to move the UV light source from its first vertical position (see FIGS. 48B and 48C) upwardly to a second vertical position within the container 4. Container 4, UV lamp(s) 5, frame 6, central post 16, top plate 42, opening 77 of container 4, handle 91, wheels 114, pivot 118. Not all parts of UV device Model BM3 are shown in figure. Description of parts is as in FIGS. 46A-E and as described herein.

DETAILED DESCRIPTION OF THE INVENTION

I. Definitions

Throughout the present specification and the accompanying claims the words "comprise" and "include" and variations thereof, such as "comprises," "comprising," "includes," and "including" are to be interpreted inclusively. That is, these words are intended to convey the possible inclusion of other elements or integers not specifically recited, where the context allows. No language in the specification should be construed as indicating any non-claimed element essential to the practice of the invention.

The terms "a" and "an" and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, another embodiment includes from the one particular value and/or to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the skilled artisan. For example, if the value "10" is disclosed, the "less than or equal to 10" as well as "greater than or equal to 10" is also disclosed.

All methods described herein can be performed in any suitable order unless otherwise indicated herein or otherwise clearly contradicted by context. The use of any and all examples, or exemplary language (e.g., "such as" or "e.g.," or "for example") provided herein is intended merely to better illuminate the invention and does not pose a limitation on the scope of the invention otherwise claimed.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

The abbreviations used herein have their conventional meaning within the mechanical, chemical, and biological arts.

As used herein, the term "about" refers to a range of values of plus or minus 10% of a specified value. For example, the phrase "about 200" includes plus or minus 10% of 200, or from 180 to 220, unless clearly contradicted by context.

As used herein, the terms "amount effective" or "effective amount" mean an amount, which produces a desired effect, such as a biological effect. In particular, an effective amount of a UV dosage is an amount, which inhibits the growth of a microorganism by at least 90% (by at least 1 log reduction), by at least 99% (by at least 2 log reduction), by at least 99.9% (by at least 3 log reduction), by at least 99.99% (by at least 4 log reduction), by at least 99.999% (at least 5 log reduction), or by at least 99.9999% (at least 6 log reduction).

As used herein, the terms "attach to" or "attached to" or grammatical equivalents thereof mean to fasten on, fasten together, affix to, mount to, mount on, connect to, to join, to position onto, position into, place onto, or place into. "Attachment" means the act of attaching or the condition of being attached. Attachment can be direct or indirectly. For example a part A may be attached directly to part B. Alternatively, part A may be attached indirectly to part B through first attaching part A to part C and then attaching part C to part B. More than one intermediary part can be used to attach part A to part B. Attaching can be permanent, temporarily, or for a prolonged time. For example, a UV device of the present invention may be attached to a container temporarily for the time necessary to perform a method of the invention. Alternatively, a UV device of the present invention may be attached to a container or to an object or structure in a room, a space or defined environment for a prolonged time, e.g., also when a method of the present invention is not performed. Also, a UV device of the present invention may be attached permanently to a container or to an object or structure in a room, a space or defined environment.

The terms "container," "vessel," or "tank" are used interchangeably herein.

As used herein, the terms "germicidal lamp" or "germicidal UV lamp" refer to a type of lamp, which produces ultraviolet (UV) light. Short-wave UV light disrupts DNA base pairing causing thymine-thymine dimers leading to death of bacteria and other microorganisms on exposed surfaces.

As used herein, the terms "inhibiting the growth of a microorganism," "inhibiting the growth of a population of microorganisms," "inhibiting the growth of one or more species of microorganisms" or grammatical equivalents thereof refer to inhibiting the replication of one or more microorganisms and may include destruction of the microorganism(s). Assays for determining inhibiting the growth of a microorganism are known in the art and are described herein.

As used herein, the terms "microorganism" or "microbe" comprise a diverse group of microscopic organisms, including, but not limited to, bacteria, fungi, viruses, archaea, and protists.

The terms "optional" or "optionally" as used throughout the specification means that the subsequently described event or circumstance may but need not occur, and that the description includes instances where the event or circumstance occurs and instances in which it does not. The terms also refer to a subsequently described composition that may but need not be present, and that the description includes instances where the composition is present and instances in which the composition is not present.

As used herein, the term "portable" in the context of a UV device refers to a UV device of the present invention that can be carried by a person and that can be temporarily (e.g., for the duration of a sanitization cycle) attached to a container. As such, a portable UV device of the present invention does not include a UV device that is temporarily or permanently affixed to a structure (other than a container to be sanitized), such as a wall, or a ceiling and being employed to sanitize containers that are transported in front of or underneath a UV light source by, e.g., a conveyer belt.

As used herein, the term "radiation" or grammatical equivalents refer to energy, which may be selectively applied, including energy having a wavelength of between $10^{-14}$ and $10^4$ meters including, for example, electron beam radiation, gamma radiation, x-ray radiation, light such as ultraviolet (UV) light, visible light, and infrared light, microwave radiation, and radio waves. A preferred radiation is UV light radiation. "Irradiation" refers to the application of radiation to a surface.

As used herein, the terms "sterile" or "sterilization" and grammatical equivalents thereof refer to an environment or an object, which is free or which is made free of detectable living cells, viable spores, viruses, and other microorganisms. Sometimes the process of sterilization is also referred herein to as "disinfection" or "sanitization."

As used herein the term "ultraviolet" and the abbreviation "UV" refer to electromagnetic radiation with wavelengths shorter than the wavelengths of visible light and longer than those of X-rays. The UV part of the light spectrum is situated beyond the visible spectrum at its violet end.

As used herein, the abbreviation "UV-A" refers to ultraviolet light in the range of 315-400 nanometers (nm).

As used herein, the abbreviation "UV-B" refers to ultraviolet light in the range of 280-315 nanometers (nm).

As used herein, the abbreviation "UV-C" refers to ultraviolet light in the range of 200-280 nanometers (nm).

As used herein, the term "UV dose" refers to an amount of UV irradiation absorbed by an exposed population of microbes, typically in units of $mJ/cm^2$ ($mJ/cm^2$=1,000 $\mu W/cm^2$ per second).

As used herein, the terms "UV intensity" or "UV irradiance" refer to the irradiance field of a UV germicidal irradiation system (such as a UV light source described herein), i.e., the total radiant energy incident on a surface from all directions. It is measured in $\mu W/cm^2$ at 1 m. The UV intensity greatly depends on the distance from the UV emitter and the transmittance of the medium.

As used herein, the terms "ultraviolet radiation" or "UV radiation" refer to radiation having a wave-length or wavelengths between from 160 to 400 inn. If a range is specified, a narrower range of radiation is meant within the 160 to 400 nm range. The range specified, unless otherwise indicated, means radiation having a wavelength or wavelengths within this specified range.

In the following description it is to understood that terms such as "forward," "rearward," "front," "back," "right," "left," "upward," "downward," "horizontal," "vertical," "longitudinal," "lateral," and the like are words of convenience and are not to be construed as limiting terms.

The present invention generally relates to compositions, systems and methods for ultraviolet (UV) sterilization, and more specifically, to compositions, systems and methods for UV sterilization of a container, and more particularly to compositions, systems and methods for UV sterilization of a container used in the process of fermentation for an alcoholic beverage. A system as described herein comprises a UV device and a container.

II. UV Devices

Figure 2:
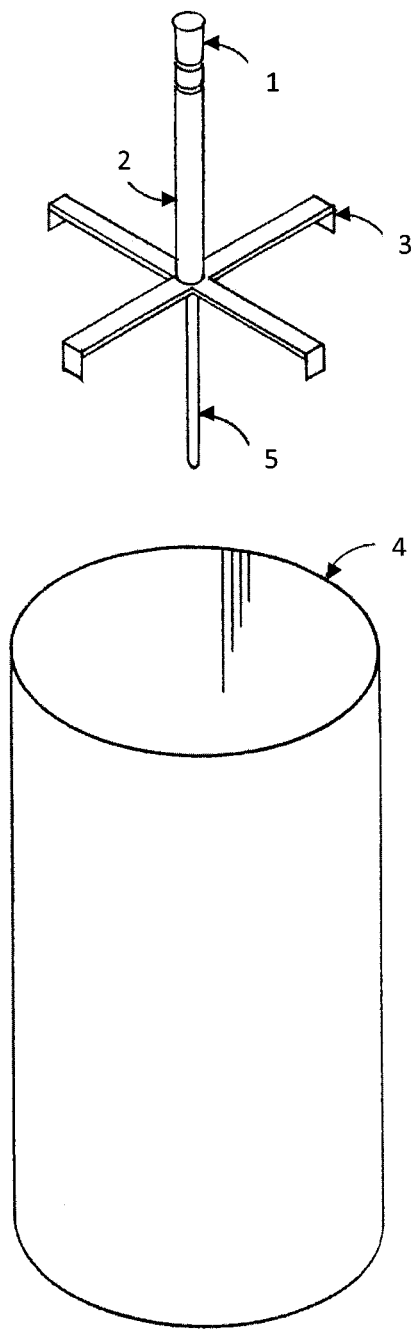
FIG. 2 schematically depicts a UV device of the present invention above a container 4, here a cylindrical fermentation vessel. In this embodiment, the UV lamp 5 is being lowered from within a housing 2, here a protective sleeve. The UV lamp 5 can be suspended above the container 4 via a mounting bracket 3. The UV lamp 5 can be raised and lowered by a motorized unit 1 mounted on top of the housing 2.
Figure 3:
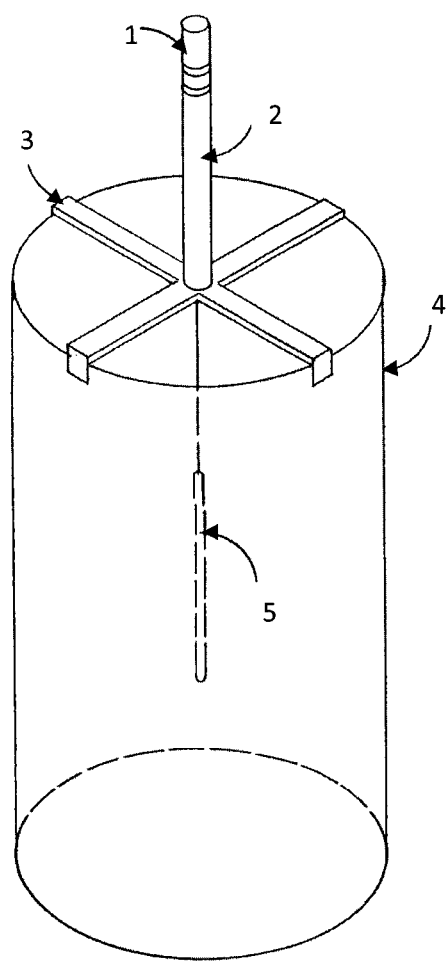
FIG. 3 schematically depicts a UV device of the present invention placed on a container 4, here a cylindrical fermentation vessel. In this embodiment, the UV lamp 5 is being lowered into the interior of the container 4. The UV device is supported by a mounting bracket 3. The UV lamp is being lowered from a housing 2, here a protective sleeve, by a motorized unit 1 mounted on top of the housing 2.
Figure 4:
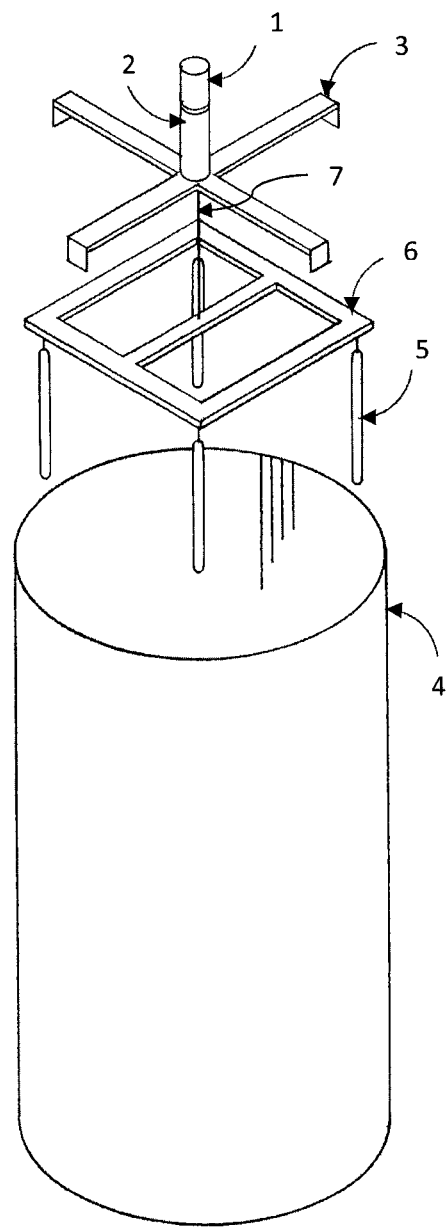
FIG. 4 schematically depicts a UV device of the present invention comprising four UV lamps 5 mounted on a frame 6, which can be attached to a motorized unit 1 by a rigid rod or flexible cable 7. In this embodiment, four UV lamps were chosen as an example to demonstrate that the use of more than one UV lamp 5 in various un-clustered positions is encompassed by the present invention. In this embodiment, the UV lamps 5 are being lowered into the interior of the container 4, here a cylindrical fermentation vessel. The UV device is supported by a mounting bracket 3. The cable or rigid rod 7 supporting the frame 6 is lowered from within a housing 2, here a protective sleeve, by a motorized unit 1 mounted on top of the housing 2.
Figure 5:
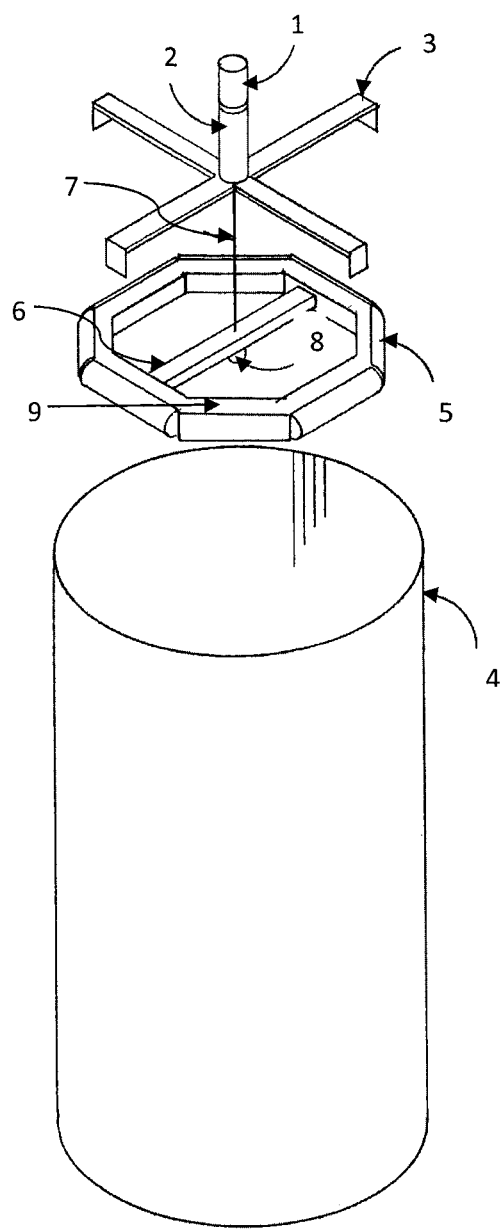
FIG. 5 schematically depicts a UV device of the present invention showing a different configuration of LTV lamps 5. In this embodiment, eight UV lamps 5 are mounted on an octagonal bracket 9, which can be attached to a motorized unit 1 by a rigid rod or flexible cable 7. In this figure, the UV lamps 5 are being lowered into the interior of the container 4, here a cylindrical fermentation vessel. The UV device is supported by a mounting bracket 3. The cable or rigid rod 7 attached to a connecting plate 6 is lowered from within a housing 2, here a protective sleeve, by a motorized unit 1 mounted on top of the housing 2. An additional UV lamp 8 may optionally be placed at the bottom of the connecting plate 6. The UV lamp 8 will be attached to a position on the connecting plate 6 such that the lower surface of the container 4 will receive sufficient UV radiation to kill or inhibit the growth of all desired microorganisms by the end of the sterilization cycle. In another embodiment, a reflective lid is positioned horizontally between the octagonal bracket 9 and the UV lamp 8 may be fixed to the surface of the octagonal bracket 9 to increase the intensity of UV light directed at the lower surface and pointing downwards to ensure the bottom surface of the container 4 is exposed to sufficient UV radiation.
Figure 6:
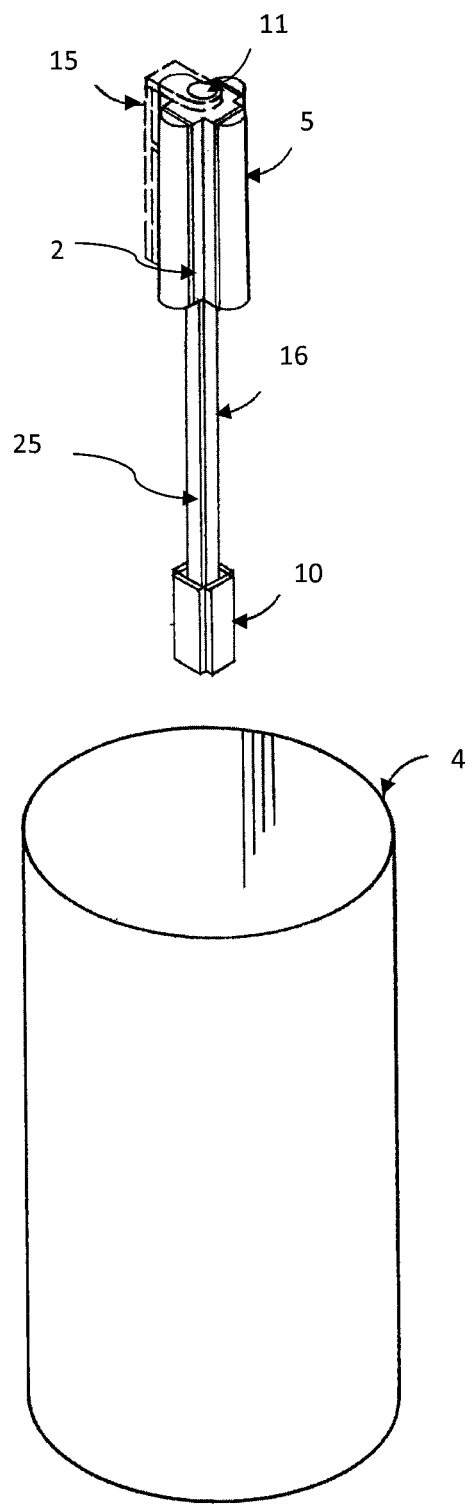
FIG. 6 schematically depicts a UV device of the present invention showing a different configuration of UV lamps 5. The UV device is supported by a folding base plate 10, which is attached to a central post 16 having a track 25. The device is inserted through the top opening of a container 4, here a cylindrical fermentation vessel. The intensity of the UV radiation is monitored by a UV detector 11, which optionally is attached to an adjustable bracket 15 allowing the detector 11 to be placed as close to the inner surface of the container 4 as possible. The UV lamps 5 are optionally covered in this configuration by an acrylic covering that does not absorb UV-C light. The lamps 5 are supported by a housing 2, which as shown in FIG. 7 may fold open. The position and angle of the lamps 5 may be adjusted as depicted in FIG. 7.
Figure 7:
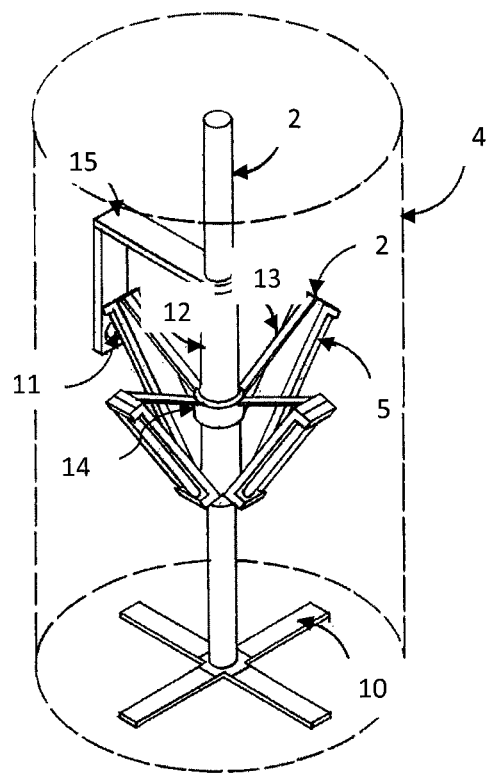
FIG. 7 schematically depicts a UV device of the present invention showing a different configuration of UV lamps 5. The UV device is supported by a folding base plate 10. The UV device is inserted through the top opening of a container 4, here a cylindrical fermentation vessel. The LTV lamps 5 are held in housings 2, which fold open. The housings 2 are attached to a central sleeve 12 via connecting rods 13. The position of the central sleeve 12 may be adjusted to adjust the angle that the UV lamps 5 protrude from the central axis. In this embodiment, the central sleeve 12 is mounted in turn on another centrally mounted motorized sleeve 14, which can move the entire UV device up and down within the container 4. The intensity of the UV radiation is monitored by a UV detector 11, which is attached to an adjustable bracket 15 allowing the detector 11 to be placed as close to the inner surface of the container as possible. The angling of the lamps 5 also ensures the base of the container is irradiated with UV.
Figure 8:
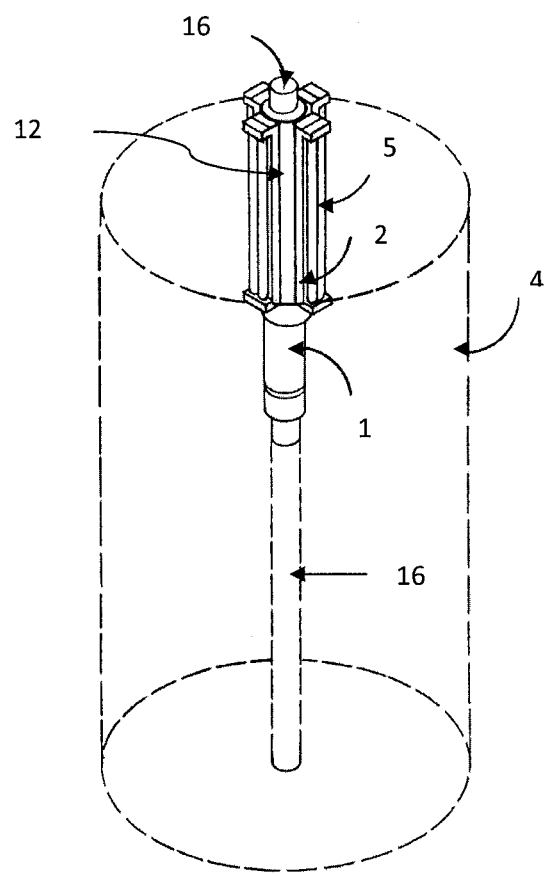
FIG. 8 schematically depicts a UV device of the present invention showing a different configuration of UV lamps 5. In this embodiment, four UV lamps 5 mounted in housings 2 are mounted to a central sleeve 12, which can be moved up and down within the container 4, here a cylindrical fermentation vessel, on a central post 16, via a motorized unit 1 attached to the central sleeve 12. The lamp housings 2 are affixed to two parallelogramming arms (not shown in this Figure, shown in FIG. 9), which can move in a circular motion and adjust the position of the UV lamps 5 and their proximity to the inner surface of container 4 of varying diameter.
Figure 9:
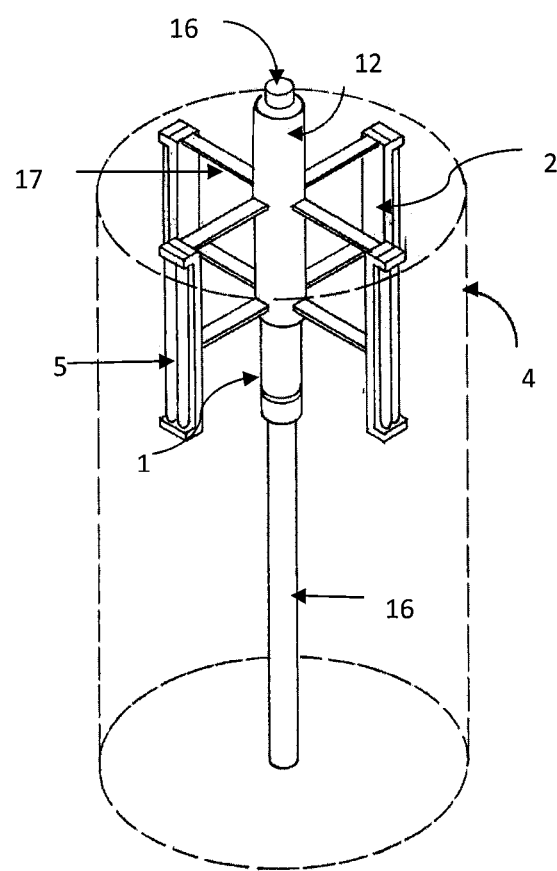
FIG. 9 schematically depicts a UV device of the present invention showing a different position of UV lamps 5 (same as FIG. 8, but with UV lamps 5 extended). In this embodiment, four UV lamps 5 mounted in housings 2 are mounted to a central sleeve 12, which can be moved up and down within the container 4, here a cylindrical fermentation vessel on a central post 16, via a motorized unit 1 attached to the central sleeve 12. The lamp housings 2 are affixed to two parallelogramming arms 17, which can move in a circular motion and adjust the position of the UV lamps 5 and their proximity to the inner surface of containers 4 of varying diameter. In this figure the parallelogramming arms 17 are shown fully extended. Arms 17 may also not be fully extended, i.e., form they an angle between 0 and 90 degrees and be positioned within the closed position (shown in FIG. 8) and the open position (shown in FIG. 9).
Figure 10:
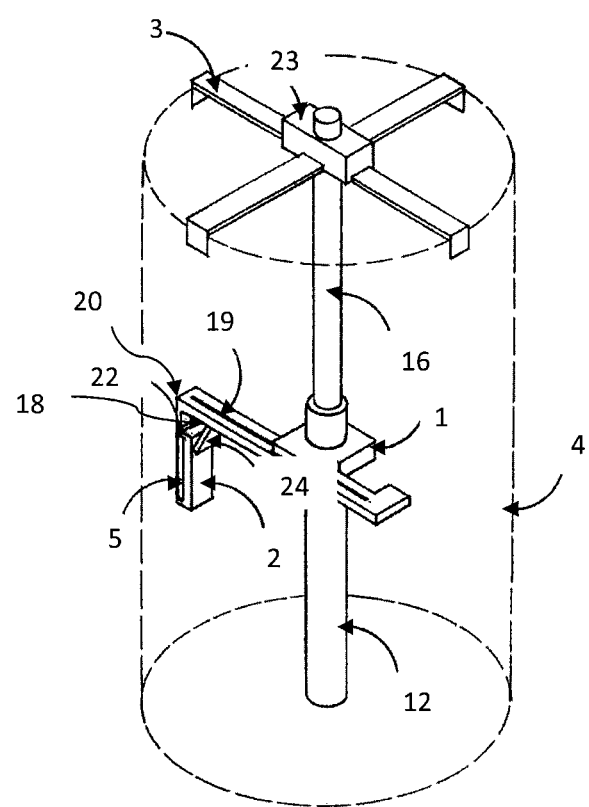
FIG. 10 schematically depicts a UV device of the present invention showing a different configuration using a pulsed UV lamp 5. In this embodiment, the pulsed UV lamp 5 is shown within a housing 2, which contains a fan cooling system (not shown) in order to maintain the lamp temperature within an optimal range. The entire UV device is supported by a bracket 3, mounted on top of the container 4, here a cylindrical fermentation vessel. The assembly holding the UV lamp 5 is attached via an arm 18, with a track 19, that allows the position of the UV light to be adjusted horizontally via a motorized unit 1. The positioning of the UV pulsed lamp 5 can be optimized by a range-finding device 20 (also referred to as a guide) mounted at position 22. The motorized unit 1 can also move up and down a central sleeve 12, adjusting the position vertically. Central sleeve 12 also moves up and down on central post 16, and can telescope up covering central post 16 in order to decrease the overall size of the device facilitating transport. Motor unit 23 mounted at the top of the central post 16 spins the central post 16 enabling the pulsed UV lamp 5 to irradiate the entire surface of the container 4 (by moving vertically and rotating). Adjusting bracket 24 can adjust the position of the pulsed UV lamp 5 from vertical to horizontal (shown in FIG. 11) by moving along a track 19 at the bottom of arm 18.
Figure 11:
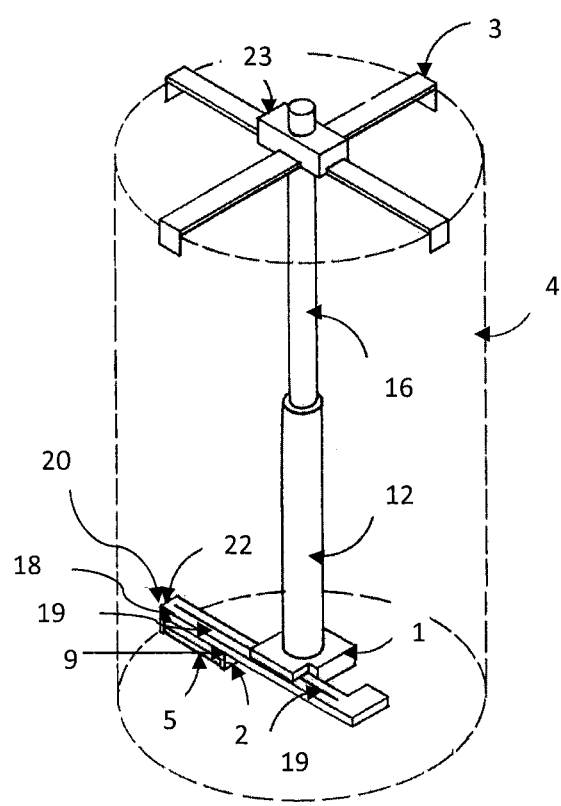
FIG. 11 schematically depicts a UV device of the present invention showing a different position using a pulsed UV lamp 5 (same as embodiment as FIG. 10, but with UV lamps 5 in horizontal position). In this embodiment, the pulsed UV lamp 5 is shown within a housing 2, which contains a fan cooling system (not shown) in order to maintain the lamp temperature within an optimal range. The UV device is supported by a bracket 3 placed or mounted on top of a container 4, here a cylindrical fermentation vessel. The assembly holding the UV lamp 5 is attached via an arm 18, with a track 19, that allows the position of the UV light to be adjusted horizontally via a motorized unit 1. The positioning of the UV pulsed lamp 5 can be optimized by range-finding device 20 mounted at position 22. The motorized unit 1 can also move up and down a central sleeve 12 adjusting the position vertically. Central sleeve 12 also moves up and down on central post 16 and can telescope up covering central post 16 in order to decrease the overall size of the device facilitating transport. Motor unit 23 mounted at the top of the central post 16 spins the central post 16 enabling the pulsed UV lamp 5 to irradiate the entire surface of the container 4 (by moving vertically and rotating). Adjusting bracket 24 (hidden) can adjust the position of the pulsed UV lamp 5 from vertical to horizontal (shown in FIG. 12) by moving along a track 19 at the bottom of arm 18. In the embodiment shown, the UV lamp 5 is held horizontally allowing the of the vessel to be bottom surface of the vessel to be irradiated with pulsed UV light.
Figure 12:
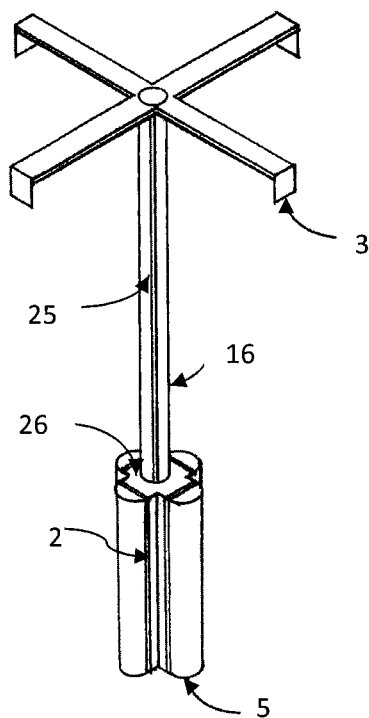
FIG. 12 schematically depicts a UV device of the present invention showing a different configuration using four clustered UV lamps 5. In this embodiment, the UV lamps 5 are mounted to a housing 2 (the housing may or may not have reflectors of various cross sections e.g. parabolic, elliptical, or circular). The UV device is supported to the top of a container (not shown) by a four-armed bracket 3. The clustered UV lamps 5 can move up and down a central post 16 along a track 25. This is accomplished by a motorized unit (not shown here) located between the clustered UV lamps 5 in position 26. The bracket 3 can be used to attach the UV device to a container. Alternatively, the bracket 3 can also function as a base plate or stand similar to base plate 10 as shown, e.g., in FIG. 7 In such configuration, the UV device may be positioned on a surface of a container, e.g., on an interior bottom surface of a container (e.g., see FIG. 7) or on an upper exterior surface of a container (e.g., see FIGS. 25, 29).
Figure 13:
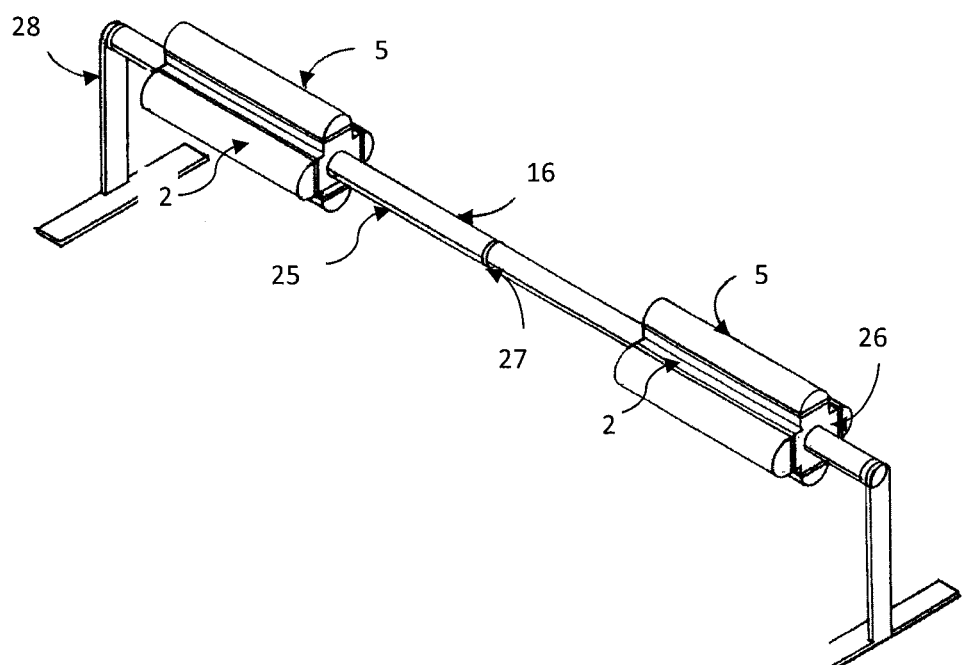
FIG. 13 schematically depicts a UV device of the present invention showing a different configuration using two sets of four clustered UV lamps 5. In this embodiment, the UV lamps 5 are mounted to a housing 2 (the housing may or may not have reflectors of various cross sections e.g., parabolic, elliptical, or circular). This embodiment is preferred for use within a horizontal container. The UV device is supported to the top of a container (not shown) by a horizontal stand 28 The clustered UV lamps 5 can move horizontally along a central post 16 along a track 25. This is accomplished by a motorized unit located between the clustered lamps in position 26. The central post 16 is telescoping allowing one half to slide into the other at position 27. This allows the length of the UV device to be adjusted to the length of the container. Two clusters of UV lamps 5 are shown to demonstrate that more than one cluster of UV lamps 5 can be used.
Figure 14:
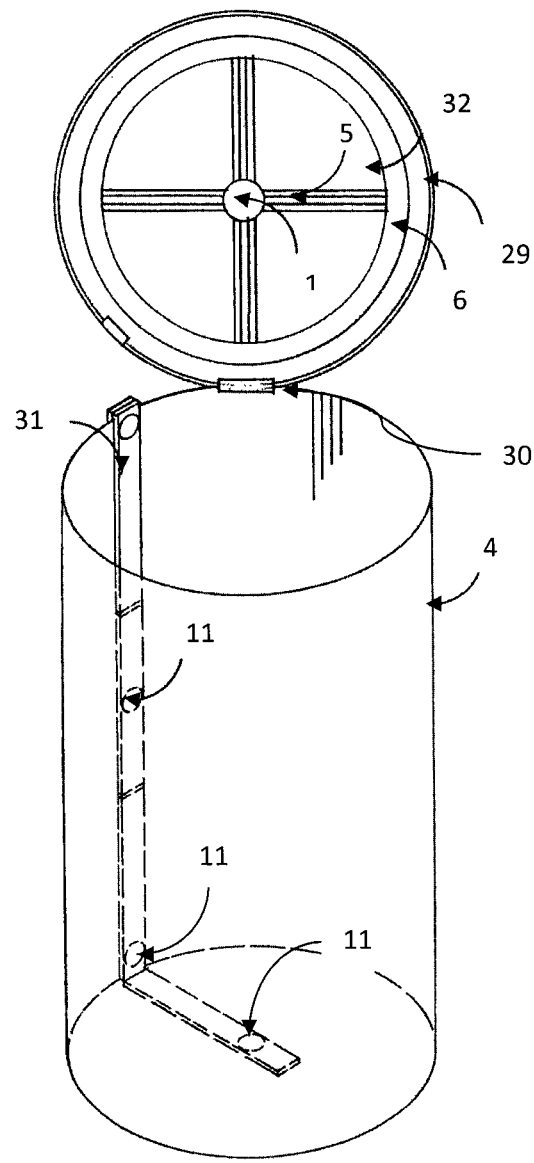
FIG. 14 schematically depicts a UV device of the present invention showing a different configuration of UV lamps 5. In this embodiment, the UV lamps 5 are mounted on a lid 29, such as a hinged lid 30, to a container 4, here a cylindrical fermentation vessel. A removable bracket 31 providing support for a system comprising one or more UV detectors 11 is mounted along the inner surface of the container 4. These UV detectors 11 ensure sufficient intensity of UV radiation required to kill or inhibit growth of unwanted microorganisms has reached all interior surfaces of the container 4. In this embodiment, the UV lamps 5 are mounted to frame 6 and lowered via a cable 7 (not shown, shown in FIG. 15) attached to a motorized unit 1. A reflector 32 may optionally be mounted to the lower surface of the lid 29.
Figure 15:
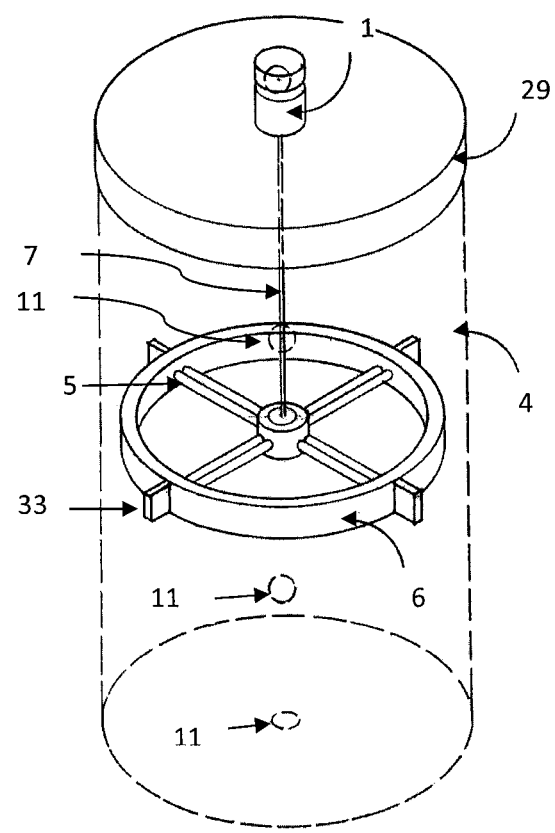
FIG. 15 schematically depicts a UV device of the present invention showing a different position of UV lamps 5 (same embodiment as FIG. 14 but now with the frame 6 and UV lamps 5 lowered). A removable bracket 31 (not shown here, shown in FIG. 14) providing support for a system comprising one or more UV detectors 11 (shown in FIG. 14) is mounted along the inner surface of the container 4. These UV detectors 11 ensure sufficient intensity of UV radiation required to kill or inhibit growth of unwanted microorganisms has reached all surfaces of the container 4. In this embodiment, the UV lamp assembly is guided down the container 4 by nylon blocks 33 attached to frame 6. The lowering of the UV lamp assembly occurs via a motorized unit 1, to which the UV lamp assembly is attached via a cable 7. The lowering of the UV lamp assembly is optional. It can remain at the top of the vessel situated just below the lid 29. In some embodiments, the motorized unit moves the UV lamp assembly in a circular manner.
Figure 16:
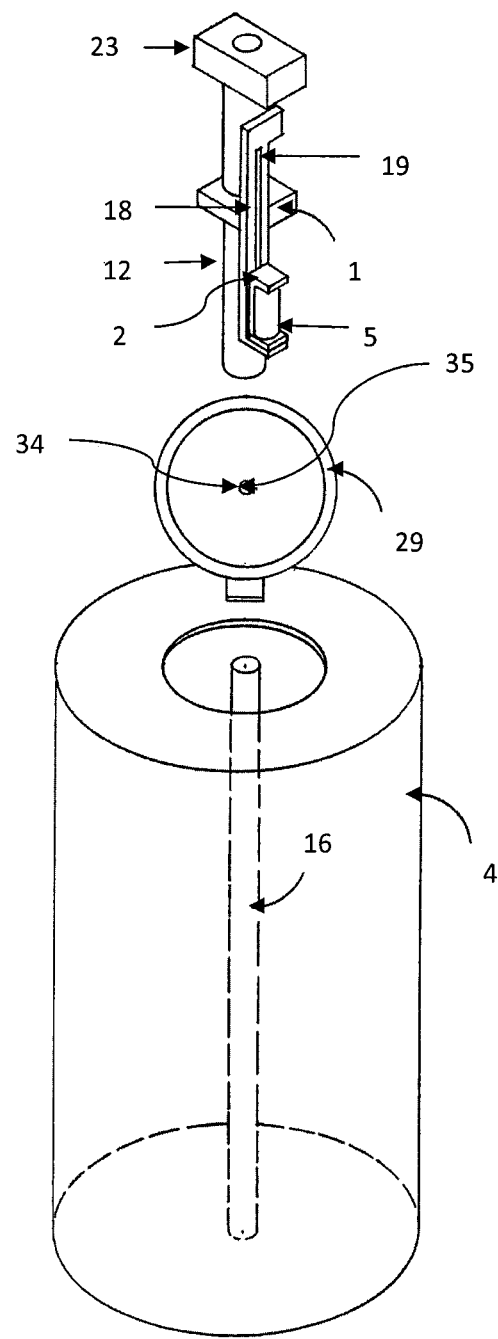
FIG. 16 schematically depicts a UV device of the present invention showing a different configuration of a pulsed UV lamp 5. The pulsed UV lamp 5 is shown within a housing 2, which contains a fan cooling system (not shown) in order to maintain the lamp temperature within an optimal range. The assembly holding the UV lamp 5 (e.g., a pulsed UV lamp) attached via an arm 18 with a track 19 that allows the position of the UV lamp 5 to be adjusted horizontally via a motorized unit 1. The motorized unit 1 can also move up and down a central sleeve 12 adjusting the position vertically. Central sleeve 12 also moves up and down on central post 16 that can be a permanent integral component of the container 4, here a cylindrical fermentation vessel. Motor unit 23 mounted at the top of the central sleeve 12 spins the central sleeve 12 enabling the pulsed UV lamp 5 to irradiate the entire surface of the container (by moving vertically and rotating). The assembly holding the UV lamp 5 is attached via an arm 18 with a track 19 that allows the position of the UV lamp 5 to be adjusted horizontally via a motorized unit 1. A post or boss 34 at position 35 further enhances the stability of central post 16 once the UV device is mounted and lid 29 is closed.
Figure 18A:
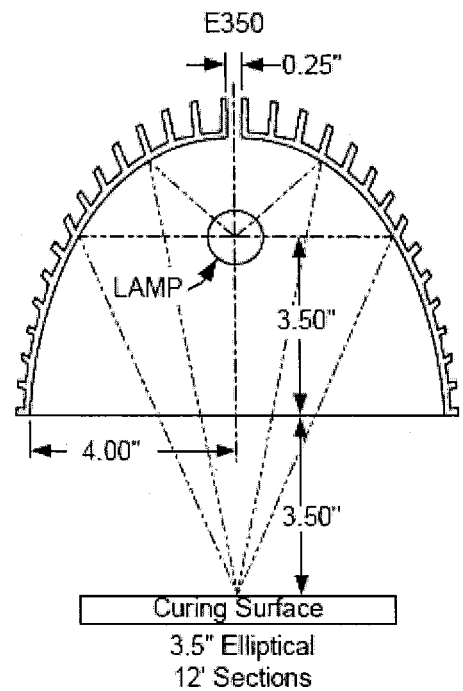
FIGS. 18A-D schematically depict cross sections of four commercially available reflectors (Hill Technical Sales Corp.) for use in the present invention. The upper two cross sections of the reflectors shown in FIG. 18A and FIG. 18B are elliptical and provide a line source of UV light. One focal point of the ellipse is located at the center of the UV lamp the other focal point is positioned approximately 1.75" or 3.5" (depending on reflector used) from the bottom edge of the reflector to the surface being irradiated. The lower two cross sections of the reflectors shown in FIG. 18C and FIG. 18D are parabolic and provide a collimated UV radiation source. The reflectors bottom edge preferably are located 4 to 5 inches from the surface being irradiated.
Figure 18B:
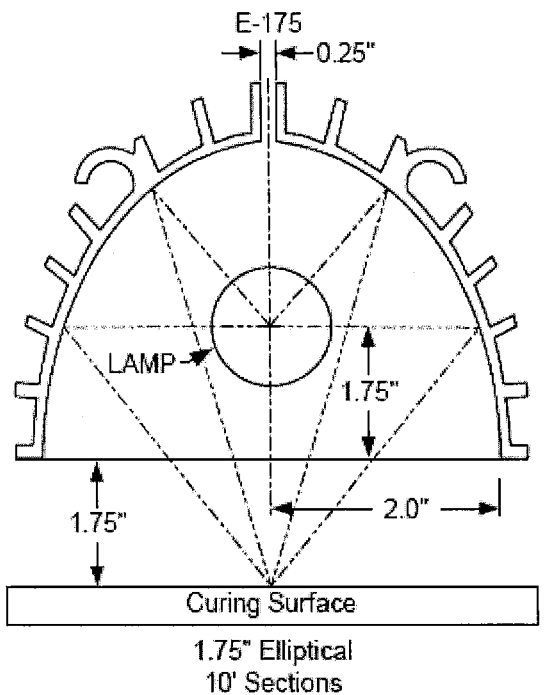
Figure 18C:
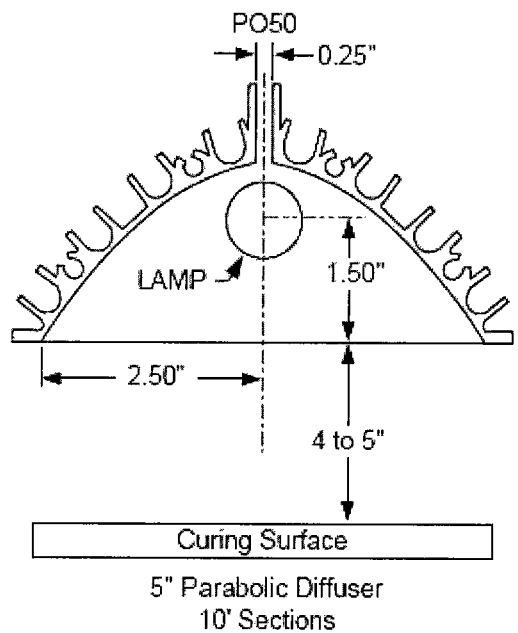
Figure 18D:
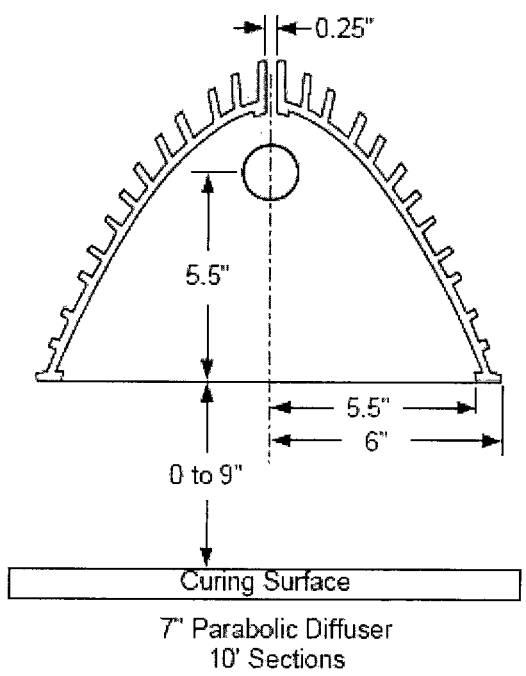
Figure 19A:
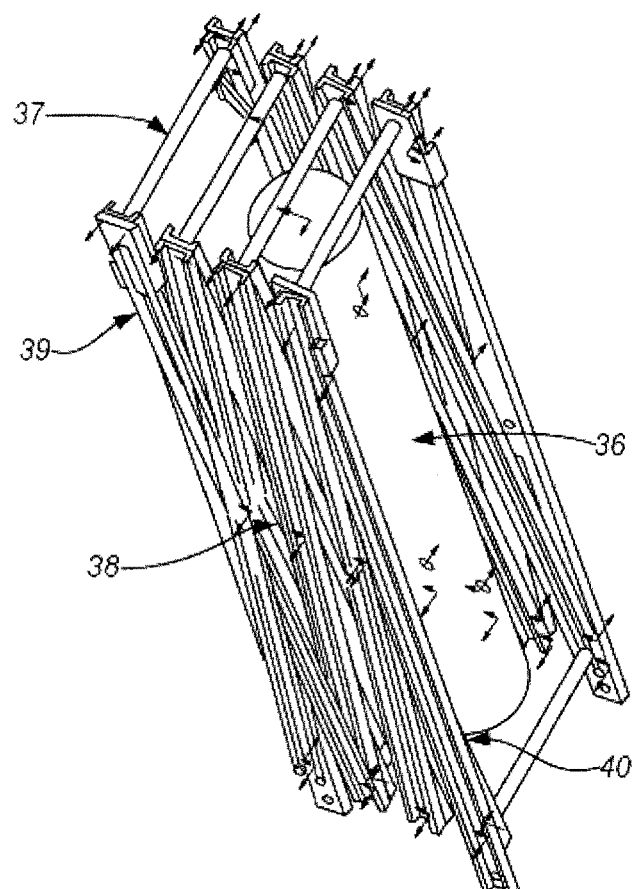
FIGS. 19A and B schematically depict an embodiment of a UV device of the present invention referred to herein as linear actuator or scissor boom wherein the central post 16 is a scissor boom. Two configurations are shown.
Figure 38B:
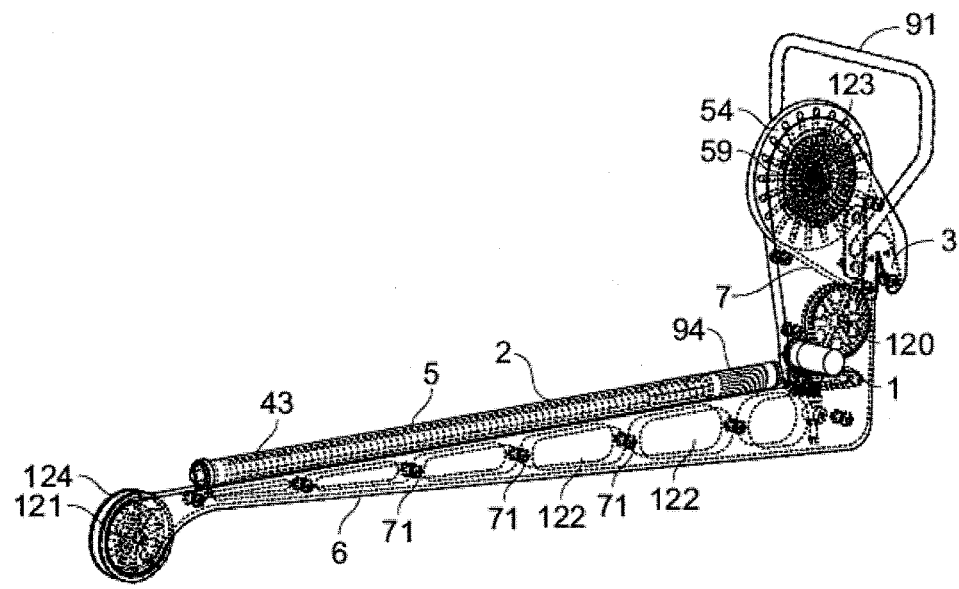

The present invention describes a variety of UV devices. In some embodiments of the present invention, a UV device is a UV device as depicted in FIG. 1, 2 or 3. In some embodiments of the present invention, a UV device is a UV device as depicted in FIG. 4. In some embodiments of the present invention, a UV device is a UV device as depicted in FIG. 5. In some embodiments of the present invention, a UV device is a UV device as depicted in FIG. 4. In some embodiments of the present invention, a UV device is a UV device as depicted in FIG. 6 or 7. In some embodiments of the present invention, a UV device is a UV device as depicted in FIG. 8 or 9. In some embodiments of the present invention, a UV device is a UV device as depicted in FIG. 10. In some embodiments of the present invention, a UV device is a UV device as depicted in FIG. 11. In some embodiments of the present invention, a UV device is a UV device as depicted in FIG. 12. In some embodiments of the present invention, a UV device is a UV device as depicted in FIG. 13. In some embodiments of the present invention, a UV device is a UV device as depicted in FIG. 14 or 15. In some embodiments of the present invention, a UV device is a UV device as depicted in FIG. 16. In some embodiments of the present invention, a UV device is a UV device as depicted in FIG. 19. In some embodiments of the present invention, a UV device is a UV device as depicted in FIG. 20. In some embodiments of the present invention, a UV device is a UV device as depicted in FIGS. 21-25. In some embodiments of the present invention, a UV device is a UV device as depicted in FIG. 27. In some embodiments of the present invention, a UV device is a UV device as depicted in FIG. 28. In some embodiments of the present invention, a UV device is a UV device as depicted in FIG. 29. In some embodiments of the present invention, a UV device is a UV device as depicted in FIG. 30. In some embodiments of the present invention, a UV device is a UV device as depicted in FIG. 31. In some embodiments of the present invention, a UV device is a UV device as depicted in FIG. 32. In some embodiments of the present invention, a UV device is a UV device as depicted in FIG. 33. In some embodiments of the present invention, a UV device is a UV device as depicted in FIG. 34. In some embodiments of the present invention, a UV device is a UV device as depicted in FIG. 35. In some embodiments of the present invention, a UV device is a UV device as depicted in FIG. 37. In some embodiments of the present invention, a UV device is a UV device as depicted in FIGS. 38A and 38B. In some embodiments of the present invention, a UV device is a UV device as depicted in FIGS. 39A-C. In some embodiments of the present invention, a UV device is a UV device as depicted in FIGS. 40A-C. In some embodiments of the present invention, a UV device is a UV device as depicted in FIG. 42. In some embodiments of the present invention, a UV device is a UV device as depicted in FIG. 43. In some embodiments of the present invention, a UV device is a UV device as depicted in FIG. 44. In some embodiments of the present invention, a UV device is a UV device as depicted in FIG. 45. In some embodiments of the present invention, a UV device is a UV device as depicted in FIGS. 46A-E. In some embodiments of the present invention, a UV device is a UV device as depicted in FIG. 47A-C. UV devices depicted in FIGS. 1-16, 19-25, 27-35, and 37-48 are portable UV devices.

UV light sources of the present invention include pulsed UV light sources and continuous wavelength mode UV light sources. In some embodiments of the present invention, a UV light source is a pulsed UV light source. In some embodiments of the present invention, a UV light source is a continuous wavelength mode UV light source.

A UV device comprises a UV light source, also referred to as UV lamp.

In some embodiments of the present invention, a UV light source comprises a lamp selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.

Notably, any number of UV lamps including low pressure, medium pressure, high pressure, and ultra-high pressure lamps, which are made of various materials, e.g., most commonly mercury (Hg) can be used with the system configuration according to the present invention and in the methods described herein.

In some embodiments, a UV light source of the present invention comprises a low pressure mercury lamp. In some embodiments, a UV light source of the present invention comprises a medium pressure mercury lamp. In some embodiments, a UV light source of the present invention comprises a high pressure mercury lamp. In some embodiments, a UV light source of the present invention comprises an ultra-high pressure mercury lamp. Such mercury lamps are known in the art and are commercially available, e.g., Sterili Aire Model SE series UVC Emitters™.

In some embodiments, a UV light source of the present invention comprises a low pressure short arc xenon lamp. In some embodiments, a UV light source of the present invention comprises a medium pressure short arc xenon lamp. In some embodiments, a UV light source of the present invention comprises a high pressure short arc xenon lamp. In some embodiments, a UV light source of the present invention comprises an ultra-high pressure short arc xenon lamp. Short arc xenon lamps are known in the art and are commercially available, e.g., Ushio #5000371-UXL-75XE Xenon Short Arc Lamp.

In some embodiments, a UV light source of the present invention comprises a low pressure long arc xenon lamp. In some embodiments, a UV light source of the present invention comprises a medium pressure long arc xenon lamp. In some embodiments, a UV light source of the present invention comprises a high pressure long arc xenon lamp. In some embodiments, a UV light source of the present invention comprises an ultra-high pressure long arc xenon lamp. Long arc xenon lamps are known in the art and are commercially available, e.g., Lumi-Max XLA1500W Long Arc Xenon Lamp.

In some embodiments, a UV light source of the present invention comprises a low pressure metal halide lamp. In some embodiments, a UV light source of the present invention comprises a medium pressure metal halide lamp. In some embodiments, a UV light source of the present invention comprises a high pressure metal halide lamp. In some embodiments, a UV light source of the present invention comprises an ultra-high pressure metal halide lamp. Metal halide lamps are known in the art and are commercially available, e.g., Venture Lighting product number 32519, open rated 175 watt probe start lamp.

In some embodiments, a UV light source of the present invention comprises a halogen lamp. A halogen lamp includes, but is not limited to a tungsten halogen lamp, a quartz halogen lamp and a quartz iodine lamp. Halogen lamps are known in the art and are commercially available, e.g., General Electric model 16751.

In some embodiments, a UV light source of the present invention comprises a sodium lamp. A sodium lamp includes, but is not limited to a high pressure sodium lamp. Sodium lamps are known in the art and are commercially available, e.g., General Electric ED 18, 400 W, high pressure sodium lamp.

In some embodiments, a UV light source of the present invention comprises an incandescent lamp. An incandescent lamp includes, but is not limited to an electric light filament lamp. Incandescent lamps are known in the art and are commercially available, e.g., Philips 60-Watt Household Incandescent Light Bulb.

In some embodiments, a UV light source of the present invention comprises a light emitting diode (LED) or a solid state light emitting device, including, but not limited to a semiconductor laser. LEDs are known in the art and are commercially available, e.g., Model L-A3W Energy Efficient UV 110V LED Spot light from Battery Junction.

Additionally, spectral calibration lamps, electrodeless lamps, and the like can be used.

A. Germicidal UV Light Source

Ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, UV light, and in particular, UV-C light is "germicidal," i.e., it deactivates the DNA of microorganism, such as bacteria, viruses and other pathogens and thus, destroys their ability to multiply and cause disease, effectively resulting in sterilization of the microorganisms. While susceptibility to UV light varies, exposure to UV energy for about 20 to about 34 milliwatt-seconds/cm$^2$ is adequate to deactivate approximately 99 percent of the pathogens. In some embodiments of the present invention, a UV light source is a germicidal UV light source. A UV light source, also referred to herein as UV lamp, is indicated in the drawings and respective legends as 5.

In some embodiments of a UV device of the present invention, the UV light source is a germicidal UV light source. In some embodiments of a UV device of the present invention, the UV light source is a UV-C light source. In some embodiments of a UV device of the present invention, the UV light source is a UV-B light source. In some embodiments of a UV device of the present invention, the UV light source is a UV-A light source.

In some embodiments of a UV device of the present invention, a UV light source comprises one UV lamp. In some embodiments of a UV device of the present invention, a UV light source comprises one or more UV lamps. If a UV light source comprises more than one UV lamp, e.g., two, three, four, five, six, seven, eight or more UV lamps, it is also referred to as a "UV lamp cluster," "UV cluster" "UV lamp assembly" or "UV assembly."

1. Pulsed Germicidal UV Light Source

In some embodiments of the present invention, a germicidal UV light source is a pulsed germicidal UV light source. Pulsed UV light is composed of a wide spectrum of light ranging from the UV region to the infrared (Wang and MacGregor, 2005, *Water Research* 39(13):2921-25). A large portion of the spectrum lies below 400 nm and as such has germicidal properties. Pulsed UV light has proven equally if not more effective (same sterilization levels achieved more rapidly) at sterilizing surfaces when compared with traditional germicidal UV-C lights (Bohrerova et al., 2008, *Water Research* 42(12):2975-2982). In a pulsed UV system, UV-light is pulsed several times per second, each pulse lasting between 100 μs (nanosecond) and 2 ms (millisecond). An additional advantage of a pulsed UV light system is that it obviates the need for the toxic heavy metal mercury, which is used in traditional germicidal UV lamps. A pulsed UV system requires less power than a mercury UV lamp and as such, is more economical.

The peak intensity of a pulsed UV lamp is typically one to two orders of magnitude higher than that of a mercury UV lamp of similar wattage. These high peak energies are achieved by storing energy in the high voltage storage capacitor and releasing this energy in a very short burst through the flash lamp. Pulse widths of 10 μs (microsecond) to 300 us are common in today's industrial flashlamp systems. Peak energy levels range from 300 kilowatts to over a megawatt. (Kent Kipling Xenon Corporation Wilmington, Mass.). Sterilization is achieved because the intensity of the light produced by the pulsed lamp is greater than that of conventional UV-C lamps. Further, pulsed UV achieves sterilization via the rupture and disintegration of micro-organisms caused by overheating following absorption UV photons emitted in the light pulse (Wekhof et al., "Pulsed UV Disintegration (PUVD): a new sterilization mechanism for packaging and broad medical-hospital applications." The First International Conference on Ultraviolet Technologies. Jun. 14-16, 2001; Washington, D.C., USA).

2. Low Pressure UV Lamp

In some embodiments of the present invention, a germicidal UV light source is a low pressure UV lamp. Low-pressure UV lamps are very similar to a fluorescent lamp, with a wavelength of 253.7 nm. Low pressure lamps are most effective, because they emit most of the radiant energy in the germicidal wavelength of 253.7 nm also known as the UV-C part of the spectrum. This is why low pressure lamps are mostly used in germicidal UV applications. The most common form of germicidal lamp looks similar to an ordinary fluorescent lamp but the tube contains no fluorescent phosphor. In addition, rather than being made of ordinary borosilicate glass, the tube is made of fused quartz. These two changes combine to allow the 253.7 nm UV light produced by the mercury arc to pass out of the lamp unmodified (whereas, in common fluorescent lamps, it causes the phosphor to fluoresce, producing visible light). Germicidal lamps still produce a small amount of visible light due to other mercury radiation bands. In some embodiments, a low pressure UV lamp looks like an incandescent lamp but with the envelope containing a few droplets of mercury. In this design, the incandescent filament heats the mercury, producing a vapor which eventually allows an arc to be struck, short circuiting the incandescent filament. Some low pressure lamps are shown in FIG. 17. Each of those low pressure UV lamp can be used in the present invention.

Preferred UV lamps for use in a portable UV device are low pressure mercury amalgam bulb supplied by, e.g., Z-E-D Ziegler Electronic Devices GmbH, D 98704 Langewiesen, Germany ("Z-E-D") and Heraeus Noblelight Fusion UV Inc. 910 Clopper Road Gaithersburg, Md., 20878 USA.

Various UV lamps may be used in the UV devices, systems and methods described herein. Preferred are UV lamps from Z-E-D. Two of those are particularly preferred. Both have the same external dimensions of 1500 mm length and 32 mm diameter. The lamp current for the less powerful bulb is 5.0 A, the lamp power is 550 W with a 170 W (at 253.7 nm) UVC output, 136 W UVC (at 253.7 nm) output when coated with Teflon. The life is 16,000 hours with a 15% loss at 253.7 nm after 12,000 hours. The second more powerful lamp draws a 6.5 A current and has a total output of 700 W and 200 W UVC (at 253.7 nm). The life is 15,000 hours with a 15% loss at 253.7 nm after 12,000 hours. Both are low pressure mercury amalgam bulbs 3. Medium and High Pressure UV Lamps In some embodiments of the present invention, a germicidal UV light source is a medium-pressure UV lamp. Medium-pressure UV lamps are much more similar to high-intensity discharge (HID) lamps than fluorescent lamps. Medium-pressure UV lamps radiate a broad-band UV-C radiation, rather than a single line. They are widely used in industrial water treatment, because they are very intense radiation sources. They are as efficient as low-pressure lamps. A medium-pressure lamps typically produces very bright bluish white light. In some embodiments of the present invention, a germicidal UV light source is a high pressure UV lamp.

Preferred UV lamps for use in a portable UV device are medium pressure mercury arc lamps provided by, e.g., Baldwin UV limited, 552 Fairlie Road, Trading Estate, Bershire, SL1 4PY, England.

4. Dimension of Germicidal UV Light Source

Different sized and shaped UV light sources may be used to practice a method of the present invention, largely depending on the shape of the container and the desired duration of the sterilization cycle. In some embodiments, a longer and more powerful UV lamp will provide for shorter duration cycles.

In some embodiments of the present invention, the UV light source is a UV-C lamp of 64" in length with an output of 190 microwatts/cm$^2$ at 254 nm (American Air and Water®, Hilton Head Island, S.C. 29926, USA). Other useful UV-C lamps for use in the systems and methods of the present invention are shown in FIG. 17.

In some embodiments of the present invention, a germicidal UV lamp is a hot cathode germicidal UV lamp, examples of which are shown in FIG. 17.

In some embodiments of the present invention, a germicidal UV lamp is a slimline germicidal UV lamp, examples of which are shown in FIG. 17.

In some embodiments of the present invention, a germicidal UV lamp is a high output germicidal UV lamp, examples of which are shown in FIG. 17.

In some embodiments of the present invention, a germicidal UV lamp is a cold cathode germicidal UV lamp, examples of which are shown in FIG. 17.

In some embodiments of the present invention, a germicidal UV lamp is an 18" single ended low pressure mercury lamp, e.g., as made commercially available by Steril-Aire.

5. Power Output and UV Intensity of Germicidal UV Light Sources

UV disinfection is a photochemical process. The effectiveness of UV-C is directly related to intensity and exposure time. Environmental factors, such as, air flow, humidity, airborne mechanical particles and distance of microorganism to the UV light source can also affect the performance of a UV device. While those environmental factors when present make it somewhat difficult to calculate the effective UV dosage required to kill or to inhibit the growth of a microorganism of interest, it has been shown that UV light will kill or inhibit the growth of any microorganism given enough UV dosage.

For UV disinfection and sterilization, the microorganisms present in a container or on a surface of a room, a space or defined environment are exposed to a lethal dose of UV energy. UV dose is measured as the product of UV light intensity times the exposure time within the UV lamp array. The microorganisms are exposed for a sufficient period of time to a germicidal UV light source in order for the UV rays to penetrate the cellular membrane and breaking down the microorganisms' genetic material. The following tables provide the approximate required intensities to kill or growth inhibit ("Kill Factor") either 90% or 100% of microorganisms (American Water & Air® Inc., Hilton Head Island, S.C. 29926, USA):

Table 1 provides the approximate required intensities to kill or growth inhibit ("Kill Factor") either 90% or 99% of mold spores (American Water & Air® Inc., Hilton Head Island, S.C. 29926, USA):

| | Energy Dosage of UV Radiation (UV Dose) in μWs/cm$^2$ Needed for Kill Factor | |
|---|---|---|
| Mold Spores | 90% (1 log Reduction) | 99%* (2 log Reduction) |
| *Aspergillius flavus* | 60,000 | 99,000 |
| *Aspergillius glaucus* | 44,000 | 88,000 |
| *Aspergillius niger* | 132,000 | 330,000 |
| *Mucor racemosus* A | 17,000 | 35,200 |
| *Mucor racemosus* B | 17,000 | 35,200 |
| *Oospora lactis* | 5,000 | 11,000 |
| *Penicillium expansum* | 13,000 | 22,000 |
| *Penicillium roqueforti* | 13,000 | 26,400 |
| *Penicillium digitatum* | 44,000 | 88,000 |
| *Rhisopus nigricans* | 111,000 | 220,000 |

*it is noted that American Ultraviolet Company (Lebanon, IN, USA) states that the energy dosage of UV radiation (UV Dose) shown above to kill 99% of the indicated mold spores, is sufficient to achieve a 100% kill factor of the indicated mold spores.

Table 2 provides the approximate required intensities to kill or growth inhibit ("Kill Factor") either 90% or 99% of bacteria (American Water & Air® Inc., Hilton Head Island, S.C. 29926, USA):

| | Energy Dosage of UV Radiation (UV Dose) in μWs/cm$^2$ Needed for Kill Factor | |
|---|---|---|
| Bacteria | 90% (1 log Reduction) | 99%* (2 log Reduction) |
| *Bacillus anthracis* - Anthrax | 4,520 | 8,700 |
| *Bacillus anthracis* spores - Anthrax spores | 24,320 | 46,200 |
| *Bacillus magaterium* sp. (spores) | 2,730 | 5,200 |
| *Bacillus magaterium* sp. (veg.) | 1,300 | 2,500 |
| *Bacillus paratyphusus* | 3,200 | 6,100 |
| *Bacillus subtilis* spores | 11,600 | 22,000 |
| *Bacillus subtilis* | 5,800 | 11,000 |
| *Clostridium tetani* | 13,000 | 22,000 |
| *Corynebacterium diphtheriae* | 3,370 | 6,510 |
| *Ebertelia typhosa* | 2,140 | 4,100 |
| *Escherichia coli* | 3,000 | 6,600 |
| *Leptospiracanicola* - infectious Jaundice | 3,150 | 6,000 |
| *Microccocus candidus* | 6,050 | 12,300 |
| *Microccocus sphaeroides* | 1,000 | 15,400 |
| *Mycobacterium tuberculosis* | 6,200 | 10,000 |
| *Neisseria catarrhalis* | 4,400 | 8,500 |
| *Phytomonas tumefaciens* | 4,400 | 8,000 |
| *Proteus vulgaris* | 3,000 | 6,600 |
| *Pseudomonas aeruginosa* | 5,500 | 10,500 |
| *Peudomonas fluorescens* | 3,500 | 6,600 |
| *Salmonella enteritidis* | 4,000 | 7,600 |
| *Salmonela paratyphi* - Enteric fever | 3,200 | 6,100 |
| *Salmonella typhosa* - Typhoid fever | 2,150 | 4,100 |
| *Salmonella typhimurium* | 8,000 | 15,200 |
| *Sarcina lutea* | 19,700 | 26,400 |
| *Serratia marcescens* | 2,420 | 6,160 |
| *Shigella dyseteriae* - Dysentery | 2,200 | 4,200 |
| *Shigella flexneri* - Dysentery | 1,700 | 3,400 |

-continued

| Bacteria | Energy Dosage of UV Radiation (UV Dose) in μWs/cm² Needed for Kill Factor | |
|---|---|---|
| | 90% (1 log Reduction) | 99%* (2 log Reduction) |
| Shigella paradysenteriae | 1,680 | 3,400 |
| Spirillum rubrum | 4,400 | 6,160 |
| Staphylococcus albus | 1,840 | 5,720 |
| Staphylococcus aerius | 2,600 | 6,600 |
| Staphylococcus hemolyticus | 2,160 | 5,500 |
| Staphylococcus lactis | 6,150 | 8,800 |
| Streptococcus viridans | 2,000 | 3,800 |
| Vibrio comma - Cholera | 3,375 | 6,500 |

*it is noted that American Ultraviolet Company (Lebanon, IN, USA) states that the energy dosage of UV radiation (UV Dose) shown above to kill 99% of the indicated microorganisms, is sufficient to achieve a 100% kill factor of the indicated microorganism.

Table 3 provides the approximate required intensities to kill or growth inhibit ("Kill Factor") either 90% or 99% of protozoa (American Water & Air® Inc., Hilton Head Island, S.C. 29926, USA):

| Protozoa | Energy Dosage of UV Radiation (UV Dose) in μWs/cm² Needed for Kill Factor | |
|---|---|---|
| | 90% (1 log Reduction) | 99%* (2 log Reduction) |
| Chlorella vulgaris (Algae) | 13,000 | 22,000 |
| Nematode Eggs | 45,000 | 92,000 |
| Paramecium | 11,000 | 20,000 |

*it is noted that American Ultraviolet Company (Lebanon, IN, USA) states that the energy dosage of UV radiation (UV Dose) shown above to kill 99% of the indicated protozoa, is sufficient to achieve a 100% kill factor of the indicated protozoa.

Table 4 provides the approximate required intensities to kill or growth inhibit ("Kill Factor") either 90% or 99% of viruses (American Water & Air® Inc., Hilton Head Island, S.C. 29926, USA):

| Virus | Energy Dosage of UV Radiation (UV Dose) in μWs/cm² Needed for Kill Factor | |
|---|---|---|
| | 90% (1 log Reduction) | 99%* (2 log Reduction) |
| Bacteriophage - E. Coli | 2,600 | 6,600 |
| Infectious Hepatitis | 5,800 | 8,000 |
| Influenza | 3,400 | 6,600 |
| Poliovirus - Poliomyelitis | 3,150 | 6,600 |
| Tobacco mosaic | 240,000 | 440,000 |

*it is noted that American Ultraviolet Company (Lebanon, IN, USA) states that the energy dosage of UV radiation (UV Dose) shown above to kill 99% of the indicated viruses, is sufficient to achieve a 100% kill factor of the indicated viruses.

Table 5 provides the approximate required intensities to kill or growth inhibit ("Kill Factor") either 90% or 99% of yeast (American Water & Air® Inc., Hilton Head Island, S.C. 29926, USA):

| Yeast | Energy Dosage of UV Radiation (UV Dose) in μWs/cm² Needed for Kill Factor | |
|---|---|---|
| | 90% (1 log Reduction) | 99% (2 log Reduction) |
| Brewers yeast | 3,300 | 6,600 |
| Common yeast cake | 6,000 | 13,200 |
| Saccharomyces carevisiae | 6,000 | 13,200 |
| Saccharomyces ellipsoideus | 6,000 | 13,200 |
| Saccharomyces spores | 8,000 | 17,600 |

*it is noted that American Ultraviolet Company (Lebanon, IN, USA) states that the energy dosage of UV radiation (UV Dose) shown above to kill 99% of the indicated yeast, is sufficient to achieve a 100% kill factor of the indicated yeast.

By way of example, using a germicidal UV lamp with 190 microwatts/cm² output at 254 nm, it would take approximately about 1 minute and 26 seconds to kill or growth inhibit ("Kill Factor") 100% of Saccharomyces sp. (which requires 17,600 microwatt/cm²) at a distance of 36" and 3 minutes 41 seconds at a distance of 60".

In some embodiments a IN lamp within a UV device has a polymer coating. The polymer coating will prevent small glass pieces from falling into a container in case of accidental shattering during use of a UV device in a method of the present invention.

B. Detector

The present invention describes a variety of LTV devices. In some embodiments of the present invention, a UV device comprises a detector. In the drawings, showing exemplary embodiments, detectors are shown by 11. The use of a detector ensures that in addition to the algorithm (taking into account vessel size and shape, size and shape of a room, a space or defined environment, lamp intensity, distance of lamp or lamps from surfaces to be sterilized) a required or predetermined UV light intensity is achieved. Further, a detector ensures that all areas known to specifically accumulate microorganisms also receive the required or predetermined dose of UV radiation.

The use of a detector solves a significant problem existing using the chemical and ozone disinfection methods. When those methods are used, there is no established protocol for verifying the level of sterilization achieved. In contrast thereto, methods of the present invention comprising the use of a detector offers a unique, quick, and reliable means of providing verifiable levels of the sterilization achieved. As described herein, once set at a predetermined UV dose, the detector will shut of the UV lamp when this predetermined amount of UV radiation has been attained.

In some embodiments of the present invention, a UV light source is connected to one or more UV detectors. In some embodiments of the present invention, a germicidal light source is connected to one or more UV detectors. As shown in the exemplary UV devices in FIGS. 6, 7, 14, and 15, one or more detectors may be mounted to a different position within the UV assembly or onto a removable bracket.

A variety of commercially available detectors can be used. UV-C detectors commercially available include, e.g., a PMA2122 germicidal UV detector (Solar Light Company, Inc., Glenside, Pa. 19038, USA). Detectors, such as the PMA2122 Germicidal UV detector, provide fast and accurate irradiance measurements of the effective germicidal radiation. A LTV producing lamp is monitored to insure that the microorganisms, such as bacteria, are receiving a desired dose of germicidal UV radiation. Using a detector, the UV lamps can also be monitored to get maximum life out of the lamp before replacement. A germicidal UV detector can also be used to insure that the proper lamp has been installed after replacement.

In some embodiments of the present invention, a germicidal light source is connected electrically to one or more UV detectors. In some embodiments, a UV detector is connected by wire to a radiation meter, which in turn can communicate via the wire with a UV lamp and instruct it to turn off, e.g., when a desired radiation level has been attained.

In some embodiments of the present invention, a germicidal light source is connected to one or more UV detectors via a signal.

In some embodiments, a detector is placed at a location within a container where microorganisms, which negatively impact production and flavor of an alcoholic beverage, a dairy product, a liquid dairy, a liquid dairy composition, or a dry dairy composition, are known to accumulate. In some embodiments, a detector is placed within a room, a space or defined environment.

In some embodiments of the present invention, the one or more UV detectors are placed in conjunction with a UV light source, preferably, a germicidal UV light source, so that the one or more detectors ensure that a desired UV intensity has been attained and/or maintained. In some embodiments, a detector is placed strategically in corners or on uneven surfaces of containers such as weld seams where microorganisms may accumulate.

In some embodiments, a detector is arranged so that it is both furthest away from the UV lamp and closest to the most uneven interior surface of a container (e.g., weld seam or a corner), a room, a space or defined environment. The purpose of the detector is to ensure that the required or predetermined UV dose is attained at a given interior location of a container, room, space or defined environment in order to achieve the desired log reduction of microorganisms. By placing a detector or more than one detector (i.e., at least two detectors) in one or more positions in the interior of the container or within a room, a space or defined environment to be sanitized, it will be ensured that the even surfaces and those closer to the UV lamp will receive more than sufficient UV radiation to achieve the desired log reduction of microorganisms and that the more problematic interior surfaces of a container (e.g., weld seams and corners) or uneven surfaces in a room, a space or defined environment will receive the required or predetermined UV dose.

In some embodiments of the present invention, a UV light source communicates back and forth with a detector so that the UV light source is shut off when a desired specified germicidal level of UV radiation has been attained. As will be appreciated by one of skill in the art, a desired specified germicidal level is dependent on the log reduction or percentage reduction of microorganisms desired. If sterilization is required, a six log reduction in microorganisms may be specified. In the interest of saving time and electricity, however, a five log reduction or a four-log reduction may be desired. Once the desired UV intensity has been attained, the detector will cause the UV light source to shut off.

One of skill in the art using a detector in combination with a UV device to sterilize a container, a room, a space or defined environment according to a method of the present invention would not need to know the diameter of the container or dimension of a room, a space or defined environment as the detector would automatically detect the appropriate UV dose necessary to achieve a predetermined sterilization rate (log reduction value).

The use of a detector, however, is optional. Detectors are not required to practice methods of the present invention provided that the timing of the sterilization cycle has been calculated correctly. Detectors can be used as a redundant system if the shape of the container and/or lamp does allow the skilled artisan to apply a simple programmable calculation of the sterilization cycle duration.

C. Housing

In some embodiments of the present invention, a UV device comprises a housing. Various housings for UV lamps are shown in the exemplary UV devices in FIGS. 1-13, 16, 21-25, 28-35, 37-45 by 2. In some embodiments of the present invention, a germicidal UV light source is residing in a housing. In some embodiments of the present invention, a germicidal UV light source is positioned within a housing. In some embodiments of the present invention, the housing surrounds or encloses the germicidal UV light source. An exemplary surrounding or enclosure of a UV light source by a housing is shown in FIGS. 1-3, 7, 9, 21, 22, 23, 24, 25, 28, 29, 31, 34, 35, and 37-45. The surrounding or enclosure may be complete or partial. An exemplary complete surrounding or enclosure of a UV light source by a housing is shown in FIGS. 1-3, 21, 22, 23, 24, 25, 28, 29, 31, and 38-41. An exemplary partial surrounding or enclosure of a UV light source by a housing is shown in FIGS. 7, 9, 34, 35, 37 and 42-45. Housings are designed to protect the UV light source from damage during transport or when it is retracted from a container according to a method of the present invention. A UV light source can also be directly or indirectly attached to a housing or alternatively, resides within a housing. Housings, however, are not necessary for a UV device of the present invention to function. For example, UV device Model BM3, schematically depicted in FIGS. 46-48, does not comprise a housing.

The housing can be of a variety of materials. It can be made from a polymer (e.g., plastic) or metal depending on the desired weight. In some embodiments, a housing is made of DuPont Teflon®FEP (Fluorinated Ethylene Propylene).

The housing can have various shapes and forms. In some embodiments of the present invention, the housing is a mesh cage allowing the UV light to pass through. An exemplary mesh cage housing is shown in FIGS. 21-25. The housing 2 in FIGS. 42-45, e.g., comprises one or more circular structures, such as metal rings, within the UV light source resides. When using housings that allow passing through of the UV light, the UV light source does not need to be released from the housing to practice a method of the invention.

In some embodiments of the present invention, the housing is a housing which does not allow the UV light to pass through or which only allows the UV light to pass through partly. When using such a housing in the methods of the present invention, the UV light source is being released from a housing. Upon release of the germicidal UV light source from the housing, the germicidal UV light source may be stationary or mobile. The housing can be of any shape. The shape of the housing is largely depending on the size and shape of the UV light source (e.g., see FIGS. 1-13, 16, 21-25, 27, and 38-45). FIGS. 21-25 and 42-45 show a UV lamp cluster (comprising 8 UV lamps) arranged at an angle and a correspondingly shaped housing. FIG. 27 shows five UV lamp clusters each comprising three UV lamps arranged at an angle and in a square or rectangular housing.

In some embodiments a single longitudinal UV lamp is used as a UV light source. In those embodiments, the housing may surround or enclose the UV lamp either completely or partially. In some embodiments, a housing comprises two arms, a first arm and a second arm, e.g., as schematically shown in FIGS. 34 and 35. The first arm may be positioned in a fixed position, while the second arm may be movably attached to the first arm. In some embodiments the second arm can reside completely or partially within the first arm. The movable attachment of the second arm to the first arm may be through a pivot point. In some embodiments, a UV lamp is attached to such housing through an opening in the second arm and further connected to a part of the UV device through a rope, string, or a power cord. In a configuration wherein the second arm resides within the first arm, the UV lamp would then reside within the second arm. The rope, string or power cord could also prevent the second arm of the housing from moving downwardly. Upon lowering the rope, string, or power cord, the UV lamp along with the second arm will be release from the first arm of the housing. The rope, string or power cord can be lowered to the point whereupon the second and first arm form a 90 degree angle (e.g., see FIG. 34B). Thereby the UV light source can be moved into almost any position within the confines of a container (FIG. 34B). As one of ordinary skill in the art will appreciate, such positioning depends on the length of the first arm, the length of the second arm and the angle formed between the first and second arm. The inventions contemplates various lengths of the first and second arms depending on the diameter and height of a container which should be sterilized. For example, if the diameter of a container is about 5 meters, then a second arm having a length of about 2.5 meters could position a UV device approximately in the middle of the container when the UV device is attached to an outer part on top of the container (see FIGS. 34B, 34C). The height positioning of a UV light source within a container can then be controlled conveniently by the extent to which the rope, string or power cord is further lowered (compare FIG. 34B to FIG. 34C). Lowering of the UV lamp can be achieved as described herein by use of a motorized unit (e.g., see FIGS. 34 and 35).

D. Guides, Range-Finding Devices, and Circuit Boards

In some embodiments of the present invention, a UV device or system comprises a range-finding device or guide, such as a laser range finder. A range-finding device may be placed or aligned at some point along the longitudinal axis of the UV device in order to prevent the UV lamp(s) or UV device from contacting either the top or bottom surface of the container (depending on the embodiment the device may be suspended from the top of the container or supported from below by a mount). If the embodiment uses lateral movement to position the UV lamp(s) closer to the internal surface the container or to a predetermined position in a room, a space or defined environment, the rangefinder may be aligned in the same orientation ensuring that the UV lamp(s) is positioned at the desired distance depending on the internal diameter of the container or dimension of the room, space or defined environment. In some embodiments of the present invention, a range-finding device is used in conjunction with the system to guarantee that the UV lamp(s) is in correct distance from the interior surface of a container to be sterilized or the surface, walls or ceilings of a room, a space or defined environment to be sterilized as well as preventing the UV lamp from impacting the interior surfaces of the container, room, space or defined environment. Range-finding devices or guides are indicated by 20 in exemplary UV devices herein, e.g., in FIGS. 11, 12 and 35.

In some embodiments of the present invention, a range-finding device 20 is a radiofrequency identifier (RFID), which is used to position a UV light source to a desired or predetermined position within a container. An RFID receives information about the dimensions of a container to be sterilized, such as depth and radius of the container. An RFID may be attached to a UV device of the present invention. In some embodiments, an RFID is attached to the container to be sterilized.

For example, as described herein, an RFID determines the depth of moving a UV light source from its load position into its payout position. FIG. 35 schematically depicts a laser depth guide attached in proximity of a UV lamp.

FIGS. 26A-D schematically depict a circuit board used in an embodiment of a UV device of the present invention. FIGS. 36A-D schematically depict a circuit board used in UV device UV55 described further herein. FIG. 28E schematically depicts an exemplary positioning of a circuit board 103 within a circuit board cavity 99 within a central sleeve 12. A circuit board may also be enclosed in a box 127, as shown in FIGS. 42-45.

A circuit board for use in a UV device of the present invention may have a variety of functionalities. In some embodiments, a functionality of a circuit board comprises a functionality selected from the group consisting of communicating with a radiofrequency identifier, controlling a movement of the germicidal UV light source within the container, controlling a rate of descent of the germicidal UV light source within the container, controlling a rate of ascent of the germicidal UV light source within the container, controlling a positioning of the germicidal UV light source within the container, controlling activation and deactivation of the germicidal UV light source, relaying UV light intensity via a sensor to the container; uploading and relaying information from the radiofrequency identifier, generating a report on time of sanitization cycle, generating a report on duration of sanitization cycle, generating a report on UV light intensity attained during sanitization cycle, emailing, phoning or texting a report on time of sanitization cycle, emailing, phoning or texting a report on duration of sanitization cycle, emailing, phoning or texting a report on UV light intensity attained during sanitization cycle, and emailing, phoning or texting an alert to an individual that sanitization cycle is complete.

In some embodiments of the present invention, the functionality of the circuit board is communicating with a radiofrequency identifier.

In some embodiments of the present invention, the functionality of the circuit board is controlling a movement of the germicidal UV light source within the container.

In some embodiments of the present invention, the functionality of the circuit board is controlling a rate of descent of the germicidal UV light source within the container In some embodiments of the present invention, the functionality of the circuit board is controlling a rate of ascent of the germicidal UV light source within the container.

In some embodiments of the present invention, the functionality of the circuit board is controlling a positioning of the germicidal UV light source within the container.

In some embodiments of the present invention, the functionality of the circuit board is controlling activation and deactivation of the germicidal UV light source.

In some embodiments of the present invention, the functionality of the circuit board is relaying UV light intensity via a sensor to the container.

In some embodiments of the present invention, the functionality of the circuit board is uploading and relaying information from the radiofrequency identifier.

In some embodiments of the present invention, the functionality of the circuit board is generating a report on time of sanitization cycle.

In some embodiments of the present invention, the functionality of the circuit board is generating a report on duration of sanitization cycle.

In some embodiments of the present invention, the functionality of the circuit board is generating a report on UV light intensity attained during sanitization cycle.

In some embodiments of the present invention, the functionality of the circuit board is relaying a message to an individual. A message relayed by a circuit board of a UV device of the present invention may be an email notification, an automated telephone voice mail message or a special message system to a hand held device such as a cell phone or tablet type device. The individual can receive an email notification that documents or reports generated are available to view and download online.

In some embodiments of the present invention, the functionality of the circuit board is emailing, phoning or texting a report on time of sanitization cycle.

In some embodiments of the present invention, the functionality of the circuit board is emailing, phoning or texting a report on duration of sanitization cycle.

In some embodiments of the present invention, the functionality of the circuit board is emailing, phoning or texting a report on UV light intensity attained during sanitization cycle.

In some embodiments of the present invention, the functionality of the circuit board is emailing, phoning or texting an alert to an individual that sanitization cycle is complete.

E. Means for Attaching a UV Device

The UV devices described herein can be used to practice the methods described herein. A UV device of the present invention can be attached movably, adjustably, temporarily, or permanently to a container, surface of an object, floor, ceiling or wall of a room, a space or defined environment by using various attachment means, such as fasteners, screws, mounting tabs, etc. In some embodiments of the present invention, a UV device is positioned on top of a container 4, as e.g., schematically depicted in FIGS. 1-5, 10, 11, 25, 29, 41, and 44. In some embodiments of the present invention, a UV device is positioned on the bottom of a container 4, as e.g., schematically depicted in FIGS. 6-9, 32, 33, and 48A-D. In some embodiments of the present invention, a UV device is attached to a lid 29 of a container 4, as e.g., schematically depicted in FIGS. 14 and 15. In some embodiments of the present invention, a UV device is attached to a wall or ceiling, as e.g., schematically depicted in FIG. 27.

The UV devices described herein can be attached temporarily to a container, e.g., for the time required to perform a method described herein. The UV devices described herein can also be attached to a container for a prolonged time, e.g., for the time required to perform a method described herein and an extended period of time before or after practicing the method. The UV devices described herein can also be attached permanently to a container.

In some embodiments of a UV device of the present invention, a UV device comprises a means for attaching the UV device to a container. This invention provides various means for attaching the UV device to a container, including, but not limited to a bracket, a hanger, and the like.

The means for attaching the UV device to a container essentially serves to attach the UV device on an outer perimeter of the opening of the container so that the UV light source and other parts of the UV device necessary to perform a method of the present invention can be movably inserted through the opening of the container into the interior part of the container. In some embodiments of the present invention, the means for attaching the UV device to a container is a bracket, also referred to as mounting bracket. In some embodiments of the present invention, a housing is affixed to a bracket. In some embodiments, the bracket supports the housing in the desired position and allows the UV lamp to project and descend from the housing into the desired positions for the "sterilization cycle." In some embodiments, the bracket supports the housing centrally. In some embodiments, the bracket supports the housing asymmetrically. The bracket may be in the form of a base, tripod or stand if the device is to be supported from the bottom of the fermentation vessel. The arms of the bracket may be adjustable to accommodate containers of various diameters and dimensions. Exemplary bracket embodiments 3 are depicted in the exemplary UV devices shown in FIGS. 1-5, 10-12, 33, and 28-45.

In some embodiments of the present invention, a means for attaching the UV device to a container is a hanger as shown, e.g., in FIGS. 21-25. A hanger may comprise one or more of the following: a clamp post 53, a hanger support bar 52, and a tightening screw 78. A preferred configuration of those parts is shown in FIGS. 21-24. Another hanger-like means for attachment of a UV device to a container is depicted in FIGS. 38-45. A hanger can have any shape or size as long as it can be used to attached the UV device to the container to be sterilized, for example, FIGS. 21-24 schematically show an L-shaped hanger.

In some embodiments, the hanger is attached to a pulley mount arm 51 (e.g., see FIGS. 21-24). In some embodiments, the hanger is attached to a telescopic arm pivot 73 (e.g., see FIGS. 21-24). In some embodiments, a hanger is attached to a frame 6 (e.g., see FIGS. 38-54).

In some embodiments of the present invention, the housing enclosing the UV lamp is attached to a UV impermissible lid or cover that is placed on top of the opening of a container so that the UV lamp can be moved downwards into the container through the housing (movement similarly as shown in FIGS. 1-3). In some embodiments, as the UV lamp is retracted, the impermissible lid descends via gravity. A person standing close by will not be exposed to UV irradiation but rather be shielded from irradiation because of the UV impermissible lid or cover.

FIG. 27 shows a UV device that can be mounted to a surface, wall, floor or ceiling of a room, a space or defined environment. Preferably the device shown in FIG. 27 is mounted to the ceiling of a room.

F. Optical Components

To increase the UV intensity over a reduced area, to focus the UV intensity, or to control the UV intensity, in some embodiments of the present invention, a UV device of the present invention comprises an optical component. Optical components include, but are not limited to, a reflector, a shutter, a lens, a splitter, a mirror, and the like. The optical component may be of any shape. In some embodiments of the present invention, a UV device comprises a reflector. A reflector can have a variety of configurations. In some embodiments, the reflector is a parabolic reflector. In some embodiments, the reflector is an elliptical reflector. In some embodiments, the reflector is a circular reflector. Exemplary embodiments comprising a reflector are depicted in the exemplary UV devices shown in FIGS. 12-14 and 37.

Reflectors are generally provided by the manufacturer of UV light sources. For example, reflectors of circular, elliptical and parabolic cross sections can be purchased from Hill Technical Sales Corp (Arlington Heights, Ill., USA). Exemplary reflectors are schematically shown in FIG. 18. A preferred supplier for parabolic reflector is Baldwin UV limited, 552 Farilie Road, Trading Estate, Berkshire, SL1 4PY, England.

UV devices comprising a reflector are schematically shown in FIGS. 14 and 37. However, as one of ordinary skill in the art will appreciate, a reflector can be configured into other UV devices described herein. In the exemplary UV device schematically shown in FIG. 37, the UV device comprises a UV lamp cluster having eight UV lamps arranged in a circular arrangement, wherein each reflector partially surrounds a UV lamp. Other suitable UV lamp clusters are described herein. UV lamps and reflectors may be attached to a housing as schematically depicted in FIG. 37C. In some embodiments, reflectors individually and partially surrounding a UV lamp may form a continuous reflecting wall as schematically depicted in FIG. 37B. Such a reflecting wall may be connected to a central sleeve.

The UV device schematically shown in FIG. 37 can be inserted through an opening of a container, e.g., an opening located on top of a container so that the reflectors and UV lamps move inwardly into the container and the housing rests on the opening of the lid while the sterilization cycle is being performed. In some embodiments, the UV lamp cluster of such device is arranged so that it can be moved through the opening of the container, while the diameter of the housing of the UV device is larger than the diameter of the opening of the container so that the UV device can be positioned on top of the container opening. In some embodiments, both the housing and the UV lamp cluster can be moved through an opening of a container. In such embodiment, the housing is attached to a cover (or plate) which has a larger diameter than the housing and the UV lamp cluster and the housing is attached to the cover (or plate) through a cable, which can be extended so that both the housing and UV lamp cluster can move further downwards into the container upon release of the cable. The cover then remains positioned on top of the container opening. The cover (or plate) can have various shapes, such as round, oval, square, rectangular, hexagonal, etc. A handle attached to such cover (or plate) conveniently allows the user to place the UV device onto an opening of a container.

In some embodiments of the present invention, the UV device schematically shown in FIG. 37 is inserted inwardly into a container from an opening located at the bottom or side of a container (e.g., see FIGS. 31-33).

G. Additional Components of a UV Device

FIGS. 1-16, 19-25, 27-35, and 37-48 depict exemplary embodiments of exemplary UV devices of the present invention and uses thereof. Those figures also show additional components of UV devices of the present invention, their positioning and how those components may be connected to a container, a UV lamp, a UV detector, a frame, a bracket, a housing, and a range-finding device, which are described in detail above. As one of ordinary skill in the art will appreciate individual components described herein can be combined in various ways in a UV device for a use described herein without deviating from the scope of the present invention.

In some embodiments of the present invention, a UV device comprises a motorized unit (indicated by 1 in the figures). In some embodiments of the present invention, a UV device comprises a second motor unit (indicated by 23 in the figures; different from the motorized unit "1"). A motorized unit can provide various functions, including, but not limited to positioning a UV lamp within a container. A motorized unit may move a UV lamp within a container to a horizontal position, a vertical position or combination of both. As one of ordinary skill in the art will appreciate the moving of a UV lamp within a container depends on parameters, such as size and power of a UV lamp, diameter and height of a container and areas within the container a practitioner desires to sterilize as described herein.

In some embodiments of the present invention, a UV device comprises a cable or rigid rod (indicated by 7 in the figures). A cable or rigid rod is also useful for the positioning of a UV lamp within a container. For example, as schematically depicted in FIGS. 4, 5 38-45, a cable 7 is used to lower the UV lamps 5 of the UV devices shown inwardly into the container 4. In some embodiments, a cable 7 is a power cord 90 as, e.g., schematically shown in FIGS. 34 and 35. In some embodiments of a UV device of the present invention, a rigid rod, such as an extension of the central post 16, may be used to move a UV light source upwardly within a container 4 (e.g., see FIG. 48D).

In some embodiments of the present invention, a UV device comprises a base plate (indicated by 10 in the figures. A base plate can have many different shapes and configurations as schematically depicted in the figures herein. A function of a base plate is to allow the UV device be positioned onto or into a container or allow the UV device be attached to a container (although attachment of a UV device to a container can also be done by other means as described herein). Exemplary embodiments of base plates are schematically depicted in FIGS. 6, 7, 28, 29, 31-33, and 35. The base plate 10 of the UV device embodiments shown in those figures allows the UV device to stand upright on a surface, e.g., within a container (see, FIGS. 7, 32, 33), on top of a container (see FIGS. 28 and 29) or on a floor and the container is slided onto the UV device (see FIG. 31). The base plate 10 of the UV device shown in FIGS. 28 and 29, is partially circular and has a straight part allowing the UV device to be positioned vertically on a surface (e.g., when servicing it) without rolling away. The base plate 10 of the exemplary UV device embodiments depicted in FIGS. 31 and 32 has a tripod-like configuration. The base plate 10 of the exemplary UV device embodiment depicted in FIG. 35 is round. It can be oval, rectangular, hexagonal, etc. as well.

In some embodiments of the present invention, a UV device comprises a central sleeve (indicated by 12 in the figures). A central sleeve can have various configurations and shapes. Typically, the central sleeve 12 is round. A central sleeve can have various configurations and can be connected to other components of a UV device in various ways. For example, as shown in FIG. 7, a central sleeve 12 is connected to a housing 2. In some embodiments, a central sleeve 12 can slide over a housing 2. As depicted exemplary in FIG. 8, more than one housing 2 can be attached to a central sleeve 12. Attachment of the housings 2 to the central sleeve can be direct or indirect. For example, as depicted in FIG. 9, the housings 2 are attached to a central sleeve 12 via parallelogramming arms 17. Various components of a UV device can be attached directly or indirectly to a central sleeve 12 as shown in figures. For example, as depicted in FIGS. 28 and 29, a central sleeve 12 is movably attached to a housing 2. In some embodiments of the present invention (see e.g., FIGS. 28, 29, 37), a UV lamp 5 is attached to a central sleeve 12. The attachment of a UV lamp 5 to a central sleeve 12 may be achieved via pins 93 and a UV lamp socket or adaptor 94. The device depicted in FIGS. 28 and 29, referred to as UV55, is described in more detail below.

In some embodiments of the present invention, a UV device comprises one or more connecting rods (indicated by 13 in the figures).

In some embodiments of the present invention, a UV device comprises a motorized sleeve (indicated by 14 in the figures), In some embodiments of the present invention, a UV device comprises an adjustable bracket (indicated by 15 in the figures).

In some embodiments of the present invention, a UV device comprises a central post (indicated by 16 in the figures). In some embodiments of the present invention, the central post 16 is a scissor boom. In some embodiments of the present invention, the central post 16 is a central bar 44. In some embodiments of the present invention the central post 16 is surrounded by a central sleeve 12. In some embodiments of the present invention, a central post 16 may be extendible and permit positioning of a UV light source attached thereto to be moved from a first position (e.g., a first vertical position) to a second position (e.g., second vertical position) within a container (e.g., see FIG. 48).

In some embodiments of the present invention, a UV device comprises parallelogramming arms (indicated by 17 in the figures).

In some embodiments of the present invention, a UV device comprises an arm (indicated by 18 in the figures; distinguished from "17").

In some embodiments of the present invention, a UV device comprises a track on the arm (indicated by 19 in the figures).

In some embodiments of the present invention, a UV device comprises an "adjustable bracket" or "mounting frame" (indicated by 24 in the figures).

In some embodiments of the present invention, a UV device comprises a track on a central post (indicated by 25 in the figures).

In some embodiments of the present invention, a UV device comprises a removable bracket (indicated by 31 in the figures).

In some embodiments of the present invention, a UV device comprises a reflector (indicated by 32 in the figures).

In some embodiments of the present invention, a UV device comprises one or more nylon blocks (indicated by 33 in the figures).

In some embodiments of the present invention, a UV device comprises a post or boss (indicated by 34 in the figures).

In some embodiments of the present invention, a UV device comprises a hanging hook (indicated by 84 in the figures). A hanging hook provides a convenient way of storing a UV device when not in use, by e.g., hanging it on hook. A hanging hook can be attached to a UV device at various locations. Form, shape, positioning and function of an exemplary hanging hook 84 are described in detail in the UV device embodiment UV55 (see FIGS. 28 and 29 and below). A handle 91, e.g., as shown in FIGS. 39-40 and 46-48, can also be used as a hanging hook. As such, the terms hanging hook 84 and handle 91 are used interchangeably herein.

In some embodiments of the present invention, a UV device comprises an on/off or reset button (indicated by 85 in the figures). As one of ordinary skill in the art an on/off or reset button provides for the activation of the UV device. An on/off or reset button can be attached to a UV device at various locations. Form, shape, positioning and function of an exemplary on/off or reset button 85 are described in detail in the UV device embodiment UV55 (see FIGS. 28 and 29 and below).

In some embodiments of the present invention, a UV device comprises a central sleeve tightening knob (indicated by 86 in the figures). A central sleeve tightening knob, for example, allows the precise sliding of a central sleeve 12 into a housing 2 or onto a housing 2. Typically, a central sleeve tightening knob is tightened by a person to maintain a central sleeve in a predetermined position. It is loosened by a person to allow the central sleeve to be moved from a first position to a second position. In the exemplary UV device embodiment UV55 (see below) and others, movement of the central sleeve can be upwardly or downwardly. A central sleeve tightening knob can be attached to a UV device at various locations. Form, shape, positioning and function of an exemplary central sleeve tightening knob 86 are described in detail in the UV device embodiment UV55 (see FIGS. 28 and 29 and below).

In some embodiments of the present invention, a UV device comprises a translucent plastic ring (indicated by 87 in the figures). In some embodiments of the present invention, a plurality of LED lights are located behind the translucent plastic ring. Upon activation of the LED light, the light can be seen through the translucent plastic ring. The appearance of a light signal may indicate to a user of the UV device the time of use of the UV device to perform the sterilization of a container, the termination of a sterilization cycle, etc. A translucent plastic ring can be attached to a UV device at various locations. Form, shape, positioning and function of an exemplary translucent plastic ring 87 are described in detail in the UV device embodiment UV55 (see FIGS. 28 and 29 and below).

In some embodiments of the present invention, a UV device comprises a stopping plate (indicated by 88 in the figures). A stopping plate can be attached to a UV device at various locations. Form, shape, positioning and function of an exemplary stopping plate 88 are described in detail in the UV device embodiment UV55 (see FIGS. 28 and 29 and below).

In some embodiments of the present invention, a UV device comprises a metal disc (indicated by 89 in the figures). A metal disc can be attached to a UV device at various locations. Form, shape, positioning and function of an exemplary metal disc 89 are described in detail in the UV device embodiment UV55 (see FIGS. 28 and 29 and below).

In some embodiments of the present invention, a UV device comprises a power cord (indicated by 90 in the figures). A power cord can be attached to a UV device at various locations. Form, shape, positioning and function of an exemplary power cord 90 are described in detail in the UV device embodiment UV55 (see FIGS. 28 and 29 and below).

In some embodiments of the present invention, a UV device comprises a handle (indicated by 91 in the figures). A handle provides for the convenient transport of a UV device by a user. A handle can be part of a central sleeve 12, such as an extension of a central sleeve 12 (e.g., see FIGS. 28 and 29) A handle 91 can also be part of a frame 6, an extension of a frame 6 or attached to a frame 6 (e.g., see FIGS. 38-41 and 46-48). The handle may be of a different thickness than the central sleeve or frame. The handle and the central sleeve or frame can be made of the same material. A preferred material is a plastic. A preferred plastic is Delrin. Another preferred material for a handle is a metal, preferably, a light-weight metal. A handle can be attached to a UV device at various locations. Form, shape, positioning and function of an exemplary handle 91 are described in detail in the UV device embodiment UV55 (see FIGS. 28 and 29 and below), in FIG. 37, in UV device Model BM1 (see FIGS. 38-41) and in UV device BM3 (see FIGS. 46-48).

In some embodiments of the present invention, a UV device comprises a handle cap (indicated by 92 in the figures). A handle cap is attached to a handle 91. In some embodiments of the present invention, a handle cap houses an acoustic speaker. Thus, in some embodiments of the present invention, a UV device comprises an acoustic speaker. A handle cap can be attached to a UV device at various locations. Form, shape, positioning and function of an exemplary handle cap 92 are described in detail in the UV device embodiment UV55 (see FIGS. 28 and 29 and below).

In some embodiments of the present invention, a UV device comprises one or more pins for attaching a UV lamp 5 to a UV lamp socket or adaptor 94 (indicated by 93 in the figures). Pins 93 can be attached to a UV lamp 5 at various locations, preferably at an end of a UV lamp 5. Form, shape, positioning and function of exemplary pins 93 are described in detail in the UV device embodiment UV55 (see FIGS. 28 and 29 and below).

In some embodiments of the present invention, a UV device comprises one or more UV lamp sockets or adaptors (indicated by 94 in the figures). A UV lamp socket or adaptor 94 attaches a UV lamp 5 to a UV device, preferably through pins 93. A UV lamp socket or adaptor can be attached to a UV device at various locations. Typically, each UV lamp 5 is attached to a UV lamp socket or adaptor 94. Form, shape, positioning and function of an exemplary UV lamp socket or adaptor 94 are described in detail in the UV device embodiment UV55 (see FIGS. 28 and 29 and below), UV device Model BM1 (see FIGS. 38, 29, and 41), UV device Model BM2 (see FIG. 45), and UV device Model BM3 (see FIG. 47A).

In some embodiments of the present invention, a UV device comprises a metal sleeve attachment ring (indicated by 95 in the figures). A metal sleeve attachment ring can be attached to a UV device at various locations. For example, it can be attached to a housing 2. Form, shape, positioning and function of an exemplary metal sleeve attachment ring 95 are described in detail in the UV device embodiment UV55 (see FIGS. 28 and 29 and below).

In some embodiments of the present invention, a UV device comprises a power supply of UV lamp ballast (indicated by 96 in the figures). A power supply 96 can be attached to a UV device at various locations. Preferably, a power supply is not visible from the outside of a UV device and housed in an inner compartment (e.g., see box 127 in FIGS. 42-45) or cavity within the UV device. A preferred cavity for housing a power supply 96 is a power supply cavity 100. Typically, the power supply cavity is covered by a power supply access plate 97 so that the power supply is not visible from the outside. Form, shape, positioning and function of an exemplary power supply 96 are described in detail in the UV device embodiment UV55 (see FIGS. 28 and 29 and below). A ballast/power supply 96 may power one or more UV lamps 5. In some embodiments, a single ballast/power supply 96 powers a UV lamp cluster. In some embodiments, a single ballast/power supply 96 powers eight (8) UV lamps 5. In some embodiments, a single ballast/power supply 96 powers four (4) UV lamps 5, i.e., when eight (8) UV lamps 5 are configured into a UV device, two ballasts/power supplies 96 may be employed. In some embodiments, the ballast/power supply 96 powers each UV lamp 5 separately, i.e., each UV lamp is powered by a separate electrical cable, wire or connector connecting the ballast/power supply 96 with that particular UV lamp 5. In some embodiments, the ballast/power supply 96 in parallel a plurality of UV lamps 5, i.e., a plurality of UV lamps 5 is powered by a single electrical cable, wire or connector connecting the ballast/power supply 96 with the plurality of UV lamps 5. In some embodiments, the ballast/power supply 96 powers in parallel a UV lamps 5 of a UV lamp cluster, i.e., the UV lamps 5 of the UV lamp cluster are powered by a single electrical cable, wire or connector connecting the ballast/power supply 96 with the UV lamps 5 of the UV lamp cluster.

In some embodiments, the ballasts/power supplies 96 are separated from the UV lamps 5. That distance can vary. Distances can be about 1 m, about 2 m, about 3 m, about 4 m, about 5 m, about 6 m, about 7 m, about 8 m, about 9 m, about 10 m, about 11 m, about 12 m or even more.

In some embodiments of the present invention, a LTV device comprises a power supply access plate (indicated by 97 in the figures). A power supply access plate 97 can be attached to a UV device at various locations. A power supply access plate covers a power supply, which is housed in an inner compartment or cavity within the UV device. A power supply cavity access plate may be screwed to a UV device with one or more screws. Form, shape, positioning and function of an exemplary power supply access plate 97 are described in detail in the UV device embodiment UV55 (see FIGS. 28 and 29 and below).

In some embodiments of the present invention, a UV device comprises an optical switch (indicated by 98 in the figures). An optical switch, also referred to as cycle time count reset sensor, can be attached to a UV device at various locations. Form, shape, positioning and function of an exemplary optical switch 98 are described in detail in the UV device embodiment UV55 (see FIGS. 28 and 29 and below).

As described herein, in some embodiments of the present invention, a UV device comprises a circuit board (indicated by 103 in the figures; see also FIGS. 26A-D and 36A-D). A circuit board 103 can be attached to a UV device at various locations. Preferably, a circuit board is not visible from the outside of a UV device and housed in an inner compartment or cavity within the UV device. A preferred cavity for housing a circuit board 103 is a circuit board cavity 99. Typically, the circuit board cavity is covered by a plate. Conveniently, a power supply access plate 97 may also cover the circuit board so that the circuit board is not visible from the outside. Form, shape, positioning and function of an exemplary circuit board 103 and circuit board cavity 99 are described in detail in the UV device embodiment UV55 (see FIGS. 28 and 29 and below).

In some embodiments of the present invention, a UV device comprises an AC to DC power converter (indicated by 101 in the figures). An AC to DC power converter can be attached to a UV device at various locations. Form, shape, positioning and function of an exemplary AC to DC power converter 101 are described in detail in the UV device embodiment UV55 (see FIGS. 28 and 29 and below).

In some embodiments of the present invention, a UV device comprises an electronic component (indicated by 102 in the figures). An AC to DC power converter can be attached to a UV device at various locations. Form, shape, positioning and function of an exemplary electronic component 102 are described in detail in the UV device embodiment UV55 (see FIGS. 28 and 29 and below).

In some embodiments of the present invention, a UV device comprises one or more connectors or wires (indicated by 104 in the figures) to connect to e.g., an LED, an optical switch, or an acoustic speaker. Connectors and wires 104 can be attached to a UV device at various locations. Form, shape, positioning and function of an exemplary connectors and wires 104 are described in detail in the UV device embodiment UV55 (see FIGS. 28 and 29 and below).

In some embodiments of the present invention, a UV device comprises one or more connectors or wires (indicated by 105 in the figures) to connect to a UV light source, such as a UV lamp 5. Connectors and wires 105 can be attached to a UV device at various locations. Form, shape, positioning and function of an exemplary connectors and wires 105 are described in detail in the UV device embodiment UV55 (see FIGS. 28 and 29 and below).

In some embodiments of the present invention, a UV device comprises one or more connectors or wires (indicated by 106 in the figures) to connect to the power supply 96. Connectors and wires 106 can be attached to a UV device at various locations. Form, shape, positioning and function of an exemplary connectors and wires 106 are described in detail in the UV device embodiment UV55 (see FIGS. 28 and 29 and below).

In some embodiments of the present invention, a UV device comprises an anchor (indicated by 107 in the figures). An anchor 107 can be attached to a UV device at various locations. Form, shape, positioning and function of an exemplary anchor 107 are described in detail in the UV device embodiment depicted in FIG. 30 and below.

In some embodiments of the present invention, a UV device comprises an anchor line (indicated by 108 in the figures). An anchor line 108 can be attached to a UV device at various locations. Form, shape, positioning and function of an exemplary anchor line 108 are described in detail in the UV device embodiment depicted in FIG. 30 and below.

In some embodiments of the present invention, a UV device comprises an anchor connector (indicated by 109 in the figures). An anchor connector 109 can be attached to a UV device at various locations. Form, shape, positioning and function of an exemplary anchor connector 109 are described in detail in the UV device embodiment depicted in FIG. 30 and below.

In some embodiments of the present invention, a container 4 comprises manhole or port (indicated by 77 in the figures) as an opening. A manhole or port 77, typically is found at large containers 4, such as tanks and fermenters having a solid lid 29 or are otherwise fully enclosed (other than the manhole or port 77 itself). A manhole or port 77 can be positioned at a container 4 at various locations, preferably at a position close to the periphery of the upper part of the container 4 as exemplary depicted in FIGS. 25, 30, 32-34, 41, 44 and 48. A manhole or port can also be located at a lower portion of a side wall of a container 4, as exemplary depicted in FIGS. 32, 33, 41, and 48. The manhole or port 77 is wide enough to allow insertion of a UV device of the present invention (e.g., see FIGS. 25, 30, 32-34, 41, 44, and 48).

In some embodiments of the present invention, a UV device comprises a UV lamp cluster line (indicated by 111 in the figures). A UV lamp cluster line 111 can be attached to a UV device at various locations. Form, shape, positioning and function of an exemplary UV lamp cluster line 111 are described in detail in the UV device embodiment depicted in FIG. 30 and below.

In some embodiments of the present invention, a UV device comprises a twist lock (indicated by 116 in the figures). A twist lock 116 can be attached to a UV device at various locations. Form, shape, positioning and function of an exemplary twist lock 116 are described in detail in the UV device embodiment depicted in FIG. 34 and below.

In some embodiments of the present invention, a UV device comprises an interface (indicated by 117 in the figures). An interface, e.g., permits a user to activate a UV device, by e.g., pushing a start button. An interface, e.g., permits a user to inactivate a UV device, by e.g., pushing a stop button. An interface, e.g., permits a user to set the time it takes to perform a sterilization cycle. An interface, e.g., permits a user to read the time remaining to complete a sterilization cycle. An interface 117 can be attached to a UV device at various locations. Form, shape, positioning and function of an exemplary interface 117 are described in detail in the UV device embodiment depicted in FIG. 34 and below.

Some UV devices of the present invention comprise an easily accessible control box with an on-off switch to activate and shut off (deactivate) the UV lamps. Further, UV devices comprise circuitry for activating and shutting off (deactivating) the UV lamps. The control box may include a lamp indicator light to show whether power is being sent to the UV device.

H. Positioning of a UV Light Source

As will be appreciated by one of ordinary skill in the art, the positioning of a UV light source at a desired or predetermined position for the UV sterilization of a container will be determined by e.g., the shape and volume (dimension) of the container, vessel, steel type used, and the shape, size and power output of the UV light source. Given the guidance provided herein, one of ordinary kill in the art will be able to properly position one or more UV lamps to achieve a desired level of sanitization, a desired killing or growth inhibition of one or more microorganisms using a method of the invention.

In some embodiments of the present invention, a UV light source is suspended from a removable lid of a container of various dimensions.

In other embodiments of the present invention, a UV light source is suspended from a fixed or hinged lid of a container of various dimensions.

In some embodiments of the present invention, the UV device is portable. A portable IN device can be transported between different vessels, vats and facilities.

Figure 25A:
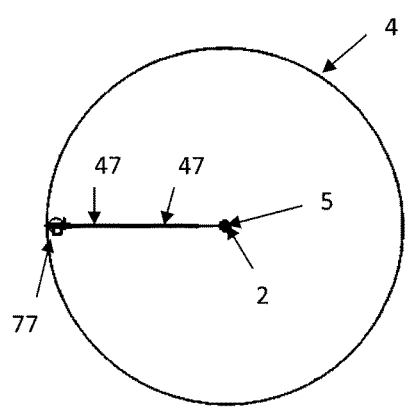
FIG. 25A schematically depicts a top view of a UV device attached to a container 4 and having a telescopic arm in its UV lamp down position.
Figure 25C:
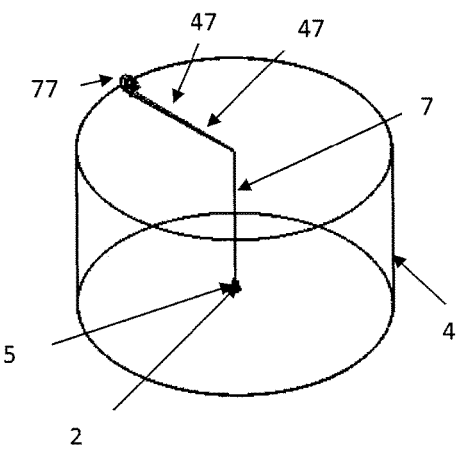
FIG. 25C shows a schematic isometric view of a UV device attached to a container 4 and having a telescopic arm in its UV lamp down position. Individual parts are shown and numbered as described in FIGS. 21A-F.
Figure 25B:
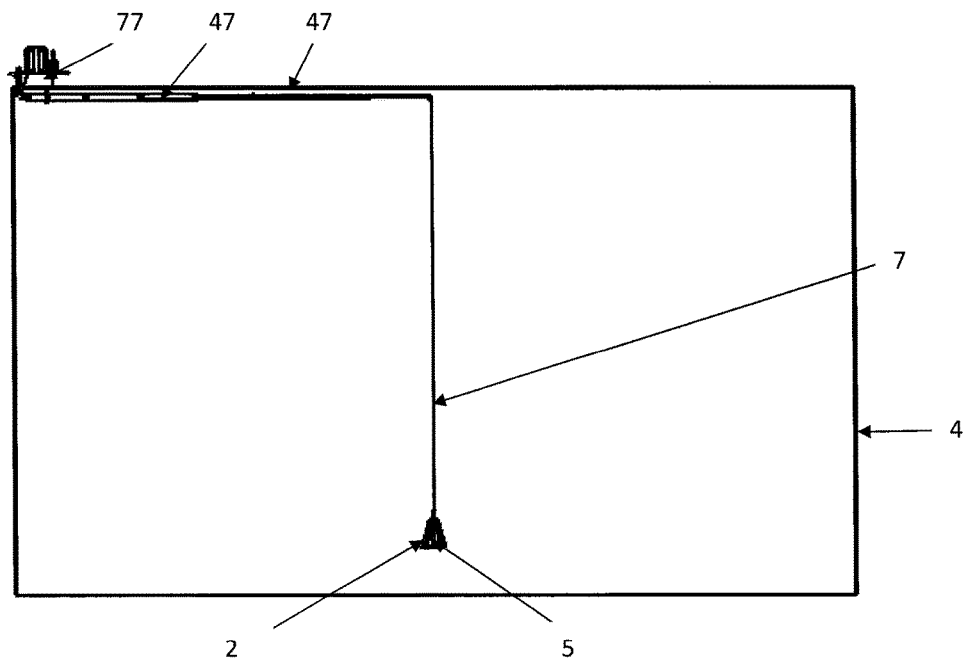
FIG. 25B shows a schematic side view of a UV device attached to the container 4 and having a telescopic arm in its UV lamp down position.
Figure 26B:
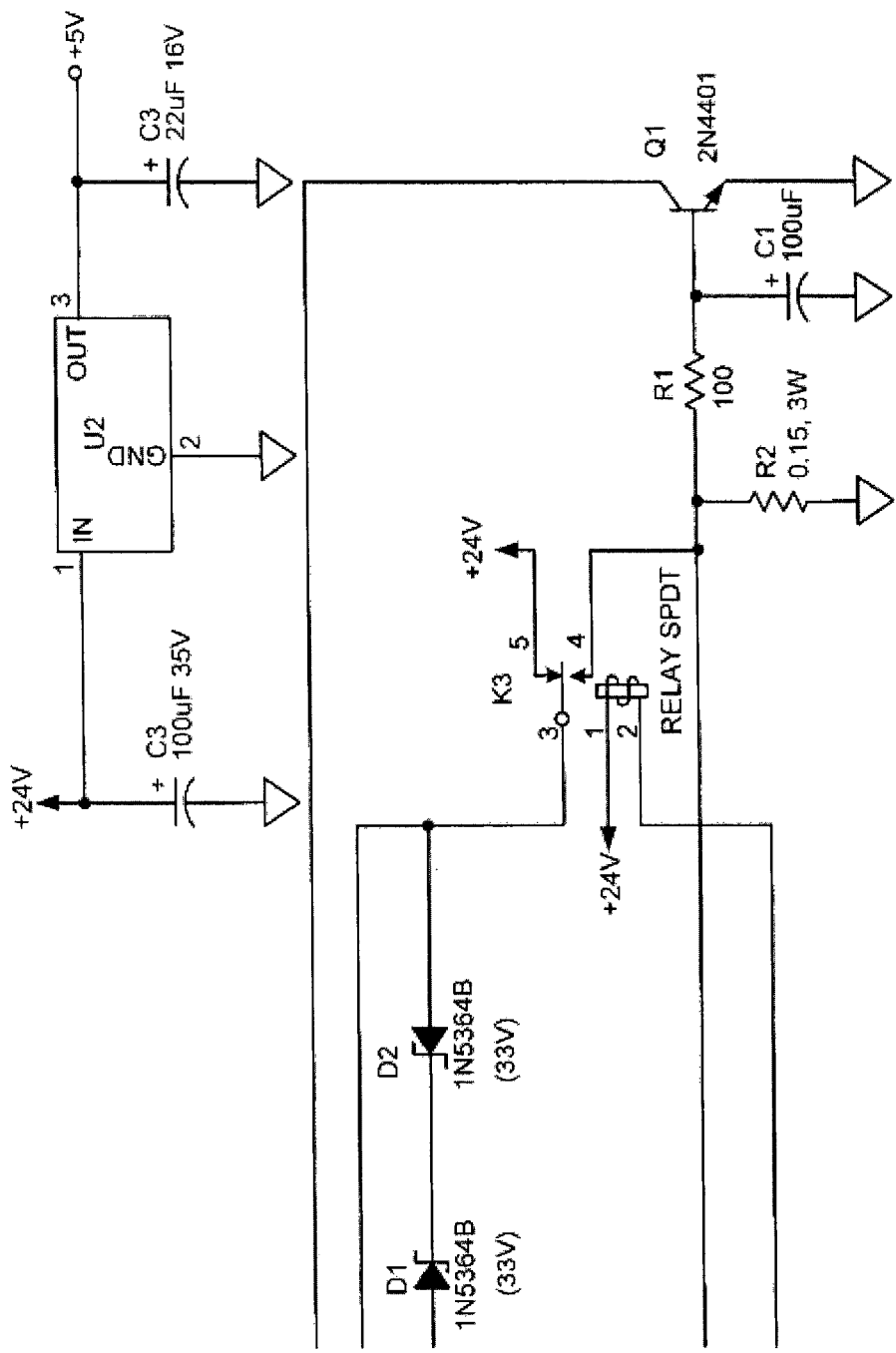
FIG. 26 consists of FIG. 26A, FIG. 26B, FIG. 26C and FIG. 26D arranged as shown and schematically depicts a circuit board used in an embodiment of the present invention. The circuit board, which provides for several functionalities, can be attached to a UV device and, e.g. communicates with an RFID chip that can be mounted to an interior wall of the container. Once information is retrieved from the RFID chip, the circuit board will control movement, the length of which the telescopic arm descends (i.e., the length to which the telescoping units 47 move the UV light source into, a vertical downwards position) and the rate of descent based on tank dimensions stored in the RFD chip. As one of ordinary skill in the art will appreciate, the exemplary circuit board shown, comprises a TI module (part number shown) and a serial port. Also shown on the board are relays to control a motor and the positioning of the UV light source. In some embodiments is also a 5 VDC regulator to power the electronics. In the circuit board shown, the RFID tag part number is also shown. Other functionalities of a circuit board are described herein.
Figure 26C:
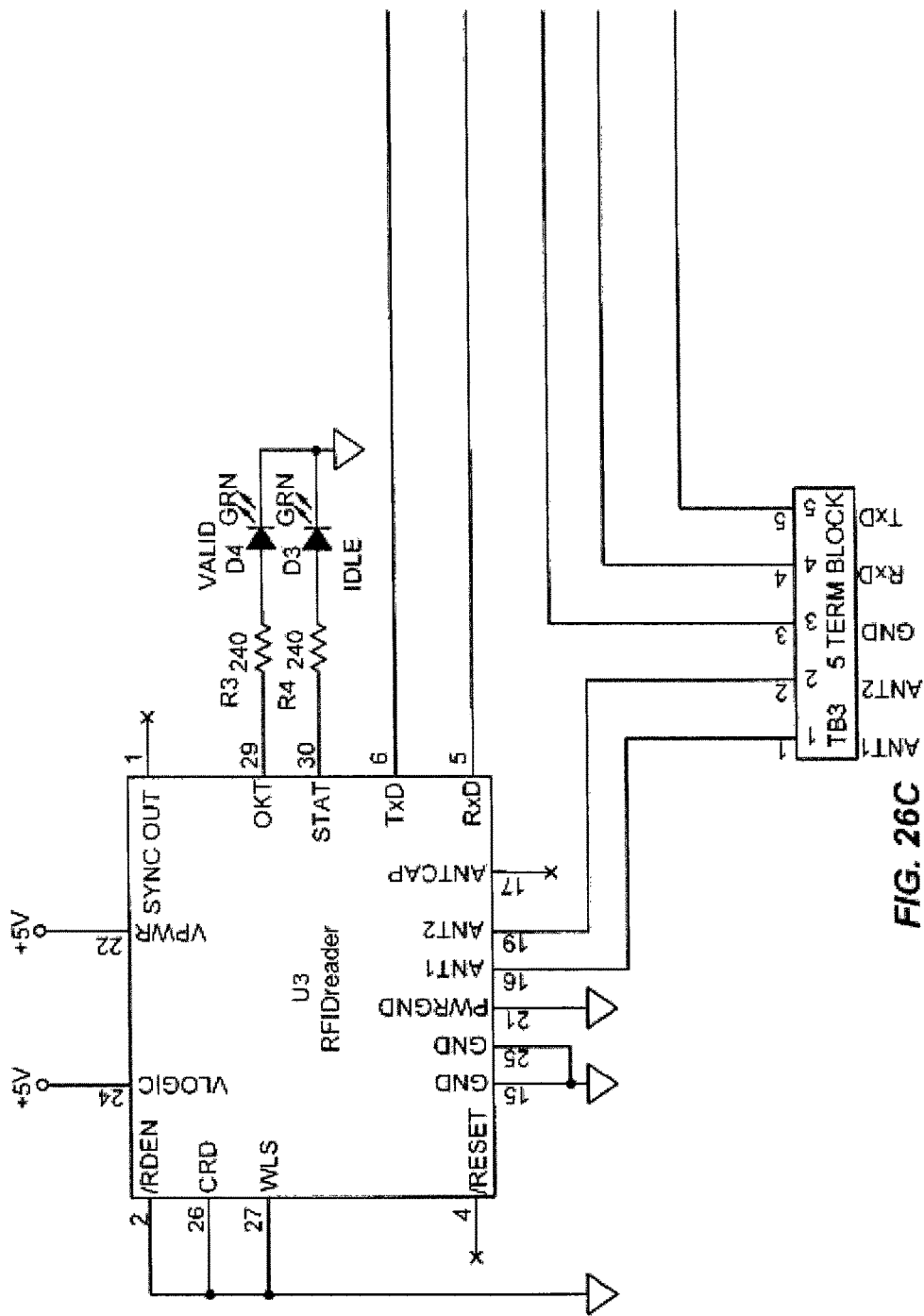
Figure 26D:
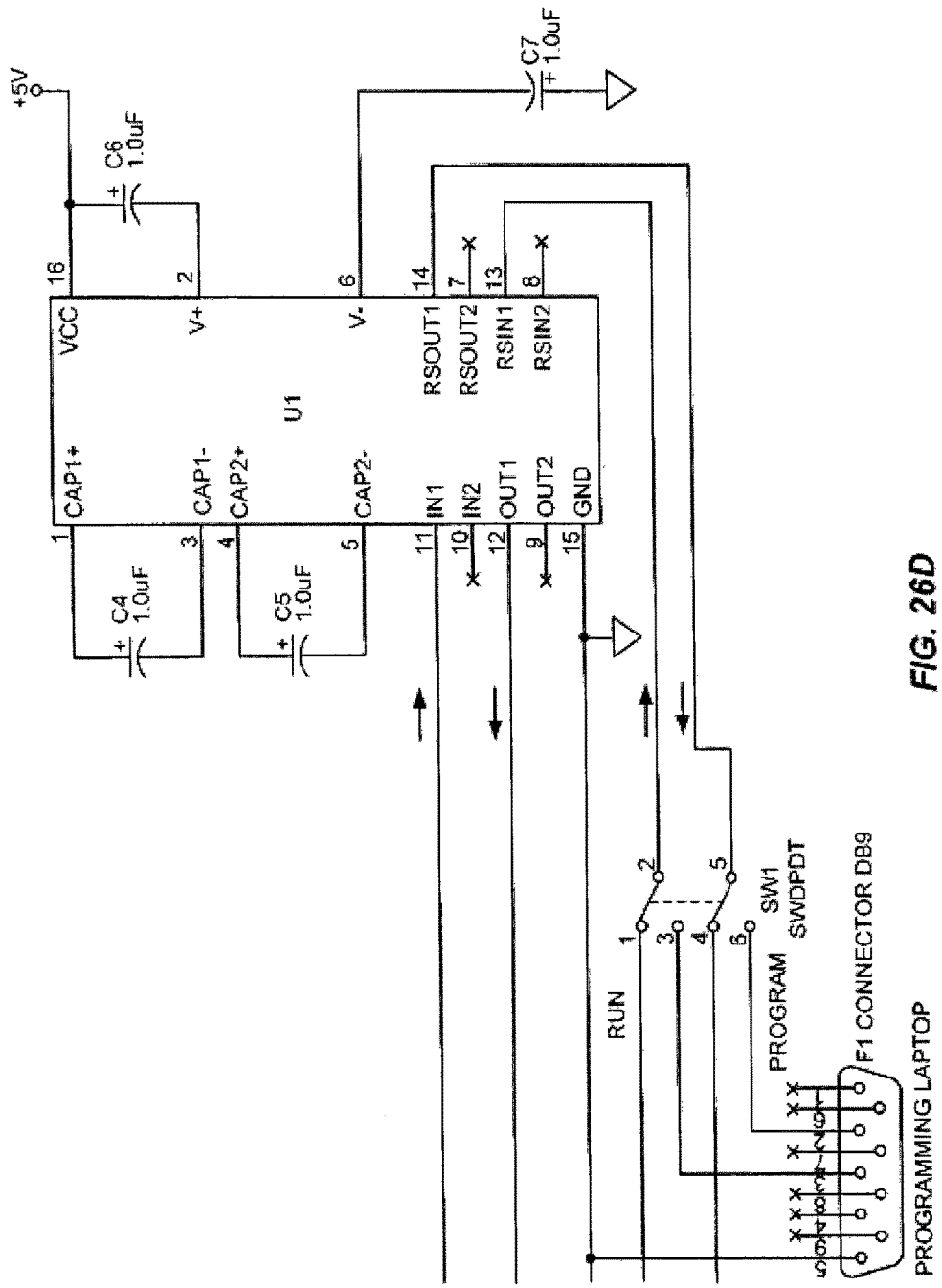

In some embodiments of the present invention, e.g., when a UV device is used to sterilize a rather large container, the UV light source may be moved within the container from a first position to a second position and from a second position to a third position. This is demonstrated, for example in FIGS. 21 to 25, showing a UV device in various positions and configurations, e.g., folded position (FIG. 21), load position (FIG. 22), payout position or first vertical downwards position (FIG. 23), horizontal position (FIG. 24), and lamp down position or second vertical downwards position (FIG. 25). For example, as shown in FIGS. 25, 29, 41, 44, and 48, the UV light source is positioned in the approximate middle (center position) of a container 4 to practice a method of the invention. The height within a container at which a UV light source is positioned may also depend on the shape and volume (dimension) of the container, vessel, steel type used, and the shape, size and power output of the UV light source. For example, UV device Models BM1 and BM2 (described below in greater detail) permit descending a UV light source to a desired position within a container 4 by moving the UV light source from a first vertical position downwardly to a second vertical position within the container 4. Likewise, UV device Model BM3 (described below in greater detail) optionally permits ascending a UV light source to a desired position within a container 4 by moving the UV light source from a first vertical position upwardly to a second vertical position within the container 4.

Further, as demonstrated by UV device Model BM3, when placed on the floor of a container 4 (see FIG. 48), a plurality of wheels 114 attached to the frame of that device, permits the UV device to be moved into any desired position on the floor of the container 4 and subsequently deploy the UV light source so that it can be positioned at any desirable position within the container.

As will be appreciated by one of ordinary skill in the art, the positioning of a UV light source at a desired or predetermined position for the UV sterilization of a room, a space or defined environment will be determined by, e.g., the shape and dimension of the room, space or defined environment to be sanitized, and the shape, size and power output of the UV light source. Given the guidance provided herein, one of ordinary kill in the art will be able to properly position one or more UV lamps to achieve the desired killing or growth inhibition of one or more microorganisms using a method of the invention.

In some embodiments of the present invention, a UV light source is suspended from a the ceiling of a room of various dimensions. In other embodiments of the present invention, a UV light source is suspended from a fixed or hinged connecting part within a housing of various dimensions. An exemplary embodiment is shown in FIG. 27.

In some embodiments of the present invention, the UV device is portable. A portable UV device can be transported between different rooms, spaces and defined environments.

In some embodiments of the present invention, e.g., when a UV device is used to sterilize a rather large room, space or defined environment, the UV light source may be moved within the room, space or defined environment from a first position to a second position and from a second position to a third position.

I. Multiple UV Lamps

For use in the methods of the present invention, UV light sources, also referred to herein as UV lamps, can be configured in a variety of ways in a UV device. The configuration of one or more UV lamps within a UV device is referred to herein also as a UV lamp assembly or UV lamp cluster. In some embodiments of the present invention more than one UV lamp is used for the sterilization of a container, a room, a space or defined environment. Multiple UV lamps can be clustered together or spaced apart either symmetrically or asymmetrically in order to achieve the desired reduction in microorganisms in a timely and efficient manner.

For example, FIGS. 2 and 3 depict embodiments of the present invention where the UV assembly consists of a single UV lamp. FIG. 4 depicts an embodiment of the present invention showing a UV lamp assembly having four UV lamps. FIG. 5 depicts an embodiment of the present invention showing a UV lamp assembly having eight UV lamps arranged in an octagonal configuration. In addition, as depicted in FIG. 5, an additional UV lamp may be attached to a support plate. Those UV lamps are typically mounted to a frame 6, as shown, e.g., in FIGS. 4, 5, 14, 15 and 21-25. FIGS. 21-25 and 42-48 depict an embodiment of the present invention showing eight UV lamps attached to a frame 3 and an upper plate 42. Alternatively, those UV lamps are attached to or enclosed in a housing 2, as shown, e.g., in FIGS. 2, 3, 6-13, 16, 21-25 and 42-45. When more than one UV lamp is used in an UV assembly or in a method of the present invention, each UV lamp may be the same or different.

In some embodiments of the present invention a UV device comprises more than one UV lamp. In some embodiments, at least two UV lamps are clustered together. In some embodiments, at least three UV lamps are clustered together. In some embodiments, at least four UV lamps are clustered together. In some embodiments, four UV lamps are clustered together. In some embodiments, five UV lamps are clustered together. In some embodiments, six UV lamps are clustered together. In some embodiments, seven UV lamps are clustered together. In some embodiments, eight UV lamps are clustered together. The clustering of the lamps may be at perpendicular angles as shown in FIG. 4 or at any other angle (e.g., FIGS. 21-25, 27, 32, 33, 45, and 48). The more than one UV lamps in a UV lamp cluster can be positioned to each other at various angles ranging from about 5 to about 45 degree, preferably from about 10 to about 30 degree, more preferably from about 15 to about 20 degree. In some embodiments of the present invention, the more than two UV lamps are positioned to each other in an about 5 degree angle. In some embodiments of the present invention, the more than two UV lamps are positioned to each other in an about 10 degree angle. In some embodiments of the present invention, the more than two UV lamps are positioned to each other in an about 15 degree angle. In some embodiments of the present invention, the more than two UV lamps are positioned to each other in an about 20 degree angle. In some embodiments of the present invention, the more than two UV lamps are positioned to each other in an about 25 degree angle.

In some embodiments, more than one UV lamp is attached to a bracket. In some embodiments, at least two UV lamps are attached to a bracket. In some embodiments, at least three IN lamps are attached to a bracket. In some embodiments, at least four UV lamps are attached to a bracket. In some embodiments, four UV lamps are attached to a bracket. In some embodiments, five UV lamps are attached to a bracket. In some embodiments, six UV lamps are attached to a bracket. In some embodiments, seven UV lamps are attached to a bracket. In some embodiments, eight UV lamps are attached to a bracket. The UV lamps may be attached to a means for attaching the UV device to a container, e.g., a bracket as shown in FIGS. 1-5, and 10-15, which typically, but not always, comprises mounting the UV lamp to a housing or frame and mounting the housing or frame to the bracket. Other embodiments for attaching a UV light source, such as a UV lamp cluster, to a means for attaching the UV device to a container, are shown in FIGS. 21-25 and 42-48.

In some embodiments, more than one UV lamp is attached to a frame. In some embodiments, at least two UV lamps are attached to a frame. In some embodiments, at least three UV lamps are attached to a frame. In some embodiments, at least four UV lamps are attached to a frame. Four UV lamps may be attached to a frame as shown exemplary in FIGS. 4-9, 12, and 15. In some embodiments, at least five UV lamps are attached to a frame. In some embodiments, at least six UV lamps are attached to a frame. In some embodiments, at least seven UV lamps are attached to a frame. In some embodiments, at least eight UV lamps are attached to a frame. Eight UV lamps may be attached to a frame as shown exemplary in FIGS. 5, 13, 21-25 and 42-48. In the embodiments shown in FIGS. 21-25 and 42-48, the UV lamps are also attached to an upper plate 42.

In some embodiments, more than one UV lamp is attached to a housing. In some embodiments, at least two UV lamps are attached to a housing. In some embodiments, at least three UV lamps are attached to a housing. In some embodiments, at least four UV lamps are attached to a housing. In some embodiments, at least five UV lamps are attached to a housing. In some embodiments, at least six UV lamps are attached to a housing. In some embodiments, at least seven UV lamps are attached to a housing. In some embodiments, at least eight UV lamps are attached to a housing. FIG. 27 depicts an embodiment of the present invention where a UV assemble comprises 15 UV lamps, arranged in five UV lamp clusters each having three UV lamps and of which one UV lamp cluster is stationary and four UV lamp clusters are movable. In this embodiment, a light box 79, comprising a back wall 80 for mounting to the ceiling of a room is considered an equivalent of a housing 2. FIG. 27 depicts a UV device mountable to a ceiling or wall of a room, a space or defined environment.

J. UV Lamp Cluster

In some embodiments of the present invention, a UV lamp is configured into a UV lamp cluster. Increasing the number of UV lamps increases the intensity of UV light emitted throughout the tank or container. For packaging purposes, multiple short UV lamps are preferable to fewer long UV lamps. The increased UV intensity decreases the time necessary for sterilization or sanitization.

Exemplary UV lamp clusters of a UV device are shown in FIGS. 2-25, 27, 30, 32, 33, and 37-48. While FIG. 20 shows that the UV lamps are not in a housing, in some embodiments UV lamps may be in a protective housing (e.g., FIGS. 21-25, 27, 28-35, 37-40A, 42, and 43). UV lamps assembled into a UV lamp cluster may be spring loaded. As they emerge from the housing, they spring out to a relatively optimal angle of 15 degrees. Other preferred angles are 10 degrees, 11 degrees, 12 degrees, 13 degrees, 14 degrees, 16 degrees, 17 degrees, 18 degrees, 19 degrees, and 20 degrees. These angles are preferred as they allow for good UV coverage on both horizontal and vertical surfaces of a container.

In some embodiments of the present invention, UV lamp clusters can move out of a housing due to being attached via a hinge mechanism, i.e., wherein the UV device comprises, for example, a hinge or a UV lamp module swing 81, allowing the so attached UV lamps/UV lamp cluster to move from a closed position (e.g., when not in use) into an exposed position (i.e., for sanitization). An exemplary embodiment of such a UV device is shown in FIG. 27.

In some embodiments, a LTV lamp cluster is lowered into a container on a rope.

K. Scissor Boom

In some embodiments of a UV device of the present invention, the UV device comprises one or more means for moving a UV light source to a predetermined position, typically to a predetermined position within a container, a room, a space or defined environment. A means for moving the UV light source can be a means for moving the UV light source to vertical downwards position in a container, room, space or defined environment. Another means for moving the UV light source can be a means for moving the UV light source to a horizontal position in a container, a room, a space or defined environment. In some embodiments of the present invention, a UV device comprises more than one means for moving a UV light source to a predetermined position within a container, a room, a space or defined environment. For example, a UV device may comprise a means for moving the UV light source to a first vertical downwards position within a container, a room, a space or defined environment. The UV device may also comprise a means for moving the UV light source from the first vertical position to a horizontal position within a container, a room, a space or defined environment. The UV device may also comprise a means for moving the UV light source from the horizontal position to a second vertical downwards position within a container, a room, a space or defined environment.

In some embodiments of the present invention, a UV device comprises a means for moving a UV light source to a predetermined position within a container, a room, a space or defined environment and is referred to as a scissor boom.

A scissor boom comprises a first end and a second end. The first end is also referred to as inner end, and the second end is also referred to as outer end.

In some embodiments, the scissor boom comprises at least one scissor unit between its first end and second end. In some embodiments, the scissor boom comprises at least two scissor units between its first end and second end. In some embodiments, the scissor boom comprises at least three scissor units between its first end and second end. In some embodiments, the scissor boom comprises at least four scissor units between its first end and second end. In some embodiments, the scissor boom comprises at least five scissor units between its first end and second end. In some embodiments, the scissor boom comprises at least ten scissor units between its first end and second end. A scissor unit can be made from any material. A preferred scissor bracket is a metal bracket. In some embodiments, a metal bracket is an aluminum bracket. Aluminum brackets are particularly preferred based on low cost and low weight. Preferred are also carbon fiber brackets. The scissor units are connected to each other by pivots. The pivots allow the horizontal extension of the scissor boom units.

The dimensions of a scissor boom for use in the methods of the present invention are not limited. A scissor boom may have various dimensions and may extend for several feet. A non-limiting scissor boom constructed by the Applicant measures about 10" by 10" by 50" in its retracted position and can extend over 15 feet.

In some embodiments of the present invention, an actuator unit is mounted to the first end of the scissor boom. An exemplary, non-limiting, embodiment of a linear actuator 37 is shown in FIG. 19. An actuator of the present invention operates by conversion of a rotary motion into a linear motion. An actuator extends the scissor boom and the extent of the expansion is determined by a sensor.

In some embodiments, a UV lamp 5 is mounted to the second end of the scissor boom. In some embodiments of this UV device, the UV lamp 5 is housed in a housing (e.g., FIG. 19). In some embodiments, a UV lamp cluster 41 (i.e., more than one UV lamp) is mounted to the second end of the scissor boom. In some embodiments of the present invention, a UV lamp cluster comprises at least two germicidal UV light sources. In some embodiments of the present invention, a UV lamp cluster comprises at least three germicidal UV light sources. In some embodiments of the present invention, a UV lamp cluster comprises at least four germicidal UV light sources. In some embodiments of the present invention, a UV lamp cluster comprises at least five germicidal UV light sources. In some embodiments of the present invention, a UV lamp cluster comprises two germicidal UV light sources. In some embodiments of the present invention, a UV lamp cluster comprises three germicidal UV light sources. In some embodiments of the present invention, a UV lamp cluster comprises four germicidal UV light sources. In some embodiments of the present invention, a UV lamp cluster comprises five germicidal UV light sources.

In some embodiments of this UV device, the UV lamp cluster 41 is housed in a UV lamp cluster housing 36 (FIG. 19). In some embodiments, the first end of the scissor boom is attached to an additional bracket mounted to a container (e.g., an adjusting bracket 24 as shown in FIG. 10) so that the scissor boom can be moved up and down via sliding rails 39 located at the inner end of the scissor boom (FIG. 19).

A scissor boom of the present invention can move (a) horizontally from an interior position of a container (i.e., from its folded position, FIG. 19A) towards the inner wall of the container (i.e., into its extended position, FIG. 19B) via slide rail 40, (b) vertically along sliding rails 39 in an up and down movement, and (c) in a circular motion when the scissor boom is fixed at a desired vertical position in the container and in its extended position. In the embodiments where the UV lamp(s) are within a housing, upon reaching the desired position, the UV lamp(s) are released and the housing is removed.

L. UV Lamp Cluster Assembly Combined with Scissor Boom

In some embodiments, a UV device of the present invention comprises a UV lamp cluster and a scissor boom. In some embodiments, a UV lamp cluster comprise three UV lamps. In some embodiments, a UV lamp cluster comprise four UV lamps. In some embodiments, a UV lamp cluster comprise five UV lamps. The function of the scissor boom mechanism is to move the UV lamps horizontally across the top of a container and position the UV lamps to the central axis of the container. A linear actuator (37 in FIG. 19) pushes the scissor mechanism up and down a slide rail (39 in FIG. 19) allowing the length of the scissor to be varied according to the diameter of the container. Slide rails (40 in FIG. 19) on the second side of the scissor boom allow the system to expand and contract in length. Once in place, the UV lamp cluster is dropped from its housing, if present (36, in FIG. 19), and lowered down the central axis of the container.

Figure 19B:
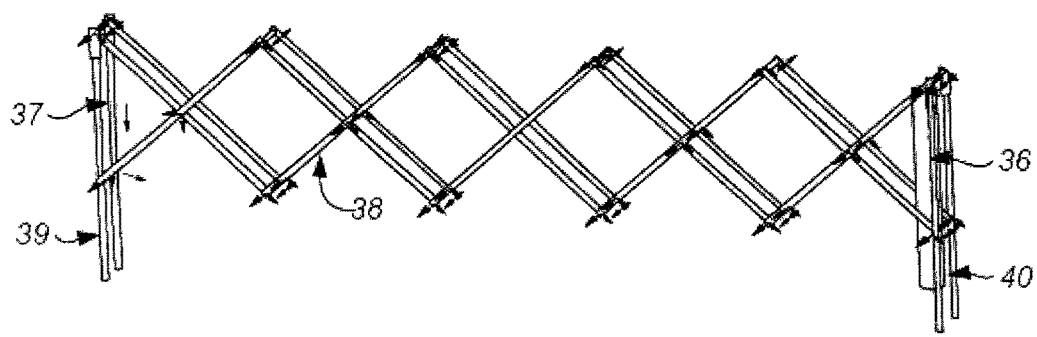
FIG. 19B, scissor boom extended. A UV lamp cluster housing 36 is attached to the outer end of the scissor boom. The UV lamp cluster housing houses a cluster of UV lamps (not shown in Figure). A linear actuator 37 pushes a scissor mechanism 38 up and down a first slide rail 39 located at the inner end (first end) of the scissor boom and allows the length of the scissor boom to be varied according to the diameter of the container into which it is inserted and/or mounted to. A second sliding rail 40, located at the outer end (second end) of the scissor boom allows the scissor boom to expand and contract in length. Once in place, the UV lamp cluster (not shown in Figure) is dropped from its UV lamp cluster housing 36 and lowered down the central axis of the container. Arrows indicate pivot points. A sensor, e.g., a range-finding device (20, not shown in Figure) may also be attached to the second end of the scissor boom and will determine the length to which the scissor boom expands.
Figure 20A:
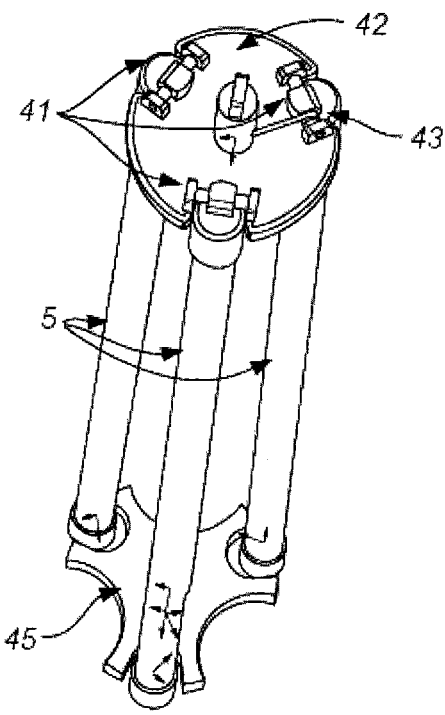
FIGS. 20A and B schematically depict an embodiment of a UV device of the present invention referred to herein as bulb cluster assembly wherein the central post 16 is a central bar.
Figure 20B:
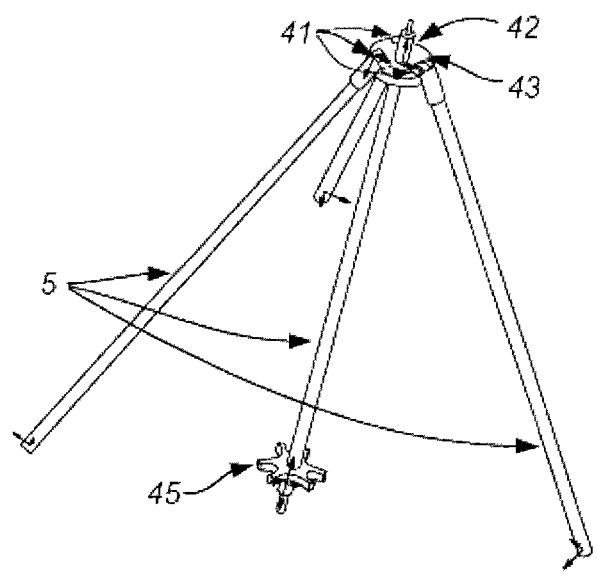
FIG. 20B, open configuration. In this embodiment, the bulb cluster assembly is shown without a protective housing. In other embodiments, the UV lamps 5 are in a protective housing when not in use. Three UV lamps 5 are attached via pins 41 to an upper plate 42. When dropped out of a protective housing (not shown), a spring 43 on each UV lamp (only shown for one UV lamp in Figure) forces the UV lamps out to a 15 degree angle. A central bar 44 attaches to a lower plate 45 to the upper plate 42. As the cluster is retracted back into the protective cover, the UV lamps are forced back into a vertical position and are held in place by the lower plate 45.

The UV lamp cluster may be housed in a protective housing 36 (FIG. 19) and can be attached to a winch at the second end of a scissor mechanism. Once the linear actuator extends the scissor boom to the central position in the tank, the winch drops the UV lamp cluster from the protective cover. As this occurs, the UV lamps will spring out into a tripod configuration in case three UV lamps were clustered (FIG. 20B). An algorithm based on the diameter and depth of the tank will determine the speed at which the winch lowers and raises the tripod configuration. These distances may be determined either by ultrasonic or laser range finders. As the winch retracts the lamp back into the protective housing, the lamps are forced back into a vertical position and secured in that position by the lower plate (FIG. 20A). The scissor arm is then retracted and the system can be removed from the tank.

The entire UV device unit can be mounted to the port of a tank via either a molding attached to the slide rails. This molding or bracket can be made from a variety of materials, including various polymers, aluminum or other metals or carbon fiber. Preferably, it will be made for the lightest and most cost effective material. The standard access port on most modern tanks is offset to one side of the tank and is 18" in diameter.

M. UV Device with Telescoping Arm

In some embodiments of a UV device of the present invention, a UV device comprises a means for moving a UV light source to a predetermined position within a container, a room, a space or defined environment and is referred to herein as a UV device with telescoping arm. In some embodiments of a UV device of the present invention, a UV device comprises a UV light source that is attached to a telescopic arm 46. In some embodiments, the telescopic arm 46 corresponds to a central sleeve 12 (as shown exemplary in FIGS. 7-11), comprising two or more movable units, referred to herein as telescoping units 47. Exemplary embodiments of a UV device comprising a telescopic arm 46 are shown in various configurations in FIGS. 21-25.

FIGS. 21-25 depict several views of an exemplary embodiment of a UV device of the present invention comprising a telescopic arm as a means for moving a UV light source or a UV lamp cluster to a desired position within a container, a room, a space or defined environment. The UV device is shown schematically in various configurations: in its folded position (FIG. 21), in its load position (FIG. 22), in its payout position (FIG. 23), in its horizontal position (FIG. 24), and in its UV lamp down position (FIG. 25). While FIGS. 21-25 show a UV device comprising a telescopic arm and a UV lamp cluster having eight UV lamps, any number of UV lamps can be attached to a UV device having a telescopic arm 46.

The telescopic arm 46 comprises two or more telescoping units 47. The number of telescoping units is not important for practicing the methods of the present invention as long as the telescoping units 47 can be used to move the UV light source to a desired position within a container (e.g., see FIGS. 21-25), a room, a space or defined environment. In some embodiments, the telescopic arm 46 comprises two or more telescoping units 47. In some embodiments, the telescopic arm 46 comprises two telescoping units 47. In some embodiments, the telescopic arm 46 comprises three telescoping units 47. In some embodiments, the telescopic arm 46 comprises four telescoping units 47. In some embodiments, the telescopic arm 46 comprises five telescoping units 47. In some embodiments, the telescopic arm 46 comprises six telescoping units 47. An example of a telescopic arm 46 comprising six telescoping units 47 is shown in FIGS. 21-25. In some embodiments, the telescopic arm 46 comprises seven telescoping units 47. In some embodiments, the telescopic arm 46 comprises eight telescoping units 47. In some embodiments, the telescopic arm 46 comprises nine telescoping units 47. In some embodiments, the telescopic arm 46 comprises ten telescoping units 47. In some embodiments, the telescopic arm 46 comprises more than ten telescoping units 47.

The form of the telescoping units 47 is not important for practicing the methods of the present invention as long as the telescoping units 47 can be used to move the UV light source to a desired (also referred to as predetermined) position within a container, a room, a space or defined environment. The telescoping units 47 can be of any form. For example, in some embodiments, the telescoping units 47 are square. In some embodiments, the telescoping units 47 are rectangular. In some embodiments, the telescoping units 47 are round. In some embodiments, the telescoping units 47 are oval. In one embodiment of a UV device of the present invention, exemplified in FIGS. 21-25, the telescoping units 47 are square.

The dimensions of the telescoping units 47 are not important for practicing the methods of the present invention as long as the telescoping units 47 can be used to move the UV light source to a desired position within a container, a room, a space or defined environment. The telescoping units 47 may have various dimensions. Typically a telescoping unit 47 having the smallest diameter, $D_1$, is surrounded by a telescoping unit 47 having a larger diameter, $D_2$, which in turn is surrounded by a telescoping unit 47 having a larger diameter, $D_3$, which in turn is surrounded by a telescoping unit 47 having a larger diameter, $D_4$, and so on. An exemplary embodiment thereof, showing six telescoping units 47 of different diameters, is shown in FIGS. 21-25. In the embodiment shown schematically in FIGS. 21-25 and produced by the inventor, the diameter $D_1$ of the inner telescoping unit 47 is about 20×20 mm, the diameter $D_2$ of the next larger telescoping unit 47 is about 30×30 mm, the diameter $D_3$ of the next larger telescoping unit 47 is about 40×40 mm, the diameter $D_4$ of the next larger telescoping unit 47 is about 50×50 mm, the diameter $D_5$ of the next larger telescoping unit 47 is about 60×60 mm, and the diameter $D_6$ of the next larger telescoping unit 47 is about 70×70 mm. In the embodiment shown schematically in FIGS. 21-25 and produced by the inventor, the length of the telescoping unit 47 is about 3 feet each. Each telescoping unit 47 may, however, be of a different length, i.e., longer or shorter than 3 feet.

Each telescoping unit 47 has two ends, a first end and a second end, with which they are connected to another telescoping unit 47 or to a UV light source with respect to the inner telescoping unit 47 or to a means for attaching the UV device to a container, such as a hanger with respect to the outer telescoping unit 47 (see FIGS. 21-25). Thus, in some embodiments of the present invention, as exemplified in FIGS. 21-25, the UV light source is connected to a first end of the inner telescoping unit 47. More specifically with respect to the embodiment shown in FIGS. 21-25, the UV light source is connected to the inner telescoping unit 47 having a diameter $D_1$, the second end of the inner (or smallest in diameter) telescoping unit 47 having a diameter $D_1$ is connected to the first end of a telescoping unit 47 having a diameter $D_2$, the second end of the telescoping unit 47 having a diameter $D_2$ is connected to the first end of a telescoping unit 47 having a diameter $D_3$, the second end of the telescoping unit 47 having a diameter $D_3$ is connected to the first end of a telescoping unit 47 having a diameter $D_4$, the second end of the telescoping unit 47 having a diameter $D_4$ is connected to the first end of a telescoping unit 47 having a diameter $D_5$, and the second end of the telescoping unit 47 having a diameter $D_5$ is connected to the first end of a telescoping unit 47 having a diameter $D_6$.

The most outer (or largest in diameter) telescoping unit 47 is attached to a telescopic arm pivot 73, which in turn is attached to the means for attaching the UV device to a container 4, such as hanger as exemplified in FIGS. 21-25. The telescopic pivot arm 73 allows the UV device to be moved from a vertical position to a horizontal position and vice versa so that the UV light source can be positioned at a desired position within a container (see FIGS. 21-25), a room, a space or defined environment.

While the embodiment of the UV device having a telescopic arm shown in FIGS. 21-25 shows the telescopic unit 47 having the smallest diameter as the inner telescoping unit 47 and attached to the UV light source, in some embodiments it is the telescopic unit 47 having the largest diameter which is attached to the UV light source. In this embodiment, the telescopic unit 47 having the smallest diameter is attached to the telescopic arm pivot.

The telescopic (used herein interchangeably with the term "telescoping") arm 46 and the telescoping units 47 can be of any material as long as the material is strong enough allowing the moving of the UV light source to a desired position as described herein. A preferred material is metal.

In the exemplary embodiment shown in FIGS. 21-25, UV lamps 5 are clustered in a UV lamp cluster and are enclosed within a housing 2, such as a LTV mesh cage, which allows the UV light to pass through. In some embodiments, the UV lamps 5 are attached to a frame 6, and to an upper plate 42. The upper plate 42 is connected to a UV lamp pivot arm 49 allowing the UV lamp cluster to be positioned in a desired position and orientation. In a preferred orientation, as shown e.g., in FIGS. 24 and 25, the UV light source points towards the bottom of a container.

In some embodiments, the UV lamp pivot arm 49 is attached to a UV lamp stop block 50. The UV lamp stop block 50 stops the UV light source from being retracted too high into the telescoping arm 46.

In some embodiments, a means for attaching the UV device to a container, i.e., referred to as hanger in FIGS. 21-25, is used to attach the UV device to a container, a room, a space or defined environment. The hanger can be attached to a pulley mount arm 51, to which also other parts of the UV device can be attached, such as the motorized unit 1 (also referred to as motor) and a winch 48. In some embodiments, the hanger comprises one or more hanger support bars 52 and a clamp post 53 for firmly attaching the UV device to a container, a room, a space or defined environment.

In some embodiments of the present invention the means for moving the UV light source to a desired position within a container, a room, a space or defined environment is the telescopic arm 46. The telescoping units 47 of the telescopic arm 46 can be moved either manually, by gravity, or with a motorized unit 1 (also referred to as motor). In some embodiments, the motorized unit 1 is attached to a reel assembly 54 and also permits moving the UV light source from a horizontal position to a vertical downwards position within the container (as described further herein) a room, a space or defined environment.

In some embodiments, the reel assembly 54 is attached to a pulley mount arm 51. In some embodiments, the reel assembly comprises one or more of the following: a reel assembly motor mount 55, a reel assembly idler post 57 for mounting the reel assembly 54 to the pulley mount bar 51, a reel assembly top plate 58, one or more reel assembly flanges 59, a reel assembly hub 60, and a reel assembly drive post 61. A preferred configuration of those parts is shown in FIGS. 21-25.

The motorized unit 1 or gravity or a winch (manually) extends the telescoping arm 46 comprising of multiple telescoping units 47 from a folded position (FIG. 21) and load position (FIG. 22) into the payout position (FIG. 23). In some embodiments, the motor 1 is connected to a reel assembly 54 (shown in greater detail in FIGS. 21 E-G). In some embodiments, the motor 1 connects to the reel assembly 54 via a reel assembly motor unit 55 and a motor coupler 56.

In some embodiments of a UV device of the present invention, a UV device comprises a means for moving a UV light source from a vertical downwards position (also referred sometimes as first vertical downwards position) into a horizontal position. In some embodiments the means for moving the UV light source from the vertical downwards position into the horizontal position is a winch 48. In other embodiments, the means for moving the UV light source from the vertical position into the horizontal position is a motorized unit or a motor. A winch 48 may be operated manually by hand.

In some embodiments, a winch 48 is attached to the pulley mount arm 51 and moves the telescoping arm 46 and the telescoping units 47 from the payout position (FIG. 23; also referred to as first vertical downward position) into a horizontal position (FIG. 24). In some embodiments, a winch 48 comprises one or more of the following: a winch pulley guide 62, a winch guide pulley shaft 63, a winch shaft 64, a winch hub 65, a winch top plate 66, one or more winch flanges 67, a winch ratchet retainer 68, a pawl 69, and a crank or handle 70. A preferred configuration of those parts is shown in FIGS. 21-25. A winch guide pulley shaft 63 allows the winch pulley guide 62 to rotate and reduce friction. In some embodiments, the winch shaft 64 allows the winch hub 65 to spin and wind and unwind a cable 7. Cable 7 typically wraps around winch hub 65. A winch top plate 66 adds structural integrity to the winch assembly 48. A winch ratchet retainer 68 keeps the ratchet from slipping off. In some embodiments, cable 7 connects the winch 48, more specifically, the winch hub 65 with the UV light source so that the UV light source can be moved e.g., from the horizontal position (FIG. 24) towards the bottom of the container, i.e., to a vertical position, more specifically, to a second vertical downwards position. The length of the cable 7 is sufficient to allow the UV light source to be moved from the horizontal position to a position close to the bottom of the container, i.e., into a second vertical downwards position and back into its horizontal position (see FIG. 25).

In some embodiments, the outer telescoping unit 47 of the telescopic arm 46 is attached to the bottom part of the pulley mount arm 51 by one or more cross member support bars 71 and a cross bar stop plate 72. One end of the outer telescopic unit 47 is connected to a telescopic arm pivot 73 allowing the telescoping arm to be moved from the loaded (FIG. 22) or layout position (FIG. 23) into a horizontal position (FIG. 24).

Figure 21A:
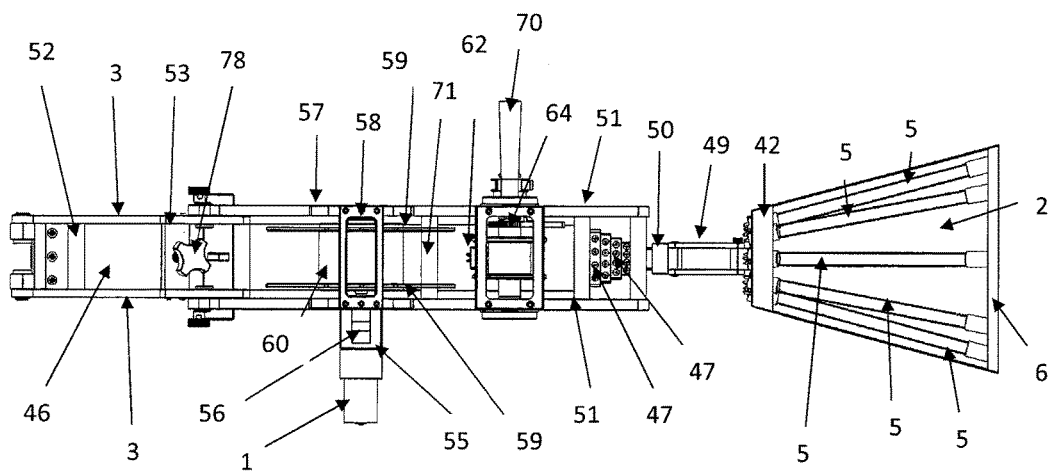
FIG. 21A schematically depicts a top view of the UV device having a telescopic arm in its folded position. UV lamps 5 are clustered in a UV lamp cluster and are within a housing 2, here a UV mesh cage, which allows UV light to pass through. The UV lamps 5 are attached to a frame 6 and an upper plate 42. The upper plate 42 is connected to a UV lamp pivot arm 49 allowing the UV lamp cluster to be positioned in a desired position. The UV lamp pivot arm 49 is attached to a UV lamp stop block 50. A mounting bracket 3, also referred to as hanger, is used to attach the UV device to a container (not shown). The mounting bracket 3 is attached to a pulley mount arm 51, to which also other parts of the UV device can be attached, such as the motorized unit 1 (also referred to as motor) and a winch 48. The mounting bracket (hanger) 3 comprises one or more hanger support bars 52, a clamp post 53 and a tightening screw 78 for firmly attaching the UV device to a container. A motorized unit 1 (also referred to as motor) is connected to a reel assembly 54, which is mounted to the pulley mount arm 51. A motorized unit 1 or gravity extends the telescoping arm 46 consisting of multiple telescoping units 47 shown here as slided into each other, from the folded and load position (FIGS. 22A-G) into the payout position (FIGS. 23A-G). As shown schematically in this embodiment, the motor 1 is connected to a reel assembly 54 (shown in greater detail in FIGS. 21 E-G). The motor 1 connects to the reel assembly 54 via a reel assembly motor unit 55 and a motor coupler 56. As shown in this embodiment, the reel assembly 54 comprises a reel assembly idler post 57 for mounting the reel assembly 54 to the pulley mount bar 51, a reel assembly top plate 58, one or more reel assembly flanges 59, a reel assembly hub 60, and a reel assembly drive post 61. A winch 48 mounted on the pulley mount arm 51 moves the telescoping arm 46 and the telescoping units 47 from a payout position (FIGS. 2A-G) into a horizontal position (FIGS. 24A-G). As shown in this embodiment, the winch 48 comprises a winch pulley guide 62, a winch guide pulley shaft 63, a winch shaft 64, a winch hub 65, a winch top plate 66, one or more winch flanges 67, a winch ratchet retainer 68, a pawl 69, and a crank or handle 70. The outer telescoping unit 47 of the telescopic arm 46 is attached to the bottom part of the pulley mount arm 51 by one or more cross member support bars 71 and a cross bar stop plate 72. One end of the outer telescopic unit 47 is connected to a telescopic arm pivot 73 allowing the telescoping arm to be moved from the loaded (FIGS. 22A-G) or layout position (FIGS. 23A-G) into a horizontal position (FIGS. 24A-G) and back into the loaded or payout position.
Figure 21B:
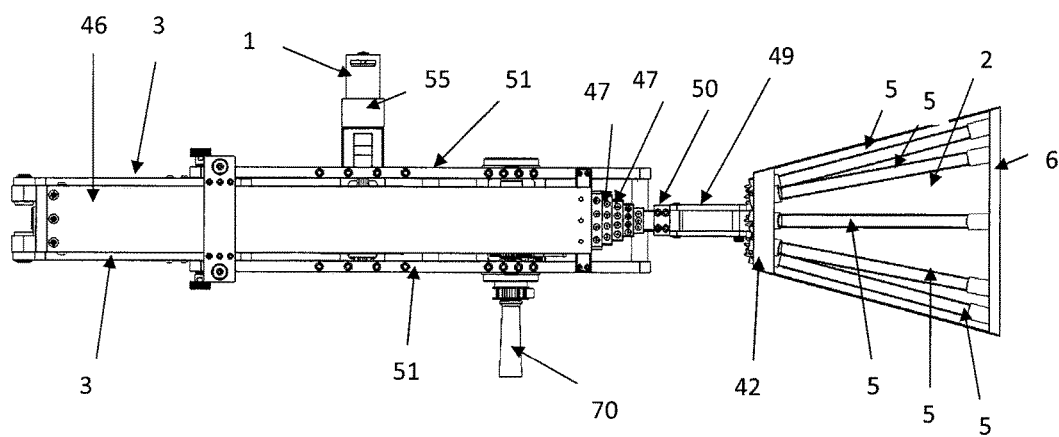
FIG. 21B schematically depicts a bottom view of a UV device having a telescopic arm in its folded position. Individual parts are shown and numbered as described in FIG. 21A. A lifting eye 74 having a lifting eye base 75 and a lifting eye side support 76 (better shown e.g., in FIGS. 21E, F) is attached to the outer telescoping unit 47 and to the pulley mount arm 51.
Figure 21C:
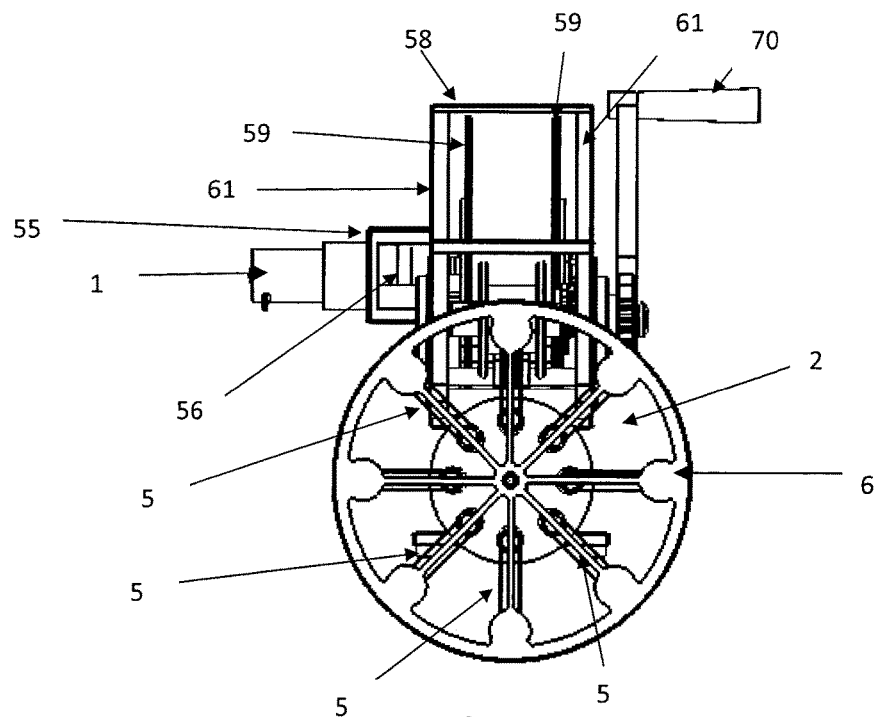
FIG. 21C schematically depicts a front view of a UV device having a telescopic arm in its folded position. Individual parts are shown and numbered as described in FIGS. 21A, B.
Figure 21D:
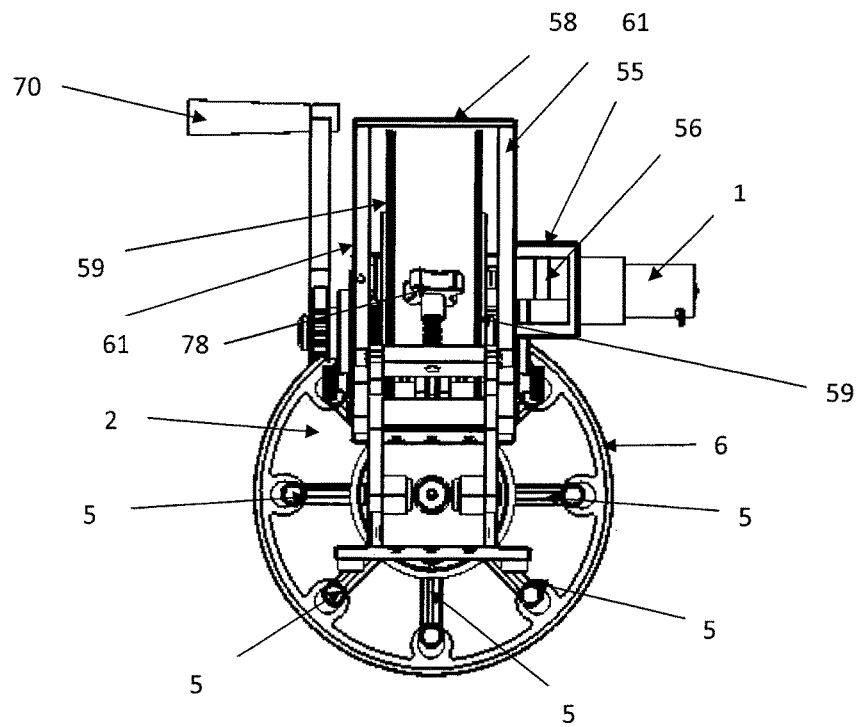
FIG. 21D schematically depicts a back view of a UV device having a telescopic arm in its folded position. Individual parts are shown and numbered as described in FIGS. 21A-C A cable 7 functions as a lamp holder and for vertically extending the position of the UV light source (here a UV lamp cluster) towards the bottom of a container (not shown). The cable 7 attaches the UV light source through the inner telescoping unit 47 to the reel assembly 54.
Figure 21E:
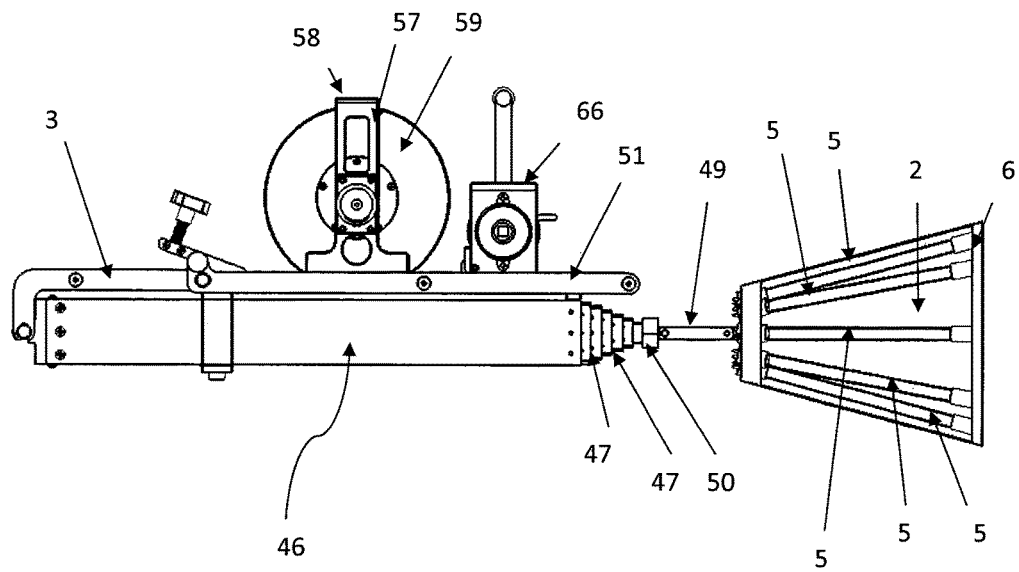
FIG. 21E schematically depicts a first side view of a UV device having a telescopic arm in its folded position. Individual parts are shown and numbered as described in FIGS. 21A-D.
Figure 21F:
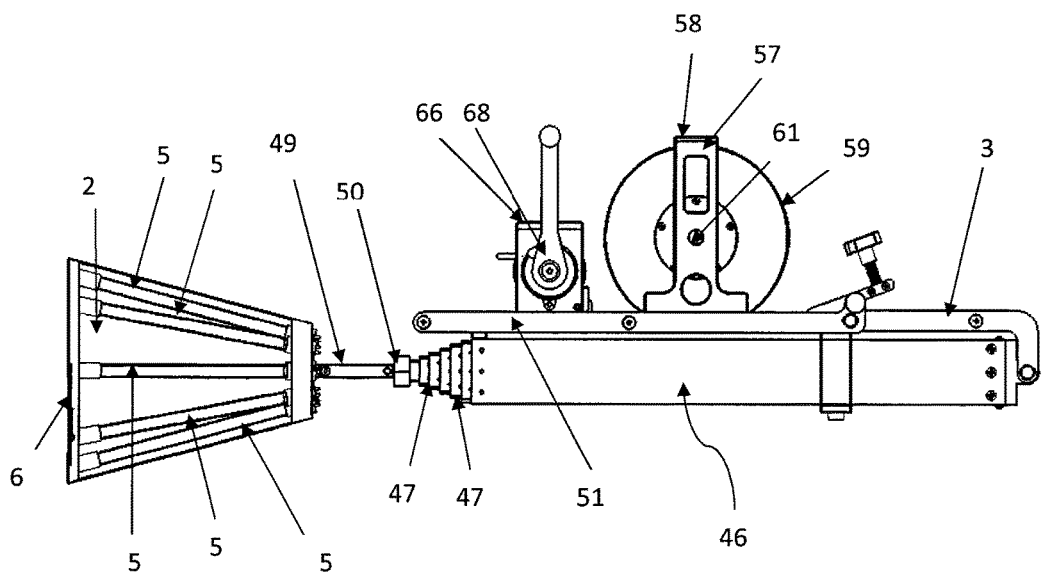
FIG. 21F schematically depicts a second side view of a UV device having a telescopic arm in its folded position. Individual parts are shown and numbered as described in FIGS. 21A-E.
Figure 21G:
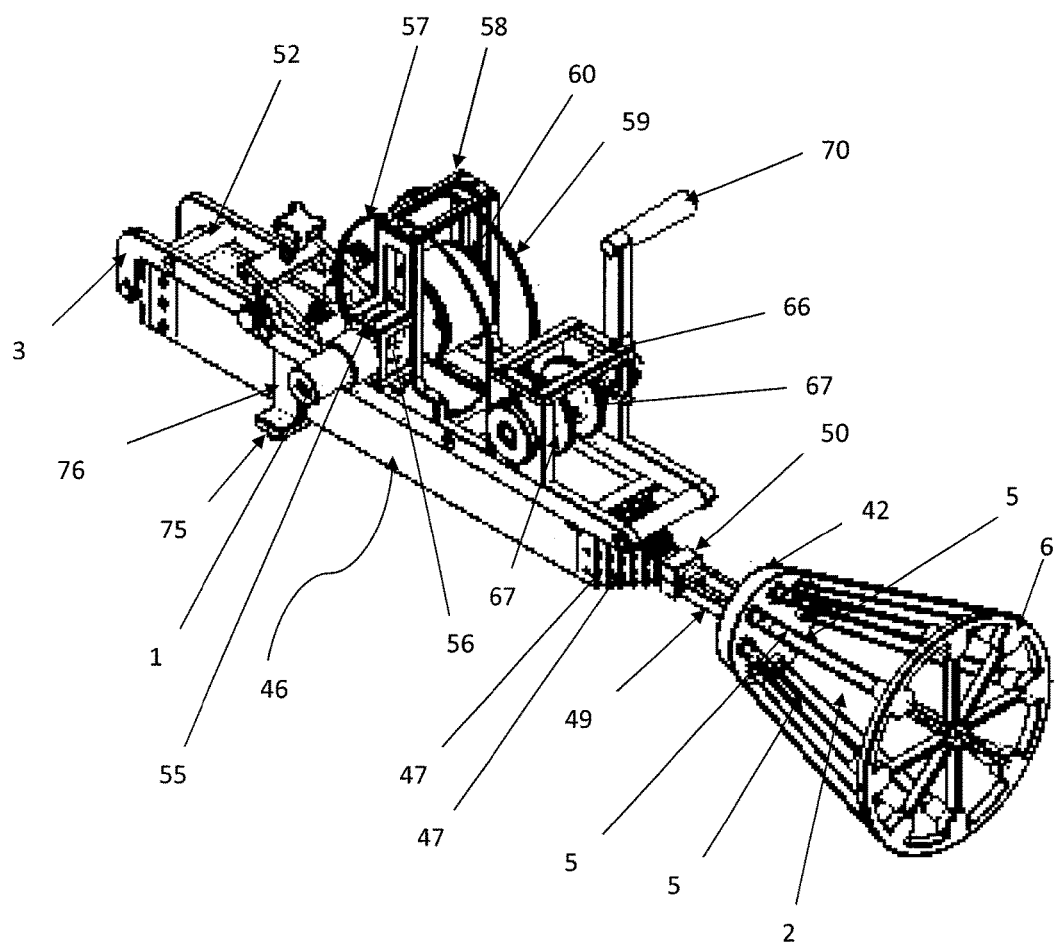
FIG. 21G schematically depicts an isometric view of a UV device having a telescopic arm in its folded position. Individual parts are shown and numbered as described in FIGS. 21A-F.
Figure 22A:
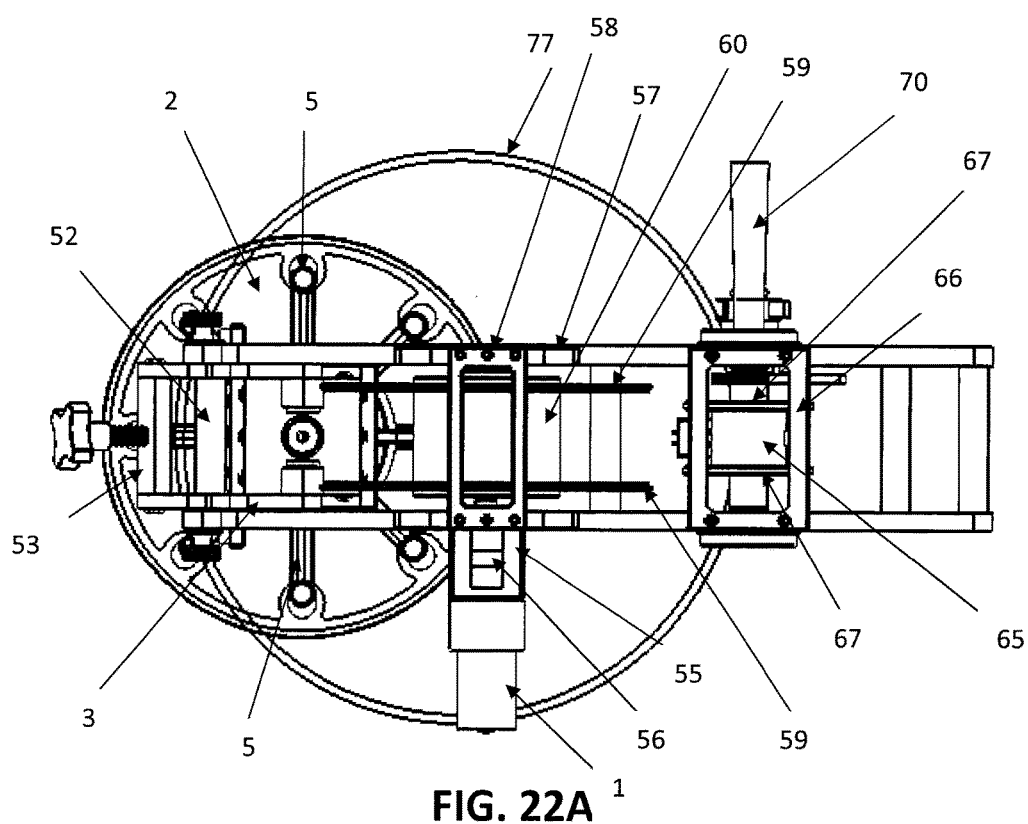
FIG. 22A schematically depicts a top view of a UV device having a telescopic arm in its load position. Individual parts are shown and numbered as described in FIGS. 21A-F. A manhole or port 77 provides for access to the container from the top of the container and allows, e.g., for pressure washing devices to be attached and for attaching of a UV device of the present invention.
Figure 22B:
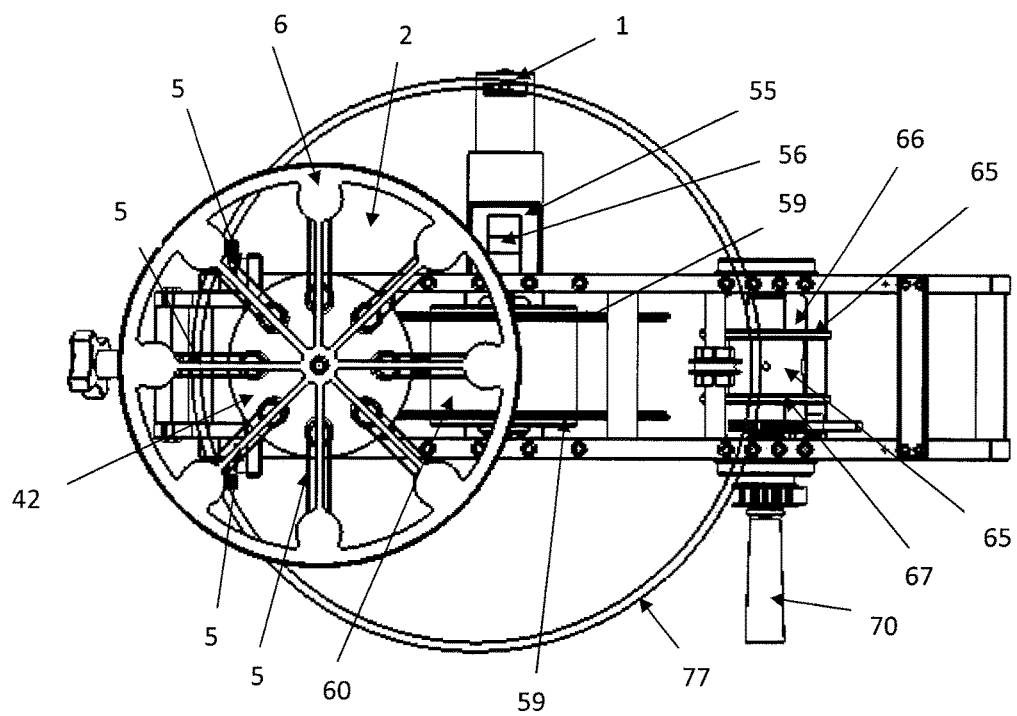
FIG. 22B schematically depicts a bottom view of a UV device having a telescopic arm in its load position. Individual parts are shown and numbered as described in FIGS. 21A-F.
Figure 22C:
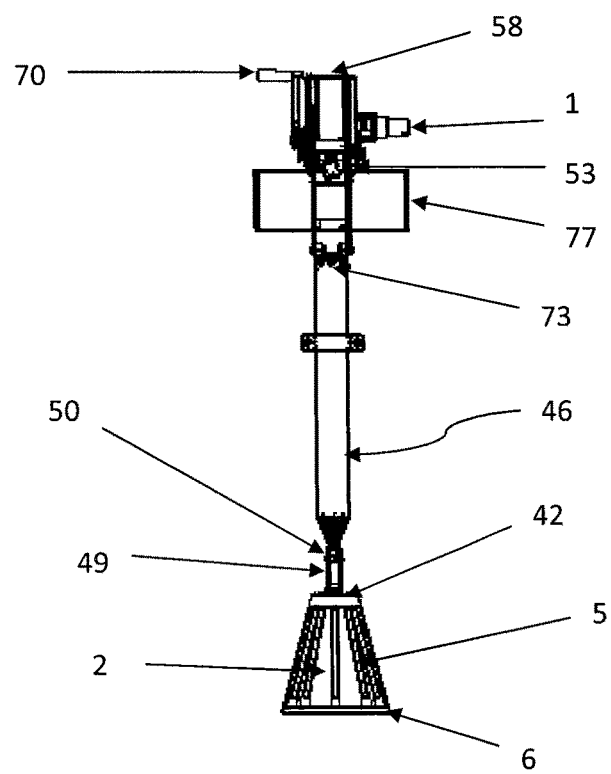
FIG. 22C schematically depicts a front view of a UV device having a telescopic arm in its load position. Individual parts are shown and numbered as described in FIGS. 21A-F.
Figure 22D:
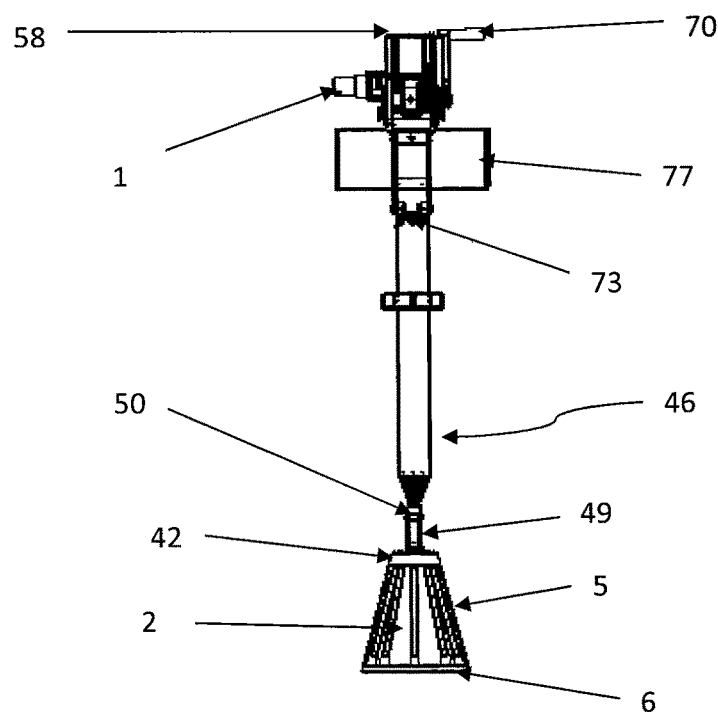
FIG. 22D schematically depicts a back view of a UV device having a telescopic arm in its load position. Individual parts are shown and numbered as described in FIGS. 21A-F.
Figure 22E:
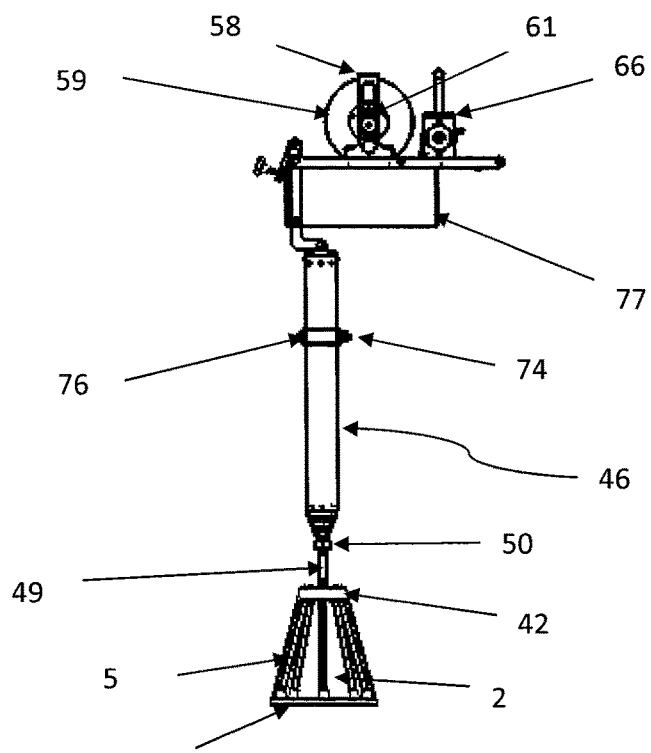
FIG. 22E schematically depicts a first side view of a UV device having a telescopic arm in its load position. Individual parts are shown and numbered as described in FIGS. 21A-F.
Figure 22F:
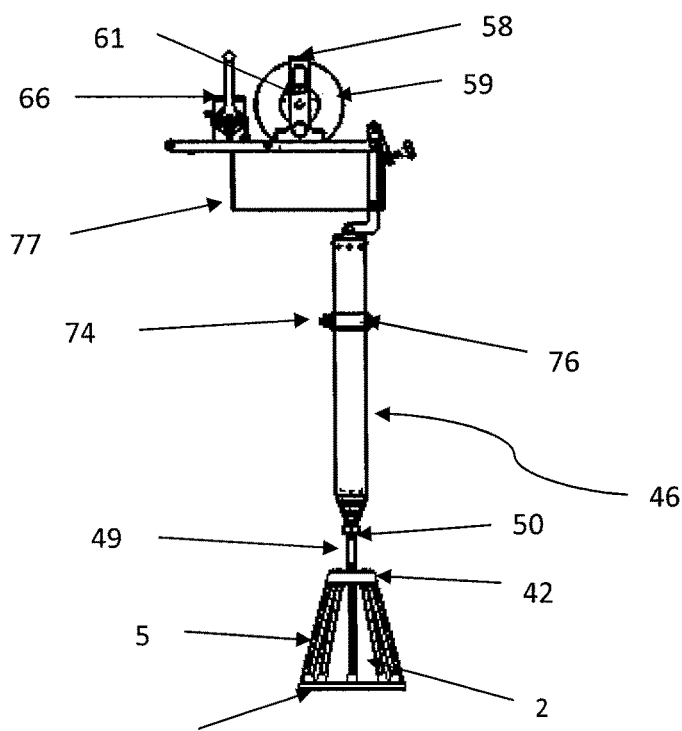
FIG. 22F schematically depicts a second side view of a UV device having a telescopic arm in its load position. Individual parts are shown and numbered as described in FIGS. 21A-F.
Figure 22G:
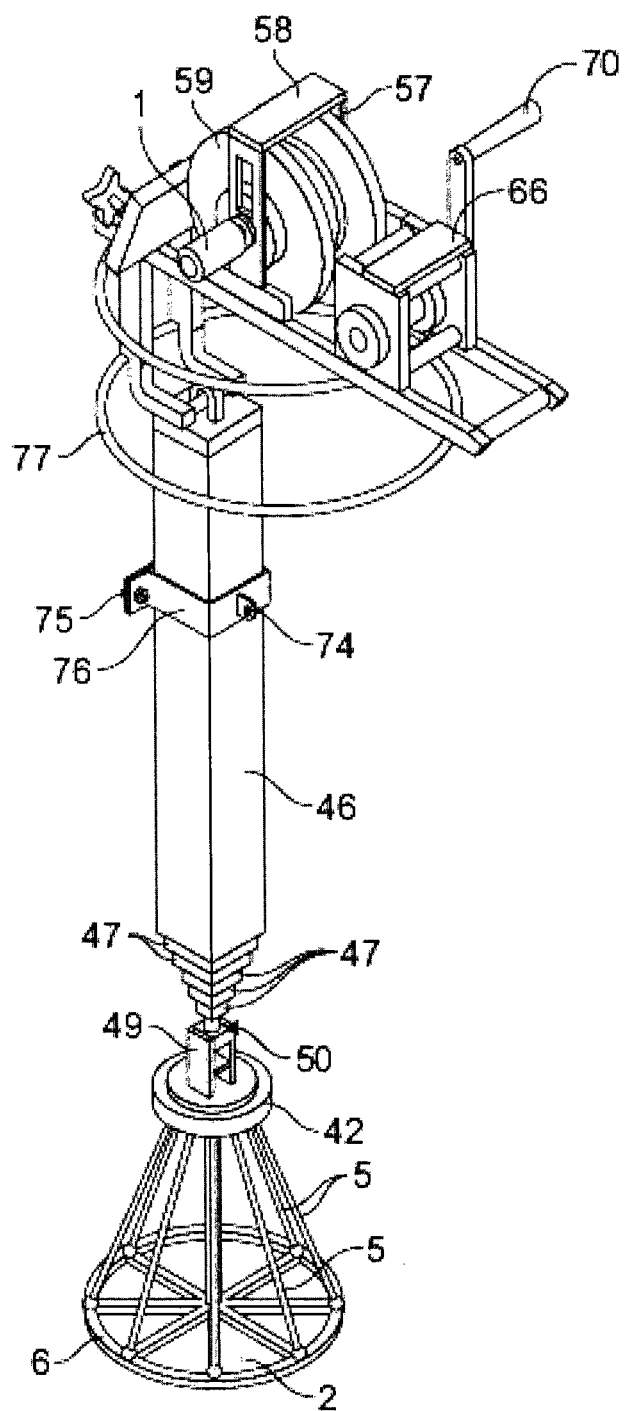
FIG. 22G schematically depicts an isometric view of a UV device having a telescopic arm in its load position. Individual parts are shown and numbered as described in FIGS. 21A-F.
Figure 23A:
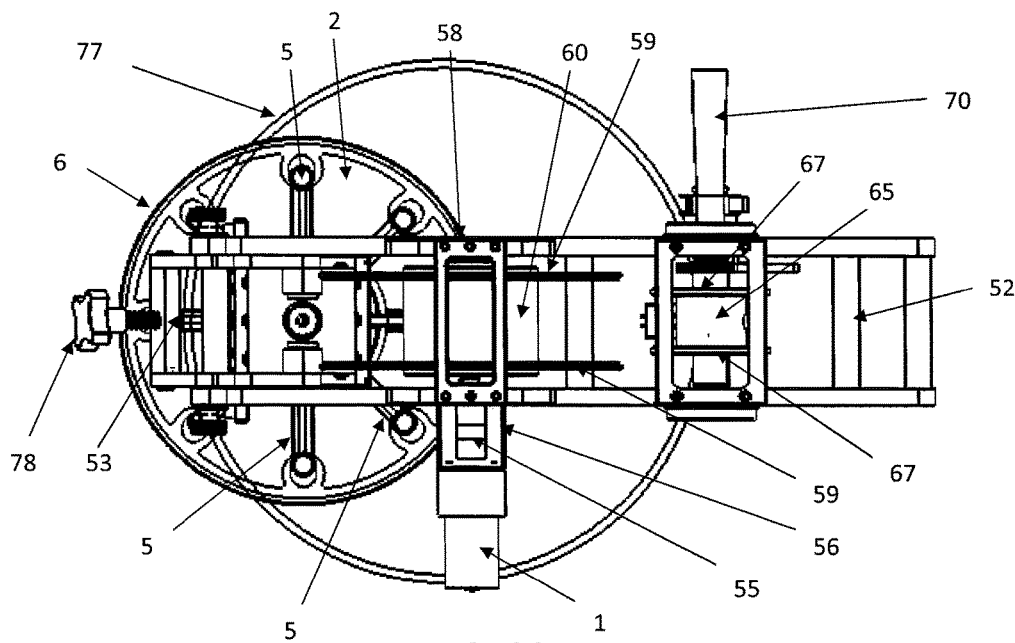
FIG. 23A schematically depicts a top view of a UV device having a telescopic arm in its payout position. Individual parts are shown and numbered as described in FIGS. 21A-F.
Figure 23B:
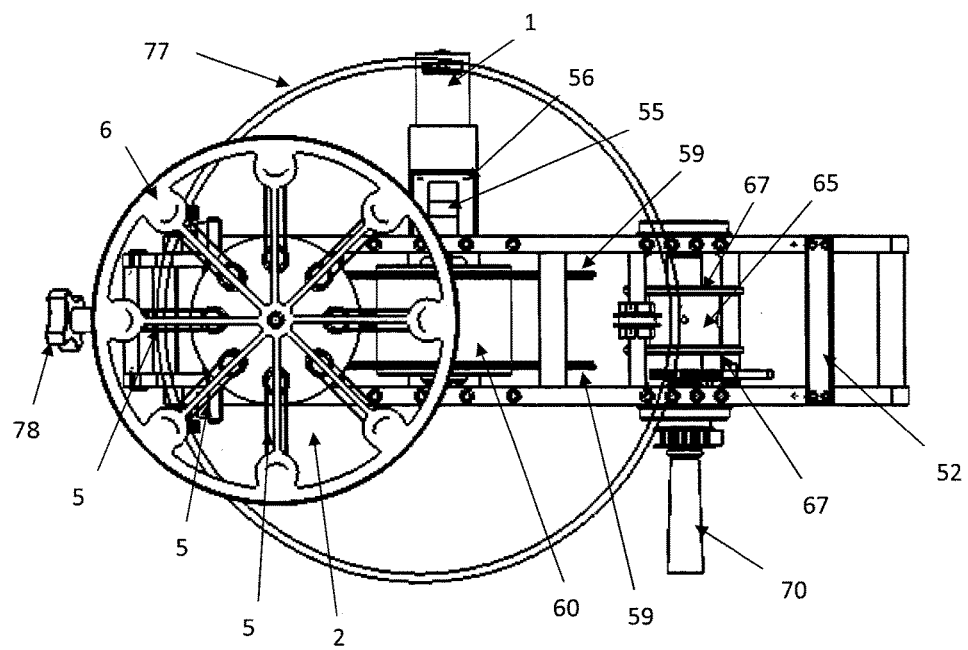
FIG. 23B schematically depicts a bottom view of a UV device having a telescopic arm in its payout position. Individual parts are shown and numbered as described in FIGS. 21A-F.
Figure 23C:
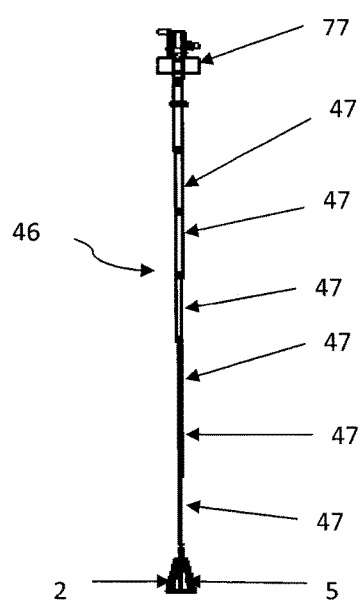
FIG. 23C schematically depicts a front view of a UV device having a telescopic arm in its payout position. Individual parts are shown and numbered as described in FIGS. 21A-F.
Figure 23D:
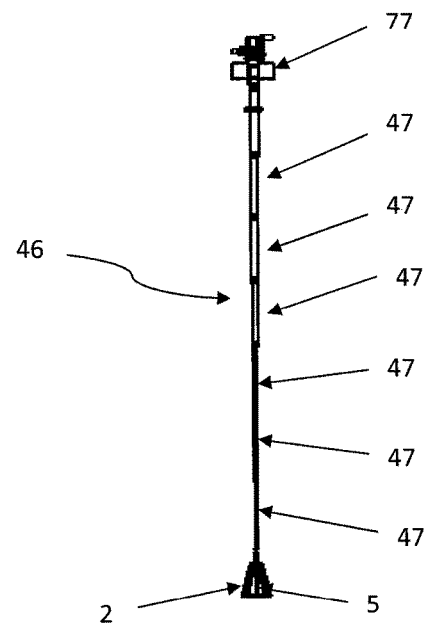
FIG. 23D schematically depicts a back view of a UV device having a telescopic arm in its payout position. Individual parts are shown and numbered as described in FIGS. 21A-F.
Figure 23E:
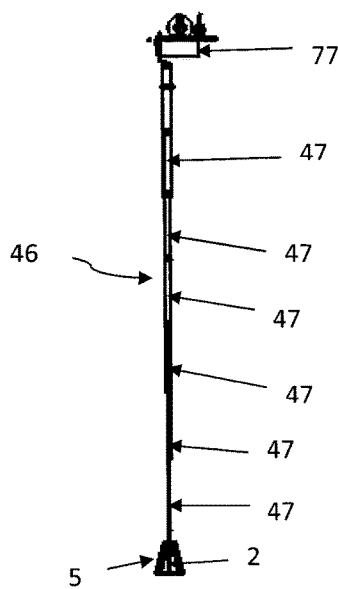
FIG. 23E schematically depicts a first side view of a UV device having a telescopic arm in its payout position. Individual parts are shown and numbered as described in FIGS. 21A-F.
Figure 23F:
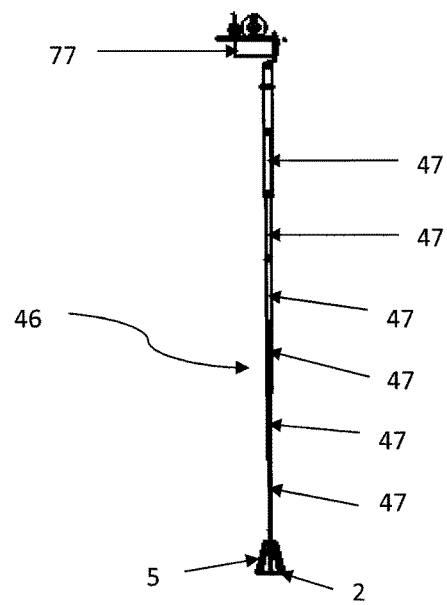
FIG. 23F schematically depicts a second side view of a UV device having a telescopic arm in its payout position. Individual parts are shown and numbered as described in FIGS. 21A-F.
Figure 23G:
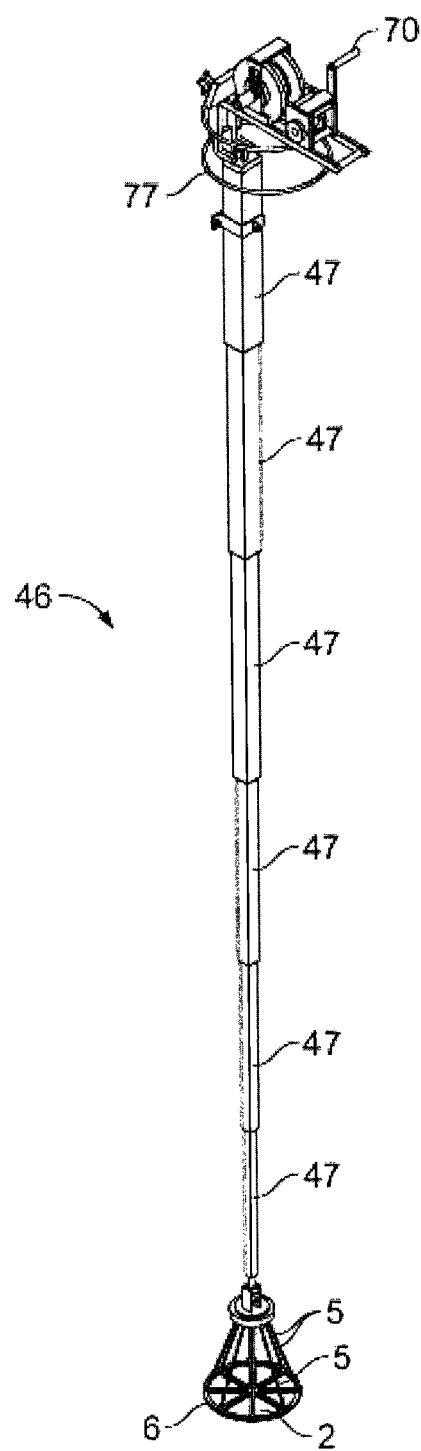
FIG. 23G schematically depicts an isometric view of a UV device having a telescopic arm in its payout position. Individual parts are shown and numbered as described in FIGS. 21A-F.
Figure 24A:
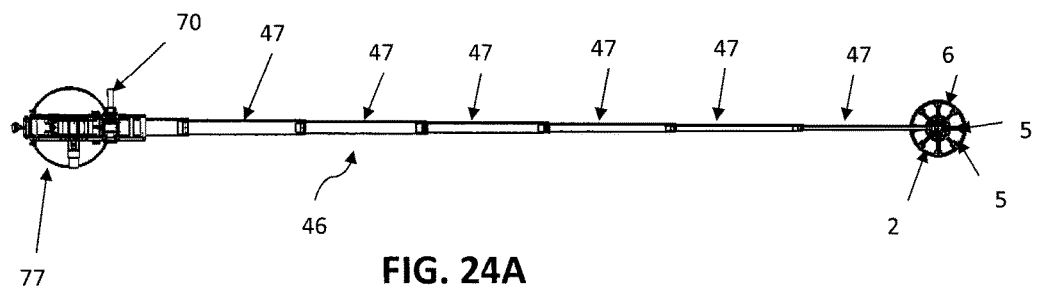
FIG. 24A schematically depicts a front view of a UV device having a telescopic arm in its horizontal position. Individual parts are shown and numbered as described in FIGS. 21A-F.
Figure 24B:
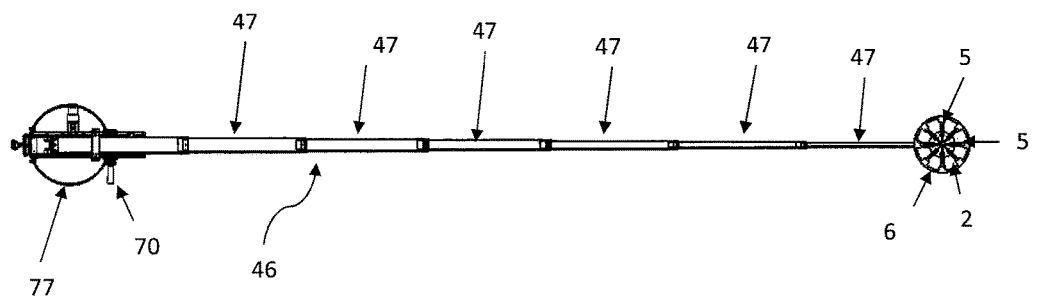
FIG. 24B schematically depicts a back view of a UV device having a telescopic arm in its horizontal position. Individual parts are shown and numbered as described in FIGS. 21A-F.
Figure 24C:
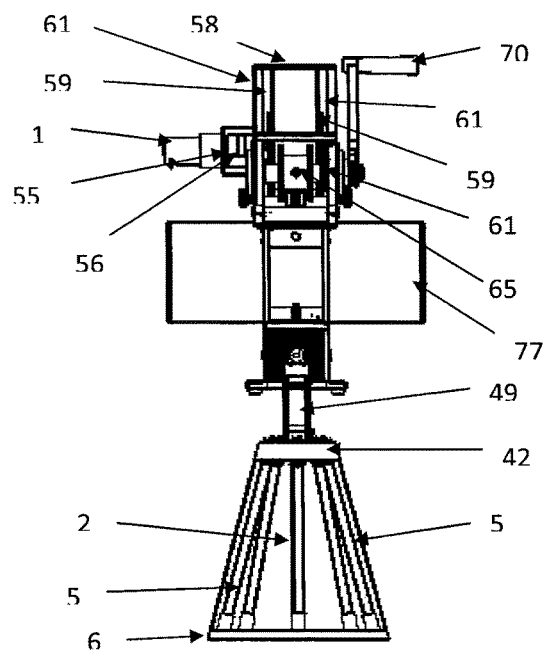
FIG. 24C schematically depicts a top view of a UV device having a telescopic arm in its horizontal position. Individual parts are shown and numbered as described in FIGS. 21A-F.
Figure 24D:
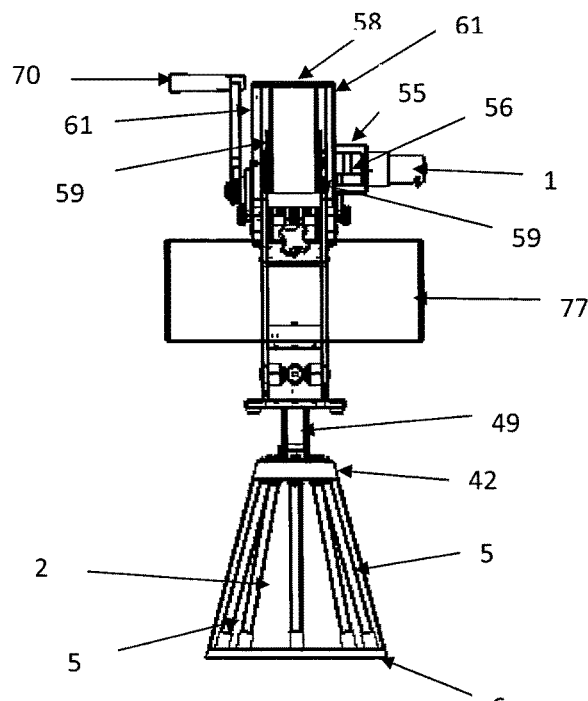
FIG. 24D schematically depicts a bottom view of a UV device having a telescopic arm in its horizontal position. Individual parts are shown and numbered as described in FIGS. 21A-F.
Figure 24E:
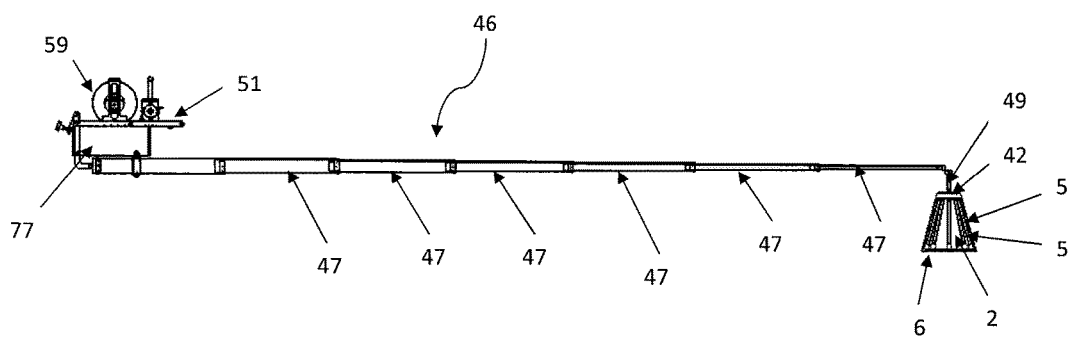
FIG. 24E schematically depicts a first side view of a UV device having a telescopic arm in its horizontal position. Individual parts are shown and numbered as described in FIGS. 21A-F.
Figure 24F:
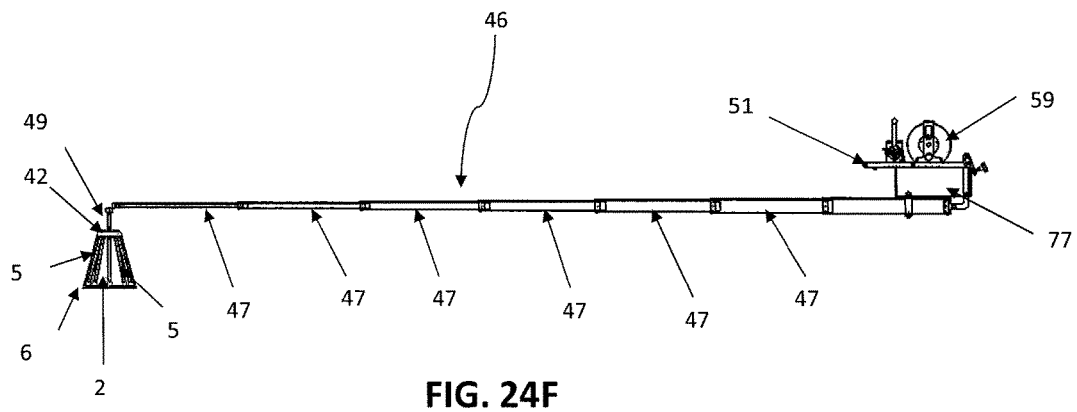
FIG. 24F schematically depicts a second side view of a UV device having a telescopic arm in its horizontal position. Individual parts are shown and numbered as described in FIGS. 21A-F.
Figure 24G:
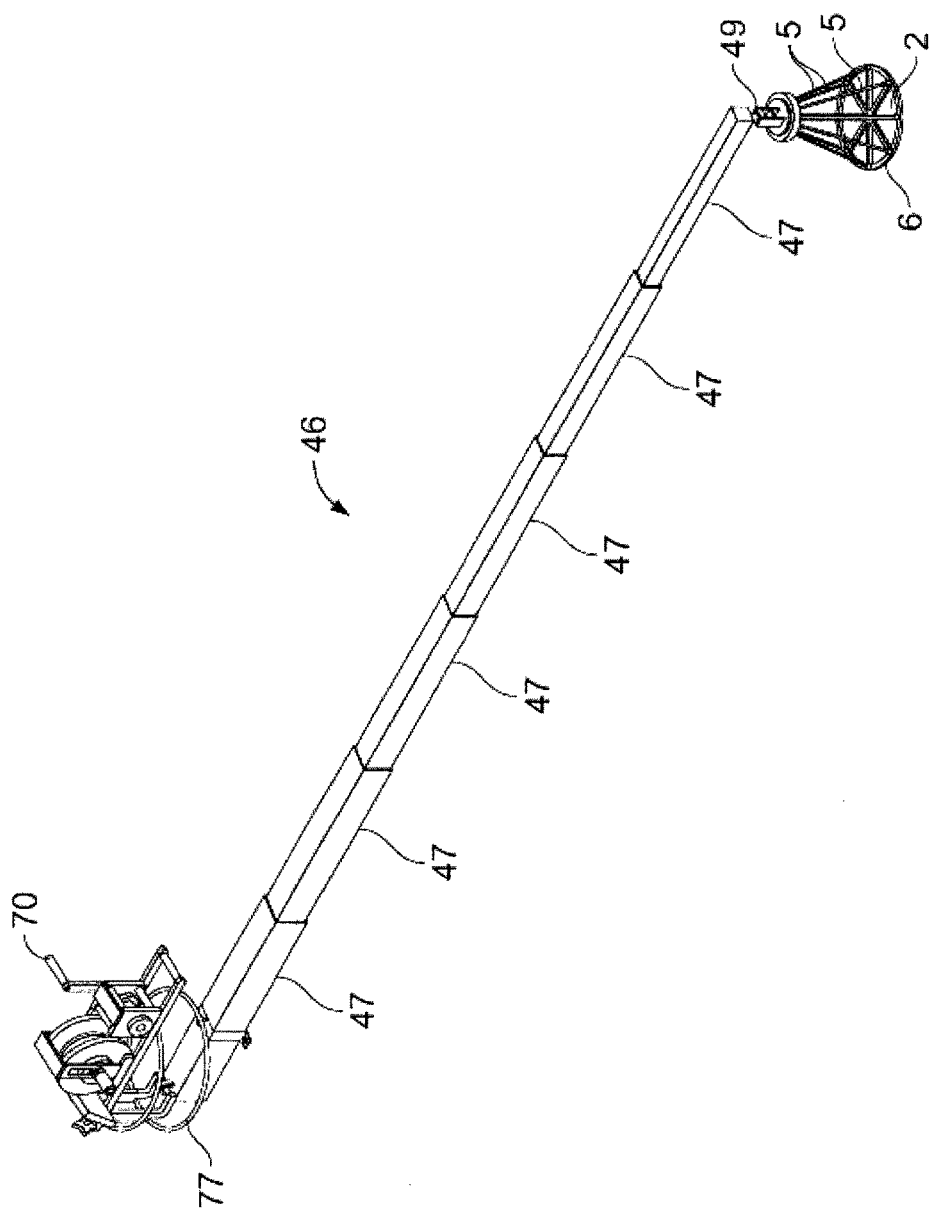
FIG. 24G schematically depicts an isometric view of a UV device having a telescopic arm in its horizontal position. Individual parts are shown and numbered as described in FIGS. 21A-F.

In some embodiments, a UV device having a telescopic arm comprises one or more of the following: a lifting eye 74 having a lifting eye base 75 and a lifting eye side support 76 (e.g., FIGS. 21E, F). In some embodiments, the lifting eye 74 is attached to the outer telescoping unit 47 and to the pulley mount arm M. The lifting eye 74 allows carrying and transporting the UV device when not in use.

1. Load Position of a UV Device Having a Telescopic Arm

Generally, the positioning of a UV light source described herein into a desired or predetermined position can be done manually, by gravity, or by using a motor.

Unless permanently attached to a container, when practicing a method of the present invention, a UV device will be attached to a container 4 In FIG. 22, the attachment is schematically shown for a UV device having a telescopic arm 46 and referred to as load position. In the load position some parts of the UV device, such as the telescopic arm 46 and the UV light source 5 are movably inserted through an opening at the container, such as a manhole or port 77 so that the telescopic arm pivot 73 is below the manhole 77.

2. Payout Position of a UV Device Having a Telescopic Arm (First Vertical Position)

Once attached to a container 4 and released from its load configuration (see, FIG. 22), the telescoping units 47 of the telescopic arm 46 can movably position the UV light source 5 (e.g., a UV lamp cluster) to any desired position within a container and for practicing the methods of the present invention. In some embodiments for practicing methods of the present invention, the UV lamp cluster is moved from its released or load configuration vertically downwards towards the bottom of the container. This vertical extension of the telescoping units 47 (units that can be moved into each other) is shown schematically in FIG. 22. One or more interior telescoping units 47 move outwards of the telescoping arm 46 into a vertical downwards position.

When practicing the invention using a UV device of the present having a telescopic arm 46, the UV device is moved from its load position into its payout position. A UV device of the present invention in its payout position is schematically shown in FIG. 23. As described herein, a means for moving the UV light source to a first vertical downwards position moves the UV source into that position. In some embodiments, the means for moving the UV light source to the first vertical downwards position is the telescopic arm 46 having telescoping units 47. In some embodiments, the means for moving the UV light source to a first vertical downwards position is gravity.

The extent of the downward movement of the UV light source is determined by a premounted radiofrequency identification chip (RFID chip) which contains information about the dimensions of the container and relays that information to a circuit board on the UV device. The extent of the first downward movement of the UV light source is determined mainly by the diameter of the container and typically is about one half of the diameter of the container. For example, if the container has a diameter of 20 feet, the extent of the first downward movement of the UV light source is about 10 feet. This will guarantee that upon moving the UV light source into the horizontal position (see below), the UV light source will be positioned in the approximate center of the container.

3. Horizontal Position of a UV Device Having a Telescopic Arm

When practicing the invention using a UV device of the present having a telescopic arm 46, the UV device (and as such, the UV light source) is moved from its payout position (i.e., first vertical downwards position) into its horizontal position. The invention contemplates various means for moving the UV light source from the first vertical downwards position to a horizontal position. A UV device of the present invention in its horizontal position is schematically shown in FIG. 24. As described herein, a means for moving the UV light source from the first vertical downwards position to a horizontal position is a winch. In some embodiments, the means for moving the UV light source from the first vertical downwards position to a horizontal position is a motorized unit, Upon activating the means for moving the UV light source from the first vertical downwards position to the horizontal position, the UV device pivots at the telescopic arm pivot 73 and the telescopic arm 46 and its telescopic units 47 move from the first vertical downwards position to the horizontal position. After positioning the UV device in its horizontal position, the UV light source faces downwards into the container and ideally is positioned within the approximate center of the container to be sterilized (see FIG. 25).

The UV light source may be activated at any time while practicing a method of the present invention. In some embodiments, when the UV light source is positioned in its horizontal position within the container, the UV light source is activated.

4. Lamp Down Position of a UV Device Having a Telescopic Arm (Second Vertical Position)

When practicing the invention using a UV device of the present having a telescopic arm 46, the UV device is moved from its horizontal position to its lamp down position, also referred to herein as second vertical downwards position. The invention contemplates various means for moving the UV light source from the horizontal downwards position to the lamp down position. A IN device of the present invention in its second vertical downwards position is schematically shown in FIG. 25. In some embodiments, the means for moving the UV light source from the horizontal position to the second vertical downwards position is a motorized unit or a motor. In other embodiments, the means for moving the UV light source from the horizontal position to the second vertical downwards position is gravity. In some embodiments, the means for moving the UV light source from the horizontal position to the second vertical downwards position is a winch.

When the UV light source is moved towards the second vertical downwards position, a cable 7 connecting the UV light source 5 with the reel assembly 54, and the reel assembly hub 60 rolls off from the reel assembly hub 60 and moves the UV light source 5 downwards towards the bottom of the container. In some embodiments, the time for the downwards movement of the UV light source is controlled by a radiofrequency identification chip (RFID chip) or tag, which contain information about the UV lamps used and dimensions of the container and relays that information to a circuit board on the UV device and/or to the motor if a motor is being used for moving the UV light source into its second vertical downwards position.

As one of ordinary skill in the art will appreciate, the larger the radius of the container is (i.e., the distance of the UV light source to the interior wall of the container), the slower the speed will be with which the UV light source is moved from its horizontal position into its second vertical downwards position. Accordingly, the larger the radius of the container is, the longer the descent will be with which the UV light source is moved from its horizontal position into its second vertical downwards position. The speed of the downwards movement or the descent of the UV light source is adjusted to guarantee that the growth of one or more microorganism located on an interior surface of the container is inhibited as described herein. In some non-limiting examples, the speed with which the UV light source is moved from its horizontal position into its second downwards vertical position is 12 inches per minute.

Once the method of the invention has been practiced, the UV device is moved from its lamp-down position (second vertical downwards position) into its horizontal position, then into its payout position (first vertical downwards position) and then into its load position. At that time, the UV device can be detached from the container or can remain attached to the container until the next use.

While moving into its second vertical downwards position, the UV light source remains activated to perform a method of the present invention, i.e., the UV sterilization of an interior surface of a container.

5. Additional Vertical Movements

In some embodiments of the present invention, a scissor boom comprises a UV lamp and a means for vertically moving the UV lamp from an upper position within a container to a lower position of the container. The same means for moving the UV lamp from the upper position within a container, room, space or defined environment to the lower position of the container, room, space or defined environment can be used to move the UV lamp from the lower position within the container, room, space or defined environment to an upper position of the container, room, space or defined environment.

In some embodiments of the present invention, a means for moving a UV lamp from an upper position within a container, room, space or defined environment to a lower position within a container, room, space or defined environment and/or from a lower position within a container, room, space or defined environment to an upper position within a container, room, space or defined environment is by using an actuator. Thus, in some embodiments, a scissor boom comprises an actuator. An exemplary scissor boom is shown in FIG. 19. A preferred means for effectuating the vertical movement of the scissor boom is an actuator.

An actuator is a mechanical device for moving a UV lamp to a desired position within a container. In some embodiments, the actuator is a linear actuator. An actuator of the present invention actuates up and down (or in a lateral direction) and moves a cross bar with it effectively extending and retracting a scissor mechanism (FIG. 19).

In some embodiments, the linear actuator is mounted to a bracket.

In some embodiments, the linear actuator 37 is a DC linear actuator. In some embodiments, the linear actuator 37 is an AC linear actuator.

The force of the actuator can vary significantly, however, will be sufficient to move a UV lamp to a desired position within a container. In some embodiments, the force of an actuator is at least 100 lbs. In some embodiments, the force of an actuator is at least 200 lbs. In some embodiments, the force of an actuator is at least 300 lbs. In some embodiments, the force of an actuator is at least 500 lbs. In some embodiments, the force of an actuator is at least 750 lbs. In some embodiments, the force of an actuator is at least 1,000 lbs. In some embodiments, the force of an actuator is at least 1,200 lbs.

6. Additional Horizontal Movements

In some embodiments of the present invention, a scissor boom comprises a UV lamp and a means for horizontally moving the UV lamp from an inner position of a container to an outer position of the container. The same means for moving the UV lamp from the inner position of the container to the outer position of the container can be used to move the UV lamp from the outer position of the container to an inner position of the container.

Effectuating a horizontal movement of a scissor boom, i.e., extending a scissor boom from its folded position to its extended position can be done manually or via a motorized unit. Manual extension of a scissor boom to a desired position can be done when the distance between the UV lamp(s) and the inner wall of the container is constant, i.e., in a container with straight walls and where the interior diameter throughout the height of a container will be constant.

Some containers, such as wooden wine barrels, however, often do not have straight walls. In those containers, the interior diameter of a container varies. The diameter typically is smallest at the top and bottom of the container and the greatest at the middle of the container. For those containers a controllable motorized extension and retraction of the scissor boom is preferred.

Thus, in some embodiments extending a scissor boom to a desired position is performed by a motorized unit, also referred to as a motor unit. In some embodiments of the present invention, a scissor boom comprises a motor unit for effectuating the horizontal movement of a UV lamp mounted to a second end of the scissor boom to an inner wall of a container. The motor unit then essentially expands the scissor units of the scissor boom so that the UV lamp(s) mounted at the opposite end (outer end) of the scissor boom than the motor unit can be positioned at a desired position within a container. Upon activation of the scissor mechanism, the one or more UV lamps attached to the outer end of the scissor boom move from its (their) folded position (FIG. 19A) towards an extended position (FIG. 19B). This movement is horizontally towards the inner wall of a container (and backwards to its folded position). In its extended position, the UV lamps of the scissor boom are close to the inner wall of the container so that when activated (switched on), the desired effect on the microorganisms present on the wall of the container will be achieved (as described herein).

In some embodiments, the motorized unit is attached to the first end of scissor boom. In some embodiments, a sensor is attached to the scissor boom. The sensor can be attached to the second end of the scissor boom, e.g., in close proximity to a UV lamp. In some embodiments, the sensor, such as a laser range finder described herein, is attached to sliding rail 40. The sensor measures the distance from the UV lamp(s) to the wall of the container. The sensor is connected to the motorized unit for extending and retracting the scissor boom. The sensor effectively guarantees that the UV lamp(s) are positioned in the same distance to the inner wall of the container. In case where the sensor senses that the UV lamp(s) is too far away from the inner wall of the container, it sends a signal to the motor unit, which then extends the scissor mechanism accordingly allowing the UV lamp(s) to be moved closer to the inner wall of the container until a desired position is achieved. Likewise, should the sensor sense that the UV lamp(s) are too close to the inner wall of the container, it sends a signal to the motor unit, which then retracts the scissor mechanism accordingly allowing the UV lamp(s) to move further away from the inner wall of the container until a desired position is achieved. Thus, the sensor is connected to the motor unit.

A preferred means for effectuating the horizontal movement of the scissor boom is an actuator.

7. Circular Movement

In some embodiments of the present invention, a scissor boom comprises a UV lamp and a means for circular moving one or more UV lamp(s) from one position within a container, room, space or defined environment to another position of the container, room, space or defined environment. A motorized unit (motor unit) can be used to effectuate the circular movement of the one or more UV lamp(s). Preferably, a sensor is attached to the second end of the scissor boom and sends signals to a second motorized unit (motor unit) for extending and/or retracting the scissor mechanisms to adjust for the respective distance between the UV lamp(s) and the inner wall of the container, room, space or defined environment.

A scissor boom can be mounted at its first end to an inner wall of a container, room, space or defined environment or to a (removable) bracket as shown e.g., in FIG. 10 for a container. When mounted to an inner wall of a container at a first position or a bracket, the circular motion of the scissor boom is somewhat limited. The UV lamp(s) will, for example, not cover, and thus, not efficiently sterilize, the wall part of the inner container to which the scissor boom is mounted, i.e., the first position. Microorganisms present at around the first position may not be growth inhibited to the extent desired. This limitation can easily be overcome by mounting the scissor boom to the opposite position of its first mounting position, i.e., into a second position, and repeat the UV sterilization process.

To overcome the need for repositioning the scissor boom and to permit a complete circular rotation, in some embodiments of the present invention, a scissor boom is mounted to a central post, which can be positioned in the center of a container. In this embodiment, the circular motion of the scissor boom is such that it allows to cover 360° of the container, room, space or defined environment i.e., the complete inner walls of the container, room, space or defined environment. The central post may reach to the bottom of the container and/or may be connected to a lid of the container or, alternatively to a bracket resting on top of the container for stabilization and desired positioning.

In some embodiments of the present invention, the circular movement of a scissor boom (when extended) is done manually by pivoting the UV device. The UV device may be set in a position upon installation in the center of a container, room, space or defined environment that will allow the scissor boom to extend from the center of the container, room, space or defined environment to the outer region of the container, room, space or defined environment. Alternatively, the UV device may be set in a position upon installation at a wall of a container, room, space or defined environment that will allow the scissor boom to extend from the wall of the container, room, space or defined environment to the outer region of the container, room, space or defined environment.

The speed of the circular motion of the scissor boom is adjusted to obtain a desired effect, i.e., the growth inhibition of microorganisms present on the inner wall of the container, or in a desired area in the room, space or defined environment.

N. UV Device UV55

In some embodiments of the present invention, a UV device is a UV device referred to herein as Model UV55. A UV55 device is schematically depicted in FIGS. 28 and 29 and explained in detail below and herein.

UV device UV55 comprises an 18" single ended low pressure mercury lamp 5 supplied by Steril-Aire (FIG. 28H). The UV lamp 5 is attached to the base of a cylindrical plastic (Delrin) central sleeve 12 by a UV lamp socket or adaptor 94 (FIG. 28G) The UV lamp pins 93 plug into the UV lamp socket or adaptor 94 (FIGS. 28 G, H) The UV lamp socket or adaptor 94 is attached to a cylindrical central sleeve 12 (FIG. 28G).

The cylindrical central sleeve 12 comprises two cavities, a circuit board cavity 99 and a power supply cavity 100 (FIG. 28E). A power supply 96 resides within the power supply cavity 100 (FIG. 28E). Within the power supply cavity 100 also reside a connector and wires 105 from the power supply 96 to the UV lamp 5 (FIG. 28E).

Within the circuit board cavity 99 reside an AC to DC power converter 101, electronic components 102, a circuit board 103 as well as a connector and wires 104 from on/off/reset switch 85 and optical switch 98 (FIG. 28E)

Also within the aforementioned cavities 99 and 100 are connector and wires 106 connecting the power supply 96 and the AC to DC power converter 101 (FIG. 28E)

Cavities 99 and 100 can be accessed through a power supply access plate 97, which is screwed by a plurality of screws to the central sleeve 12 to cover the cavities 99 and 100 and protect the power supply 96, circuit board 103 and other components residing within the cavities 99 and 100 (FIGS. 28A, E).

The top of the UV device embodiment UV55 comprises a hanging hook 84, and an on/off/reset button 85 (FIGS. 28A, B, D, F). The on/off/reset button 85 activates and terminates the UV device. The hanging hook 84 is attached to a handle cap 92, which forms the top part of a handle 91 (FIGS. 28A, B, D, F). Handle 91 is a narrower extension of the central sleeve 12 (FIGS. 28A, B, D, F).

At the lower end of handle 91 is a metal disc 89 protecting a translucent blue plastic ring 87, which may or may not comprise a plurality of LED lights inside (FIGS. 28A, B, D-F). Partially protruding from the translucent blue plastic ring 87 is an entrance for an external power cord 90 (FIGS. 28A, B, D-F).

A stainless steel housing 2 slides over the cylindrical sleeve 12 however does not extend beyond the plastic blue translucent ring 87 (FIGS. 28A, C, D-G). When the unit is not mounted on the lid 29 of a container 4 (such as a keg, a drum, a barrel, a porta tank, etc.) the stainless steel housing 2 is extended to cover the length of the UV lamp 5 so that none of it is exposed or visible from the outside when the UV device stands on its base plate 10 (FIG. 28A).

A stopping plate 88 is mounted at the bottom of the central sleeve 12 to prevent the steel housing 2 from sliding off (FIG. 28C).

A plastic (Delrin) base plate 10 is attached to the bottom of the stainless steel housing 2. This provides a stable platform for the unit to stand upright when not in use.

The UV55 device comprises a central sleeve tightening knob 86 on the side of the stainless steel housing 2. It locks the housing 2 into a position on the central sleeve 12 at a predetermined position selected by a user. It is tightened by screwing clockwise and loosened by unscrewing counter clockwise. When central sleeve tightening knob 86 is tightened on the stainless steel housing 2 in the fully extended position (housing 2 positioned at the bottom part of central sleeve 12; see FIG. 28A), the UV device can be stood upright on the plastic base plate 10. When the central sleeve tightening knob 86 is loosened, the UV device can be mounted over any 2-3" lid opening 29 and the plastic cylindrical sleeve 12 descends through the steel housing 2 (see FIGS. 28D, 29). Since the UV lamp 5 is attached to the bottom of the central sleeve 12 it will then be residing within the container 4 (FIG. 29).

As the stainless steel housing 2 passes over the optical switch 98 within the plastic sleeve 12 it starts a timer controlled by the circuit board 103. As the timer sequence begins, acoustic and visual signals are generated. The acoustic signal is made audible by an acoustic speaker residing in the handle cap 91. The optical switch does, however, not start or stop the activation of the UV device. The visual signal leads to the intermittent blinking of a plurality of LED lights residing behind the translucent plastic ring 87. The blinking of the LED lights indicates how much time has elapsed, i.e., the time a sterilization cycle has been activated.

O. UV Device BM1

In some embodiments of the present invention, a UV device is UV device depicted in FIGS. 38-41 and referred to herein as UV device Model BM1 ("BM1"). This UV device embodiment comprises a housing 2, which is attached on top of a frame 6 (see FIGS. 38A, B). The housing 2 harbors and shields a single UV lamp 5 (see FIGS. 38A, B). As such, in its undeployed state but attached to a container 4, the UV light source is positioned in a horizontal position with respect to the orientation of the container 4. The housing 2 conforms to the shape, size and length of the UV lamp 5 (see FIGS. 38A, B)

The frame 6 comprises a first side and a second side, which are connected to each other, e.g., by cross member support bars 71 (see FIGS. 38A, B). The frame 6 of BM1 may be described as having an L-shaped form wherein a motorized unit 1, a mounting bracket 3, a reel assembly 54, reel assembly flanges 59, a handle 91, a cable tightening spring 123 may be attached to the shorter arm of the L (see FIGS. 38A, B). The housing 2, a second cable guide wheel 121 may be attached to the longer arm of the L (see FIGS. 38A, B). To provide for a light-weight frame 6, in some embodiments, the frame 6 comprises one or more openings 122 (see FIGS. 38A, B). The frame 6 can be made of various materials. Non-limiting materials include aircraft aluminum and stainless steel. It can also be made from composite materials, carbon fiber, and polymers.

UV device model BM1 comprises a handle 91 attached to frame 6. Handle 91 conveniently provides for transportation (e.g., hand carrying) and storing BM1. In addition to the handle 91, BM1 also comprises a mounting bracket 3 as a means for attaching it to an opening (e.g., a manhole or port 77) of a container 4.

The UV lamp 5 of UV device Model BM1 is attached to a UV lamp socket/adaptor 94. UV lamp socket/adaptor 94 is attached to a cable 7, which in turn is attached to a reel assembly 54 (being flanked by reel assembly flanges 59). The cable 7 should not be too thick; otherwise the bend radius will too large and it will be difficult to coil the cable 7 and store it in addition to being too heavy. The cable 7 (and other parts employed in the UV devices described herein) should also be UV resistant, preferably also water resistant.

BM1 comprises two cable guide wheels, a first cable guide wheel 120 and a second cable guide wheel 121. The first cable guide wheel is positioned in close proximity to the reel assembly 54 and may have a single track for guiding cable 7. The second cable wheel 121 is positioned at the end of the long arm of the L-shaped frame 6 and may comprises a track 124.

Cable 7, unwinding from reel assembly 54 is guided onto a track on the first cable guide wheel 120. Upon releasing UV lamp 5 from the housing 2 (see below), UV lamp 5 and cable 7 move onto a first track 124 of the second cable guide wheel 121. The movement of the UV lamp 5 out of the housing 2 and onto the second cable wheel guide is schematically depicted in FIG. 40A. Upon further moving out of the housing 2, UV lamp 5 eventually completely passes over the second cable wheel guide 121 and the cable 7 continues to slide on top of the first track 124 of the second cable wheel guide 121 (see FIG. 40B). Thereby the UV lamp 5 is moved from a horizontal position (see FIG. 40A) into a first vertical position (see FIG. 40B). Upon further descending UV lamp 5 downwardly into the interior of a container, cable 7 further slides on top of the first track 124 of the second cable wheel guide 121 and the UV lamp 5 moves from the first vertical position (see FIG. 40B) downwardly into a second vertical position (see FIG. 40C).

In some embodiments of UV device Model BM1, the UV lamp 5 within the housing 2 is spring-loaded. Upon opening the spring 43, UV lamp 5 begins moving out of the housing 2. The moving of UV lamp 5 out of the housing 2 may be further aided a cable tightening spring 123 (see FIGS. 38A, B).

In some embodiments of UV device Model BM1, a motorized unit 1 activates the reel assembly 54. In some embodiments of UV device Model BM1, the UV device comprises an additional motor 133, which drives its torque perpendicular to its axis (see FIG. 39B).

FIGS. 39A-C schematically depict preferred, however, non-limiting dimensions of UV device Model BM1. For example, handle 91 may be about 20" in width and about 1" in diameter (see FIG. 39A). The first side and the second side of frame 6 may be apart by about 1.75" (see FIG. 39B). The height of UV device Model BM1, measured from the handle 91 in its vertical position and the center of the second cable wheel guide 121 is about between 33" and 34" (see FIG. 39C) The length of UV device Model BM1, measured from the outmost part of frame 6 at the lower end of its L-shaped form and the center of the second cable wheel guide 121 is about between 77" and 78" (see FIG. 39C). The second cable wheel guide 121 has a diameter of about between 7" and 8" (see FIG. 39C). Having provided the above dimensions, one of ordinary skill in the art can determine dimensions of other parts schematically depicted in FIGS. 39A-C, in addition to conveniently vary the dimensions given in FIGS. 39A-39C.

UV device Model BM1 is designed to be attached to an opening of a container 4, preferably to an opening, e.g., a manhole or port 77 of a container 4 located on the upper perimeter of the container 4 (see FIG. 41). The attachment of BM1 to the opening of the container is done using the mounting bracket 3. Once attached, the device is activated and the UV lamp 5 moves out of the housing 2 as described herein. Upon completion of the sanitization cycle, the UV lamp 5 is moved back into its undeployed configuration (see FIGS. 38A, B) by reversing the movements described above. The movements may be controlled by a motorized unit 1.

While the above described various parts and features of UV device Model BM1 (see FIGS. 38A, B), one of ordinary skill in the art will appreciate that any arrangement or positioning of parts described can be varied without deviating from the scope of the invention. In addition, UV device Model BM1 depicted schematically in FIGS. 38-41 may comprise any additional component described herein, such as a circuit board, etc.

P. UV Device BM2

In some embodiments of the present invention, a UV device is UV device depicted in FIGS. 42-45 and referred to herein as UV device Model BM2 ("BM2"). This UV device embodiment comprises a housing 2, which is attached to a pivot arm 118 (see FIGS. 42-45). The pivot arm 118 is attached to a frame 6 (see FIGS. 42-45). The housing 2 harbors and shields a UV lamp cluster comprising eight (8) UV lamp 5 (see FIGS. 42-45). In its undeployed state but attached to a container 4, the UV light source is positioned in a horizontal position with respect to the orientation of the container 4. The housing 2 conforms to the shape, size and length of the UV lamp cluster (see FIGS. 42-45). In the UV device embodiment shown in FIGS. 42-45, the housing 2 does not completely shield the UV lamp cluster, but rather provides a three ring like structure surrounding the UV lamp cluster. In other embodiments, the housing 2 completely shields the UV lamp cluster.

The frame 6 comprises a first side and a second side, which are connected to each other, e.g., by cross member support bars 71 (see FIGS. 42-45). The frame 6 of BM2 may be described as having a bended L-shaped form. To provide for a light-weight frame 6, in some embodiments, the frame 6 comprises one or more openings 122. (see FIGS. 42-45)

In some embodiments of the UV device Model BM2, a box 127 (also referred to as control box) is positioned at the end of the short arm of the "L" of frame 6. Box 127 can either be permanently attached to the UV device or be attached removably via cables or plugs. Box 127 may include other parts and components of a UV device that may be desirably not be directly attached to the frame 6. In some embodiments, box 127 comprises a circuit board having a functionality as described herein and being connected to the UV lamp ballast/power supply and motor(s) through electrical cables, wires or connectors. In some embodiments, box 127 comprises a ballast/power supply connected to the UV lamps through electrical cables, wires or connectors. In some embodiments box 127 comprises a motor controlling extension, descent, ascent, and other movements of a UV light source, the motor being connected by electrical cables or connectors to a UV light source (multiple electrical cables, wires or connectors could be integrated and combined into a singular one). The motor is also controlled by the circuit board through electrical cables, wires or connectors. In some embodiments, box 127 comprises a touch screen user interface. The touch screen user interface is connected to the circuit board by electrical cables, wires or connectors. In some embodiments of, box 127 comprises a wireless communication device. A wireless communication device includes, but is not limited to, e.g., a wireless transponder and/or transceiver to send or receive wireless signals to a user. The wireless communication device is connected to the circuit board through electrical cables, wires or connectors. In some embodiments, box 127 comprises part selected from the group consisting of a UV detector, a range-finding device, a reel assembly, reel assembly flanges, an optical switch, an AV to DC power converter, and an electronic component.

UV device model BM2 comprises a motorized unit 1 attached to frame 6 or box 127 (see FIGS. 42, 43)

BM2 also comprises a mounting bracket 3 as a means for attaching it to an opening (e.g., a manhole or port 77) of a container 4 (see FIGS. 42-45).

On their first end, the UV lamps 5 of UV device Model BM2 are attached to a UV lamp socket/adaptor 94 (see FIGS. 42, 45) UV lamp socket/adaptors 94 are attached to an upper plate 42, which in turn is attached to a cable 7. Cable 7 is attached to a reel assembly 54 located within box 127 (as such, reel assembly 54 is not shown in FIGS. 42-45). On their second end, the UV lamps 5 are attached to a lower plate 45. In some embodiments, attachment of the UV lamps to the lower plate 45 is by springs 43 (see FIG. 45).

BM2 comprises two or more cable guide wheels, a first cable guide wheel 128 and a second cable guide wheel 130, and optionally, a third cable guide wheel 132 (see FIGS. 42, 43, 45). The first cable guide wheel 128 is positioned in between the first and second sides of frame 6. The first cable guide wheel 128 has a first track 129, on which the cable 7 can slide (see FIGS. 42-45). The second cable wheel 130 is positioned at the upper end of the pivot arm 118 and comprises a second track 131 on which cable 7 can slide (see FIGS. 42-45). A third cable wheel guide may be positioned in close proximity to the reel assembly 54 and has a third track for guiding cable 7 (see FIGS. 42, 43, 45).

Cable 7, unwinding from reel assembly 54 is guided onto the first track on the first cable guide wheel 128, further onto the second track on the second cable guide wheel 130 and to its attachment at an upper plate 42, to which the UV light source is attached (see FIGS. 42-45). In some embodiments, cable 7 slides onto a third track of a third cable guide wheel 132, as schematically depicted in FIGS. 42, 43, and 45.

When UV device Model BM2 is attached to an opening of a container 4 in its undeployed position, the UV light source will be positioned in a horizontal position with respect to the container 4. BM2 comprises a pivot arm 118 as a means for moving the UV light source from the horizontal position (see FIG. 42) into a first vertical position (see FIG. 43). Upon moving the pivot arm, the housing 2, which is attached to the pivot arm also moves into a first vertical position and the second cable guide wheel 130 moves into an upwardly position (compare FIG. 42 to FIG. 43). As schematically depicted in FIG. 44, after attaching the UV device to an opening (e.g., manhole or port 77) of a container 4 and upon further unwinding of rope 7 from a reel assembly, the UV light source (in BM2 the UV light source is a cluster of eight UV lamps 5) is released from its housing 2 and moves from the first vertical position downwardly into a second vertical position. At any time during the downwardly movement to its second vertical position and upon release from its housing 2, the UV lamps 5 of the UV lamp cluster may be fully deployed and be positioned into an angled position with respect to each other (see FIG. 45). A preferred mechanism to position the UV lamps 5 in an angled arrangement is using springs 43.

Upon releasing UV lamp 5 from the housing 2, cable 7 slides onto a first track 129 of the first cable guide wheel 128 and onto the second track 131 of the second cable wheel guide 130 as schematically depicted in FIGS. 44 and 45.

In some embodiments of UV device Model BM2, a motorized unit 1 activates a reel assembly. In some embodiments of UV device Model BM2, the UV device comprises an additional motor 133, which drives its torque perpendicular to its axis (similar to UV device Model BM1 shown in FIG. 39B).

UV device Model BM2 is designed to be attached to an opening of a container 4, preferably to an opening, e.g., a manhole or port 77 of a container 4 located on the upper perimeter of the container 4 (see FIG. 44). The attachment of BM2 to the opening of the container is done using the mounting bracket 3. Once attached, the device is activated and the UV lamps 5 move out of the housing 2 as described herein. Upon completion of the sanitization cycle, the UV lamps 5 are moved back into their undeployed configuration (see FIG. 42) by reversing the movements described above. The movements may be controlled by a motorized unit 1 and/or motor 133.

While the above described various parts and features of UV device Model BM2 (see FIGS. 42-45), one of ordinary skill in the art will appreciate that any arrangement or positioning of parts described can be varied without deviating from the scope of the invention. In addition, UV device Model BM2 depicted schematically in FIGS. 42-45 may comprise any additional component described herein, such as a circuit board, etc.

Q. UV Device BM3

In some embodiments of the present invention, a UV device is UV device depicted in FIGS. 46-48 and referred to herein as UV device Model BM3 ("BM3"). This UV device embodiment may comprise an optional housing 2. The embodiments of UV device Model BM3 shown in FIGS. 46-48 do not include a housing 2. In embodiments, wherein UV device Model BM3 comprises a housing 2, the housing 2 may be manually removed from the device prior to is use.

FIGS. 46A-E schematically depict UV device BM3 from several views.

BM3 comprises a frame 6 to which other parts of the UV device are attached. The frame 6 comprises a first side and a second side, which are connected to each other, e.g., by cross member support bars 71 (not shown in figures). The frame 6 of BM3 may be described as having a long rectangular shaped form and having two ends, a first end and a second end (see FIGS. 46-48). To provide for a light-weight frame 6, in some embodiments, the frame 6 comprises one or more openings 122 (see FIG. 47C).

A handle 91 is attached to the first end of frame 6 In combination with the wheels 114 (see below), the handle allows easy maneuvering from a first position into a second position within a container 4, in addition to convenient transportation (e.g., hand carrying) and storing BM3.

At both ends of the frames are support structures attached which comprise wheels 114, preferably two wheels 114 at either side of the support structure so that UV device Model BM3 comprises a plurality of wheels 114, more specifically, four (4) wheels 114 (see FIGS. 46-48) Preferably, the plurality of wheels are swiveling so that the device can be easily maneuvered around from a first position into a second position within a container 4.

A pivot arm 118 is attached to the second end of the frame 6. The pivot arm 118 comprises two ends, a first end and a second end. The first end of the pivot arm 118 is attached to the second end of frame 6. The second end of the pivot arm 118 is attached to central post 16.

Attached to the pivot arm 118 is a central post 16. The central post 16 comprises two ends, a first end and a second end. The first end of the central post 16 is attached to the second end of the pivot arm 118. The second end of the central post 16 is attached to an upper plate 42 (see FIGS. 46-48). In some embodiments of the UV device BM3, the central post 16 is extendable so that the upper plate 42 and the UV lamps 5 attached thereto can be moved further upwardly. A central post 16 within UV device Model BM3 can also have an arrangement and configuration as schematically depicted in FIGS. 6-12

Attached to the upper plate 42 is at least one UV lamp 5. In some embodiments of UV device Model BM3, a UV lamp cluster is attached to the upper plate 42. For example, FIGS. 46-48 show the attachment of eight (8) UV lamps to the upper plate 42 of BM3. As with other UV devices described herein, the attachment of UV lamps 5 to the upper plate occurs via UV lamp socket/adaptors 94 (see FIG. 47A)

FIGS. 47A-C schematically depict preferred, however, non-limiting dimensions of UV device Model BM3. For example, deployed UV lamps 5 may be arranged having a diameter of about 40" (see FIG. 47A). The wheels 114 at one end of the frame and attached to the support structure may be apart by about 17" and the upper plate may be between 10" and 11" (see FIG. 47B). The height of UV device Model BM3, measured from the top of the upper plate 42 to the center of wheel 114 is about between 77" and 78" (see FIG. 47C). The length of UV device Model BM3, measured from the outmost part of pivot arm 118 in its upright position to the handle 91 (including) is about 90" (see FIG. 47C). The wheels 114 have a radius of about 1" (see FIG. 47C). The height of the handle 91 to the center of wheel 114 is about between 17" and 18" (see FIG. 47C). Having provided the above dimensions, one of ordinary skill in the art can determine dimensions of other parts schematically depicted in FIGS. 46-48 in addition to conveniently vary the dimensions given in FIGS. 46-48.

In some embodiments of UV device Model BM3, a motorized unit 1 activates pivot arm 118. In some embodiments of UV device Model BM3, the pivot arm is moved manually from its horizontal position into its vertical position.

UV device Model BM3 is designed to be moved inwardly through an opening of a container 4, preferably through an opening, e.g., a manhole or port 77 of a container 4 located at a lower sidewall of a container (see FIG. 48). When moved inwardly into a container 4, the UV light source of UV device Model BM3 resides on top of frame 6, i.e., in a horizontal position (see FIG. 48A). Upon moving the pivot arm 118 from its horizontal position into a vertical position, the UV lamps 5 are also moved from their initial horizontal position into a first vertical position (see FIG. 48B). Upon extending central post 16 upwardly into the interior of a container 4, the UV lamps 5 move from the first vertical position (see FIG. 48C) upwardly into a second vertical position (see FIG. 48D).

Upon completion of the sanitization cycle, the UV lamps 5 are moved back into their undeployed configuration (see FIG. 48A) by reversing the movements described above. The movements may be controlled by a motorized unit 1.

While FIGS. 46-48 schematically depict the UV lamp cluster of UV device Model BM3 open in a con-like fashion and having the UV lamps 5 pointed downwardly, in some embodiments of UV device Model BM3, the opening of the UV lamp cluster and deployment of UV lamps 5 is inverted so that the UV lamps 5 open in a cone-like fashion, but face upwardly. A similar configuration and mode of opening is schematically depicted in FIGS. 7, 32 and 33. Such an upwardly facing configuration can be accomplished, e.g., by attaching the upper plate 42 to the pivot arm 118. Upon erecting pivot arm 118 into its vertical position, the upper plate 42 to which the UV lamps 5 are attached will also be moved into a first vertical position, wherein the UV lamps are facing upwards with respect to the positioning of the upper plate 42. In that situation, the upper plate 42 may be better referred to as a lower plate. As depicted in FIG. 48D, upon extension of central post 16, the UV cluster/UV lamps 5 can then be further moved from the first vertical position to a second vertical position.

While the above described various parts and features of UV device Model BM3 (see FIGS. 46-48), one of ordinary skill in the art will appreciate that any arrangement or positioning of parts described can be varied without deviating from the scope of the invention. In addition, UV device Model BM3 depicted schematically in FIGS. 46-48 may comprise any additional component described herein, such as a circuit board, etc.

R. Additional UV Devices

In some embodiments of the present invention, a UV device is UV device depicted in FIG. 30. This UV device embodiment comprises a housing 2, a UV lamp cluster line 111 attached to a UV lamp cluster. This UV device embodiment further comprises an anchor connector 109 connecting the housing 2 to an anchor 107. An anchor line 108 connects the anchor 107 with the housing 2. The anchor 107 serves to stabilize the lamp cluster as it moves upwardly and downwardly throughout a container 4. The UV device depicted schematically in FIG. 30 may comprise any additional component described herein.

In some embodiments of the present invention, a UV device is UV device depicted in FIG. 31. This embodiment describes a UV device similar to the UV device UV55 described above, however, inverted. The UV lamp 5 is inserted into an opening of a container 4 from the bottom of the container (FIG. 31A). The base plate 10, here a support stand, is attached to the central sleeve 12. A housing 2 slides over the central sleeve 12. In this embodiment, the housing 2 is spring loaded such that, as soon as UV lamp 5 is movably inserted into the container 4 (a barrel is shown in FIG. 31), the housing 2 retracts to cover the central sleeve 12 (FIG. 31B). As the unit is removed from the container 4, a spring forces the housing 2 to slide over the UV lamp 5. The UV device depicted schematically in FIG. 31 may comprise any additional component described herein.

In some embodiments of the present invention, a UV device is UV device depicted in FIG. 32. This embodiment describes a UV device that is placed in the center of a container 4 and mounted a top of a base plate 10, here, a tripod-like support stand. The support stand supports a housing 2 and a central sleeve 12 within the housing 2 that moves upwardly and downwardly. In some embodiments, this UV device comprises a UV lamp 5. In some embodiments, this UV device comprises a UV lamp cluster. The UV device depicted schematically in FIG. 32 may comprise any additional component described herein.

In some embodiments of the present invention, a UV device is UV device depicted in FIG. 33. This embodiment describes a UV device comprising a telescoping horizontal arm 113 that enters the container 4 through an opening on the side of the container 4. As described herein, instead of a single telescoping horizontal arm 13, which can be of various length (depending on the size of the container into which the UV device is being inserted), the UV device may also have one more of the telescoping arms 47, the form and function of which has been described herein. Users are protected from UV exposure by a bracket 3 fitting over the opening. A vertical housing 2 is attached to a central sleeve 12, which can be moved upwardly and downwardly in a vertical axis. In some embodiments, this UV device comprises a UV lamp 5 attached to the central sleeve 12. In some embodiments, this UV device comprises a UV lamp cluster attached to the central sleeve 12. The UV device depicted schematically in FIG. 33 may comprise any additional component described herein. The entire UV device can be transported on a movable object 112 comprising wheels 114. The wheels are attached to supports attached to the object 112. As an non-limiting example, four supports are schematically depicted in FIG. 33. In some embodiments, the length of the supports is adjustable so that the same movable object 112 can be used to introduce a UV device in to containers having an opening a different positions. The horizontal arm 113 may be rotatably attached to the object 112 so that it can turn the UV device once inserted into the container into different angle positions and also move it upwardly, downwardly, and horizontally into any desired position.

In some embodiments of the present invention, a UV device is UV device depicted in FIG. 34A. This embodiment describes a UV device that is placed in top of a container 4 as schematically shown in FIGS. 34B and 34C. The UV device comprises a housing 2 having two arms, a first arm and a second arm (both indicated by 2 in FIG. 34A). The first arm may be in a fixed, non-movable position, whereas the second arm may be movably attached to the first arm. The two arms are connected to each other through a pivot point 118. This connection allows the two arms to provide various angles between them. When not in use, the second arm resides within the first arm. The second arm comprises an opening through which a power cord 90 (FIG. 34A) or any other rope or string 7 may be guided which may be attached to a UV lamp 5. As schematically depicted in FIG. 34A, a UV lamp 5 resides within the second arm, which partially surrounds the UV lamp 5 (when not in use and the power cord 90 is completely retracted) and which releases the UV lamp 5 upon the twist lock 116 releasing the power cord 90. The release of the power cord 90 (or string or cable or rope 7) is controlled by a twist lock 116. As one of skill will appreciate upon releasing the power cord 90 (or string or cable or rope 7), the two arms of the housing 2 separate from each other. Approaching an about 90 degree angle between the two arms of the housing 2, the UV lamp will be positioned furthest away from the fixed arm of the housing 2 (schematically shown in FIGS. 34B and 34C). In some embodiments, this UV device comprises a power cord 90 connected to the UV lamp 5 and a string or cable or rope 7 attached to the second arm of the housing 2 and the twist look 116. In this embodiment movement and positioning of the UV lamp 5 within a container can be controlled in two ways. First, upon release of the rope, cable or string 7 from a twist look 116, the second arm moves from a vertical position to an angle position (between about 0 degree and 90 degree) without releasing the power cord 90 and the UV lamp 5. The extent to which the rope, cable or string is being released determines, as one of ordinary skill in the art will appreciate, the positioning of the UV lamp 5 within the diameter of the container 4. The second movement controls the vertical positioning of the UV lamp 5 within the container 4 as is shown schematically in FIG. 35. Upon release of the power cord 90 from the twist look 116 (which can be the same or a different twist look releasing string or cable or rope 7) the UV lamp 5 moves downwardly in the container 4 towards the bottom of the container 4. As described herein, when sterilizing a wide container (i.e., a container having a large diameter), the arms of the housing 2 may be chosen to have a length permitting the positioning of the UV lamp 5 within the center of the container 4. In some embodiments, this UV device comprises a UV lamp 5. In some embodiments, this UV device comprises a UV lamp cluster. The UV device depicted schematically in FIG. 34 may comprise any additional component described herein.

In some embodiments of the present invention, a UV device is UV device depicted in FIG. 35. This embodiment describes a UV device with similar functions as the UV device shown in FIG. 34A. In the UV device schematically depicted in FIG. 35, a central sleeve 12 slides movably over the housing 2. The housing 2, similarly to that of FIG. 34 comprises two arms. The two arms are attached to each other by a pivot point 118. In this embodiment, the first arm may be attached to the UV device so that it is rotatable permitting the positioning of the UV lamp 5 (upon lowering the second arm as, e.g., described herein) into various horizontal positions (see also FIGS. 8-11, 15)

In some embodiments, this UV device comprises a UV lamp 5. In some embodiments, this UV device comprises a UV lamp cluster. The UV device depicted schematically in FIG. 32 may comprise any additional component described herein.

One of ordinary skill in the art will appreciate that the parts described herein, in particular the parts controlling the movement and positioning of a UV light source within the interior of a container provide various means for moving and positioning the UV light source, such as, a means of positioning the UV light source within the central axis of a container, a means for tilting the UV light source from a vertical axis to a horizontal axis at an upper position within the container, a means for returning the UV light source from a horizontal axis to a vertical axis at an upper position within the container, a means for lowering or raising the UV light source within the central axis of the container, a means for stopping the UV light source at a pre-determined position along the central axis within a container, a means for tilting the lamp cluster from a vertical position to a horizontal position at a lower position within a container, a means for returning the UV light source from a horizontal axis to a vertical axis at the lower position within a container, and a means for returning the UV light source from a vertical position to a horizontal position within a container.

III. Containers

In some embodiments, a UV device, preferably a UV light source, more preferably a germicidal UV light source, is introduced into a container. In some embodiments, a container is exposed to UV radiation. A container accepts a UV light source for the purpose of sterilization of the interior of the container, including any and all objects, fluids, materials, and surfaces contained within the interior of the container. In some embodiments, the objects, fluids, materials, and surfaces within the interior of the container are contained within the container temporarily. In other embodiments, they are contained within the container permanently.

The present invention provides a variety of containers. Containers, include, but are not limited to a vat, a silo, a tub, a basket, a case, a box, a barrel, a storage bin, a barrel, a keg, a tank (e.g., a Porta tank), a container for biological fluids, a beverage container, and an aquarium.

A container for biological fluid includes, but is not limited, to a container for blood, a container for blood products, a container for a fermentation product, a container for a cell culture product, or a container for a biotechnology product. In some embodiments, a fermentation product is an alcoholic beverage. In some embodiments, a fermentation product is wine.

A beverage container includes, but is not limited, to a beverage container for water, milk, coffee, tea, juice, an alcoholic beverage, or a carbonated beverage. An alcoholic beverage includes, but is not limited to beer, wine, gin, vodka, or whisky. A preferred alcoholic beverage is wine. Thus, a preferred container is a container for the fermentation of wine.

A container also includes any container for storing, transporting or selling a dairy product, a liquid dairy, a liquid dairy composition or a dry dairy composition. A "liquid dairy composition" is any source of milk or milk ingredient. In exemplary embodiments, the milk is from sheep, goats, or cows. Liquid dairy compositions include without limitations, for example, liquid milk, liquid skim milk, liquid non-fat milk, liquid low fat milk, liquid whole milk, liquid half & half, liquid light cream, liquid light whipping cream, liquid heavy cream, liquid lactose free milk, liquid reduced lactose milk, liquid sodium free milk, liquid reduced sodium milk, liquid dairy fortified with nutrients, such as vitamins A, D, E, K, or calcium, liquid high protein dairy, liquid whey protein concentrate, liquid whey protein isolate, etc. Milk concentrates and milk protein concentrates are particularly contemplated liquid dairy compositions. The term "milk concentrate" means any liquid or dried dairy-based concentrate comprising milk, skim milk, or milk proteins. Dry dairy components include without limitation, for example, whole dry milk, non-fat dry milk, low fat milk powder, whole milk powder, dry whey solids, de-mineralized whey powders, individual whey protein, casein dairy powders, individual casein powders, anhydrous milk fat, dried cream, lactose free dairy powder, dry lactose derivatives, reduced sodium dairy powder, etc. Also included are calorie-free dairy, cholesterol free dairy, low calorie dairy, low cholesterol dairy, light dairy, etc. Also included are combinations of any of the above liquid or dry dairy components in any ratio.

Containers of various sizes, shapes, heights, and diameters can be used in the methods of the present invention as long as they have at least one opening through which a UV device or a UV lamp can be introduced.

Containers of various refractive indexes can be used in the methods of the present invention.

Containers of various reflective nature can be used in the methods of the present invention. As indicated in the following table, different materials reflect different percentages of UV light (254 nm). One of skill in the art will appreciate the contribution of the reflectance of a material will have for achieving a desired UV intensity useful for UV disinfection and sterilization (see Table 6).

TABLE 6

Reflective Factors On Various Surfaces At 254 Nm Wavelength. The values are obtained at normal incidence. The percentage reflectances increases rapidly at angles greater than 75%. (American Ultraviolet Company, Lebanon, IN 46052, USA)

| Material | % Reflectance |
|---|---|
| Aluminum, etched | 88 |
| Aluminum, foil | 73 |
| Aluminum, polished commercial | 73 |
| Chromium | 45 |
| Glass | 4 |

TABLE 6-continued

Reflective Factors On Various Surfaces At 254 Nm Wavelength.
The values are obtained at normal incidence. The percentage
reflectances increases rapidly at angles greater than 75%.
(American Ultraviolet Company, Lebanon, IN 46052, USA)

| Material | % Reflectance |
| --- | --- |
| Nickel | 38 |
| Silver | 22 |
| Stainless steel | 20-30 |
| Tri-plated steel | 28 |
| Water paints | 10-30 |
| White cotton | 30 |
| White oil paint | 5-10 |
| White paper | 25 |
| White porcelain | 5 |
| White wall plaster | 40-60 |

In some embodiments of the present invention, the interior surface of a container is UV reflective.

In some embodiments of the present invention, the interior surface of a container is stainless steel.

Typically, a container for use in a method of the present invention is a closed container with one or more openings at the top (e.g., see FIGS. 1-11, 14-16, 22-25, 29, 30, 32-34, 41, 44 and 48), at a side wall (e.g., see FIG. 31), or at the bottom part of a side wall (e.g., see FIGS. 32, 33, 41 and 48). In some embodiments, this opening is referred to as manhole and is shown in, e.g., FIGS. 22-25, 30, 32-34, 41, 44 and 48. The manhole or port 77 provides access to the container from the top of the container and further allows, e.g., for the attachment of various pressure washing devices. The manhole or port also allows the positioning of a UV device, e.g., of a UV device having a telescopic arm for practicing a method of the invention. As shown in FIGS. 22-25, 30, 32-34, 41, 44 and 48, part of the UV device rests on top of the manhole or port 77 when the UV device is used for the UV sterilization of the container. In some embodiments, a pulley mount arm rests on the top of the manhole.

In some embodiments, the means for attaching the UV device to a container, attaches the UV device to the manhole or port 77. This attachment is typically done using a hanger, more specifically, using the clamp post 53 or a mounting bracket 3.

In some embodiments of the present invention, a container comprises a lid (indicated by 29 in the figures). In some embodiments of the present invention, a container comprises a hinged lid (indicated by 30 in the figures). The lid itself may have one or more openings through which a UV device or parts thereof (such as a LTV light source) may be inserted inwardly into the container. When a lid is present, upon beginning the UV sterilization process, the lid is closed so to not expose a practitioner or any other person to the UV light. If a lid cannot be completely closed because, e.g., the attachment or placement of a UV device at an opening of the container, a protective shield can be used to prevent UV light from escaping the container.

In some embodiments of the present invention, a container comprises one or more support stands (indicated by 115 in the figures).

A. Fermentation Container

In some embodiments of the present invention, a container is a container used in zymurgy or the production of an alcoholic beverage. A UV device of the present invention may be used in any large scale commercial steel vessel involved in the fermentation and production of an alcoholic beverage. The term "alcoholic beverage" is used to include the alcoholic beverage prescribed in Liquor Tax Law Chapter 1, Section 2.

A fermentation container may be of various size, shape, height, and can be used in a method of the present invention as long as it has at least one opening through which a UV device or UV lamp can be introduced.

A fermentation container may be made of a variety of materials, including stainless steel, wood, plastic, concrete, a polymer, or glass. A preferred fermentation container is made of wood.

IV. Systems

In another aspect of the present invention, systems comprising a UV device described herein, are provided. In some embodiments of the present invention, a system comprises a UV device. A UV device may include one or more components as described herein, e.g., a germicidal UV light source, a detector, a housing, a range-finding device, a bracket, an optical component, a circuit board, a frame, and/or a motorized unit. In some embodiments of the present invention, a system comprises a UV device and a container. In other embodiments of the present invention, a system comprises a UV device and a room, a space or defined environment.

In some embodiments of the present invention, a system is for use in a method for ultraviolet (UV) sterilization of an interior surface of a container. In other embodiments of the present invention, a system is for use in a method for ultraviolet (UV) sterilization of a room, a space or defined environment.

In some embodiments of the present invention, a system is for use in a method for inhibiting the growth of one or more species of microorganisms present in a container, preferably for inhibiting the growth of one or more species of microorganisms present on an interior surface of a container. In other embodiments of the present invention, a system is for use in a method for inhibiting the growth of one or more species of microorganisms present in a room, a space or defined environment, preferably for inhibiting the growth of one or more species of microorganisms present on a surface of a room, a space or defined environment.

V. Methods

In another aspect of the present invention, methods of using a UV device described herein, are provided. In some embodiments, a method of using a UV device is a method for ultraviolet (LTV) sterilization of an interior surface of a container. In some embodiments, the method for UV sterilization of an interior surface of a container comprises the steps of (a) providing a container having an opening, (b) movably inserting through the opening of the container a first germicidal UV light source and (c) activating the germicidal UV light.

In some embodiments, as described herein, the method further comprises the step of (d) moving the germicidal UV light source to a first vertical downwards position within the container.

In some embodiments, as described herein, the method further comprises the step of (e) moving the germicidal UV light source from the first vertical downwards position to a horizontal position within the container.

In some embodiments, as described herein, the method further comprises the step of (f) moving the germicidal UV light source from the horizontal position to a second vertical downwards position within the container.

In some embodiments, as described herein, the method further comprises the step of (d) moving the germicidal UV light source from a horizontal position to a first vertical position within the container. Preferably, the movement is downwardly, however, depending on the UV device employed for practicing a method, the movement can also be upwardly.

In some embodiments, as described herein, the method further comprises the step of (e) moving the germicidal UV light source from the first vertical position within the container to a second vertical position within the container. Preferably, the movement is downwardly, however, depending on the UV device employed for practicing a method, the movement can also be upwardly.

In some embodiments, as described herein, the method further comprises the step of attaching a UV device comprising the germicidal UV light source to the container. Preferably, the attachment is at an opening at the container. An opening at a container can be on top, at a side wall or at a bottom part of a side wall of the container.

In some embodiments, as described herein, the method further comprises the step of movably positioning a UV device comprising the germicidal UV light source in a container. Preferably, movably positioning a UV device in a container comprises moving a UV device trough an opening into the container. An opening at a container can be on top, at a side wall or at a bottom part of a side wall of the container. The positioning of the UV device within the container may be on the floor of the container.

In some embodiments, a method of using a UV device is a method for inhibiting the growth of one or more microorganisms present on an interior surface of a container. In some embodiments, the method for inhibiting the growth of one or more microorganisms present on an interior surface of a container comprises the steps of (a) providing a container having an opening, (b) movably inserting through the opening of the container a first germicidal UV light source and (c) activating the germicidal UV light.

In some embodiments, as described herein, the method for inhibiting the growth of one or more microorganisms present on an interior surface of a container further comprises the step of (d) moving the germicidal UV light source to a first vertical downwards position within the container.

In some embodiments, as described herein, the method for inhibiting the growth of one or more microorganisms present on an interior surface of a container further comprises the step of (e) moving the germicidal UV light source from the first vertical downwards position to a horizontal position within the container.

In some embodiments, as described herein, the method for inhibiting the growth of one or more microorganisms present on an interior surface of a container further comprises the step of (f) moving the germicidal UV light source from the horizontal position to a second vertical downwards position within the container.

In some embodiments, as described herein, the method for inhibiting the growth of one or more microorganisms present on an interior surface of a container further comprises the step of (d) moving the germicidal UV light source from a horizontal position to a first vertical position within the container. Preferably, the movement is downwardly, however, depending on the UV device employed for practicing a method, the movement can also be upwardly.

In some embodiments, as described herein, the method for inhibiting the growth of one or more microorganisms present on an interior surface of a container further comprises the step of (e) moving the germicidal UV light source from the first vertical position within the container to a second vertical position within the container. Preferably, the movement is downwardly, however, depending on the UV device employed for practicing a method, the movement can also be upwardly.

In some embodiments, as described herein, the method for inhibiting the growth of one or more microorganisms present on an interior surface of a container further comprises the step of attaching a UV device comprising the germicidal UV light source to the container. Preferably, the attachment is at an opening at the container. An opening at a container can be on top, at a side wall or at a bottom part of a side wall of the container.

In some embodiments, as described herein, the method for inhibiting the growth of one or more microorganisms present on an interior surface of a container further comprises the step of movably positioning a UV device comprising the germicidal UV light source in a container. Preferably, movably positioning a UV device in a container comprises moving a UV device trough an opening into the container. An opening at a container can be on top, at a side wall or at a bottom part of a side wall of the container. The positioning of the UV device within the container may be on the floor of the container.

In some embodiments, as described herein, the method for inhibiting the growth of one or more microorganisms present on an interior surface of a container further comprises the step of attaching a UV device comprising the germicidal UV light source to the container.

A. Providing a Container

In some embodiments, the method for UV sterilization of an interior surface of a container comprises the step of providing a container having an opening. In some embodiments, the method for inhibiting the growth of one or more microorganisms present on an interior surface of a container comprises the step of providing a container having an opening. Containers useful for practicing methods of the present invention are described herein.

B. Attaching a UV Device to a Container

In some embodiments, a method of the present invention comprises the step of attaching a UV device to a container. Attaching a UV device temporarily, for a prolonged time, or permanently to a container is described herein.

C. Inserting a UV Light Source into a Container

In some embodiments, a method of the present invention comprises the step of inserting a germicidal UV light source through an opening of the container. The opening of the container may be on top of the container as illustrated in FIGS. 1-11, 14-16, 22-25, 29, 30, 32-34, 41, 44 and 48)

Alternatively, an opening of the container may also be at the bottom of a container or at a side of a container as illustrated in FIGS. 31-33, 41 and 48). One of skill in the art reading the instant specification will appreciate that a UV light source can be inserted into a container through an opening on the top, through an opening at the bottom, or through an opening at a side. As described herein, a UV light source, once movably inserted into a container can be moved at any desired or predetermined position. One of ordinary skill in the art will appreciate that the methods described herein for positioning a UV light source within a container can be easily modified to account for the point of where the UV light source is being movably inserted into a container. Those would be considered design choices in view of the disclosure provided herewith.

In some embodiments, once the UV light is inserted into a container, it remains in a stationary position for the time of the sterilization process. In some other embodiments, once the UV light is inserted into a container, it is mobile. In some embodiments, a UV lamp moves longitudinally within the container. In some embodiments, a UV lamp moves laterally. In some embodiments, a UV lamp rotates on its own axis or about an axis. In some embodiments, a combination of movements of some or all movements is used to achieve the desired result of positioning a UV light source at a desired or predetermined position within a container. The movement of the UV lamp is achieved through use of a motorized unit, a hydraulic system, or a combination thereof.

Mobility of the UV light source may depend on the size and shape of the container and on the size, shape, and intensity of the UV lamp(s). The use of a mobile UV light source will depend on the desired sterilization rate. If, for example, a faster rate is desired, the UV lamp preferably is positioned closer to the inner surface of the container to be sterilized. Thus, in this embodiment, a means by which the UV light source is positioned in closer proximity to the inner surface is recommended. Similarly, in some embodiments, the positioning of the UV lamp is altered to avoid an obstruction, such as an internally mounted thermometer or the like. As one of skill in the art will appreciate, the longitudinal movement of a IN lamp depends on the height of the vessel. Further, the lateral movement of a UV lamp depends on the diameter of the container. In embodiments where a rotating UV lamp is used, the rate of rotation will depend on the type of UV lamp used (continuous UVC vs. pulsed UV) and on the intensity of the UV lamp.

D. Activating a UV Light Source

In some embodiments, a method of the present invention comprises the step of activating a germicidal UV light source. Thereby a necessary or predetermined dose of radiation will be delivered. Activating of the UV light source initiates the process of sterilization, disinfection and growth inhibition of the one or more microorganisms by providing a UV dose for effective sterilization of microorganisms, disinfection of the interior surface of a container, and for the growth inhibition of the one or more microorganisms.

In some embodiments, a method of the present invention comprises the step of manually activating a germicidal UV light source.

In some embodiments of the present invention, a UV device comprises an interface for activating the UV device, for inactivating the UV device, for making a user aware of the time elapsed in a sterilization cycle and/or making a user aware of the time remaining for completion of a sterilization cycle. Some interface function may be connected to a visual or audible alert or to an email notification, telephonic contacting or texting.

In some embodiments, activation of the UV light source occurs at a predetermined time and may be controlled by an RFID communicating with a circuit board attached to the UV device (e.g., FIGS. 26 and 36). In some embodiments, the information retrieved from the RFID is used by the circuit board to determine the length of extension of the telescopic arm (e.g., moving the UV light source into a first vertical downwards position; payout position, e.g., see FIG. 23) and the length of descent of the UV light source from its horizontal position into the second vertical downwards position (e.g., see FIG. 25).

In some embodiments, activation of the UV light source occurs for a predetermined time. Preferably the duration of the activation of the UV light source is provided for a time sufficient to cause an at least about 1 log reduction of microorganisms on the interior surface of a container, an at least about 2 log reduction of one or more microorganisms on the interior surface of a container, an at least about 3 log reduction of one or more microorganisms on the interior surface of a container, an at least about 4 log reduction of one or more microorganisms on the interior surface of a container, an at least about 5 log reduction of one or more microorganisms on the interior surface of a container, or an at least about 6 log reduction of one or more microorganisms on the interior surface of a container.

By inserting the UV light source into the interior of a container and by activating the UV light source, the interior surface of the container is exposed to a UV light dose.

Once the desired UV intensity has been applied to the interior surface of a container, the UV light source may be deactivated. In some embodiments, deactivation is performed by a timer, which can be set to different times depending on the desired log reduction of the desired microorganisms (see calculations of killing rates in Example B). Deactivation can also be performed by a UV detector, which would automatically shut off the UV lamp(s) when the desired UV intensity has been attained. In some embodiments of the present invention, deactivation may also be controlled by a RFID. In some embodiments of the present invention, deactivation, upon completing a sterilization cycle, is controlled by a circuit board attached to the UV device. Again, the desired UV intensity will depend on the desired log reduction of the desired microorganisms. For example, using a lamp with an output of 190 microwatts/cm$^2$ at 254 nm (at a distance of 1 meter), placed within a fermentation vessel 60" from the interior surface, if a 2 log reduction of *Shigella dysentery* is desired, 4,200 microwatt seconds/cm$^2$ would be required. Once the UV detector has detected that 4,200 microwatt seconds/cm$^2$ have been attained it would automatically shut off the UV lamp. Thus, in some embodiments, the method for UV sterilization of an interior surface of a container comprises the step deactivating a germicidal UV light source. As described herein, deactivation may occur automatically by using a preset UV detector. Alternatively, deactivation is performed manually.

In some embodiments, the process of sterilizing the interior of a container comprises the step of subjecting the interior of the container to UV radiation.

While typically a single exposure of an interior surface of a container by a necessary or predetermined UV dose is sufficient to achieve a desired log reduction of microorganisms, in some embodiments, the interior surface of the container is exposed multiple times to UV radiation.

Short-wave UV light is harmful to humans. In addition to causing sunburn and (over time) skin cancer, UV light can produce extremely painful inflammation of the cornea of the eye, which may lead to temporary or permanent vision impairment. It can also damage the retina of the eye. For this reason, the light produced by a germicidal lamp must be carefully shielded against both direct viewing and reflections and dispersed light that might be viewed. Thus, in some embodiments of the present invention, the methods of sterilization a container and methods for inhibiting the growth of one or more microorganisms present on an interior surface of a container comprise the step of covering a container with a lid, top, or cover. The lid, top or cover essentially does not allow the UV light to penetrate and thus, protects humans from the harmful UV light.

E. Releasing a Germicidal UV Light Source from a Housing

In some embodiments, a method of the present invention comprises the step of releasing a germicidal UV light source from a housing. Thereby a germicidal UV light source, e.g., a UV lamp, is released from a housing. In some embodiments, the releasing of the germicidal UV light source from the housing is accomplished by a motorized unit. The motorized unit (exemplary shown in FIGS. 1-3, 38, 39, 42, 43, 45) is connected to a rope, cable or wire 7, which is connected to a UV lamp 5 and thus, can move the UV lamp 5 in an downward direction for use and moves the UV lamp 5 in an upward direction after use. Alternatively, depending on the UV device being used, the UV lamp 5 is moved in an upwardly direction for use and in a downwardly direction after use. Various modes of releasing a UV lamp 5 from a housing 2 have been described herein in the context of the various UV devices useful for practicing a method of the present invention.

In some embodiments, upon release from the housing, the germicidal UV light source moves longitudinally into the container to a predetermined position. An example of such a longitudinally movement is depicted, e.g., in FIG. 3. In some embodiments, upon release from the housing, the germicidal UV light source moves laterally in the container to a predetermined position. An example of such a lateral movement is depicted, e.g., in FIG. 7. In some embodiments, upon release from the housing, the germicidal UV light source rotates in the container. Examples of such a rotational movement are depicted, e.g., in FIGS. 9-11.

Still other modes for releasing a germicidal UV light source from a housing are depicted, e.g., in FIGS. 27, 40, 41 and 44. In some of those embodiments, a hinge or UV lamp module swing 81, is used to move the UV light source from a closed position into an exposed (released) position.

F. Placing a UV Device on an Upper Perimeter of a Container

In some embodiments, a method of the present invention comprises the step of placing a UV device comprising a bracket to which the germicidal UV light source is attached on the upper perimeter of a container. Thereby the UV device comprising the UV light source is firmly positioned on the upper perimeter of the container is restricted from moving downwards due to the brackets. An exemplary placing of a bracket to which the germicidal UV light source is attached on the upper perimeter of a container is shown in FIGS. 3, 10, and 11. While the bracket is firmly placed on the upper perimeter of a container, as shown in FIGS. 3, 10, and 11 other parts of the UV device can be moved downwards into the container.

In some embodiments, a method of the present invention comprises the step of placing a UV device comprising a housing to which the germicidal UV light source is attached (either directly or indirectly) on the upper perimeter of a container. Thereby the UV device comprising the UV light source is firmly positioned on the upper perimeter of the container and is restricted from moving downwards, e.g., by comprising a base plate (e.g., FIGS. 28, 29). An exemplary placing of a housing and base plate to which the germicidal UV light source is attached on the upper perimeter of a container is shown in FIGS. 28 and 29. While the base plate is firmly placed on the upper perimeter of a container, as shown in FIG. 29 other parts of the UV device, such as the UV light source can be moved downwards into the container.

In some embodiments of the present invention, a subject method comprises the step of positioning a UV device on top of an opening of a container. This step is schematically depicted, e.g., in FIGS. 1-3, 10, 11, 29, 30, 34, 41, 44 and 48.

G. Movably Inserting Through an Opening of a Container a Second Germicidal UV Light Source In some embodiments of the present invention comprises the step of movably inserting through an opening of a container a second germicidal UV light source. The second germicidal UV light source can be inserted similarly as the first germicidal light source or differently. Insertion of the second germicidal UV light source can be simultaneously with the first germicidal light source or subsequently. In some embodiments, the second germicidal light source differs from the first germicidal light source in dimension and/or intensity.

H. Moving a Germicidal UV Light Source to a First Vertical Downwards Position within a Container In some embodiments, a method of the present invention comprises the step of moving a germicidal UV light source to a first vertical downwards position within the container. Moving a germicidal UV light source to a first vertical downwards position within a container is described herein.

I. Moving a Germicidal UV Light Source from a First Vertical Downwards Position to a Horizontal Position within a Container In some embodiments, a method of the present invention comprises the step of moving a germicidal UV light source from a first vertical downwards position to a horizontal position within the container. Moving a germicidal UV light source from a first vertical downwards position to a horizontal position within a container is described herein.

J. Moving a Germicidal UV Light Source from a Horizontal Position to a Second Vertical Downwards Position within a Container In some embodiments, a method of the present invention comprises the step of moving a germicidal UV light source from a horizontal position to a second vertical downwards position within the container. Moving a germicidal UV light source from a horizontal position to a second vertical downwards position within a container is described herein.

K. Moving a Germicidal UV Light Source from a Horizontal Position to a First Vertical Position within a Container In some embodiments, a method of the present invention comprises the step of moving a germicidal UV light source from a horizontal position within a container to a first vertical position within the container. Moving a germicidal UV light source from a horizontal position within a container to a first vertical position within a container is described herein.

L. Moving a Germicidal UV Light Source from a First Vertical Position to a Second Vertical Position within a Container In some embodiments, a method of the present invention comprises the step of moving a germicidal UV light source from a first vertical position within a container to a second vertical position within the container. Moving a germicidal UV light source from a first vertical position within a container to a second vertical position within a container is described herein.

M. Inhibiting Growth of Microorganisms

In some embodiments of the present invention, a germicidal light source is used to inhibit the growth of a microorganism or inhibit the growth of one or more microorganisms. The terms "inhibiting the growth of microorganisms," "growth arresting microorganisms," "reducing microorganisms," "killing microorganisms," or grammatically equivalents are used interchangeably herein.

In some embodiments of the present invention, a microorganism is a yeast species. The following provides a non-exhaustive list of yeast species that are typically found in a fermentation container, and more specifically on an interior surface of a fermentation container. Yeast species that have been investigated for wine and beer production include those from the *Candida, Kloeckera, Hanseniaspora,*

*Zygosaccharomyces, Schizosaccharomyces, Torulaspora, Brettanomyces, Pichia, Hansenula, Metschnikowia, Torulespora, Debaryomyces, Saccharrmycodes* (species *ludwigii*), and *Williopsis* genera. Cultured yeast species include *Saccharomyces cerevisiae* and *Saccharomyces bayanus*. The growth of non-*Saccharomyces* yeast in wine production is also being investigated and can be inhibited. Thus, in some embodiments, it is particularly desirable to inhibit the growth of a yeast species using a method of the present invention. For example, 17,600 μWs/cm$^2$ is necessary for a 2 log killing of *Sacchahhmycodes* and 6,600 μWs/cm$^2$ for a 2 log killing of Brewer's yeast. UV intensities required for sterilization for unknown microorganism species can be determined by one of skill in the art using methods known in the art and described herein.

Some of the microorganisms found in a fermentation container, more specifically, on an interior surface of a fermentation container, are pathogenic. In some embodiments of the present invention, a microorganism is a pathogenic microorganism. Those microorganisms include, but are not limited to, *Escherichia coli, Corynebacterium diphtheria, Salmonella paralyphi* (causing enteric fever), *Salmonella typhosa* (causing typhoid fever), *Shigella dysenteriae* (causing *dysentery*), *Shigella flexerni* (causing *dysentery*), *Staphylococcus albus, Staphylococcus aureus, Streptococcus hemolyticus, Streptococcus lactis, Streptococcus viridians* and *Vibrio comma* (causing cholera). Thus, in some embodiments, it is particularly desirable to inhibit the growth of a pathogenic microorganism using a method of the present invention.

Other microorganisms found in a fermentation container, more specifically on an interior surface of a fermentation container, are detrimental in the production of a fermented beverage. Those microorganisms include, but are not limited to, *Brettanomyces (Dekkera)*, lactic acid bacteria, *Pediococcus, Lactobacillus*, and *Oenococcus*. *Brettanomyces* species include *B. abstinens, B. anomalus, B. bruxellensis, B. claussenii, B. custersianus, B. custersii, B. intermedius, B. lambicus*, and *B. naardensis*. The genus *Dekkera* (the perfect form of *Brettanomyces*, meaning it can sporulate), includes the species *D. bruxellensis* and *D. intermedius*. Thus, in some embodiments, it is particularly desirable to inhibit the growth of a microorganism, which is detrimental in the production of a fermented beverage, using a method of the present invention.

Other microorganisms found in a fermentation container, more specifically on an interior surface of a fermentation container, that are detrimental in the production of a fermented beverage are bacterial microorganisms. Bacteria genus include, but are not limited to, *Acetobacter, Lactobacillus, Pediococcus*, and *Leuconostoc*. *Acetobacter* species include, e.g., *A. aceti, A. hansennii, A. liquefaciens*, and *A. pasteurienus*. *Lactobacillus* species (ML bacteria, spoilage) include, e.g., *L. fructivorans* and others. *Pediococcus* species (ML bacteria, spoilage) include, e.g., *P. damnosus* and others. *Leuconostoc* species (ML bacteria) include, e.g., L. o and others. Thus, in some embodiments, it is particularly desirable to inhibit the growth of a bacterial microorganism using a method of the present invention.

1. Duration of Sterilization

The duration of sterilization, i.e., the time of activating a UV light source, determines the percentage of how many microorganisms are growth arrested or killed. As one of skill in the art will appreciate, the duration of a sterilization cycle is based on the power output of the UV lamp and the distance of the UV lamp from the walls and surfaces of the container to be sterilized.

In some embodiments, the duration of sterilization is performed for a time to ensure that at least 90% of the microorganisms present on the surface of a container are growth arrested or killed. One of skill in art will appreciate that a 90% growth arrest of microorganisms corresponds to a 1 log reduction.

In some embodiments, the duration of sterilization is performed for a time to ensure that at least 99% of the microorganisms present on the surface of a container are growth arrested or killed. One of skill in art will appreciate that a 99% growth arrest of microorganisms corresponds to a 2 log reduction.

In some embodiments, the duration of sterilization is performed for a time to ensure that at least 99.9% of the microorganisms present on the surface of a container are growth arrested or killed. One of skill in art will appreciate that a 99.9% growth arrest of microorganisms corresponds to a 3 log reduction.

In some embodiments, the duration of sterilization is performed for a time to ensure that at least 99.99% of the microorganisms present on the surface of a container are growth arrested or killed. One of skill in art will appreciate that a 99.99% growth arrest of microorganisms corresponds to a 4 log reduction.

In some embodiments, the duration of sterilization is performed for a time to ensure that at least 99.999% of the microorganisms present on the surface of a container are growth arrested or killed. One of skill in art will appreciate that a 99.999% growth arrest of microorganisms corresponds to a 5 log reduction.

In some embodiments, the duration of sterilization is performed for a time to ensure that at least 99.9999% of the microorganisms present on the surface of a container are growth arrested or killed. One of skill in art will appreciate that a 99.9999% growth arrest of microorganisms corresponds to a 6 log reduction.

Examples 6 and 7, in particular, provide useful times and guidance for sanitization of various containers.

2. Extinction Depths at 254 Nm Wavelength

When practicing methods of the present invention, the extinction depths of the UV light source at 254 nm wavelength in various liquids needs to be taken into consideration, unless the surface of the container to be sterilized is completely dry. The application of UV light to sterilize a surface following a pressure wash would have to take into account the extinction depth of UV light at 254 nm in the remaining tap water. However, the depth of tap water the UV light must penetrate is minimal and would be equivalent to that of a film of water or at most interspersed water droplets. In some instances, the effect of depth of tap water on the duration of sterilization and kill rate will have to be tested using methods described herein and available in the art. This is due to the fact that following pressure washing of a container (e.g., a fermentation vessel), the remaining layer of water covering the container may not be homogeneous. Maximum depths of water drops can be used to calculate extra time needed for the sterilization cycle. Although the extinction coefficient could theoretically be used to calculate this, it would not take into account the reflection and scattering caused by uneven surfaces of the water film and water droplets, as such empirical data would be more useful for determining how to adjust sterilization timing. The following table provides guidance:

TABLE 7

Extinction Depths at 254 nm Wavelength (relationship to clear water) (American Ultraviolet Company, Lebanon, IN 46052, USA)

| Liquid | Extinction Depth |
| --- | --- |
| Apple juice | 1.0 |
| Beer | <1.3 |
| Liquid sugar | 1.0 |
| Milk - whole, raw | <0.1 |
| Vinegar | <5.0 |
| Water - concrete cistern | <75 |
| Water - distilled | 3,000 |
| Water - tap or mains | 125-180 |
| Wine | <2.5 |

N. Assessing Microbial Concentration

Microbial concentration on interior surfaces of containers may be assessed before and after performing a method of the present invention, such as the UV disinfection and UV sterilization methods described herein. A lower microbial concentration on interior surfaces of containers after a method of the present invention, e.g., performing a UV disinfection or UV sterilization method evidences the effectiveness of the method used. Methods for assessing microbial concentration are known in the art. Exemplary methods are described herein.

Preferred embodiments of this invention are described herein, including the best mode known to the inventor for carrying out the invention. Of course, variations on those preferred embodiments will become apparent to those of ordinary skill in the art upon reading the foregoing description. The inventor expects skilled artisans to employ such variations as appropriate, and the inventor intends for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

As can be appreciated from the disclosure above, the present invention has a wide variety of applications. While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention. The invention is further illustrated by the following examples, which are only illustrative and are not intended to limit the definition and scope of the invention in any way.

M. Sanitization of a Room, a Space or Defined Environment

In some embodiments, a UV device, preferably a UV light source, more preferably a germicidal UV light source, is used to sanitize a room, a space or a defined environment. The terms "sanitization" or "sanitation" and "UV sterilization" and grammatical equivalents thereof are used interchangeably herein. The meaning of a room is not limited to an enclosed room having walls, a ceiling, a floor or other barriers, but rather includes spaces open to at least one side and any defined environment. As exemplified herein, in some embodiments, a room, a space or defined environment is selected from the group consisting of a commercial kitchen, a medical facility, an acute care area, an operating room, a medical equipment storage cabinet, a clean room, a bathroom, a food production area, a nursery home, a trailer, a rail car, a grocery store display case, and a deli counter.

Thus, the present invention provides methods for sanitization (UV sterilization) of a room, a space or defined environment. In some embodiments of this method, the method comprises the step of providing a room, a space or defined environment in need of sanitization and exposing the room, space or defined environment to ultraviolet (UV) sterilization using a UV device. In some embodiments of this method, the method comprises the step of selecting a room, a space or defined environment in need of sanitization and exposing the room, space or defined environment to ultraviolet (UV) sterilization using a UV device. Suitable UV devices are described herein. Some embodiments of the method for sanitizing a room comprise the step of attaching a UV device to a wall of the room. Some embodiments of the method for sanitizing a room comprise the step of attaching a UV device to a ceiling of the room. Some embodiments of the method for sanitizing a space or defined environment comprise the step of attaching a UV device to an object or structure present in the space or defined environment. Objects or structures to which a UV device can be attached include, but are not limited to, a conveyer belt, a hood, a cabinet, a display case. A UV device can also be superimposed over or attached to a preexisting light fixture.

Some embodiments of the method for sanitizing a room, a space or defined environment comprise the step of moving a UV light source from a closed position to an exposed position.

Some embodiments of the method for sanitizing a room, a space or defined environment comprise the step of activating the UV light source.

In some embodiment of a UV device being used for the sanitization of a room, a space or defined environment, a portable UV device may be used. In some embodiments, an RFID tag is mounted to the doorway of a room, a space or defined environment intended to be sanitized. In some embodiments, an RFID tag reader is mounted to the UV device, such that when the UV device is brought into the room, space or defined environment, the tag is read. Information on the tag includes, but is not limited to, dimension and type of the room, space or defined environment, and desired log reduction. This information is uploaded into the UV device and a sanitization cycle is preprogrammed.

As one of ordinary skill in the art will appreciate some embodiments of the method for sanitizing a room, a space or defined environment comprise steps described herein for the sanitization (UV sterilization) of a container or surface of a container. Those steps are described in detail herein and one of ordinary skill in the art can easily adapt those steps for the use in the method for sanitizing a room, a space or defined environment.

In some embodiments, a room, a space or a defined environment is exposed to UV radiation. It is to be understood that the invention can be applied to any defined environment. For example, an environment may be defined by solid surfaces or barriers, such as a wall or product packaging.

A room accepts a UV light source for the purpose of sterilization of the wall, ceiling or floor, including any and all objects, fluids, materials, and surfaces contained within the room. In some embodiments, the objects, fluids, materials, and surfaces within the room are contained within the room temporarily. In other embodiments, they are contained within the room permanently.

The present invention provides for the sanitization of a variety of rooms, spaces or defined environments. Rooms, spaces or defined environments include, but are not limited to a commercial kitchen, an operating room, a clean room (ISO 1-ISO 9), a food production area, a nursery home. An exemplary application of a UV device described herein would be for sanitizing a sensitive area of a medical facility, such as an acute care area or an operating room. Other areas in a medical facility that can be sanitized using a UV device described herein include a waiting room, a bathroom, and a medical equipment storage cabinet.

A UV device described herein may also be configured into a food processing equipment so that food is treated as it moves through the equipment, for example on a conveyor belt, automatic cutters and slicers and inspection areas. The product may be tumbled to promote uniform treatment. The UV device may also be configured to be placed in containers, trailers, and rail cars or as a component to a refrigeration system of such containers, trailers, and rail cars to sanitize the air therein while providing the beneficial preservative effects of ozone to any products stored therein.

Other exemplary applications of a UV device described herein include the provision or incorporation of the UV device into grocery store display cases, such as deli counters and meat, fish and poultry display cases and floral display cases, both refrigerated and non-refrigerated.

Still other examples of areas that can be sanitized with a UV device described herein include parcels, packages, and envelopes, also when moving on a conveyor belt. The parcels, packages, and envelopes may be tumbled or turned to promote uniform treatment.

In some embodiments of a UV device, when used for sanitization of a room, one or more UV lamps are attached to the ceiling of the room in a housing. One embodiment of such UV device is shown in FIG. 27. The housing may be referred to as a box, UV light box or box-like housing. In some embodiments of the UV device, the UV device comprises UV lamps arranged in one or more UV lamp clusters, each comprising two, three, or more UV lamps. As shown in FIG. 27, the UV lamp clusters can either be stationary or retrievable. The UV device may also have combinations of stationary and retrievable UV lamp clusters, For example, FIG. 27 shows a UV device having one stationary UV lamp cluster and four retrievable UV lamp clusters. Thus, in one embodiment of the invention, a UV device is a UV device mountable to the ceiling or wall of a room, a space or defined environment and comprises at least one stationary UV lamp cluster and at least one retrievable UV lamp cluster. In other embodiments, all UV lamp clusters are retrievable. In still other embodiments, all UV lamp clusters are stationary.

As one of ordinary skill in the art will appreciate, a UV device mountable to a ceiling or wall may have different configurations with respect to height, width and length dimensions as the one shown in FIG. 27.

Figure 27A:
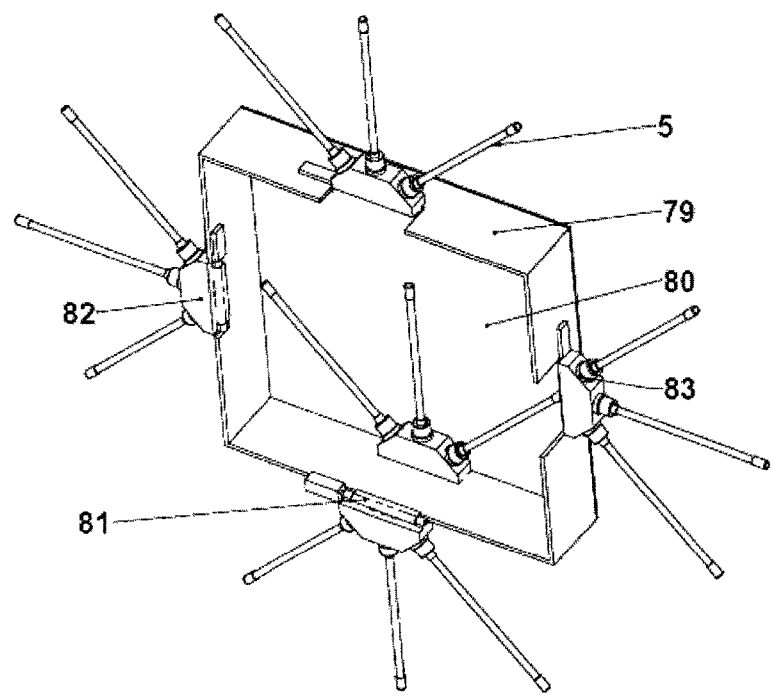
FIGS. 27A through 27G schematically depict a UV device mountable to the ceiling or wall of a room. As one of ordinary skill in the art will appreciate the UV device can also be mounted to a ceiling of an appropriately sized container. In this particular embodiment, UV lamps are arranged in UV lamp clusters. More specifically, five UV lamp clusters are shown, one stationary UV lamp cluster and four retrievable LTV lamp clusters each comprising three UV lamps 5. The UV device shown may be referred to as UV light box. In the embodiment shown, the UV device comprises (i) UV lamps, 5, (ii) a light box, 79, comprising a back wall, 80, (iii) a hinge or UV lamp module swing, 81, (iv) a UV lamp holder, and (v) a UV lamp head connector, 83, for connecting the UV lamps.
Figure 27B:
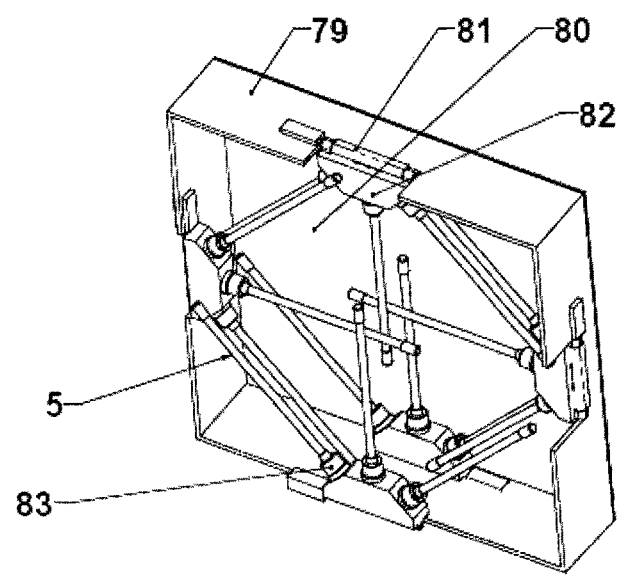
Figure 27C:
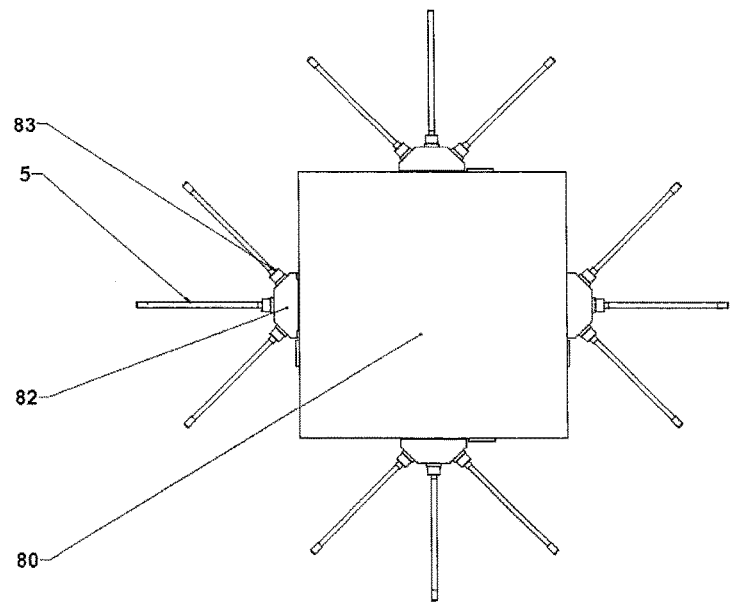
Figure 27D:
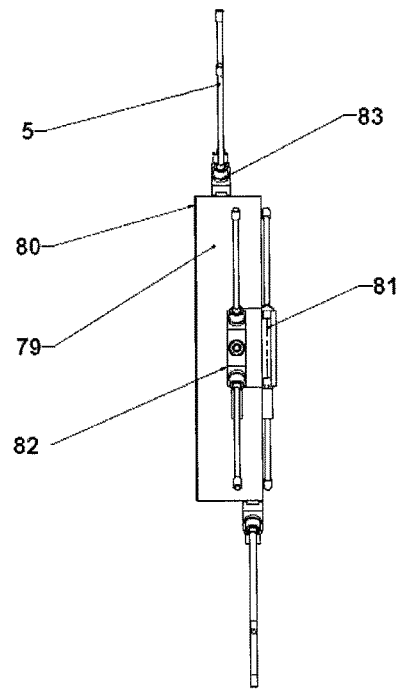
Figure 27E:
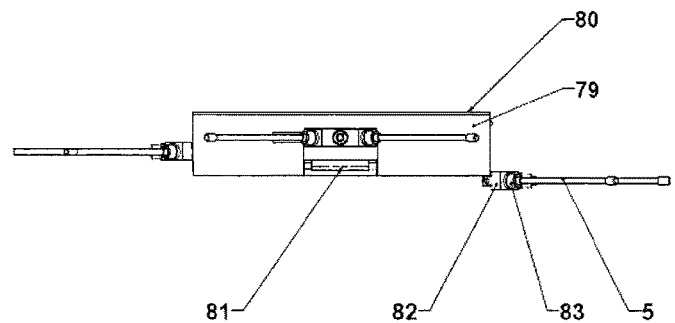
Figure 27F:
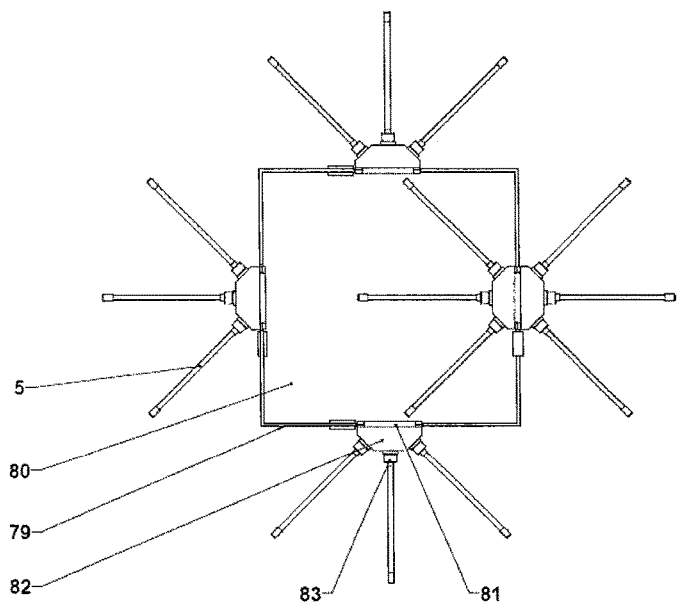
Figure 27G:
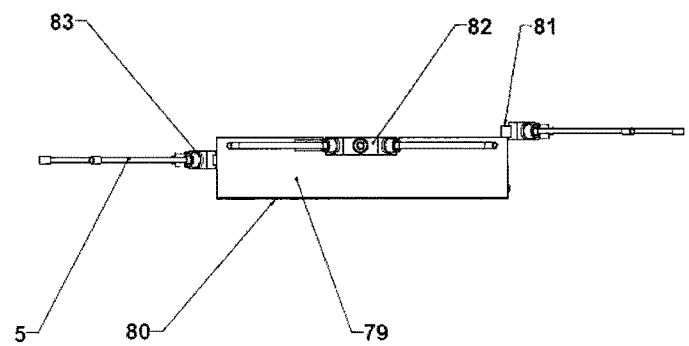

When the UV lamp clusters comprising the UV lamps 5 are in a closed, locked or folded position, they may be folded completely within a box-like housing 79 as shown in FIG. 27B. This can be easily achieved by positioning UV lamp holders 82 at slightly different height positions on the sides of the box-like housing 79 as shown in FIG. 27. A hinge or UV lamp module swing 81 serves to move the UV lamp holder into a desired position, for example from a closed, locked, or folded position into a position where the UV lamps are exposed (FIG. 27). Optionally, the UV lamp clusters may be covered temporarily with a removable lid, cover, or panel when in the closed, locked or folded position. The interior surface of box-like housing 79 may be covered with a reflective interior surface so to enhance the sanitization process.

In some embodiments of a UV device mountable to a ceiling or wall of a room, space or environment, the UV lamps or UV lamp clusters are fully enclosed in a housing when not in use. Prior to use of the UV lamps or UV lamp clusters for sanitization, the UV lamps or UV lamp clusters are moved from an enclosed position to an exposed position through one or more openings in the housing. The opening of the housing may also be covered by a flap door/hinge mechanism so that the UV lamps are not visible when the UV device is not in use.

In some embodiments, the UV lamp clusters extend from the box-like housing at varying angles.

A motor may be used to move the hinge or UV lamp module swing 81 and arrest them in a desired fixed angle position. Thus, the position of the UV lamps is adjustable vertically and horizontally in relation to the housing to optimize sanitization. Adjustments may be made hydraulically, pneumatically, electronically, mechanically, or by other equivalent means.

In some embodiments of a UV device, when used for sanitization of a room, one or more UV lamps are attached to the side of a room in a housing. The housing can be similar to the one shown in FIG. 27, however, may have different configurations with respect to height, width and length dimensions. When in use, the UV lamps may extend from the housing at varying angles. When not in use, the UV lamps may be retracted into a closed, locked, or folded position. Positioning the UV lamps into a desired position can be done by using a motor.

A UV device described herein may be configured for general room sanitization applications where the UV device, or components thereof, may be placed on a moving part, either permanently or temporarily during the sanitization procedure.

In some embodiments of a UV device, when used for sanitization of a room, area or defined environment, the UV device comprises a range finding device to determine the size of the room, space or defined environment to be sanitized. The range-finder then provides information to preprogram an effective sanitization cycle.

In some embodiments of a UV device, when used for sanitization of a room, a space or defined environment, a multi bulb UV cluster extends from the ceiling with the UV lamps extending at varying angles to optimize coverage and UV exposure of the room, space or defined environment.

In some embodiments of a UV device, when used for sanitization of a room, a space or defined environment, a multi lamp UV cluster extends from the ceiling with individual UV light coming down independently at varying angles.

In some embodiments of a UV device, when used for sanitization of a room, a space or defined environment, the UV lamp cluster and housing are permanently fixed to either the walls, floors, or ceiling of the room, space or defined environment.

In some embodiments of a UV device, when used for sanitization of a room, a space or defined environment, the UV lamp cluster is attached via a fixture to the ceiling of the room, space or defined environment. The fixture may be permanently attached and the UV bulb cluster and housing may be removable.

In some embodiments of a UV device, when used for sanitization of a room, a space or defined environment, the dimensions of the room, space or defined environment are preprogrammed into the UV device allowing the timing of sanitization to be optimized and the minimal necessary UV dose required for sanitation to be reached while minimizing power use. Preferred is an approximately 3 log reduction of microorganism determined as described herein.

In some embodiments of a UV device, when used for sanitization of a room, a space or defined environment, the UV device is linked to a motion detector. This may be helpful to ensure people and/or animals are absent from the room, space or environment prior to the beginning of the sanitization cycle. It will also be helpful for shutting off and deactivating the UV sterilization process if a person enters a room, a space or defined environment while a UV sterilization process is ongoing.

In some embodiments of a UV device, when used for sanitization of a room, a space or defined environment, multiple UV lamp clusters are spread throughout the room, space or defined environment. Based on the dimension and shape of the room, space or defined environment, the positioning of the UV lamps and angles are accounted for and this information is programmed into an algorithm allowing the timing of sanitization to be optimized and the minimal necessary UV dose required for sanitation to be reached while minimizing power use. Preferred is an approximately 3 log reduction of microorganism determined as described herein. The positioning of the UV lamps and angles can also be communicated via wireless technology. In some embodiments, a rangefinder may analyze the shape and dimension of the room, space or defined environment and input information into an algorithm allowing the timing of sanitization to be optimized and the minimal necessary UV dose required for sanitation to be reached while minimizing power use. Preferred is an approximately 3 log reduction of microorganisms determined as described herein.

In some embodiments of a device, when used for sanitization of a room, a space or defined environment, the UV bulb is attached to the bottom of a robot having wheels and follows programming allowing it to both perform an effective moving pattern on the floor covering desired areas. The robot may also have an object and wall avoiding programming and technology. The robot may move at a speed allowing an effective UV dose required for sanitization to be reached while minimizing power use. Preferred is an approximately 3 log reduction of microorganisms determined as described herein.

In some embodiments of a UV device, the UV bulb is attached to the bottom of a robot crawler that uses suction allowing it to crawl vertically on walls and horizontally on ceilings of a room, space or environment. The robot crawler may follow programming allowing it to perform an effective pattern on the wall and ceiling covering desired areas. The robot crawler may move at a speed allowing an effective UV dose required for sanitization to be reached while minimizing power use. Preferred is an approximately 3 log reduction of microorganisms determined as described herein.

It is also understood that for the methods described herein, individual steps may be performed by more than one person or more than one entity. Thus, not every step of a method described herein must be performed by the same person or entity.

VI. Examples

The below examples are meant to illustrate specific embodiments of the methods and compositions described herein and should not be construed as limiting the scope of the invention in any way.

Example 1

Assessing Microbial Concentration i. Inoculation of a Container

The following is an exemplary method for assessing microbial concentration in a tank after UV disinfection according to a method described herein and after using the standard sodium hydroxide and citric acid procedure or hypochlorite and citric acid (Emmanuel et al., 2004, *Environmental International*, 30(7): 891-900).

Four tanks (wine fermentation vessels; stainless steel) are provided. Two tanks have a 36" radius and two tanks have a 60" radius and a height of 120". The tanks are pressure washed with water and inoculated with spoilage yeast, cultured yeast, and pathogenic microorganisms (see Table 8).

TABLE 8

Exemplary Inoculating Containers (Tanks) With Microorganism

| Spoilage Yeast | Cultured Yeast | Pathogenic Microorganisms |
| --- | --- | --- |
| Brettanomyces abstinens | Saccharomyces cerevisiae | Salmonella spp |
| Brettanomyces anomalus | Saccharomyces bayanus | Clostridium botulinum |
| Brettanomyces bruxellensis | | Staphylococcus aureus |
| Brettanomyces claussenii | | Campylobacter jejuni |
| Brettanomyces custersianus | | Yersinia enterocolitica and Yersinia pseudotuberculosis |
| Brettanomyces custersii | | Listeria monocytogenes |
| Brettanomyces intermedius | | Vibrio cholerae O1 |
| Brettanomyces lambicus | | Vibrio cholerae non-O1 |
| Brettanomyces naardensis | | Vibrio parahaemolyticus and other vibrios |
| | | Vibrio vulnificus |
| | | Clostridium perfringens |
| | | Bacillus cereus |
| | | Aeromonas hydrophila and other spp |
| | | Plesiomonas shigelloides |
| | | Shigella spp |
| | | Miscellaneous enterics |
| | | Streptococcus |
| | | Escherichia coli enterotoxigenic (ETEC) |
| | | Escherichia coli enteropathogenic (EPEC) |
| | | Escherichia coli O157:H7 enterohemorrhagic (EHEC) |
| | | Escherichia coli enteroinvasive (EIEC) |

The tanks are inoculated on multiple surfaces, such as the corners, the weld seams, the bottom and sides of the tanks. After the inoculation and before the UV or chemical disinfection, samples are collected from several interior surfaces of the tanks (as described below). Those samples will be referred to as control samples or no treatment samples.

A UV light source, an American Air and Water UVC lamp 64" in length with an output of 190 microwatts/$cm^2$ at 254 nm (Model GML270) is inserted into a 36" radius tank (see, FIGS. 1-3) and activated for 1 minute and 26 seconds for each 64" interval of the tank. The UV-C lamp is moved down the 36" radius tank until the entire interior surface has been covered by the same intensity (dose) of UV-C light. After each interval of 1 minute and 26 seconds the UV lamp will be lowered by 64". In order to kill 100% of *Saccharomyces* sp. Yeast, 17,600 microwatt/cm$^2$ is needed (The timing of 1 minute and 26 seconds was based on achieving 17,600 microwatt/cm$^2$ at a distance of 36").

A UV light source, an American Air and water UVC lamp 64" in length with an output of 190 microwatts/cm$^2$ at 254 nm (Model GML270) is inserted into a 60" radius tank (see, FIGS. 1-3) and activated for 3 minute and 41 seconds for each 64" interval of the tank. The UV-C lamp is moved down the 60" radius tank until the entire interior surface has been covered by the same intensity (dose) of UV-C light. After each interval of 3 minute and 41 seconds the lamp will be lowered by 64" In order to kill 100% of *Saccharomyces* sp. Yeast, 17,600 microwatt/cm$^2$ is needed (The timing of 3 minute and 41 seconds was based on achieving 17,600 microwatt/cm$^2$ at a distance of 60").

The other 36" and 60" tanks, which have been comparably inoculated, are cleaned using the standard sodium hydroxide and citric acid solutions.

In a separate series of experiments, following inoculation, the tanks are sterilized/disinfected at different time intervals simulating alcoholic beverage production protocols (e.g., the time between tanks being emptied and then refilled).

ii. Collecting Samples from an Interior Surface of a Container

After completing the UV disinfection or the chemical disinfection as described above, the interior surfaces of the tanks are wiped using, e.g., Fellowes Surface Cleaning Wipes (STRATUS Inc., Amarillo, Tex.), which are pre-moisten antistatic wipes. Prior to the sampling, a sheet of original wipe cloth is cut to one forth size (48 cm$^2$) using sterilized scissors, placed into sterile whirl pack bags, and placed under a UV lamp for disinfection. Several areas of the tanks are wiped back and forth over the entire surface area of approximately 10 cm$^2$ using several vertical strokes, then folded with the fresh side of the wipe exposed, and several horizontal strokes were made over the same area with the other side of the wipe. After the sampling, the wipes are placed in 10 mL of phosphate buffer saline plus 0.01% Tween-80 (PBST) in 50-mL tubes. Types of sampling areas are recorded after the sampling.

iii. Microbial Assays

Collected wipe samples are assayed with culture methods to measure viable microorganisms. Selective agars, i.e. Tryptic(ase) Soy Agar (TSA) for mesophilic bacteria and thermophilic actinomycetes, Mannitol Salt Agar (MSA) for *Staphylococcus*, CHROMagar for methicillin resistant *Staphylococcus aureus* (MRSA) and Malt Extract Agar (MEA) for total fungi are used.

The log reduction of each inoculated microorganism species is recorded. Experiments are repeated to obtain statistically significant results.

iv. Pulsed UV Light

In a different series of experiments, the experiments described in i. to iii. of above, are repeated using a pulsed UV light. Xenon, SteriPulse-XL and Model RS-3000M will be used. As shown in FIG. 10, 11, or 16 one pulsed UV lamp will be mounted on laterally adjustable arms or mounts that allow the pulsed UV lamp to be brought within the optimal distance of 1.25" of the surface to be sterilized. The pulsed LTV lamp uses an elliptical window and has a footprint of 16"×1". The pulsed UV lamp will be rotated at speed such that the footprint is exposed for a duration of 1 second on the surface being sterilized. For the tank with a 36" radius that means that the rate of rotation will be 0.277 rpm. After a 16" interval of the tank has been exposed to the pulsed UV, the device will be lowered by 16" and the rotation will be repeated. This will be repeated in 16" interval until the entire surface of the vessel has been exposed.

v. Closed Top Container

In a different series of experiments, the experiments described in i. to iv. of above, are repeated using a closed top fermentation vessel. Essentially, the only difference will be that instead of supporting the UV device by a bracket from the top of the fermentation vessel, the UV device will be mounted on a tripod and inserted through a hatch at the base of the fermentation vessel.

vi. Pressure Washing at Various Times

In a different series of experiments, the experiments described in i. to v. of above, are repeated by performing the pressure washing after various times following the inoculation. In this series of experiments it is also determined what, if any, effect the presence of water droplets will have on the log reduction. This is done by employing the UV device at various times following the pressure washing.

The first set of experiments involves inoculating the tanks and pressure washing them at different time intervals following inoculation, such as 24 hours, 48 hours, 72 hours and 144 hours. The pressure washing is then immediately followed by a UV sterilization cycle. This is done to determine whether the time bacteria and yeast are allowed to grow prior to pressure washing affects the final duration of the sterilization cycle.

Another set of experiments will not vary the time between inoculation and pressure washing, but rather the time between pressure washing and UV sterilization. The objective will be to determine the effects of varying amounts of water on the inner surface of the tank and its effect on the duration of the sterilization cycle and log reduction. In this set of experiments, the UV sterilization cycle can be applied at 0 minutes following the pressure washing, 15 minutes following the pressure washing and in continually increasing 15 minute intervals following the pressure washing until the tank is completely dry.

vii. Dry Interior Surface

In a different series of experiments, the experiments described in i. to vi. of above, are repeated by including the step of allowing the interior surface of the tanks to dry after performing the pressure washing.

Example 2

Calculating Killing of Microorganisms

The following provides the steps to calculate the time needed to kill a desired microorganism using compositions and methods of the present invention. The required Energy Dosage of UV Radiation (UV Dose) in μWs/cm$^2$ needed for kill factor is provided herein in Tables 1-5. To determine the intensity of UV on a surface at various distances from a germicidal UV lamp one divides the radiant energy (shown in microwatts per square centimeter at one meter) by the intensity factor as shown in the Table 9 below.

TABLE 9

Intensity Factor (American Ultraviolet Company, Lebanon, IN 46052, USA

| | Distance from UV Lamp | | | | | | | | | |
|---|---|---|---|---|---|---|---|---|---|---|
| | 2" | 3" | 4" | 6" | 8" | 10" | 12" | 14" | 18" | 24" |
| Intensity Factor | 32.3 | 22.8 | 18.6 | 12.9 | 9.85 | 7.94 | 6.48 | 5.35 | 3.6 | 2.33 |

| | Distance from UV Lamp | | | | | | |
|---|---|---|---|---|---|---|---|
| | 36" | 39.37" (1 meter) | 48" | 60" | 80" | 100" | 120" |
| Intensity Factor | 1.22 | 1.0 | 0.681 | 0.452 | 0256 | 0.169 | 0.115 |

Using a UV lamp with an output of 190 microwatts/cm$^2$ at 254 nm (at a distance of 1 meter), placed within a fermentation vessel 36" from the interior surface, the following calculations are used for achieving 99% killing of *Saccharomyces cerevisiae* (13,200 microwatt seconds/cm$^2$ required; see Table 5). Step 1: 13,200 microwatt seconds/cm$^2$/190 microwatts/cm$^2$=69.47 seconds. Step 2: The intensity factor at 36" is 1.22 (see Table 9), therefore 69.47 seconds/1.22=56.96 seconds.

Using a lamp with an output of 190 microwatts/cm$^2$ at 254 nm (at a distance of 1 meter), placed within a fermentation vessel 60" from the interior surface, the following calculations are used for achieving 99% killing of *Shigella dysentery* (4,200 microwatt seconds/cm$^2$ required; see Table 2): Step 1. 4,200 microwatt seconds/cm$^2$/190 microwatts/cm$^2$=22.10 seconds. Step 2: The intensity factor at 60" is 0.452 (see Table 9), therefore 22.10 seconds/0.452=48.90 seconds.

Using a lamp with an output of 190 microwatts/cm$^2$ at 254 nm (at a distance of 1 meter), placed within a fermentation vessel 60" from the interior surface, the following calculations are used for achieving 99% killing of *Sarcina lutea* (26,400 microwatt seconds/cm$^2$ required; see Table 2): Step 1. 26,400 microwatt seconds/cm$^2$/190 microwatts/cm$^2$=138.94 seconds. Step 2: The intensity factor at 60" is 0.452 (see Table 9), therefore 138.94 seconds/0.452=307.40 seconds.

Since *Sarcina lutea* is one of the most UV resistant bacteria (more resistant than known species of yeast), a fermentation vessel where the UV source was 60" away from the internal surface could be left on for about 307.40 seconds at each sterilization interval within the vessel to ensure all yeast (known) and pathogenic microorganisms are killed.

Example 3

Inhibiting the Growth of *Bacillus Subtilis*

To determine the effectiveness of a method of the present invention and efficacy of a UV device of the present invention for the sanitization of a stainless steel tank used in the wine making process, the killing/growth arrest of *Bacillus subtilis* (American Type Culture Collection, ATCC Number 82TM; designations: AMC [ATCC 8037, NRS 315]) was investigated. *Bacillus subtilis* forms spores, thereby making it a more UV resistant microorganism than microorganisms that do not form spores. In this experiment 30" SE UV-C lamps (Steril-Aire) were used. Three identical UV lamps were placed in a mount and put in a spiral configuration with each UV lamp set at a 15 degrees angle.

Two coupons (per time point) were spiked with a *Bacillus subtilis* suspension to give a final concentration of 9.6×10$^6$ CFU (colony forming units)/coupon for the first three time points. The fourth (25 minute) time point was inoculated with a suspension of 1.3×10$^7$ CFU/coupon (since it was tested on a different day) and allowed to air dry inside a biological safety cabinet. The coupons were allowed to dry and attached to the inside of stainless steel tank. Then the coupons were exposed to the UV light at a distance of 60" from the UV light source for four all four (4) time points: 30 seconds, 5 minutes, 15 minutes and 25 minutes. After each exposure time was performed, the coupons were swabbed in order to perform the recovery process. Two additional stainless steel coupons were spiked to be used as positive controls.

UV readings to measure the UV-C exposure at various time points were done using a General UV512C Digital UV-C Meter (radiometer). Table 10 below provides the actual UV readings recorded for each exposure time:

TABLE 10

UV Readings per Time Point and Interval.

| 30 Seconds Time Point | | 5 Minutes Time Point | | 15 Minutes Time Point | | 25 Minutes Time Point | |
|---|---|---|---|---|---|---|---|
| Seconds | uW | Minutes | uW | Minutes | uW | Minutes | uW |
| 5 | 42 | 0.5 | 135 | 1 | 243 | 3 | 200 |
| 10 | 54 | 1 | 202 | 2 | 225 | 6 | 179 |
| 15 | 69 | 1.5 | 206 | 3 | 212 | 9 | 174 |
| 20 | 87 | 2 | 204 | 4 | 198 | 12 | 167 |
| 25 | 109 | 2.5 | 202 | 5 | 186 | 15 | 162 |
| 30 | 135 | 3 | 198 | 6 | 177 | 18 | 159 |
| | | 3.5 | 195 | 7 | 176 | 21 | 162 |
| | | 4 | 192 | 8 | 181 | 24 | 169 |
| | | 4.5 | 190 | 9 | 175 | | |
| | | 5 | 184 | 10 | 172 | | |
| | | | | 11 | 171 | | |
| | | | | 12 | 171 | | |
| | | | | 13 | 171 | | |
| | | | | 14 | 170 | | |
| | | | | 15 | 168 | | |

The recovery of *Bacillus subtilis* from the coupons after 30 seconds exposure to the UV light was 5.3×10$^5$ CFU/ml.

After 5 minutes exposure to the UV light, the recovery of *Bacillus subtilis* was reduced to 1.4×10³ CFU/ml. After 15 minutes exposure to the UV light, the recovery of *Bacillus subtilis* was further reduced to 1.5×10¹ CFU/ml. Finally, after 25 minutes exposure to the UV light, no microorganisms were recovered. The recovery positive control had a count of 6.4×10⁵ CFU/ml for the first three time points and 8.1×10⁵ CFU/ml for the fourth time point.

Table 11 below summarizes the results of the above experiment and provides the log reduction results based on calculations from *Bacillus subtilis* recovery from test coupon vs. positive control.

TABLE 11

Inhibiting the growth of *Bacillus subtilis*.

| Exposure Time | Concentration *Bacillus subtilis* Recovered (CFU/ml) | Log Reduction |
|---|---|---|
| 30 seconds | $5.3 \times 10^5$ | 0.1 |
| 5 minutes | $1.4 \times 10^3$ | 2.7 |
| 15 minutes | $1.5 \times 10^1$ | 4.6 |
| 25 minutes | 0 | 5.9 |

The results of this experiment demonstrated that the UV light source tested was effective in reducing the *Bacillus subtilis* microorganism population by about 3 logs at an exposure time of 5 minutes, by about 5 logs at an exposure time of 15 minutes and by about 6 logs at exposure time of 25 minutes.

One of skill in the art will appreciate that in view of the experiments described above, a lower UV dose will be required to kill or inhibit the growth of other microorganisms that do not produce spores. Thus, by having demonstrated that one of the most UV-resistant microorganisms can be efficiently killed or growth inhibited using a method of the present invention, one of skill in the art will appreciate that the methods of the present invention in combination with the UV devices of the present invention are useful to kill or growth inhibit other microorganism that might be present in a fermentation container, more specifically on a surface of a fermentation container Example 4

Sanitization of a Room

The following provides an exemplary procedure for UV sterilization of a room, in particular, an operating room, a clean room (ISO 1-9), a nursing home, or a kitchen (commercial or residential). The UV device for sanitizing the room will be fixed to the ceiling of, for example, a 20 ft by 20 ft room. The UV device is allowed to determine the dimensions of the room and program a sanitization cycle. The room has all of the standard equipment and features of an operating room (OR), a clean room (ISO 1-9), a nursing home, or a kitchen (commercial or residential). Radiometers and plates pre inoculated with pathogenic microorganisms (such as but not limited to: *Streptococcus* and *Pseudomonas*, and foodborne bacteria such as *Shigella, Campylobacter*, and *Salmonella*) are placed throughout the room at varying distances from the UV device to determine the UV-C intensity level attained in addition to the log reduction of microorganisms. Furthermore, swab tests are taken at those locations in addition to swabbing objects of different material composition, such as polymers, metals, papers, and fabrics. This is to determine log reductions on objects of different material. Areas of potential shading are also tested in a similar fashion in order to determine the effects of reflected light on log reductions and UV-C intensity.

These experiments are repeated in each room type, however with multiple UV devices in the room. One UV device is fixed to the ceiling, one to each wall. The UV devices are allowed to scan the respective room and communicate with one another, and program a sanitization cycle.

In some embodiments the UV device will communicate with a surface reading radar unit that will enable it to detect relative distances of objects in the room, material type and will program a sanitization cycle based on the nature of the material and the positioning of the objects and room size.

Example 5

Using UV Device UV55

The UV device UV55 has been extensively tested on 55 gallon wine drums having a 2" Tri-Clover™ fitting located on the side (see below, Examples 6, 7). The UV device UV55 is particularly well suited for use on any small container from about 15 gallon kegs to about 550 gallon Porta tanks. In addition, it has also been tested on oak barrels (see Examples 6). The UV device UV55 comprises an 18" SE lamp manufactured by Steril-Aire. As tests demonstrated, at least a 5 log reduction of microorganism growth was observed when the UV device UV55 was tested in a 55 gallon drum after 3 minutes of activation (i.e., exposure of UV radiation onto the interior surface of the container, which was spiked with microorganisms). Using UV device UV55 the following applications have been proven successful: 3 minutes of exposure for 15 gallon kegs, 6 minutes for a 55 gallon drum, 12 minutes for a Porta tank or oak barrel. Among others, testing was performed with *Pseudomonas aeruginosa*, a gram negative bacterium similar to many of the herein mentioned microbes potentially harmful to wine production.

The following provides a more detailed user guide for using UV device UV55. UV device UV55 is plugged in. The user will want to make sure that the central sleeve tightening knob 86 on the side of the metal sleeve attachment ring 95 is loosened prior to use so that the central sleeve 12 can slide downwardly and upwardly easily. For storage and protection of the UV lamp 5, the central sleeve 12 is pulled into its most upward position so that the UV lamp fully retracts beyond the position of the base plate 10. The on/off or reset button 85 at the handle cap 92 is set to an on/reset position. To turn off the UV device UV55, the on/off or reset button 85 is pressed downwards. To turn on the UV device UV55, the on/off or reset button 85 is twisted clockwise.

The user places UV device UV55 on top of a container 4 so that the housing 2 is positioned on top of an opening within the container 4. The opening on top of the container is at least wide enough to allow the insertion of the UV lamp 5. If the opening of the container is wider than the base plate 10 of the UV device, the user is advised to use an additional protective shield and cover the opening of the container (but leave an opening wide enough to allow insertion of the UV lamp 5) to not get exposed to UV irradiation during the sterilization process. The protective shield may have any shape or form or size—as long as it provides an opening through which a UV lamp 5 can be inserted and prevents exposure to UV irradiation.

Once the housing 2 is positioned on top of the opening of the container 4 and the central sleeve knob 86 is loosened, a user can lower the UV lamp 5 into the container by allowing the central sleeve 12 to move downwardly. A user may conveniently control this downward movement by holding on to the handle 91 or hanging hook 84. As the central sleeve is lowered, the optical switch 98 is activated. In addition, an audible beep will sound to indicate that a sterilization cycle has started and LED lights behind the translucent plastic ring 87 will blink. Minutes of the sterilization cycle will be indicated by a specific number of blinks. Minute one is indicated by one blink, minute two is indicated by two blinks, minute tree is indicated by three blinks, etc.

Using UV device UV55 a standard keg can be sterilized in about three minutes. Using UV device UV55 a standard drum can be sterilized in about six minutes. At 12 minutes of use, an audible beep will sound alerting the user to the amount of time which has elapsed. The UV lamp 5 will remain on until switched off (see above).

UV device UV55 will be automatically reset as the user moves the central sleeve 12 upwardly and the optical switch 98 moves upwardly out of the housing 2. The sterilization cycle of another container may be done.

Example 6

UV Sanitation of a Wooden Barrel Using UV Device UV55

A study was performed to determine the efficacy of UV device UV55 for the sanitization of wood barrel tanks used in the wine making process. The study was performed by inoculating the interior surface of wood barrel coupons (in triplicate) with a suspension of *Pseudomonas aeruginosa*. The coupons were then exposed to UV light according to Table 12.

Details of this study were as follows: Three coupons (per time point) were spiked with the *Pseudomonas aeruginosa* suspension to give a final concentration of $1.9 \times 10^7$ CFU/coupon. The coupons were placed at three different locations within the tank and exposed to the UV light (UV55) for five (5) time points: 2 minutes, 4 minutes, 6 minutes, 8 minutes, and 12 minutes. After each exposure time was performed, the coupons were immersed into 10 ml Tryptic Soy Broth to perform the enumeration/recovery process. Three additional stainless steel coupons were spiked as above and used as positive controls (no exposure to UV light).

The result of this study is shown in Table 12.

TABLE 12

Growth inhibition (log reduction) of *Pseudomonas aeruginosa* after exposure to UV light (UV device UV55).

| Exposure Time (minutes) | Concentration of *Pseudomonas aeruginosa* recoverd (CFU/coupon) | Log Reduction |
|---|---|---|
| 2 | $1.3 \times 10^5$ | 2.2 |
| 4 | $1.5 \times 10^5$ | 2.1 |
| 6 | $1.1 \times 10^5$ | 2.2 |
| 8 | $9.1 \times 10^4$ | 2.3 |
| 12 | $1.4 \times 10^3$ | 4.1 |

Based on this test, it can be concluded that the UV light source tested was effective in reducing the *Pseudomonas aeruginosa* population by about 4.1 logs at an exposure time of 12 minutes.

Example 7

A Comparative Study: UV Sanitation Using UV55 Vs. Chemical Cleaning

A study was performed to determine the efficacy of UV device UV55 for the sanitization of stainless steel tanks used in the wine making process versus a solution of sodium carbonate peroxyhydrate at a concentration of 1.56 g/L. The study was performed by inoculating the interior surface of stainless steel coupons (in triplicate) with a suspension of *Pseudomonas aeruginosa*. The coupons were then exposed to either UV light or to the chemical solution according to Table 13.

Details of UV Sanitation were as follows: Three coupons (per time point) were spiked with the *Pseudomonas aeruginosa* suspension to give a final concentration of $1.5 \times 10^8$ CFU/coupon. The coupons were placed at three different locations within the tank and exposed to the UV light (UV55) for four (4) time points: 2 minutes, 4 minutes, 6 minutes, and 8 minutes. After each exposure time was performed, the coupons were immersed into 100 ml Tryptic Soy Broth to perform the enumeration/recovery process. Three additional stainless steel coupons were spiked as above and used as positive controls (no exposure to UV light).

Details of Carbonate Solution Cleaning were as follows: Three coupons were spiked with the *Pseudomonas aeruginosa* suspension to give a final concentration of $1.5 \times 10^8$ CFU/coupon. The coupons were then immersed into 100 ml of sodium carbonate peroxyhydrate solution at a concentration of 1.56 g/L and then into 100 ml Tryptic Soy Broth to perform the enumeration/recovery process. The same positive control and suspension was used for both studies.

The result of this study is shown in Table 13.

TABLE 13

Growth inhibition (log reduction) of *Pseudomonas aeruginosa* after exposure to UV light (UV device UV55) and Treatment with sodium carbonate peroxyhydrate solution.

| UV55 Exposure Time (minutes) | Concentration of *Pseudomonas aeruginosa* recovered (CFU/coupon) | Log Reduction |
|---|---|---|
| 2 | $1.8 \times 10^3$ | 4.9 |
| 4 | $1.2 \times 10^3$ | 5.1 |
| 6 | $8.3 \times 10^2$ | 5.3 |
| 8 | $<1 \times 10^3$ | ≥5.2 |
| Sodium Carbonate Solution | $3 \times 10^6$ | 1.7 |

Based on this test, it can be concluded that the UV light source tested was effective in reducing growth of the *Pseudomonas aeruginosa* population by >5.2 logs at an exposure time of 8 minutes. The sodium carbonate solution used as a rinse was effective in reducing growth of the *Pseudomonas aeruginosa* population by about 1.7 log.

Example 8

Vertical vs. Horizontal Irradiation of a Tank

A study was performed to determine whether a container could be more efficiently UV sterilized when a UV light source is inserted into the container and positioned either in a parallel (i.e., horizontal) position with respect to the bottom or top of the container or in a perpendicular (i.e., vertical) position with respect to the bottom and top of a the container. The container used in this study was a tank of 450 cm in diameter. A total UV lamp output of 300 W was employed in the testing. The 300 W output could either be a single UV lamp or a cluster of lamps. No assumptions on light blocking by mounts, cables or shields were made.

The calculations were made for various lamp distances from the floor (or top) of the container of 50 cm (highest peak), 100 cm (second highest peak), 150 cm (third highest peak) and 200 cm (fourth highest peak) or from the floor (or top) of the container of 0 cm (highest peak), 50 cm (second highest peak), 100 cm (third highest peak) and 150 cm (fourth highest peak). A comparative study aiming to determine if the positioning of UV lamps in a container, horizontal vs. vertical affects significantly the irradiation received at the corner of the container also was performed: (i) corner irradiance, horizontal arrangement of UV lamps at 0 degree; (ii) corner irradiance, horizontal arrangement of UV lamps at 90 degree; and (iii) corner irradiance, vertical arrangement of UV lamps. While the overall distribution of irradiance was highly dependent on the orientation of the UV lamps (i.e., horizontal vs. vertical), the irradiance at the corners of the container (the more difficult area to UV sterilize) was not affected by the orientation of the UV lamps (data not shown). Under the testing parameters, it was found that the limiting irradiance for almost all configurations is around 200 uW/cm$^2$. Assuming a required dose of 100,000 uJ/cm2, the required illumination time for achieving a 4 log reduction of bacterial growth is about 500 sec.

Example 9

Irradiation Study of a Tank

A ray tracing analysis was performed using ZEMAX® software in order to determine irradiance times and distribution within a cylindrical tank having a diameter of 38.8 ft and 40 ft in height. The UV lamps were arranged in a cluster configuration at an angle of 15 degrees with the vertical axis. The UV lamps were 1500 mm in length and 32 mm in diameter. UV-C output per bulb was 134 W. The study assumed zero reflectivity within the tank offering a worst case scenario. The optical study software (ZEMAX®) placed 4 detector plates in the orientations of North, South, East and West. 1,000,000 analysis rays were used to determine UV light distribution. The base of the LTV lamps were positioned 6" off the lower surface of the tank and at a fixed distance of 10' from the lower port regardless of tank size. The time necessary for all surfaces to reach a minimum irradiance level of 100,000 uJ/cm$^2$ was determined to be approximately 166 min (data not shown). This same bulb configuration was applied to tanks of lesser dimensions and volumes and times determined to reach the aforementioned minimum level of radiance. Respective irradiation times were determined for tanks of 202,000 gallons, 120,000 gallons, 100,000 gallons and 23,000 gallons. These times were 59 minutes, 47 minutes, 30 minutes and 18.5 minutes, respectively (data not shown).

What is claimed is:

1. A method for ultraviolet (UV) sterilization of a surface within a room, a space or a defined environment, the method comprising the steps of:
(a) attaching a UV device comprising a germicidal UV light source to a floor, a wall, a ceiling, a structure, or an object within a room, a space or a defined environment;
(b) movably and inwardly positioning the germicidal UV light source of the UV device into the room, the space or the defined environment; and
(c) activating the germicidal UV light source, whereby sterilization of the surface within the room, the space or the defined environment is initiated;
wherein the germicidal UV light source comprises at least one UV lamp;
wherein the UV device comprises a circuit board; and
wherein the circuit board comprises a functionality selected from the group consisting of:
(A) comprising a radiofrequency identifier reader;
(B) communicating with a radiofrequency identifier;
(C) controlling the movement of the germicidal UV light source within the room, the space or the defined environment;
(D) controlling the rate of descent of the germicidal UV light source within the room, the space or the defined environment;
(E) controlling the positioning of the germicidal UV light source within the room, the space or the defined environment;
(F) controlling an on/off status of a motor, wherein the motor controls the positioning of the germicidal UV light source within the room, the space or the defined environment;
(G) controlling an on/off status of the germicidal UV light source based on measuring whether a pre-determined UV intensity has been attained;
(H) controlling extension of the germicidal UV light source from a housing;
(I) controlling retraction of the germicidal UV light source into the housing;
(J) responding to a jammed position status of the germicidal UV light source;
(K) controlling an optical sensor which initiates a timer upon inserting the germicidal UV light source into the room, the space or the defined environment;
(L) controlling a speaker emitting an audible signal at the beginning or completion of a sterilization cycle;
(M) controlling a plurality of LED lights indicting a status of a sterilization cycle;
(N) relaying UV light intensity via a sensor to the room, space or defined environment;
(O) uploading and relaying information from the radiofrequency identifier;
(P) generating a report on time of a sterilization cycle;
(Q) generating a report on duration of a sterilization cycle;
(R) generating a report on UV light intensity attained during a sterilization cycle;
(S) emailing, phoning or texting a report on time of a sterilization cycle;
(T) emailing, phoning or texting a report on duration of a sterilization cycle;
(U) emailing, phoning or texting a report on UV light intensity attained during a sterilization cycle; and
(V) emailing, phoning or texting an alert to an individual that a sterilization cycle is complete.

2. The method according to claim 1, wherein the method further comprises the step of:
(d) moving the germicidal UV light source within the room, the space or the defined environment to a pre-determined position.

3. The method according to claim 1, wherein the method further comprises the step of:

(d) moving the germicidal UV light source within the room, the space or the defined environment from a horizontal position to a vertical position.

4. The method according to claim 1, wherein the method further comprises the step of:
(d) moving the germicidal UV light source within the room, the space or the defined environment into an angular position.

5. The method according to claim 1, wherein the method further comprises the step of:
(d) moving the germicidal UV light source longitudinally within the room, the space or the defined environment.

6. The method according to claim 1, wherein the method further comprises the step of:
(d) moving the germicidal UV light source laterally within the room, the space or the defined environment.

7. The method according to claim 1, wherein the method further comprises the step of:
(d) rotating the germicidal UV light source within the room, the space or the defined environment.

8. The method according to claim 1, wherein the method further comprises the step of:
(d) programming the UV device to obtain a predetermined UV light intensity.

9. The method according to claim 8, wherein step (d) comprises an algorithm taking into account one or more of a parameter selected from the group consisting of size of the room, the space or the defined environment, shape of the room, the space or the defined environment, intensity of the at least one UV lamp, and distance of the at least one UV lamp from the surface of the room, the space or the defined environment to be sterilized.

10. The method according to claim 1, wherein the UV device is a portable UV device.

11. The method according to claim 1, wherein the UV device is attached to the ceiling within the room, the space or the defined environment.

12. The method according to claim 1, wherein the UV device is attached to the structure within the room, the space or the defined environment.

13. The method according to claim 1, wherein the surface within the room, the space or the defined environment comprises etched aluminum, foil aluminum, polished aluminum, chromium, glass, nickel, silver, stainless steel, tri-plated steel, water paint, white cotton, white oil paint, white paper, white porcelain or white wall plaster.

14. The method according to claim 1, wherein the germicidal UV light source comprises a plurality of UV lamps.

15. The method according to claim 14, wherein members of the plurality of UV lamps are arranged in a cluster.

16. The method according to claim 15, wherein the cluster is selected from a cluster comprising at least two UV lamps, a cluster comprising at least three UV lamps, a cluster comprising at least four UV lamps, a cluster comprising at least five UV lamps, a cluster comprising at least six UV lamps, a cluster comprising at least seven UV lamps, and a cluster comprising at least eight UV lamps.

17. The method according to claim 15, wherein members of the plurality of UV lamps are arranged adjustably so that they can be positioned at varying angles with respect to each other.

18. The method according to claim 17, wherein the angles are between 0 and 90 degrees.

19. The method according to claim 15, wherein a member of the plurality of UV lamps can be moved from a closed configuration position into an open configuration position.

20. The method according to claim 14, wherein the plurality of UV lamps comprises a first UV lamp and a second UV lamp.

21. The method according to claim 20, wherein the first UV lamp and the second UV lamp are spaced apart.

22. The method according to claim 20, wherein the first UV lamp and the second UV lamp are arranged perpendicular with respect to each other.

23. The method according to claim 20, wherein the first UV lamp and the second UV lamp are arranged adjustably so that they can move in a circular motion.

24. The method according to claim 1, wherein the at least one UV lamp is selected from the group consisting of a hot cathode lamp, a slimline lamp, a high output lamp, and a cold cathode lamp.

25. The method according to claim 1, wherein the at last one UV lamp is selected from the group consisting of a low pressure UV lamp, a medium pressure UV lamp and a high pressure UV lamp.

26. The method according to claim 1, wherein the germicidal UV light source is a pulsed germicidal UV light source.

27. The method according to claim 1, wherein the at least one UV lamp is a mercury UV lamp.

28. The method according to claim 1, wherein the UV device further comprises a frame and wherein the germicidal UV light source is attached to the frame.

29. The method according to claim 1, wherein the UV device further comprises a spring, a hinge or a UV lamp module swing and wherein the spring, the hinge or the UV lamp module swing permits the at least one UV lamp to move from a closed position into an exposed position for sterilization.

30. The method according to claim 1, further comprising the step of:
(d) placing a detector at an interior location within the room, the space or the defined environment, wherein the detector is configured to measure a UV intensity level.

31. The method according to claim 1, wherein the UV device further comprises a detector.

32. The method according to claim 31, wherein the detector is configured to measure a UV intensity level.

33. The method according to claim 31, wherein the detector is connected to the germicidal UV light source.

34. The method according to claim 32, wherein the germicidal UV light source is shut off when a specified UV intensity level is attained.

35. The method according to claim 1, wherein the UV device further comprises a housing.

36. The method according to claim 35, wherein the housing is selected from the group consisting of a mesh cage, a housing, which allows UV light to pass through, a housing comprising a protective sleeve, a housing comprising a fan cooling system, a housing comprising a reflector, a housing attached to a bracket, a housing attached to a parallelogramming arm, a housing attached to a central sleeve, a housing attached to a scissor boom, a removable housing, and a housing which may fold open.

37. The method according to claim 35, wherein the housing surrounds the at least one UV lamp.

38. The method according to claim 35, wherein the housing is made of a polymer.

39. The method according to claim 35, wherein the housing is made of teflon.

40. The method according to claim 35, wherein the housing permits passing through of UV light without the at least one UV lamp being released from the housing.

41. The method according to claim 35, wherein the housing is a housing which does not allow UV light to pass through and wherein the at least one UV lamp can be released from the housing.

42. The method according to claim 1, wherein the UV device further comprises a motor, wherein the motor controls the positioning of the germicidal UV light source within the room, space or the defined environment.

43. The method according to claim 1, wherein the UV device further comprises an optical component selected from the group consisting of a reflector, a shutter, a lens, a splitter, and a minor.

44. The method according to claim 1, wherein the UV device comprises a rope, a wire, or a cable, wherein the rope, the wire or the cable is connected to the UV light source and wherein the rope, the wire or the cable permits moving the UV light source from a first position within the room, the space or the defined environment to a second position within the room, the space or the defined environment.

45. The method according to claim 1, wherein the UV device comprises a control box comprising an on/off switch to activate and/or shut off the germicidal UV light source.

46. The method according to claim 45, wherein the control box further comprises a lamp indicator showing whether power is sent to the germicidal UV light source.

47. The method according to claim 1, wherein one or more species of microorganisms is present on the surface within the room, the space or the defined environment and wherein the activation of the germicidal UV light source results in inhibiting the growth of the one or more species of microorganisms.

48. The method according to claim 47, wherein the one or more species of microorganisms is selected from the group consisting of *Candida, Kloeckera, Hanseniaspora, Zygosaccharomyces, Schizosaccharomyces, Torulaspora, Brettanomyces, Pichia, Hansenula, Metschnikowia, Debaryomyces, Saccharomycodes, Williopsis, Saccharomyces cerevisiae, Saccharomyces bayanus, Escherichia coli, Corynebacterium diphtheria, Salmonella paratyphi, Salmonella typhosa, Shigella dysenteriae, Shigella flexerni, Staphylococcus albus, Staphylococcus aureus, Streptococcus hemolyticus, Streptococcus lactis, Streptococcus viridians, Vibrio comma, Brettanomyces (Dekkera),* lactic acid bacteria, *Pediococcus, Lactobacillus, Oenococcus, Acetobacter,* and *Leuconostoc.*

49. The method according to claim 1, wherein the UV light source produces a UV light intensity within a range of between 1,300 $\mu Ws/cm^2$ to 440,000 $\mu Ws/cm^2$.

50. The method according to claim 1, wherein the functionality of the circuit board is (G) controlling the on/off status of the germicidal UV light source based on measuring whether a predetermined UV intensity has been attained.

51. The method according to claim 1, wherein the room, space or defined environment is selected from the group consisting of a commercial kitchen, a medical facility, an acute care area, an operating room, a medical equipment storage cabinet, a clean room, a bathroom, a waiting room, a food production area, a food processing area, a nursery home, a trailer, a rail car, a grocery store display case, a deli counter, a fish display case, a poultry display case, a floral display case, a refrigerated display case, a non-refrigerated display case, and a conveyor belt.

52. The method according to claim 15, wherein the UV cluster extends from the ceiling of the room, space or defined environment and wherein individual members of the UV lamp cluster protrude downwards at varying angles.

53. The method according to claim 15, wherein the UV cluster extends from the ceiling of the room, space or defined environment and wherein individual members of the UV lamp cluster protrude downwards at varying angles.

54. The method according to claim 1, wherein the surface within the room, space or defined environment comprises a liquid layer.

55. The method according to claim 54, wherein the liquid layer comprises a liquid selected from the group consisting of apple juice, beer, liquid sugar, milk, vinegar, water, and wine.

56. A method for ultraviolet (UV) sterilization of a surface within a room, a space or a defined environment, the method comprising the steps of:
(a) attaching a UV device comprising a germicidal UV light source to a room, a space or a defined environment;
(b) movably and inwardly positioning the germicidal UV light source of the UV device into the room, the space or the defined environment; and
(c) activating the germicidal UV light source, whereby sterilization of the surface within the room, the space or the defined environment is initiated;
wherein the germicidal UV light source comprises at least one UV lamp;
wherein the UV device comprises a circuit board;
wherein the circuit board comprises a functionality selected from the group consisting of:
(A) comprising a radiofrequency identifier reader;
(B) communicating with a radiofrequency identifier;
(C) controlling the movement of the germicidal UV light source within the room, the space or the defined environment;
(D) controlling the rate of descent of the germicidal UV light source within the room, the space or the defined environment;
(E) controlling the positioning of the germicidal UV light source within the room, the space or the defined environment;
(F) controlling an on/off status of a motor, wherein the motor controls the positioning of the germicidal UV light source within the room, the space or the defined environment;
(G) controlling an on/off status of the germicidal UV light source based on measuring whether a pre-determined UV intensity has been attained;
(H) controlling extension of the germicidal UV light source from a housing;
(I) controlling retraction of the germicidal UV light source into the housing;
(J) responding to a jammed position status of the germicidal UV light source;
(K) controlling an optical sensor which initiates a timer upon inserting the germicidal UV light source into the room, the space or the defined environment;
(L) controlling a speaker emitting an audible signal at the beginning or completion of a sterilization cycle;
(M) controlling a plurality of LED lights indicting a status of a sterilization cycle;
(N) relaying UV light intensity via a sensor to the room, space or defined environment;
(O) uploading and relaying information from the radiofrequency identifier;
(P) generating a report on time of a sterilization cycle;
(Q) generating a report on duration of a sterilization cycle;

(R) generating a report on UV light intensity attained during a sterilization cycle;
(S) emailing, phoning or texting a report on time of a sterilization cycle;
(T) emailing, phoning or texting a report on duration of a sterilization cycle;
(U) emailing, phoning or texting a report on UV light intensity attained during a sterilization cycle; and
(V) emailing, phoning or texting an alert to an individual that a sterilization cycle is complete; and
wherein the UV light source is attached to a robot having wheels.

57. The method according to claim 56, wherein programming of the UV device permits the UV light source to move on the floor within the room, the space, or the defined environment.

58. The method according to claim 56, wherein the surface within the room, space or defined environment comprises a liquid layer.

59. The method according to claim 58, wherein the liquid layer comprises a liquid selected from the group consisting of apple juice, beer, liquid sugar, milk, vinegar, water, and wine.

60. The method according to claim 56, wherein the room, space or defined environment is selected from the group consisting of a commercial kitchen, a medical facility, an acute care area, an operating room, a medical equipment storage cabinet, a clean room, a bathroom, a waiting room, a food production area, a food processing area, a nursery home, a trailer, a rail car, a grocery store display case, a deli counter, a fish display case, a poultry display case, a floral display case, a refrigerated display case, a non-refrigerated display case, and a conveyor belt.

61. A method for ultraviolet (UV) sterilization of a surface within a room, a space or a defined environment, the method comprising the steps of:
   (a) attaching a UV device comprising a germicidal UV light source to a room, a space or a defined environment;
   (b) movably and inwardly positioning the germicidal UV light source of the UV device into the room, the space or the defined environment; and
   (c) activating the germicidal UV light source, whereby sterilization of the surface within the room, the space or the defined environment is initiated;
      wherein the germicidal UV light source comprises at least one UV lamp;
      wherein the UV device comprises a circuit board;
      wherein the circuit board comprises a functionality selected from the group consisting of:
   (A) comprising a radiofrequency identifier reader;
   (B) communicating with a radiofrequency identifier;
   (C) controlling the movement of the germicidal UV light source within the room, the space or the defined environment;
   (D) controlling the rate of descent of the germicidal UV light source within the room, the space or the defined environment;
   (E) controlling the positioning of the germicidal UV light source within the room, the space or the defined environment;
   (F) controlling an on/off status of a motor, wherein the motor controls the positioning of the germicidal UV light source within the room, the space or the defined environment;
   (G) controlling an on/off status of the germicidal UV light source based on measuring whether a pre-determined UV intensity has been attained;
   (H) controlling extension of the germicidal UV light source from a housing;
   (I) controlling retraction of the germicidal UV light source into the housing;
   (J) responding to a jammed position status of the germicidal UV light source;
   (K) controlling an optical sensor which initiates a timer upon inserting the germicidal UV light source into the room, the space or the defined environment;
   (L) controlling a speaker emitting an audible signal at the beginning or completion of a sterilization cycle;
   (M) controlling a plurality of LED lights indicting a status of a sterilization cycle;
   (N) relaying UV light intensity via a sensor to the room, space or defined environment;
   (O) uploading and relaying information from the radiofrequency identifier;
   (P) generating a report on time of a sterilization cycle;
   (Q) generating a report on duration of a sterilization cycle;
   (R) generating a report on UV light intensity attained during a sterilization cycle;
   (S) emailing, phoning or texting a report on time of a sterilization cycle;
   (T) emailing, phoning or texting a report on duration of a sterilization cycle;
   (U) emailing, phoning or texting a report on UV light intensity attained during a sterilization cycle; and
   (V) emailing, phoning or texting an alert to an individual that a sterilization cycle is complete; and
   wherein the UV light source is attached to a robot crawler having a plurality of suctions permitting it to crawl either vertically on the wall within the room, the space, or the defined environment or horizontally on the ceiling within the room, the space, or the defined environment.

62. The method according to claim 61, wherein the surface within the room, space or defined environment comprises a liquid layer.

63. The method according to claim 62, wherein the liquid layer comprises a liquid selected from the group consisting of apple juice, beer, liquid sugar, milk, vinegar, water, and wine.

64. The method according to claim 61, wherein the room, space or defined environment is selected from the group consisting of a commercial kitchen, a medical facility, an acute care area, an operating room, a medical equipment storage cabinet, a clean room, a bathroom, a waiting room, a food production area, a food processing area, a nursery home, a trailer, a rail car, a grocery store display case, a deli counter, a fish display case, a poultry display case, a floral display case, a refrigerated display case, a non-refrigerated display case, and a conveyor belt.

* * * * *